US008252795B2

(12) United States Patent
Fink et al.

(10) Patent No.: US 8,252,795 B2
(45) Date of Patent: Aug. 28, 2012

(54) IMIDAZOPYRIDAZINECARBONITRILES USEFUL AS KINASE INHIBITORS

(75) Inventors: Brian E. Fink, Yardley, PA (US); Libing Chen, Newtown, PA (US); Ashvinikumar V. Gavai, Princeton Junction, NJ (US); Liqi He, Furlong, PA (US); Soong-Hoon Kim, Titusville, NJ (US); Andrew James Nation, Scotch Plains, NJ (US); Yufen Zhao, Pennington, NJ (US); Litai H. Zhang, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 202 days.

(21) Appl. No.: 12/575,589

(22) Filed: Oct. 8, 2009

(65) Prior Publication Data

US 2010/0113458 A1 May 6, 2010

Related U.S. Application Data

(60) Provisional application No. 61/104,045, filed on Oct. 9, 2008.

(51) Int. Cl.
*A01N 43/58* (2006.01)
*A61K 31/50* (2006.01)
*C07D 487/00* (2006.01)

(52) U.S. Cl. ........................................ 514/250; 544/236

(58) Field of Classification Search .................. 514/250; 544/236

See application file for complete search history.

(56) References Cited

U.S. PATENT DOCUMENTS

2007/0078140 A1 4/2007 Borzilleri et al.
2008/0045536 A1 2/2008 Vaccaro et al.

FOREIGN PATENT DOCUMENTS

WO WO98/08847 A1 3/1998
WO WO01/83481 A1 11/2001
WO WO2004/017950 A2 3/2004
WO WO2004/046331 A2 6/2004
WO WO2005/080355 A1 9/2005
WO WO2007/025043 A2 3/2007
WO WO2007/025090 A2 3/2007
WO WO2007/035428 A1 3/2007
WO WO2007/038314 A2 4/2007
WO WO2008/008539 A2 1/2008
WO WO2008/025822 A1 3/2008
WO WO2008/029152 A2 3/2008
WO WO2008/030579 3/2008

OTHER PUBLICATIONS

Pinedo et al.*

McMahon et al.*

Stalter et al., "Asymmetric expression of protein kinase CK2 subunits in human kidney tumors," Biochem. Biophys. Res. Commun. 202, 141-147 [1994].

Landesman-Bollag et al., "Protein kinase CK2 in mammary gland tumorigenesis," Oncology, 20' 3247-3257 [2001].

Daya-Makin et al., "Activation of a tumor-associated protein kinase (p40TAK) and casein kinase 2 in human squamous cell carcinomas and adenocarcinomas of the lung," Cancer Research 54, 2262-2268 [1994].

Faust et al., "Antisense oligonucleotides against protein kinase CK2-α inhibit growth of squamous cell carcinoma of the head and neck in vitro," Head & Neck 22, 341-346 [2000].

Wang et al., "Role of protein kinase CK2 in the regulation of tumor necrosis factor-related apoptosis inducing ligand-induced apoptosis in prostate cancer cells," Cancer Research 66, 2242-2249 [2006].

Nie et al., "Structure-based design, synthesis, and study of pyrazolo[1,5-a][1,3,5]triazine derivatives as potent inhibitors of protein kinase CK2," Bioorganic & Medicinal Chemistry Letters 17:4191-4195 (2007).

Nie et al., "Structure-based design, synthesis of novel macrocyclic pyrazolo[1,5-α][1,3,5]triazine compounds as potent inhibitors of protein kinase CK2 and their anticancer activities," Bioorganic & Medicinal Chemistry Letters 18:619-623 (2008).

"*Design of Prodrugs*," edited by H. Bundgaard, (Elsevier, 1985).

Widder et al., *Methods in Enzymology*, vol. 112, pp. 309-396, (Academic Press, 1985).

H. Bundgaard, Chapter 5, "Design and Application of Prodrugs," A Textbook of Drug Design and Development, pp. 113-191, P. Krosgaard-Larsen et al., eds. Harwood Academics Publishers, (1991).

H. Bundgaard, *Advanced Drug Delivery Reviews*, 8, pp. 1-38 (1992).

Y. Guari et al., "Palladium-Catalyzed Animation of Aryl Bromides and Aryl Triflates Using Diphosphane Ligands: A Kinetic Study," *Chem. Eur. J.* 7: 475-482 (2001).

K. Suzuki et al., "A New Hybrid Phosphine Ligand for Palladium-Catalyzed Amination of Aryl Halides," Adv. Synth. Catal., 350, pp. 652-656 (2008).

* cited by examiner

*Primary Examiner* — Paul V. Ward
(74) *Attorney, Agent, or Firm* — Hong Liu

(57) ABSTRACT

The invention provides compounds of Formula (I)

(I)

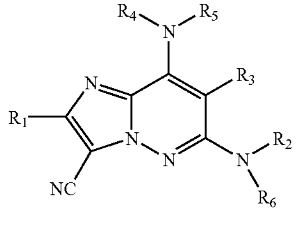

and pharmaceutically acceptable salts thereof. The Formula (I) imidazopyridazines inhibit protein kinase activity thereby making them useful as anticancer agents.

11 Claims, No Drawings

IMIDAZOPYRIDAZINECARBONITRILES USEFUL AS KINASE INHIBITORS

RELATED APPLICATIONS

This application claims priority benefit of U.S. provisional application Ser. No. 61/104,045, filed on Oct. 9, 2008, the disclosure of which is hereby incorporated by reference in its entirety.

FIELD OF THE INVENTION

The invention relates to novel substituted imidazopyridazine compounds useful as protein kinase inhibitors. The invention also relates to methods of using the compounds in the treatment of proliferative and other types of diseases and to pharmaceutical compositions containing the compounds.

BACKGROUND OF THE INVENTION

The invention relates to fused heterocyclic compounds which inhibit protein kinase enzymes, compositions which contain protein kinase inhibiting compounds and methods of using inhibitors of protein kinase enzymes to treat diseases which are characterized by an overexpression or upregulation of protein kinases. Protein kinases mediate intracellular signal transduction. They do this by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell. An extracellular stimulus may effect one or more cellular responses related to cell growth, migration, differentiation, secretion of hormones, activation of transcription factors, muscle contraction, glucose metabolism, control of protein synthesis and regulation of cell cycle.

Many diseases are associated with abnormal cellular responses triggered by protein kinase-mediated events. These diseases include autoimmune diseases, inflammatory diseases, neurological and neurodegenerative diseases, cancer, cardiovascular diseases, allergies and asthma, Alzheimer's disease or hormone-related diseases. Accordingly, there has been a substantial effort in medicinal chemistry to find protein kinase inhibitors that are effective as therapeutic agents.

Serine/threonine kinases are a class of protein kinases that are among the most promising drug targets for future small molecule inhibitors. Inhibition of serine/threonine kinases is likely to have relevance to the treatment of cancer, diabetes and a variety of inflammatory disorders. The successful development of GLEEVEC® as a Bcr/Abl protein kinase inhibitor has provided further evidence that protein kinases including protein kinase CK2 are valid drug targets for potential cancer therapies.

Protein kinase CK2 (formerly known as casein kinase II) is a highly conserved serine/threonine kinase. Protein kinase CK2 is ubiquitously distributed and constitutively active in eukaryotes. In mammals, the enzyme exists in two isozymic forms due to variations in the catalytic subunits of the enzyme. The CK2 holoenzyme is a heterotetrameric complex composed of two catalytic α (CK2A1) subunits or α' (CK2A2) subunits and two regulatory β-subunits. The formation of CK2 complexes containing the catalytic subunits requires dimerization of the regulatory β-subunits. CK2 interacts with a variety of cellular proteins and has been implicated in cell replication such as cell proliferation and differentiation, cellular survival, and tumorigenesis. With respect to tumorigenesis, protein kinase CK2 has been implicated in kidney tumors (Stalter et al., "Asymmetric expression of protein kinase CK2 subunits in human kidney tumors", *Biochem. Biophys. Res. Commun.,* 202:141-147 (1994)), mammary gland tumors (Landesman-Bollag et al., "Protein kinase CK2 in mammary gland tumorigenesis", *Oncology,* 20:3247-3257 (2001)), lung carcinoma (Daya-Makin et al., "Activation of a tumor-associated protein kinase (p40TAK) and casein kinase II in human squamous cell carcinomas and adenocarcinomas of the lung", *Cancer Res.,* 54:2262-2268 (1994)), head and neck carcinoma (Faust et al., "Antisense oligonucleotides against protein kinase CK2-α inhibit growth of squamous cell carcinoma of the head and neck in vitro", *Head Neck,* 22:341-346 (2000)), and prostate cancer (Wang et al., "Role of protein kinase CK2 in the regulation of tumor necrosis factor-related apoptosis inducing ligand-induced apoptosis in prostate cancer cells", *Cancer Res.,* 66:2242-2249 (2006)).

Inhibitors of protein kinases are widely sought and small molecule compounds capable of modulating protein kinases have been reported. For example, pyrazolotriazines as CK2 kinase inhibitors were reported in Nie et al. (*Bioorganic & Medicinal Chemistry Letters,* 17:4191-4195 (2007); 18:619-623 (2008)) and imidazopyridazines as IRAK kinase modulators were reported in PCT Publication WO 2008/030579. In addition, certain imidazopyridazine compounds were disclosed in WO 2007/038314, published Apr. 5, 2007, WO 2008/0045536, published Feb. 21, 2008, both assigned to the present assignee. The present invention relates to a new class of imidazopyridazine-carbonitriles found to be effective inhibitors of protein kinases, particularly the CK2 kinase. These novel compounds are provided to be useful as pharmaceuticals with desirable stability, bioavailability, therapeutic index and toxicity values that are important to their drugability.

SUMMARY OF THE INVENTION

The invention is directed to fused heterocyclic compounds of Formulae (I)-(X) or stereoisomers, tautomers, pharmaceutically acceptable salts, solvates or prodrugs thereof, which inhibit protein kinase enzymes, especially protein kinase CK2 for the treatment of cancer.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibiting the activity of protein kinase CK2 comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for inhibiting angiogenesis or treating cancers comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, in preparing a medicament for the treatment of cancer in a human patient, particularly a cancer receptive to treatment via inhibition of the CK2 enzyme.

These and other features of the invention will be set forth in the expanded form as the disclosure continues.

DETAILED DESCRIPTION OF THE INVENTION

The invention provides for novel imidazopyridazine compounds useful as therapeutic agents, pharmaceutical compositions employing such novel compounds and for methods of using such compounds.

In accordance with the invention, there are disclosed compounds of Formula (I) including enantiomers, diastereomers, tautomers, pharmaceutically-acceptable salts, prodrugs, hydrates, or solvates thereof, (I)

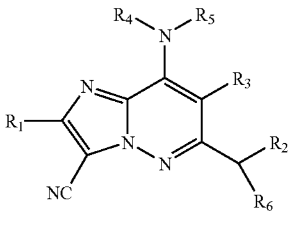

wherein $R_1$ is selected from H, F, Cl, Br, CN, and $C_{1-6}$alkyl;

$R_2$ is selected from aryl substituted with 0-5 $R_{2a}$ and heteroaryl substituted with 0-5 $R_{2a}$;

$R_{2a}$, at each occurrence, is independently selected from H, F, Cl, Br, =O, CN, $NO_2$, —$OR_b$, —$S(O)_pR_c$, —$C(=O)R_d$, —$NR_aR_a$, —$(CR_{2b}R_{2c})_rC(=O)NR_aR_a$, —$NR_aC(=O)R_d$, —$NR_aC(=O)OR_b$, —$OC(=O)NR_aR_a$, —$NR_aC(=O)NR_aR_a$, —$(CR_{2b}R_{2c})_rC(=O)OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_{2b}R_{2c})_r$—$C_{3-6}$-carbocyclyl substituted with 0-5 $R_e$, and —$(CR_{2b}R_{2c})_r$-heterocyclyl substituted with 0-5 $R_e$;

$R_{2b}$, at each occurrence, is independently selected from H and $C_{1-6}$alkyl substituted with 0-5 $R_e$;

$R_{2c}$, at each occurrence, is independently selected from H and $C_{1-6}$alkyl substituted with 0-5 $R_e$;

$R_3$ is selected from H, F, Cl, Br, CN, —$OR_b$, —$NR_aR_a$, —$C(=O)NR_aR_a$, —$NR_aS(O)_2R_c$, —$NR_aC(=O)R_d$, —$NR_aC(=O)OR_b$, and $C_{1-6}$alkyl substituted with 0-5 $R_e$;

$R_4$ is selected from H, $C_{1-6}$alkyl substituted with 0-5 $R_e$, —$(CR_{4b}R_{4c})_rOR_b$, —$(CR_{4b}R_{4c})_rS(O)_pR_c$, —$(CR_{4b}R_{4c})_rC(=O)R_d$, —$(CR_{4b}R_{4c})_rNR_aR_a$, —$(CR_{4b}R_{4c})_rC(=O)NR_aR_a$, —$(CR_{4b}R_{4c})_rNR_aC(=O)R_d$, —$(CR_{4b}R_{4c})_rNR_aC(=O)OR_b$, —$(CR_{4b}R_{4c})_rOC(=O)NR_aR_a$, —$(CR_{4b}R_{4c})_rNR_aC(=O)NR_aR_a$, —$(CR_{4b}R_{4c})_rC(=O)OR_b$, —$(CR_{4b}R_{4c})_rS(O)_2NR_aR_a$, —$(CR_{4b}R_{4c})_rNR_aS(O)_2NR_aR_a$, —$(CR_{4b}R_{4c})_rNR_aS(O)_2R_c$, —$(CR_{4b}R_{4c})_r$—$C_{3-6}$carbocyclyl substituted with 0-5 $R_{4a}$, —$(CR_{4b}R_{4c})_r$-heterocyclyl substituted with 0-5 $R_{4a}$;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, =O, CN, —$SO_3H$, —$S(O)_pR_c$, —$S(O)_2NR_aR_a$, —$NR_aS(O)_2R_c$, —$OR_b$, —$NR_aR_a$, —$NR_aC(=O)R_d$, —$NR_aC(=O)NR_aR_a$, —$C(=O)OR_b$, —$C(=O)R_d$, —$OC(=O)R_d$, —$C(=O)NR_aR_a$, $C_{3-6}$cycloalkyl, heterocyclyl, and aryl;

$R_{4b}$, at each occurrence, is independently selected from H and $C_{1-6}$alkyl substituted with 0-5 $R_e$;

$R_{4c}$, at each occurrence, is independently selected from H and $C_{1-6}$alkyl substituted with 0-5 $R_e$;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$-carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$-carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H, $C_{1-6}$ alkyl substituted with 0-5 $R_e$, $C_{2-6}$alkenyl substituted with 0-5 $R_e$, $C_{2-6}$alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOC_{1-5}$ alkyl, —$(CH_2)_rOH$, SH, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring;

p, at each occurrence, is independently selected from zero, 1, and 2; and r, at each occurrence, is independently selected from zero, 1, 2, 3, and 4.

In another aspect, there are disclosed compounds of Formula (II) including enantiomers, diastereomers, tautomers, pharmaceutically-acceptable salts, prodrugs, hydrates, or solvates thereof, (II)

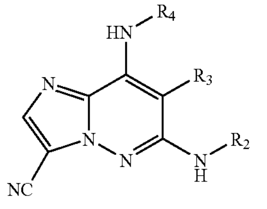

wherein $R_2$ is selected from aryl substituted with 0-4 $R_{2a}$ and heteroaryl substituted with 0-4 $R_{2a}$, wherein said heteroaryl comprises carbon atoms and 1-4 heteroatoms selected from N, O, and $S(O)_p$;

$R_{2a}$, at each occurrence, is independently selected from H, F, Cl, Br, =O, CN, —$OR_b$, —$S(O)_pR_c$, —$C(=O)R_d$, —$NR_aR_a$, —$(CR_{2b}R_{2c})_rC(=O)NR_aR_a$, —$NR_aC(=O)R_d$, —$NR_aC(=O)OR_b$, —$OC(=O)NR_aR_a$, —$NR_aC(=O)$ $NR_aR_a$, $—(CR_{2b}R_{2c})_rC(=O)OR_b$, $—S(O)_2NR_aR_a$, $—NR_aS(O)_2NR_aR_a$, $—NR_2S(O)_2R_c$, $C_{1-4}$ alkyl substituted with 0-3 $R_e$, $—(CR_{2b}R_{2c})_r—C_{3-6}$carbocyclyl substituted with 0-3 $R_e$, and $—(CR_{2b}R_{2c})_r$-heterocyclyl substituted with 0-3 $R_e$;

$R_{2b}$, at each occurrence, is independently selected from H and $C_{1-4}$alkyl;

$R_{2c}$, at each occurrence, is independently selected from H and $C_{1-4}$alkyl;

$R_4$ is selected from H, $C_{1-4}$alkyl substituted with 0-5 $R_e$, $—(CR_{4b}R_{4c})_rOR_b$, $—(CR_{4b}R_{4c})_rS(O)_pR_c$, $—(CR_{4b}R_{4c})_rC(=O)R_d$, $—(CR_{4b}R_{4c})_rNR_aR_a$, $—(CR_{4b}R_{4c})_rC(=O)NR_aR_a$, $—(CR_{4b}R_{4c})_rNR_aC(=O)R_d$, $—(CR_{4b}R_{4c})_rNR_aC(=O)OR_b$, $—(CR_{4b}R_{4c})_rOC(=O)NR_aR_a$, $—(CR_{4b}R_{4c})_rNR_aC(=O)NR_aR_a$, $—(CR_{4b}R_{4c})_rC(=O)OR_b$, $—(CR_{4b}R_{4c})_rNR_aS(O)_2R_a$, $—(CR_{4b}R_{4c})_r—C_{3-6}$carbocyclyl substituted with 0-4 $R_{4a}$, $—(CR_{4b}R_{4c})_r$-heterocyclyl substituted with 0-4 $R_{4a}$;

$R_{4a}$, at each occurrence, is independently selected from F, Cl, Br, $C_{1-6}$alkyl substituted with 0-3 $R_e$, $C_{2-6}$alkynyl substituted with 0-3 $R_e$, $—SR_c$, $—S(O)_2R_c$, $—S(O)_2NR_aR_a$, $—NR_aS(O)_2R_c$, $—OR_b$, $—NR_aR_a$, $—NR_aC(=O)R_d$, $—NR_aC(=O)NR_aR_a$, $—C(=O)OR_b$, $—C(=O)R_d$, $—OC(=O)R_d$, $—C(=O)NR_aR_a$, $C_{3-6}$cycloalkyl, heterocyclyl, and aryl;

$R_{4b}$, at each occurrence, is independently selected from H and $C_{1-4}$alkyl;

$R_{4c}$, at each occurrence, is independently selected from H and $C_{1-4}$alkyl; and r, at each occurrence, is independently selected from zero, 1, 2, and 3.

In another embodiment, there are disclosed compounds including enantiomers, diastereomers, tautomers, pharmaceutically-acceptable salts, prodrugs, hydrates, or solvates thereof, wherein $R_2$ is selected from 4- to 7-membered monocyclic or 8- to 12-membered bicyclic aryl substituted with 1-4 $R_{2a}$ and 4- to 7-membered monocyclic or 7- to 12-membered bicyclic heteroaryl substituted with 0-4 $R_{2a}$;

$R_{2a}$, at each occurrence, is independently selected from H, F, Cl, Br, =O, CN, $—OR_b$, $—S(O)_pR_c$, $—C(=O)R_d$, $—NR_aR_a$, $—(CH_2)_rC(=O)NR_aR_a$, $—NHC(=O)R_d$, $—NHC(=O)OR_b$, $—OC(=O)NR_aR_a$, $—NHC(=O)NR_aR_a$, $—(CH_2)_rC(=O)OR_b$, $—S(O)_2NR_aR_a$, $—NHS(O)_2NR_aR_a$, $—NHS(O)_2R_c$, or $C_{1-6}$ alkyl substituted with 0-3 $R_e$, $—(CH_2)_r—C_{3-6}$ carbocyclyl substituted with 0-3 $R_e$, and $—(CH_2)_r$-heterocyclyl substituted with 0-3 $R_e$;

$R_4$ is selected from H, $C_{1-4}$alkyl substituted with 0-5 $R_e$, $—(CH_2)_rOR_b$, $—(CH_2)_rS(O)_pR_c$, $—(CH_2)_rC(=O)R_d$, $—(CH_2)_rNR_aR_a$, $—(CH_2)_rC(=O)NR_aR_a$, $—(CH_2)_rNR_aC(=O)R_d$, $—(CH_2)_rNR_aC(=O)OR_b$, $—(CH_{2c})_rOC(=O)NR_aR_a$, $—(CH_2)_rNR_aC(=O)NR_aR_a$, $—(CH_2)_rC(=O)OR_b$, $—(CH_2)_rNR_aS(O)_2R_c$, $—(CH_2)_r—C_{3-6}$cycloalkyl substituted with 0-3 $R_{4a}$, $—(CH_2)_r$-aryl substituted with 0-3 $R_{4a}$, $—(CH_2)_r$-heterocyclyl substituted with 0-3 $R_e$;

$R_{4a}$, at each occurrence, is independently selected from $C_{1-6}$alkyl substituted with 0-3 $R_e$, $—SR_c$, $—S(O)_2R_c$, $—S(O)_2NR_aR_a$, $—NHS(O)_2R_c$, $—OR_b$, $—NR_aR_a$, $—NHC(=O)R_d$, $—NHC(=O)NR_aR_a$, $—C(=O)OR_b$, $—C(=O)R_d$, $—OC(=O)R_d$, $—C(=O)NR_aR_a$, $C_{3-6}$cycloalkyl, heterocyclyl, and aryl.

In another embodiment, there are disclosed compounds of formula (III) including enantiomers, diastereomers, tautomers, pharmaceutically-acceptable salts, prodrugs, hydrates, or solvates thereof, (III)

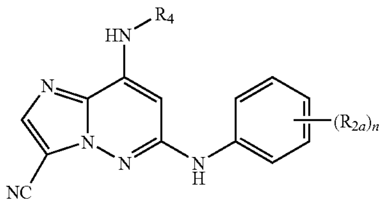

wherein $R_{2a}$, at each occurrence, is independently selected from H, F, Cl, Br, =O, CN, $—OR_b$, $—S(O)_pR_c$, $—C(=O)R_d$, $—NR_aR_a$, $—(CH_2)_rC(=O)NR_aR_a$, $—NHC(=O)R_d$, $—NHC(=O)OR_b$, $—OC(=O)NR_aR_a$, $—NHC(=O)NR_aR_a$, $—(CH_2)_rC(=O)OR_b$, $—S(O)_2NR_aR_a$, $—NHS(O)_2NR_aR_a$, $—NHS(O)_2R_c$, or $C_{1-4}$ alkyl substituted with 0-3 $R_e$, $—(CH_2)_r—C_{3-6}$ carbocyclyl substituted with 0-3 $R_e$, and $—(CH_2)_r$-heterocyclyl substituted with 0-3 $R_e$;

$R_4$ is selected from H, $C_{1-6}$alkyl substituted with 0-5 $R_e$, $—(CH_2)_rOR_b$, $—(CH_2)_rNR_aR_a$, $—(CH_2)_r—C_{3-6}$cycloalkyl substituted with 0-3 $R_{4a}$, $—(CH_2)_r$-aryl substituted with 0-3 $R_{4a}$, and $—(CH_2)_r$-heterocyclyl substituted with 0-3 $R_{4a}$;

$R_{4a}$, at each occurrence, is independently selected from $C_{1-6}$alkyl substituted with 0-3 $R_e$, $—SR_c$, $—S(O)_2NR_aR_a$, $—NHS(O)_2R_c$, $—OR_b$, $—NR_aR_a$, $—NHC(=O)R_d$, $—NHC(=O)NR_aR_a$, $—C(=O)OR_b$, $—C(=O)R_d$, $—OC(=O)R_d$, $—C(=O)NR_aR_a$, $C_{3-6}$cycloalkyl, heterocyclyl, and aryl;

$R_a$, at each occurrence, is independently selected from H, CN, $C_{1-6}$ alkyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;

$R_c$, at each occurrence, is independently selected from $C_{1-6}$ alkyl substituted with 0-5 $R_f$, $C_{3-6}$carbocyclyl, and heterocyclyl;

$R_d$, at each occurrence, is independently selected from H, $C_{1-6}$ alkyl substituted with 0-5 $R_e$, $—(CH_2)_r—C_{3-10}$carbocyclyl substituted with 0-5 $R_e$, and $—(CH_2)_r$-heterocyclyl substituted with 0-5 $R_e$;

$R_e$, at each occurrence, is independently selected from $C_{1-6}$ alkyl substituted with 0-5 $R_f$, $—(CH_2)_r—C_{3-6}$ cycloalkyl, F, Cl, Br, CN, $NO_2$, =O, $CO_2H$, $—(CH_2)_rOC_{1-5}$alkyl, $—(CH_2)_rOH$, SH, and $—(CH_2)_rNR_fR_f$;

$R_f$, at each occurrence, is independently selected from H, $C_{1-5}$ alkyl, and phenyl, or $R_f$ and $R_f$ together with the nitrogen atom to which they are both attached form a heterocyclic ring; and n, at each occurrence, is independently selected from zero, 1, 2, 3, and 4.

In another embodiment, there are disclosed compounds of Formula (III) including enantiomers, diastereomers, tautomers, pharmaceutically-acceptable salts, prodrugs, hydrates, or solvates thereof, wherein $R_4$ is selected from H, $C_{1-6}$alkyl substituted with 0-3 $R_e$, $—(CH_2)_rOR_b$, $—(CH_2)_rNR_aR_a$, $—C_{3-6}$cycloalkyl substituted with 0-3 $R_{4a}$, aryl substituted with 0-3 $R_{4a}$; 4-, 5-, or 6-membered non-aromatic monocyclic heterocyclyl substituted with 0-3 $R_{4a}$, and 5- or 6-membered heteroaryl substituted with 0-3 $R_{4a}$;

$R_{4a}$, at each occurrence, is independently selected from $C_{1-6}$alkyl substituted with 0-3 $R_e$, —$S(O)_2NR_aR_a$, —$NHS(O)_2R_c$, —$OR_b$, —$NR_aR_a$, —$NHC(=O)R_d$, —$NHC(=O)NR_aR_a$, —$C(=O)OR_b$, —$C(=O)R_d$, —$OC(=O)R_d$, —$C(=O)NR_aR_a$, $C_{3-6}$cycloalkyl, heterocyclyl, and aryl;

$R_a$, at each occurrence, is independently selected from H, CN, $C_{1-4}$ alkyl substituted with 0-3 $R_e$, —$(CH_2)_r$-heterocyclyl substituted with 0-3 $R_e$; or $R_a$ and $R_a$ together with the nitrogen atom to which they are both attached form a monocyclic heterocyclic ring substituted with 0-3 $R_e$;

$R_b$, at each occurrence, is independently selected from H and $C_{1-4}$ alkyl substituted with 0-3 $R_e$, and heterocyclyl;

$R_c$, at each occurrence, is independently selected from $C_{1-4}$ alkyl substituted with 0-3 $R_e$ and heterocyclyl;

$R_d$, at each occurrence, is independently selected from H, $C_{1-4}$ alkyl substituted with 0-3 $R_e$, —$(CH_2)_r$—$C_{3-10}$carbocyclyl substituted with 0-3 $R_e$, and —$(CH_2)_r$-heterocyclyl substituted with 0-3 $R_e$;

$R_e$, at each occurrence, is independently selected from $C_{1-4}$ alkyl substituted with 0-4 $R_f$, F, Cl, Br, CN, $NO_2$, =O, $CO_2H$, —$(CH_2)_rOC_{1-5}$ alkyl, —$(CH_2)_rOH$, SH, and —$(CH_2)_rNR_fR_f$;

$R_f$, at each occurrence, is independently selected from H and $C_{1-4}$alkyl or $R_f$ and $R_f$ together with the nitrogen atom to which they are both attached form a heterocyclic ring.

In another embodiment, there are disclosed compounds of Formula (III) including enantiomers, diastereomers, tautomers, pharmaceutically-acceptable salts, prodrugs, hydrates, or solvates thereof, wherein $R_{2a}$, at each occurrence, is independently selected from H, F, Cl, Br, CN, =O, O—$C_{1-4}$alkyl substituted with 0-3 $R_e$, —$O(CH_2)_rNR_aC_{1-4}$alkyl —O—$(CH_2)_rOC_{1-4}$alkyl, —$O(CH_2)_r$-heterocyclyl, —$S(O)_2C_{1-4}$alkyl, —$C(=O)C_{1-4}$ alkyl, —$NH_2$, —$N(C_{1-4}alkyl)_2$, —NHCN, —$NR_a(CH_2)_rNR_aC_{1-4}$alkyl, —$NR_a(CH_2)_rOC_{1-4}$alkyl, —$NH(CH_2)_r$-heterocyclyl, —$(CH_2)_rC(=O)NH_2$, —$C(=O)NH$-heterocyclyl, —$C(=O)NH(CH_2)_rN(C_{1-4}alkyl)_2$, —$C(=O)$-heterocyclyl, —$NHC(=O)C_{1-4}$alkyl, —$NHC(=O)OC_{1-4}$alkyl, —$NHC(=O)NHC_{1-4}$alkyl, $C(=O)OC_{1-4}$alkyl, —$(CH_2)_rC(=O)OH$, —$S(O)_2NH_2$, —$S(O)_2NH$-heterocyclyl, —$S(O)_2NHC_{1-4}$alkyl, —$S(O)_2$-heterocyclyl substituted with 0-3 $R_e$, —$NH_2S(O)_2NH_2$, —$NHS(O)_2C_{1-4}$alkyl, $C_{1-4}$alkyl, $CF_3$, —$(CH_2)_rOH$, $C_{3-6}$-carbocyclyl substituted with 0-3 $R_e$, non-aromatic heterocyclyl substituted with 0-3 $R_e$, and 5- or 6-membered heteroaryl substituted with 0-3 $R_e$.

In another embodiment, there are disclosed compounds of Formula (II) including enantiomers, diastereomers, tautomers, pharmaceutically-acceptable salts, prodrugs, hydrates, or solvates thereof, wherein $R_2$ is selected from

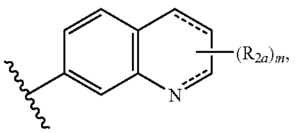

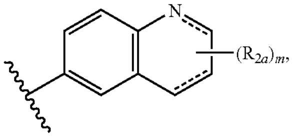

-continued

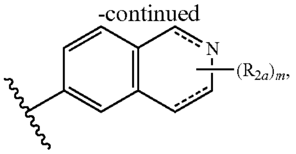

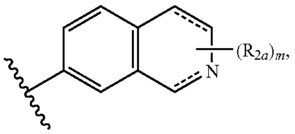

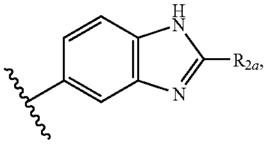

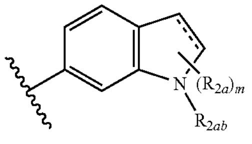

,

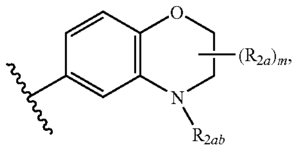

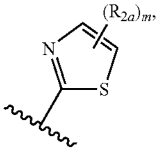

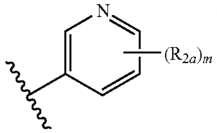

,

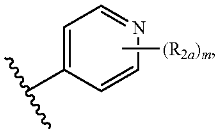

and

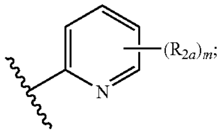

---- represents an optional bond;

$R_{2ab}$, at each occurrence, is independently selected from $C_{1-4}$ alkyl substituted with 0-3 $R_e$, —$S(O)_pR_c$, —$C(=O)R_d$, $C(=O)OR_b$; and m, at each occurrence, is independently selected from zero, 1, 2, and 3.

In another embodiment, there are disclosed compounds of Formula (II) including enantiomers, diastereomers, tautomers, pharmaceutically-acceptable salts, prodrugs, hydrates, or solvates thereof, wherein $R_4$ is selected from H, $C_{1-4}$alkyl substituted with 0-5 $R_e$, —$(CH_2)_rOR_b$, —$(CH_2)_rNR_aR_a$, —$(CH_2)_r$—$C_{3-6}$cycloalkyl substituted with 0-3 $R_{4a}$, —$(CH_2)_r$-aryl substituted with 0-3 $R_{4a}$, and —$(CH_2)_r$-heterocyclyl substituted with 0-3 $R_{4a}$.

In another embodiment, there are disclosed compounds of Formula (II) including enantiomers, diastereomers, tautomers, pharmaceutically-acceptable salts, prodrugs, hydrates, or solvates thereof, wherein $R_2$ is selected from phenyl substituted with 1-3 $R_{2a}$ and heteroaryl substituted with 0-3 $R_{2a}$;

$R_{2a}$, at each occurrence, is independently selected from H, F, Cl, Br, =O, CN, —$OR_b$, —$S(O)_2R_c$, —$C(=O)R_d$, —$NR_aR_a$, —$(CH_2)_rC(=O)NR_aR_a$, —$NHC(=O)R_d$, —$NHC(=O)OR_b$, —$NHC(=O)NR_aR_a$, —$(CH_2)_rC(=O)OR_b$, —$S(O)_2NR_aR_a$, —$NHS(O)_2NR_aR_a$, —$NHS(O)_2R_c$, $C_{1-4}$alkyl substituted with 0-3 $R_e$, non-aromatic heterocyclyl substituted with 0-3 $R_e$, and heteroaryl substituted with 0-3 $R_e$;

$R_4$ is selected from H, $C_{1-6}$alkyl substituted with 0-3 $R_e$, —$(CH_2)_rOR_b$, —$C_{3-6}$cycloalkyl substituted with 0-3 $R_{4a}$, aryl substituted with 0-3 $R_{4a}$, —$(CH_2)_r$-4- to 6-membered saturated monocyclic heterocyclyl substituted with 0-3 $R_{4a}$, and —$(CH_2)_r$-5- to 6-membered heteroaryl substituted with 0-3 $R_{4a}$;

$R_{4a}$, at each occurrence, is independently selected from $C_{1-4}$alkyl substituted with 0-3 $R_e$, —$OR_b$, and $C(=O)NR_aR_a$;

$R_a$, at each occurrence, is independently selected from H, CN, $C_{1-4}$ alkyl substituted with 0-5 $R_e$, —$(CH_2)_r$-heterocyclyl substituted with 0-3 $R_e$; or $R_a$ and $R_a$ together with the nitrogen atom to which they are both attached form a heterocyclic ring, having 1 to 3 heteroatoms selected from N, O, S, and substituted with 0-3 $R_e$;

$R_b$, at each occurrence, is independently selected from H, $C_{1-4}$ alkyl substituted with 0-3 $R_e$, and heterocyclyl;

$R_c$, at each occurrence, is independently $C_{1-4}$ alkyl substituted with 0-3 $R_e$;

$R_d$, at each occurrence, is independently selected from H and $C_{1-4}$ alkyl substituted with 0-3 $R_e$;

$R_e$, at each occurrence, is independently selected from $C_{1-4}$ alkyl substituted with 0-4 $R_f$, F, Cl, Br, =O, —$(CH_2)_rOC_{1-5}$ alkyl, —$(CH_2)_rOH$, and —$(CH_2)_rNR_fR_f$; and $R_f$, at each occurrence, is independently selected from H and $C_{1-3}$alkyl or $R_f$ and $R_f$ together with the nitrogen atom to which they are both attached form a heterocyclic ring;

r, at each occurrence, is independently selected from zero, 1, 2, and 3; and m, at each occurrence, is independently selected from zero, 1, 2, and 3.

In another embodiment, there are disclosed compounds of Formulae (IV) and (V) including enantiomers, diastereomers, tautomers, pharmaceutically-acceptable salts, prodrugs, hydrates, or solvates thereof, (IV)

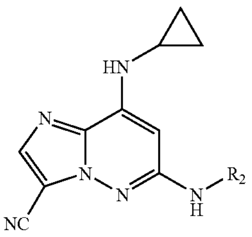

or (V)

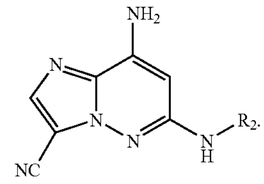

In another embodiment of the compounds of Formulae (I) and (II), $R_2$ is heteroaryl selected from pyridyl, pyrimidinyl, pyrazinyl, pyridazinyl, triazinyl, furyl, quinolinyl, dihydroquinolinyl, tetrahydroquinolinyl, isoquinolinyl, thienyl, imidazolyl, thiazolyl, indolyl, pyrrolyl, oxazolyl, benzofuryl, benzothienyl, benzthiazolyl, benzoxazinyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane, each of which is substituted with 0-4 $R_{2a}$.

In another embodiment, there are disclosed compounds of Formula (VI) or (VII), including enantiomers, diastereomers, tautomers, pharmaceutically-acceptable salts, prodrugs, hydrates, or solvates thereof, (VI)

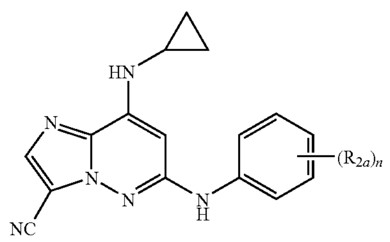

or (VII)

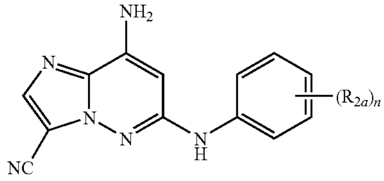

wherein $R_{2a}$, at each occurrence, is independently selected from H, F, Cl, Br, =O, CN, —$OR_b$, —$S(O)_pR_c$, —C(=O)$R_d$, —$NR_aR_a$, —$(CH_2)_rC$(=O)$NR_aR_a$, —$NR_aC$(=O)$R_d$, —$NR_aC$(=O)$OR_b$, —OC(=O)$NR_aR_a$, —$NR_aC$(=O)$NR_aR_a$, —$(CH_2)_rC$(=O)$OR_b$, —$S(O)_2NR_aR_a$, —$NR_aS(O)_2NR_aR_a$, —$NR_aS(O)_2R_c$, or $C_{1-6}$ alkyl substituted with 0-3 $R_e$, —$(CH_2)_r$—$C_{3-6}$ carbocyclyl substituted with 0-3 $R_e$, and —$(CH_2)_r$-heterocyclyl substituted with 0-3 $R_e$;

$R_a$, at each occurrence, is independently selected from H, CN, $C_{1-4}$ alkyl substituted with 0-3 $R_e$, —$(CH_2)_r$-heterocyclyl substituted with 0-3 $R_e$; or $R_a$ and $R_a$ together with the nitrogen atom to which they are both attached form a monocyclic heterocyclic ring substituted with 0-3 $R_e$;

$R_b$, at each occurrence, is independently selected from H and $C_{1-4}$ alkyl substituted with 0-3 $R_e$, and heterocyclyl;

$R_c$, at each occurrence, is independently selected from $C_{1-4}$ alkyl substituted with 0-3 $R_e$, $C_{2-4}$ alkenyl substituted with 0-3 $R_e$, and $C_{2-4}$ alkynyl substituted with 0-3 $R_e$;

$R_d$, at each occurrence, is independently selected from H, $C_{1-4}$ alkyl substituted with 0-3 $R_e$, —$(CH_2)_r$—$C_{3-10}$carbocyclyl substituted with 0-3 $R_e$, and —$(CH_2)_r$-heterocyclyl substituted with 0-3 $R_e$;

$R_e$, at each occurrence, is independently selected from $C_{1-4}$ alkyl substituted with 0-4 $R_f$, F, Cl, Br, CN, $NO_2$, =O, $CO_2H$, —$(CH_2)_rOC_{1-5}$ alkyl, —$(CH_2)_rOH$, SH, and —$(CH_2)_rNR_fR_f$;

$R_f$, at each occurrence, is independently selected from H and $C_{1-4}$alkyl or $R_f$ and $R_f$ together with the nitrogen atom to which they are both attached form a heterocyclic ring;

n, at each occurrence, is independently selected from zero, 1, 2, 3, and 4; and r, at each occurrence is independently selected from zero, 1, 2, and 3.

In another embodiment of the compounds of Formulae (VI) and (VII), $R_{2a}$, at each occurrence, is independently selected from H, F, Cl, Br, CN, =O, O—$C_{1-4}$alkyl substituted with 0-3 $R_e$, —$O(CH_2)_rNR_aC_{1-4}$alkyl —O—$(CH_2)_rOC_{1-4}$ alkyl, —$O(CH_2)_r$-heterocyclyl, —$S(O)_2C_{1-4}$alkyl, —C(=O) $C_{1-4}$alkyl, —$NH_2$, —$N(C_{1-4}alkyl)_2$, —NHCN, —$NR_a(CH_2)_rNR_aC_{1-4}$alkyl, —$NR_a(CH_2)_rOC_{1-4}$alkyl, —$NH(CH_2)_r$-heterocyclyl, —$(CH_2)_rC$(=O)$NH_2$, —C(=O)NH-heterocyclyl, —C(=O)$NH(CH_2)_rN(C_{1-4}alkyl)_2$, —C(=O)-heterocyclyl, —NHC(=O)$C_{1-4}$alkyl, —NHC(=O)$C_{1-4}$alkyl, —NHC(=O)$NHC_{1-4}$alkyl, C(=O)$OC_{1-4}$ alkyl, —$(CH_2)_rC$(=O)OH, —$S(O)_2NH_2$, —$S(O)_2$NH-heterocyclyl, —$S(O)_2NHC_{1-4}$alkyl, —$S(O)_2$-heterocyclyl substituted with 0-3 $R_e$, —$NH_2S(O)_2NH_2$, —$NHS(O)_2C_{1-4}$ alkyl, $C_{1-4}$alkyl, $CF_3$, —$(CH_2)_r$OH, $C_{3-6}$carbocyclyl substituted with 0-3 $R_e$, non-aromatic heterocyclyl substituted with 0-3 $R_e$, and 5- or 6-membered heteroaryl substituted with 0-3 $R_e$.

In another embodiment of the compounds of Formula (I), $R_1$ is H;

$R_2$ is selected from phenyl substituted with 1-4 $R_{2a}$ and heteroaryl substituted with 0-4 $R_{2a}$;

$R_{2a}$, at each occurrence, is independently selected from H, F, Cl, Br, =O, CN, —$OR_b$, —$S(O)_pR_c$, —C(=O)$R_d$, —$NR_aR_a$, —$(CH_2)_r$C(=O)$NR_aR_a$, —$NR_a$C(=O)$R_d$, —$NR_a$C(=O)$OR_b$, —OC(=O)$NR_aR_a$, —$NR_a$C(=O)$NR_aR_a$, —$(CH_2)_r$C(=O)$OR_b$, —$S(O)_2NR_aR_a$, —$NR_aS(O)_2NR_aR_a$, —$NR_2S(O)_2R_e$, $C_{1-6}$ alkyl substituted with 0-3 $R_e$, —$(CH_2)_r$—$C_{3-6}$carbocyclyl substituted with 0-3 $R_e$, and —$(CH_2)_r$-heterocyclyl substituted with 0-3 $R_e$;

$R_3$ is selected from H and $C_{1-4}$alkyl;

$R_4$ is selected from H, $C_{1-6}$alkyl substituted with 0-5 $R_e$, —$(CR_{4b}R_{4c})_rOR_b$, —$(CR_{4b}R_{4c})_rNR_aR_a$, —$(CR_{4b}R_{4c})_r$—$C_{3-6}$cycloalkyl substituted with 0-3 $R_{4a}$, —$(CR_{4b}R_{4c})_r$-aryl substituted with 0-3 $R_{4a}$, and —$(CR_{4b}R_{4c})_r$-heterocyclyl substituted with 0-3 $R_{4a}$;

$R_{4a}$, at each occurrence, is independently selected from F, Cl, Br, CN, $C_{1-6}$-alkyl substituted with 0-3 $R_e$, —$OR_b$, and C(=O)$NR_aR_a$;

$R_{4b}$, at each occurrence, is independently selected from H and $C_{1-4}$-alkyl;

$R_{4c}$, at each occurrence, is independently selected from H and $C_{1-4}$alkyl;

$R_5$ is H;

$R_6$ is H;

$R_a$, at each occurrence, is independently selected from H, CN, $C_{1-6}$ alkyl substituted with 0-5 $R_e$, —$(CH_2)_r$-heterocyclyl substituted with 0-3 $R_e$; or $R_a$ and $R_a$ together with the nitrogen atom to which they are both attached form a heterocyclic ring, having 1 to 3 heteroatoms selected from N, O, S, and substituted with 0-3 $R_e$;

$R_b$, at each occurrence, is independently selected from H, $C_{1-6}$ alkyl substituted with 0-3 $R_e$, and heterocyclyl;

$R_c$, at each occurrence, is independently selected from $C_{1-6}$ alkyl substituted with 0-3 $R_e$, $C_{2-6}$ alkenyl substituted with 0-3 $R_e$, and $C_{2-6}$ alkynyl substituted with 0-3 $R_e$;

$R_d$, at each occurrence, is independently selected from H, $C_{1-6}$ alkyl substituted with 0-3 $R_e$, $C_{2-6}$ alkenyl substituted with 0-3 $R_e$, $C_{2-6}$ alkynyl substituted with 0-3 $R_e$, —$(CH_2)_r$—$C_{3-10}$carbocyclyl substituted with 0-3 $R_e$, and —$(CH_2)_r$-heterocyclyl substituted with 0-3 $R_e$;

$R_e$, at each occurrence, is independently selected from $C_{1-4}$ alkyl substituted with 0-4 $R_f$, F, Cl, Br, CN, $NO_2$, =O, $CO_2H$, —$(CH_2)_rOC_{1-5}$ alkyl, —$(CH_2)_r$OH, SH, and —$(CH_2)_rNR_fR_f$;

$R_f$, at each occurrence, is independently selected from H and $C_{1-4}$alkyl or $R_f$ and $R_f$ together with the nitrogen atom to which they are both attached form a heterocyclic ring;

p, at each occurrence, is independently selected from zero, 1, and 2; and r, at each occurrence, is independently selected from zero, 1, 2, and 3.

In another embodiment of the compounds of Formula (I), $R_2$ is selected from phenyl substituted with 1-3 $R_{2a}$ and

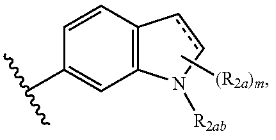
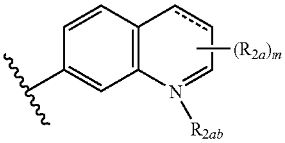
,
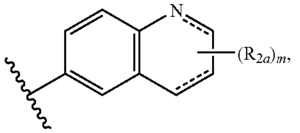
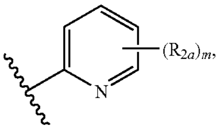
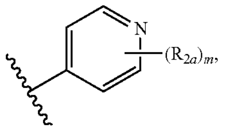
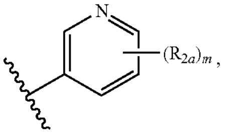
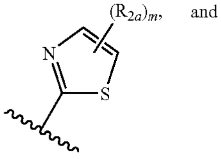
and
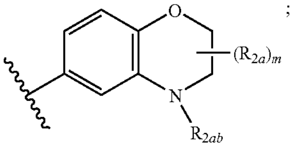
;

---- represents an optional bond;

$R_{2a}$, at each occurrence, is independently selected from H, F, Cl, Br, =O, CN, —$OR_b$, —$S(O)_2R_c$, —C(=O)$R_d$, —$NR_aR_a$, —$(CH_2)_r$C(=O)$NR_aR_a$, —NHC(=O)$R_d$, —NHC(=O)$OR_b$, —NHC(=O)$NR_aR_a$, —$(CH_2)_r$C(=O)$OR_b$, —$S(O)_2NR_aR_a$, —$NHS(O)_2NR_aR_a$, —$NHS(O)_2R_c$, $C_{1-4}$alkyl substituted with 0-3 $R_e$, non-aromatic heterocyclyl substituted with 0-3 $R_e$, and heteroaryl substituted with 0-3 $R_e$;

$R_{2ab}$, at each occurrence, is independently selected from $C_{1-4}$ alkyl substituted with 0-3 $R_e$, —$S(O)_pR_c$, —C(=O)$R_d$, C(=O)$OR_b$;

$R_4$ is selected from H, $C_{1-6}$alkyl substituted with 0-3 $R_e$, —$(CH_2)_rOR_b$, —$C_{3-6}$cycloalkyl substituted with 0-3 $R_{4a}$, aryl substituted with 0-3 $R_{4a}$, —$(CH_2)_r$-4- to 6-membered saturated monocyclic heterocyclyl substituted with 0-3 $R_{4a}$, and —$(CH_2)_r$-5- to 6-membered heteroaryl substituted with 0-3 $R_{4a}$;

$R_{4a}$, at each occurrence, is independently selected from $C_{1-4}$alkyl substituted with 0-3 $R_e$, —$OR_b$, and C(=O)$NR_aR_a$;

$R_a$, at each occurrence, is independently selected from H, CN, $C_{1-4}$ alkyl substituted with 0-5 $R_e$, —$(CH_2)_r$-heterocyclyl substituted with 0-3 $R_e$; or $R_a$ and $R_a$ together with the nitrogen atom to which they are both attached form a heterocyclic ring, having 1 to 3 heteroatoms selected from N, O, S, and substituted with 0-3 $R_e$;

$R_b$, at each occurrence, is independently selected from H, $C_{1-4}$ alkyl substituted with 0-3 $R_e$, and heterocyclyl;

$R_c$, at each occurrence, is independently $C_{1-4}$ alkyl substituted with 0-3 $R_e$;

$R_d$, at each occurrence, is independently selected from H and $C_{1-4}$ alkyl substituted with 0-3 $R_e$;

$R_e$, at each occurrence, is independently selected from $C_{1-4}$ alkyl substituted with 0-4 $R_f$, F, Cl, Br, =O, —$(CH_2)_rOC_{1-5}$ alkyl, —$(CH_2)_r$OH, and —$(CH_2)_rNR_fR_f$; and $R_f$, at each occurrence, is independently selected from H and $C_{1-3}$alkyl or $R_f$ and $R_f$ together with the nitrogen atom to which they are both attached form a heterocyclic ring;

r, at each occurrence, is independently selected from zero, 1, 2, and 3; and m, at each occurrence, is independently selected from zero, 1, 2, and 3.

In still another embodiment, $R_2$ is substituted with 1-5 $R_{2a}$ and is selected from phenyl and naphthyl.

In another embodiment, $R_2$ is substituted with 0-5 $R_{2a}$ and is heteroaryl selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

In another embodiment, $R_2$ is selected from

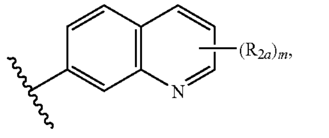

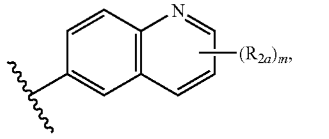

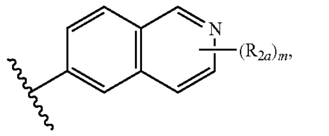

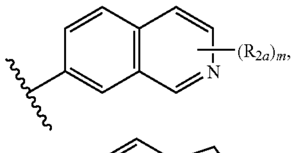 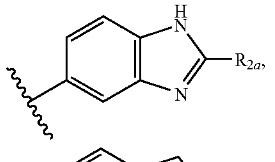

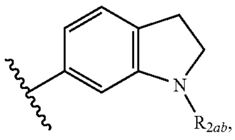 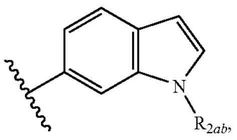

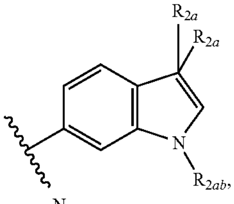 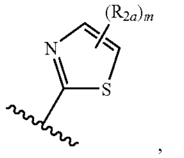 ,

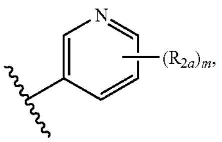 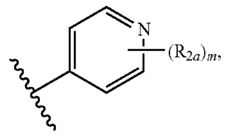 and

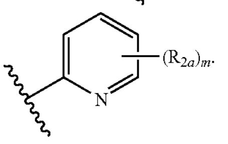

In another embodiment, $R_{2a}$, at each occurrence, is independently selected from F, Cl, Br, —$OCF_3$, —$OCHF_2$, —$CF_3$, CN, $NO_2$, $CH_3$, —OH, —$OCH_3$, $NH_2$, —$N(CH_2CH_3)_2$, —$NHC(=O)CH_3$, —$NHS(O)_2CH_3$, —$NHC(=O)OCH_3$, —$NHC(=O)CH(CH_3)_2$, —$NHC(=O)CH_2CH_3$, —$C(=O)OH$, —$C(=O)OCH_3$, $C(=O)NH_2$, —$C(=O)NHCH_3$, —$S(O)_2CH_3$, —$S(O)_2NHCH_3$, —$N(CH_3)C(=O)CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$. Non-limiting examples of the heterocyclyl include pyrrolidine, imidazole, pyrazole, oxazole, oxadiazole, thiazole, triazole, tetrazole, piperazine, piperidine, and morpholine.

In another embodiment, $R_{2a}$ is substituted with 0-2 $R_e$ and is selected from:

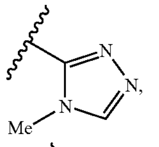 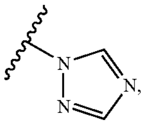 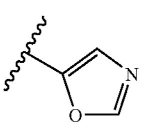

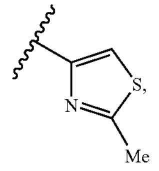 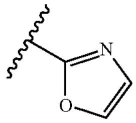 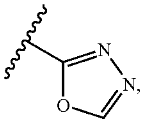

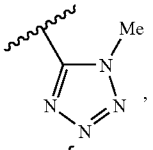 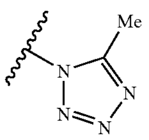 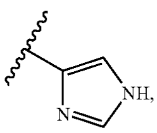

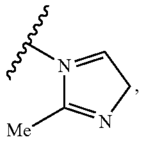 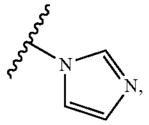 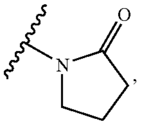

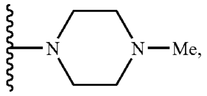 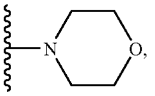 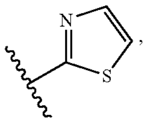 and

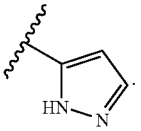

In another embodiment, $R_3$ is selected from H, F, Cl, Br, CN, —$OR_b$, —$NR_aR_a$, and $C_{1-6}$alkyl substituted with 0-5 $R_e$.

In another embodiment, $R_3$ is selected from H and $C_{1-6}$alkyl substituted with 0-5 $R_e$.

In another embodiment, $R_3$ is H.

In another embodiment, $R_4$ is selected from H, $C_{1-6}$alkyl substituted with 0-5 $R_e$, —$(CR_{4b}R_{4c})_rOR_b$, —$(CR_{4b}R_{4c})_rNR_aR_a$, —$(CR_{4b}R_{4c})_r$—$C_{3-6}$cycloalkyl substituted with 0-3 $R_{4a}$, —$(CR_{4b}R_{4c})_r$-heterocyclyl substituted with 0-3 $R_{4a}$, and —$(CR_{4b}R_{4c})_r$-aryl substituted with 0-3 $R_{4a}$;

In another embodiment, $R_4$ is selected from —$(CH_2)OR_b$, —$(CH_2CH_2)OR_b$, —$(CH(CH_3)CH_2)OR_b$, —$(C(CH_3)_2CH_2)OR_b$, —$(CH_2CH(CH_3))OR_b$, —$(CH_2C(CH_3)_2)OR_b$, —$(CH_2)NR_aR_a$, —$(CH_2CH_2)NR_aR_a$, —$(CH(CH_3)CH_2)NR_aR_a$, —$(C(CH_3)_2CH_2)NR_aR_a$, —$(CH_2CH(CH_3))NR_aR_a$, and —$(CH_2C(CH_3)_2)NR_aR_a$, wherein $R_a$, at each occurrence, is independently selected from H and $C_{1-6}$ alkyl substituted with 0-3 $R_e$; or $R_a$ and $R_a$ together with the nitrogen atom to which they are attached form a heterocyclic ring selected from imidazolidinyl, imidazolinyl, imidazolyl, indazolyl, indolinyl, indolizinyl, indolyl, isoquinolinyl, isoxazolyl, morpholinyl, oxadiazolyl, oxazolyl, pyrimidinyl, piperazinyl, pyrazinyl, pyrazolyl, pyridazinyl, pyridinyl, pyrimidinyl, pyrrolidinyl, pyrrolinyl, pyrrolyl, quinazolinyl, quinolinyl, tetrazolyl, thiazolyl, triazinyl, and triazolyl.

In another embodiment, $R_4$ is substituted with 0-3 $R_{4a}$ and is selected from phenyl, naphthyl, biphenyl, cyclopropyl, cyclobutyl, cyclopentyl, cyclohexyl, and cycloheptyl.

In another embodiment, $R_4$ is —$(CH_2)_{0-2}$-heterocyclyl substituted with 0-3 $R_{4a}$, wherein said heterocyclyl is selected from azetidinyl, thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl.

In another embodiment, $R_{4a}$, at each occurrence, is independently selected from F, Cl, Br, $C_{1-6}$-alkyl substituted with 0-5 $R_e$, $C_{2-6}$-alkenyl, $C_{2-6}$alkynyl, $NO_2$, OH, CN, —$SO_3H$, —$S(O)_pR_c$, —$S(O)_2NR_aR_a$, —$NR_aS(O)_2R_c$, —$OR_b$, —$NR_aR_a$, —$NR_aC(=O)R_d$, —$NR_aC(=O)NR_aR_a$, —$C(=O)OR_b$, —$C(=O)R_d$, —$OC(=O)R_d$, —$C(=O)NR_aR_a$, $C_{3-6}$cycloalkyl, heterocyclyl, and aryl.

All aspects of the compounds, including individual variable definitions, may be combined with other aspects to form additional compounds. For example, in one embodiment of Formula (I), $R_1$ is hydrogen and $R_3$ is hydrogen or $C_{1-4}$alkyl substituted with 0-5 $R_e$. In another embodiment, $R_1$ can be hydrogen and $R_3$ can be $OR_b$, —$NR_aR_a$, —$C(=O)NR_aR_a$, —$NHS(O)_2R_c$, —$NHC(=O)R_d$, or —$NHC(=O)OR_b$. In still another embodiment, $R_1$ is hydrogen, and $R_3$, $R_5$, and $R_6$ are all hydrogen.

In certain embodiments, the present invention includes compounds of Formula (I), or stereoisomers, tautomers, pharmaceutically acceptable salts, solvates, or prodrugs thereof, wherein:

$R_1$ is H;

$R_2$ is substituted with 0-5 $R_{2a}$ and is selected from phenyl and naphthyl;

$R_{2a}$, at each occurrence, is independently selected from F, Cl, Br, —$OCF_3$, —$OCHF_2$, —$CF_3$, CN, $NO_2$, $CH_3$, —OH, —$OCH_3$, $NH_2$, —$N(CH_2CH_3)_2$, —$NHC(=O)CH_3$, —$NHS(O)_2CH_3$, —$NHC(=O)OCH_3$, —$NHC(=O)CH(CH_3)_2$, —$NHC(=O)CH_2CH_3$, —$C(=O)OH$, —$C(=O)OCH_3$, $C(=O)NH_2$, —$C(=O)NHCH_3$, —$S(O)_2CH_3$, —$S(O)_2NHCH_3$, —$N(CH_3)C(=O)CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$. Non-limiting examples of the heterocyclyl include pyrrolidine, imidazole, pyrazole, oxazole, oxadiazole, thiazole, triazole, tetrazole, piperazine, piperidine, and morpholine;

$R_4$ is selected from H, $C_{1-6}$alkyl substituted with 0-5 $R_e$, —$(CR_{4b}R_{4c})_rOR_b$, —$(CR_{4b}R_{4c})_rNR_aR_a$, —$(CR_{4b}R_{4c})_r$—$C_{3-6}$cycloalkyl substituted with 0-3 $R_{4a}$, —$(CR_{4b}R_{4c})_r$-heterocyclyl substituted with 0-3 $R_{4a}$, and —$(CR_{4b}R_{4c})_r$-aryl substituted with 0-3 $R_{4a}$;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, =O, CN, —$SO_3H$, —$S(O)_pR_c$, —$S(O)_2NR_aR_a$, —$NR_aS(O)_2R_c$, —$OR_b$, —$NR_aR_a$, —$NR_aC(=O)R_d$, —$NR_aC(=O)NR_aR_a$, —$C(=O)OR_b$, —$C(=O)R_d$, —$OC(=O)R_d$, —$C(=O)NR_aR_a$, $C_{3-6}$cycloalkyl, heterocyclyl, and aryl;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$.

In certain embodiments, the present invention includes compounds of Formula (I), or stereoisomers, tautomers, pharmaceutically acceptable salts, solvates, or prodrugs thereof, wherein:

$R_1$ is H;

$R_2$ is substituted with 0-5 $R_{2a}$ and is heteroaryl selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, benzimidazolyl, benzothiazolyl, benzotriazolyl, quinolinyl, and isoquinolinyl;

$R_{2a}$, at each occurrence, is independently selected from F, Cl, Br, —$OCF_3$, —$OCHF_2$, —$CF_3$, CN, $NO_2$, $CH_3$, —OH, —$OCH_3$, $NH_2$, —$N(CH_2CH_3)_2$, —$NHC(=O)CH_3$, —$NHS(O)_2CH_3$, —$NHC(=O)OCH_3$, —$NHC(=O)CH(CH_3)_2$, —$NHC(=O)CH_2CH_3$, —$C(=O)OH$, —$C(=O)OCH_3$, —$C(=O)NH_2$, —$C(=O)NHCH_3$, —$S(O)_2CH_3$, —$S(O)_2NHCH_3$, —$N(CH_3)C(=O)CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$;

$R_3$ is selected from H, F, Cl, Br, CN, —$OR_b$, —$NR_aR_a$, and $C_{1-6}$alkyl substituted with 0-5 $R_e$;

$R_4$ is selected from H, $C_{1-6}$alkyl substituted with 0-5 $R_e$, —$(CR_{4b}R_{4c})_rOR_b$, —$(CR_{4b}R_{4c})_rNR_aR_a$, —$(CR_{4b}R_{4c})_r$—$C_{3-6}$cycloalkyl substituted with 0-3 $R_{4a}$, —$(CR_{4b}R_{4c})_r$—heterocyclyl substituted with 0-3 $R_{4a}$, and —$(CR_{4b}R_{4c})_r$ aryl substituted with 0-3 $R_{4a}$;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, =O, CN, —$SO_3H$, —$S(O)_pR_c$, —$S(O)_2NR_aR_a$, —$NR_aS(O)_2R_c$, —$OR_b$, —$NR_aR_a$, —$NR_aC(=O)R_d$, —$NR_aC(=O)NR_aR_a$, —$C(=O)OR_b$, —$C(=O)R_d$, —$OC(=O)R_d$, —$C(=O)NR_aR_a$, $C_{3-6}$cycloalkyl, heterocyclyl, and aryl;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$.

In certain embodiments, the present invention includes compounds of Formula (I), or stereoisomers, tautomers, pharmaceutically acceptable salts, solvates, or prodrugs thereof, wherein:

$R_1$ is H;

$R_2$ is selected from aryl substituted with 0-4 $R_{2a}$ and heteroaryl substituted with 0-4 $R_{2a}$;

$R_{2a}$, at each occurrence and when valence allows, is independently selected from F, Cl, Br, —$CF_3$, CN, $NO_2$, $CH_3$, —OH, —$OCH_3$, $NH_2$, —$N(CH_2CH_3)_2$, —$NHC(=O)CH_3$, —$NHS(O)_2CH_3$, —$NHC(=O)OCH_3$, —$NHC(=O)CH(CH_3)_2$, —$NHC(=O)CH_2CH_3$, —$C(=O)OH$, —$C(=O)OCH_3$, —$C(=O)NH_2$, —$C(=O)NHCH_3$, —$S(O)_2CH_3$, —$S(O)_2NHCH_3$, —$N(CH_3)C(=O)CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$;

$R_4$ is selected from —$(CH_2)OR_b$, —$(CH_2CH_2)OR_b$, —$(CH(CH_3)CH_2)OR_b$, —$(C(CH_3)_2CH_2)OR_b$, —$(CH_2CH(CH_3))OR_b$, —$(CH_2C(CH_3)_2)OR_b$, —$(CH_2)NR_aR_a$, —$(CH_2CH_2)NR_aR_a$, —$(CH(CH_3)CH_2)NR_aR_a$, —$(C(CH_3)_2CH_2)NR_aR_a$, —$(CH_2CH(CH_3))NR_aR_a$, and —$(CH_2C(CH_3)_2)NR_aR_a$, wherein $R_a$, at each occurrence, is independently selected from H and $C_{1-6}$ alkyl substituted with 0-3 $R_e$; or $R_a$ and $R_a$ together with the nitrogen atom to which they are attached form a heterocyclic ring selected from imidazolidinyl, imidazolinyl, imidazolyl, indazolyl, indolinyl, indolizinyl, indolyl, isoquinolinyl, isoxazolyl, morpholinyl, oxadiazolyl, oxazolyl, pyrimidinyl, piperazinyl, pyrazinyl, pyrazolyl, pyridazinyl, pyridinyl, pyrimidinyl, pyrrolidinyl, pyrrolinyl, pyrrolyl, quinazolinyl, quinolinyl, tetrazolyl, thiazolyl, triazinyl, and triazolyl;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, OH, CN, —$SO_3H$, —$S(O)_pR_c$, —$S(O)_2NR_aR_a$, —$NR_aS(O)_2R_e$, —$OR_b$, —$NR_aR_a$, —$NR_aC$(=O)$R_d$, —$NR_aC$(=O)$NR_aR_a$, —C(=O)$OR_b$, —C(=O)$R_d$, —OC(=O)$R_d$, —C(=O)$NR_aR_a$, $C_{3-6}$cycloalkyl, heterocyclyl, and aryl;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$.

In certain embodiments, the present invention includes compounds of Formula (I), or stereoisomers, tautomers, pharmaceutically acceptable salts, solvates, or prodrugs thereof, wherein:

$R_1$ is H;

$R_2$ is selected from aryl substituted with 0-4 $R_{2a}$ and heteroaryl substituted with 0-4 $R_{2a}$;

$R_{2a}$, at each occurrence and when valence allows, is independently selected from F, Cl, Br, —$CF_3$, CN, $NO_2$, $CH_3$, —OH, —$OCH_3$, $NH_2$, —$N(CH_2CH_3)_2$, —NHC(=O)$CH_3$, —$NHS(O)_2CH_3$, —NHC(=O)$OCH_3$, —NHC(=O)CH$(CH_3)_2$, —NHC(=O)$CH_2CH_3$, —C(=O)OH, —C(=O)$OCH_3$, —C(=O)$NH_2$, —C(=O)$NHCH_3$, —$S(O)_2CH_3$, —$S(O)_2NHCH_3$, —$N(CH_3)C$(=O)$CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$;

$R_4$ is substituted with 0-3 $R_{4a}$ and is selected from phenyl, naphthyl, biphenyl, cyclopropyl, cyclobutyl, cyclopentyl, cyclohexyl, and cycloheptyl;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, =O, CN, —$SO_3H$, —$S(O)_pR_c$, —$S(O)_2NR_aR_a$, —$NR_aS(O)_2R_e$, —$OR_b$, —$NR_aR_a$, —$NR_aC$(=O)$R_d$, —$NR_aC$(=O)$NR_aR_a$, —C(=O)$OR_b$, —C(=O)$R_d$, —OC(=O)$R_d$, —C(=O)$NR_aR_a$, $C_{3-6}$cycloalkyl, heterocyclyl, and aryl;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$.

In other embodiments, the present invention includes compounds of Formula (I), or stereoisomers, tautomers, pharmaceutically acceptable salts, solvates, or prodrugs thereof, wherein:

$R_2$ is selected from aryl substituted with 0-4 $R_{2a}$ and heteroaryl substituted with 0-4 $R_{2a}$;

$R_{2a}$, at each occurrence and when valence allows, is independently selected from F, Cl, Br, —$CF_3$, CN, $NO_2$, $CH_3$, —OH, —$OCH_3$, $NH_2$, —$N(CH_2CH_3)_2$, —NHC(=O)$CH_3$, —$NHS(O)_2CH_3$, —NHC(=O)$OCH_3$, —NHC(=O)CH$(CH_3)_{25}$—NHC(=O)$CH_2CH_3$, —C(=O)OH, —C(=O)$OCH_3$, —C(=O)$NH_2$, —C(=O)$NHCH_{35}$—$S(O)_2CH_3$, —$S(O)_2NHCH_3$, —$N(CH_3)C$(=O)$CH_3$, —$NHS(O)_2NH_2$, —C(=O)-heterocyclyl substituted with 0-5 $R_e$, —$(CH_2)_r$-5- to 6-membered heterocyclyl comprising carbon atoms and 1-4 heteroatoms selected from N, O, and $S(O)_p$, wherein said heterocyclyl is substituted with 0-5 $R_e$;

$R_4$ is —$(CH_2)_{0-2}$-heterocyclyl substituted with 0-3 $R_{4a}$, wherein said heterocyclyl is selected from azetidinyl, thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, and tetrahydroisoquinolinyl;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, OH, CN, —$SO_3H$, —$S(O)_pR_c$, —$S(O)_2NR_aR_a$, —$NR_aS(O)_2R_c$, —$OR_b$, —$NR_aR_a$, —$NR_aC$(=O)$R_d$, —$NR_aC$(=O)$NR_aR_a$, —C(=O)$OR_b$, —C(=O)$R_d$, —OC(=O)$R_d$, —C(=O)$NR_aR_a$, $C_{3-6}$cycloalkyl, heterocyclyl, and aryl;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$.

Further embodiments of the invention relate to compounds of Formulae (VIII), (IX), and (X), below, wherein the variables $R_2$ and $R_{2a}$, where they appear, can be selected from any of the embodiments as set forth above for compounds of Formula (I), (II), (III), (IV), (V), (VI) and/or (VII) (including as recited in any of the further embodiments).

(VIII)

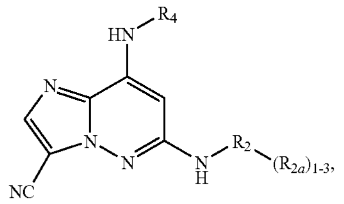

(IX)

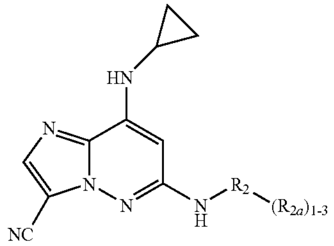

(X)

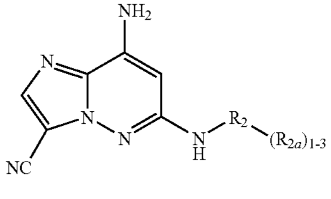

Compounds of the invention include, without limitation, the following:

6-((3-cyano-4-methylphenyl)amino)-8-(2-pyridinylamino)imidazo[1,2-b]pyridazine-3-carbonitrile.

N-(5-((3-cyano-8-(cyclopropylamino)imidazo[1,2-b]pyridazin-6-yl)amino)-2-(trifluoromethoxy)phenyl)acetamide, 3-cyano-5-((3-cyano-8-(cyclopropylamino)imidazo[1,2-b]pyridazin-6-yl)amino)benzenesulfonamide, N-(3-cyano-5-((3-cyano-8-(cyclopropylamino)imidazo[1,2-b]pyridazin-6-yl)amino)phenyl)acetamide, 6-((5-cyano-2-methoxyphenyl)amino)-8-(cyclopropylamino)imidazo[1,2-b]pyridazine-3-carbonitrile, methyl (5-((3-cyano-8-(cyclopropylamino)imidazo[1,2-b]pyridazin-6-yl)amino)-2-methylphenyl)carbamate, 3-((6-((3-acetamido-4-methylphenyl)amino)-3-cyanoimidazo[1,2-b]pyridazin-8-yl)amino)-N-(2-(dimethylamino)ethyl)benzamide, 8-(cyclobutylamino)-6-((3-methoxy-5-(4H-1,2,4-triazol-4-yl)phenyl)amino)imidazo[1,2-b]pyridazine-3-carbonitrile, 6-((1-acetyl-2,3-dihydro-1H-indol-6-yl)amino)-8-(cyclopropylamino)imidazo[1,2-b]pyridazine-3-carbonitrile, 6-((3-cyano-5-((4-methyl-1-piperazinyl)sulfonyl)phenyl)amino)-8-(cyclopropylamino)imidazo[1,2-b]pyridazine-3-carbonitrile, 6-((2-chloro-5-cyano-4-methylphenyl)amino)-8-(2-pyridinylamino)imidazo[1,2-b]pyridazine-3-carbonitrile, 8-(cyclopropylamino)-6-((1,4-dimethyl-2-oxo-1,2-dihydro-7-quinolinyl)amino)imidazo[1,2-b]pyridazine-3-carbonitrile, 3-cyano-5-((3-cyano-8-(cyclopropylamino)imidazo[1,2-b]pyridazin-6-yl)amino)-N-ethylbenzenesulfonamide, 8-(cyclopropylamino)-6-((3-(4-(2-hydroxyethyl)-1-piperazinyl)-5-(4H-1,2,4-triazol-4-yl)phenyl)amino)imidazo[1,2-b]pyridazine-3-carbonitrile, 8-((5-methoxy-2-pyridinyl)amino)-6-((3-methoxy-5-(4H-1,2,4-triazol-4-yl)phenyl)amino)imidazo[1,2-b]pyridazine-3-carbonitrile, 6-((2-chloro-5-cyanophenyl)amino)-8-(cyclopropylamino)imidazo[1,2-b]pyridazine-3-carbonitrile, methyl (3-((3-cyano-8-(cyclopropylamino)imidazo[1,2-b]pyridazin-6-yl)amino)-5-(methylsulfonyl)phenyl)carbamate, 6-((5-cyano-2-methoxyphenyl)amino)-8-(cyclobutylamino)imidazo[1,2-b]pyridazine-3-carbonitrile, 6-((5-cyano-2-methylphenyl)amino)-8-(cyclopropylamino)imidazo[1,2-b]pyridazine-3-carbonitrile, 8-(cyclopropylamino)-6-((3-(2-(dimethylamino)ethoxy)-5-(4H-1,2,4-triazol-4-yl)phenyl)amino)imidazo[1,2-b]pyridazine-3-carbonitrile, 6-((2-chloro-5-cyano-4-methylphenyl)amino)-8-(cyclopropylamino)imidazo[1,2-b]pyridazine-3-carbonitrile, 8-amino-6-((5-cyano-2-methoxyphenyl)amino)imidazo[1,2-b]pyridazine-3-carbonitrile, 8-amino-6-((3-cyano-4-methylphenyl)amino)imidazo[1,2-b]pyridazine-3-carbonitrile, N-(5-((3-cyano-8-(cyclopropylamino)imidazo[1,2-b]pyridazin-6-yl)amino)-2-methylphenyl)acetamide, 6-((2-chloro-5-cyanophenyl)amino)-8-(cyclobutylamino)imidazo[1,2-b]pyridazine-3-carbonitrile, N-(5-((3-cyano-8-(cyclopropylamino)imidazo[1,2-b]pyridazin-6-yl)amino)-2,4-difluorophenyl)acetamide, 6-((4-fluoro-3-(4H-1,2,4-triazol-4-yl)phenyl)amino)-8-((5-methoxy-2-pyridinyl)amino)imidazo[1,2-b]pyridazine-3-carbonitrile, N-(5-((3-cyano-8-((5-(2-hydroxyethoxy)-2-pyridinyl)amino)imidazo[1,2-b]pyridazin-6-yl)amino)-2-methylphenyl)acetamide, N-(5-((3-cyano-8-((5-methoxy-2-pyridinyl)amino)imidazo[1,2-b]pyridazin-6-yl)amino)-2-methylphenyl)acetamide, 8-(cyclopropylamino)-6-((4-(2-(methylamino)ethoxy)-3-(4H-1,2,4-triazol-4-yl)phenyl)amino)imidazo[1,2-b]pyridazine-3-carbonitrile, N-(5-((3-cyano-8-(cyclopropylamino)imidazo[1,2-b]pyridazin-6-yl)amino)-2-methoxyphenyl)acetamide, 6-((5-cyano-2-(2-(4-morpholinyl)ethoxy)phenyl)amino)-8-(cyclopropylamino)imidazo[1,2-b]pyridazine-3-carbonitrile, 8-((2-methoxyethyl)amino)-6-((3-methoxy-5-(4H-1,2,4-triazol-4-yl)phenyl)amino)imidazo[1,2-b]pyridazine-3-carbonitrile, 6-((3-cyano-4-(4-morpholinyl)phenyl)amino)-8-(cyclopropylamino)imidazo[1,2-b]pyridazine-3-carbonitrile, methyl (5-((8-amino-3-cyanoimidazo[1,2-b]pyridazin-6-yl)amino)-2-methylphenyl)carbamate, 8-(cyclopropylamino)-6-((3-methoxy-5-(4H-1,2,4-triazol-4-yl)phenyl)amino)imidazo[1,2-b]pyridazine-3-carbonitrile, methyl (5-((3-cyano-8-(cyclopropylamino)imidazo[1,2-b]pyridazin-6-yl)amino)-2,4-difluorophenyl)carbamate, methyl (5-((3-cyano-8-(cyclopropylamino)imidazo[1,2-b]pyridazin-6-yl)amino)-2-fluorophenyl)carbamate, 6-((5-cyano-2-(trifluoromethoxy)phenyl)amino)-8-(cyclopropylamino)imidazo[1,2-b]pyridazine-3-carbonitrile, N-(3-cyano-5-((3-cyano-8-(cyclopropylamino)imidazo[1,2-b]pyridazin-6-yl)amino)phenyl)methanesulfonamide, N-(2-chloro-5-((3-cyano-8-(cyclopropylamino)imidazo[1,2-b]pyridazin-6-yl)amino)phenyl)acetamide, 8-(cyclopropylamino)-6-((4-fluoro-3-(4H-1,2,4-triazol-4-yl)phenyl)amino)imidazo[1,2-b]pyridazine-3-carbonitrile, 8-(cyclopropylamino)-6-((4-(4-morpholinyl)-3-(4H-1,2,4-triazol-4-yl)phenyl)amino)imidazo[1,2-b]pyridazine-3-carbonitrile, 8-(cyclopropylamino)-6-((3-methyl-5-(1H-1,2,4-triazol-1-yl)phenyl)amino)imidazo[1,2-b]pyridazine-3-carbonitrile, 8-(cyclopropylamino)-6-((4-(3-(dimethylamino)propoxy)-3-(4H-1,2,4-triazol-4-yl)phenyl)amino)imidazo[1,2-b]pyridazine-3-carbonitrile, 6-((4-cyano-2-pyridinyl)amino)-8-(cyclopropylamino)imidazo[1,2-b]pyridazine-3-carbonitrile, 3-cyano-5-((3-cyano-8-(cyclopropylamino)imidazo[1,2-b]pyridazin-6-yl)amino)-N-(tetrahydro-2H-pyran-4-yl)benzenesulfonamide, 8-(cyclopropylamino)-6-((2-fluoro-5-(1H-1,2,4-triazol-1-yl)phenyl)amino)imidazo[1,2-b]pyridazine-3-carbonitrile, and N-(3-((3-cyano-8-(cyclopropylamino)imidazo[1,2-b]pyridazin-6-yl)amino)-4-methylphenyl)acetamide.

The compounds of Formulae (I)-(X) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formulae (I)-(X) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the Formulae (I)-(X) may also have prodrug forms. Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Various forms of prodrugs are well known in the art. For examples of such prodrug derivatives, see:

a) *Design of Prodrugs*, H. Bundgaard, ed., Elsevier (1985), and *Methods in Enzymology,* 112:309-396, K. Widder et al., eds., Academic Press (1985);

b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and c) Bundgaard, H., *Adv. Drug Deliv. Rev.,* 8:1-38 (1992).

It should further be understood that solvates (e.g., hydrates) of the compounds of Formulae (I)-(X) are also within the scope of the invention. Methods of solvation are generally known in the art. The inventive compounds may either be in the free or hydrate form.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C═N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Definitions

The following are definitions of terms used in this specification and appended claims. The initial definition provided for a group or term herein applies to that group or term throughout the specification and claims, individually or as part of another group, unless otherwise indicated.

In accordance with a convention used in the art,

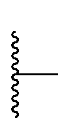

is used in structural formulas herein to depict the bond that is the point of attachment of the moiety or substituent to the core or backbone structure.

A dash "-" that is not between two letters or symbols is used to indicate a point of attachment for a substituent. For example, $—CONH_2$ is attached through the carbon atom.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "halogen" or "halo" refers to fluorine (F), chlorine (Cl), bromine (Br) and iodine.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

As used herein, "carbocycle," "carbocyclic residue," or "carbocyclyl" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle," "carbocyclic residue," or "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

The term "aryl" refers to monocyclic, bicyclic, tricyclic aromatic hydrocarbon groups having 6 to 15 carbon atoms in the ring portion, such as phenyl, naphthyl, biphenyl and diphenyl groups, each of which may be substituted. Aryl groups which are bicyclic or tricyclic must include at least one fully aromatic ring but the other fused ring or rings may be aromatic or non-aromatic. When an aryl is substituted with a further heterocyclic ring, said ring may be attached to the aryl through a carbon atom or a heteroatom and said ring in turn is optionally substituted with one to two substituents as valence allows.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

An "alkylidene" group refers to an alkylene group consisting of at least two carbon atoms and at least one carbon-carbon double bond. Substituents on this group include those in the definition of "substituted alkyl".

The term "cycloalkyl" refers to an optionally substituted, saturated cyclic hydrocarbon ring systems, preferably containing 1 to 3 rings and 3 to 7 carbons per ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

As used herein, the term "heterocycle," "heterocyclyl," "heterocyclic ring" or "heterocyclic group" is intended to mean a stable 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle," "heterocyclyl," "heterocyclic ring" or "heterocyclic group" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and $S(O)_p$) and the nitrogen atoms may optionally be quaternized.

Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, dihydroisoquinolinyl, tetrahydroquinolinyl, isoquinolinyl, benzimidazolyl, benzopyranyl, benzoxazinyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and the like.

Exemplary tricyclic heteroaryl groups include carbazolyl, benzidolyl, phenanthrollinyl, acridinyl, phenanthridinyl, xanthenyl and the like.

The term "heteroatoms" shall include oxygen, sulfur and nitrogen.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

When any variable occurs more than one time in any constituent or formula for a compound, its definition at each occurrence is independent of its definition at every other occurrence. Thus, for example, if a group is shown to be substituted with 0-3 $R_e$, then said group may optionally be substituted with up to three $R_e$ groups and $R_e$ at each occurrence is selected independently from the definition of $R_e$. Also, combinations of substituents and/or variables are permissible only if such combinations result in stable compounds.

Utility

The compounds of the invention may be used to modulate kinase activities. Types of kinases include, but are not limited to, AAK1, ABL, ACK, ACTR2, ACTR2B, ADCK3, ADCK4, AKT1, AKT2, AKT3, ALK, ALK1, ALK2, ALK4, AMPKA1, AMPKA2, ARG, AURA, AURB, AURC, AXL, BCR-ABL, BIKE, BLK, BMPR1A, BMX, BRAF, BRSK2, BRK, BTK, CAMK1A, CAMK2A, CAMK2B, CAMK1D, CAMK2D, CAMK1G, CAMK2G, CAMKK1, CAMKK2, CDK1, CDK2, CDK5, CHK2, CK1A2, CK1D, CK1E, CK1G1, CK1G2, CK2A1, CK2A2, CLK1, CLK2, CLK3, CLK4, CSK, DAPK2, DAPK3, DCAMKL3, DDR2, DMPK1, DRAK1, DRAK2, DYRK1, DYRK2, EGFR, EPHA1, EPHA2, EPHA3, EPHA4, EPHA5, EPHA6, EPHA7, EPHA8, EPHB1, EPHB2, EPHB3, EPHB4, ERK1, ERK2, FAK, FER, FES, FGFR1, FGFR2, FGFR3, FGFR4, FGR, FLT1, FLT3, FLT4, FMS, FRK, FYN, FUSED, GAK, $GCN^2$, GPRK4, GPRK5, GPRK6, GSK3A, GSK3B, HCK, HPK1, HER2/ERBB2, HER4/ERBB4, HH498, IGF1R, IKKα, IKKβ, INSR, IRR, IRAK4, ITK, JAK1, JAK2, JAK3, JNK1, JNK2, JNK3, KDR, KHS1, KHS2, KIT, LCK, LIMK1, LIMK2, LKB1, LOK, LTK, LYN, MAP3K4, MAP3K5, MAPK1, MAPKAP-K2, MARK1, MARK2, MARK4, MEK1, MER, MET, MKK4, MKK6, MLK3, MNK2, MPSK1, MRCKA, MSK1, MSK2, MST1, MST2, MST3, MST4, MUSK, MYT1, NDR2, NEK2, NEK6, NEK7, NEK9, NLK, P38A, P38B, P38G, PAK1, PAK2, PAK3, PAK4, PAK5, PAK6, PCTAIRE1, PDGFRA, PDGFRB, PDK1, PHKG1, PHKG2, PIM1, PIM2, PKA, PKACA, PKACB, PKCA, PKCD, PKCH, PKCl, PKCT, PKCZ, PKD2, PKG1, PKG2, PKN2, PLK1, PLK3, PLK4, PRKX, PYK2, QIK, RAF1, RET, RIPK2, ROCK-I, ROCK-II, RON, ROS, RSK1, RSK2, RSK4, SAPK2a, SAPK2b, SAPK3, SAPK4, SGK, SIK, SLK, SKMLCK, SRC, SRPK1, STK33, SYK, TESK1, TGFBR1, TIE2, TLK1, TLK2, TNK1, TRKA, TRKB, TRKC, TTK, TXK, TYK2, TYRO3, ULK3, WNK3, YANK2, YANK3, YES, YSK1, ZAP70, ZC1/HGK, ZC2/TNIK, and mutants thereof.

Applicants have discovered that compounds of Formulae (I)-(X) have particular utility in treating proliferative conditions associated with the modulation of kinase activity, and particularly the inhibition of serine/threonine kinase activities. The compounds of the present invention can be used to treat proliferative disorders associated with abnormal kinase activity. As used herein, the terms "treating" and "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

Accordingly, one aspect of the invention is the use of a compound of the Formulae (I)-(X), or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of Formulae (I)-(X) or a pharmaceutically acceptable salt thereof as defined herein before.

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. Compounds of Formulae (I)-(X) may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, ZOLADEX®; matrix metalloproteinase inhibitors; VEGF inhibitors, such as anti-VEGF antibodies (AVASTIN®) and small molecules such as ZD6474 and SU6668; Vatalanib, BAY-43-9006, SU11248, CP-547632, and CEP-7055; HER 1 and HER 2 inhibitors including anti-HER2 antibodies (HERCEPTIN®); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g., GLEEVEC® and dasatinib; CASODEX® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and anti-vascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (ixabepilone), [1S-[1R*,3R*(E),7R*,10S*,11R*,12R*,16S]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione, and derivatives thereof; other CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g., 6-thioguanine and 6-mercaptopurine; glutamine antagonists, e.g., DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein may be surgery, radiotherapy or chemotherapy. Such chemotherapy may cover three main categories of therapeutic agent:

(i) antiangiogenic agents that work by different mechanisms from those defined herein before (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as AVASTIN® (bevacizumab) and ERBITUX® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide, nitrosoureas, thiotepa; antimitotic agents (for example, vinca alkaloids like vincristine, vinorelbine, vinblastine and vinflunine) and taxoids such as TAXOL® (paclitaxel), Taxotere (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as VELCADE® (bortezomib).

As stated above, the Formulae (I)-(X) compounds of the invention are of interest for their antiproliferative effects. Such compounds of the invention are expected to be useful in a wide range of disease states including cancer, psoriasis, and rheumatoid arthritis.

More specifically, the compounds of Formulae (I)-(X) are useful in the treatment of a variety of cancers, including (but not limited to) the following:

carcinoma, including that of the prostate, pancreatic ductal adenocarcinoma, breast, colon, lung, ovary, pancreas, and thyroid;

tumors of the central and peripheral nervous system, including neuroblastoma, glioblastoma, and medulloblastoma; and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neurofibromatosis, pulmonary fibrosis, arthritis, psoriasis, glomerulonephritis, restenosis following angioplasty or vascular surgery, hypertrophic scar formation and inflammatory bowel disease.

The compounds of Formula (I)-(X) are especially useful in treatment of tumors having a high incidence of serine/threonine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of Formula (I)-(X) may also be useful in the treatment of other cancerous diseases (such as acute myelogenous leukemia) that may be associated with signal transduction pathways operating through kinases such as DYRK1a, CDK, and GSK3β. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I)-(X) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed. (1985), which is incorporated herein by reference in its entirety.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS® Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

The compounds of Formulae (I)-(X) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

When a compound according to this invention is administered into a human subject, the daily dosage will normally be determined by the prescribing physician with the dosage generally varying according to the age, weight, sex and response of the individual patient, as well as the severity of the patient's symptoms. Exemplary dosage amounts for a mammal may include from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of protein kinase enzyme levels.

If formulated as a fixed dose, a combination product can, for example, utilize a dosage of the compound of Formulae (I)-(X) within the dosage range described above and the dosage of another anti-cancer agent/treatment within the approved dosage range for such known anti-cancer agent/treatment. If a combination product is inappropriate, the compounds of Formulae (I)-(X) and the other anti-cancer agent/treatment can, for example, be administered simultaneously or sequentially. If administered sequentially, the present invention is not limited to any particular sequence of administration. For example, compounds of Formulas (I)-(X) can be administered either prior to, or after, administration of the known anti-cancer agent or treatment.

Biological Assays

A. CK2 Kinase Assay

The effectiveness of compounds of the present invention as inhibitors of protein kinases can be readily tested by assays known to those skilled in the art. For example, in vitro protein kinase assays may be conducted with a relevant purified protein kinase and an appropriate synthetic substrate to determine the inhibitory activity of the compounds. Assays for inhibition of CK2 by the instant compounds were performed in 384-well plates with reaction mixtures containing 10 μM of peptide substrate (RRRADDSDDDDD-NH2), [$\gamma$-$^{33}$P]ATP (10 μCi) at 25 μM (CK2A1) or 5 μM (CK2A2), 20 mM Hepes (pH 7.4), 100 mM NaCl, 10 mM $MgCl_2$, 0.25 mM dithiothreitol, Brij-35 at 0.015%, and recombinant CK2A1 (10 nM, Invitrogen) or CK2A2 (5 nM, Upstate Biotechnology). Reaction mixtures were incubated at 30° C. for 1 hour, and reaction products were captured by binding to phosphocellulose (P81) filter plates. Incorporation of radioactive phosphate into the peptide substrate was determined by liquid scintillation counting. The potency of compounds in inhibiting CK2 is expressed as $IC_{50}$, defined as the concentrations of compounds required to inhibit the enzymatic activity by 50%.

The inhibitory activity of the instant compounds may also be measured by recombinant CK2 holoenzyme kinase assays. The assays were performed in U-bottom 384-well plates. The final assay volume was 30 μl prepared from 15 μl additions of enzyme and substrates (fluoresceinated peptide FL-RRRADDSDDDDD-NH2 and ATP) and test compounds in assay buffer (20 mM HEPES pH 7.4, 10 mM $MgCl_2$, 100 mM NaCl, 0.015% Brij35 and 0.25 mM DTT). The reaction was initiated by the combination of bacterially expressed, CK2$\alpha$/$\beta$ or CK2 $\alpha'$/$\beta$ holoenzyme with substrates and test compounds. The reaction was incubated at room temperature for 60 minutes and terminated by adding 30 μl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The final concentration of reagents in the CK2 $\alpha$/$\beta$ assay was 25 μM ATP, 1.5 μM FL-RRRADDSDDDDD-NH2, 50 pM CK2$\alpha$/$\beta$ holoenzyme, and 1.6% DMSO. The final concentration of reagents in the CK2 $\alpha'$/$\beta$ assay was 10 μM ATP, 1.5 μM FL-RRRADDSDDDDD-NH2, 100 pM CK2 $\alpha'$/$\beta$ holoenzyme, and 1.6% DMSO. Dose response curves were generated to determine the concentration required inhibiting 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

B. Cell Proliferation Inhibition Assay

Compounds were evaluated for their ability to inhibit cell proliferation, using an assay that measures mitochondrial metabolic activity, that is directly correlated with cell numbers. Cells were plated at 2000 cells/well in 96-well plates and were cultured for 24 h in RPMI-1640 supplemented with 2% fetal bovine serum, before test compounds were added. Compounds were diluted in culture medium such that the final concentration of dimethyl sulfoxide never exceeded 1%. Following the addition of compounds, the cells were cultured for an additional 72 h before cell viability was determined by measuring the conversion of 3-(4,5-dimethylthiazol-2-yl)-2,5-diphenyltetrazolium bromide (MTT) dye using the CellTiter96 kit (Promega) or by measuring the conversion of [3-(4,5-dimethylthiazol-2-yl)-5-(3-carboxymethoxyphenyl)-2-(4-sulfophenyl)-2H-tetrazolium (MTS) dye using the CELLTITER 96® AQueous (Promega).

The following compounds were found to have the $IC_{50}$ described in Table 1 when measured in the assays described above.

TABLE 1

| Example No. | CK2A1 (CK2$\alpha$/$\beta$) ($IC_{50}$, μM) | CK2A2 (CK2$\alpha'$/$\beta$) ($IC_{50}$, μM) | HCT116 ($IC_{50}$, μM) |
|---|---|---|---|
| 1 | 0.0060 | 0.0075 | 0.030 |
| 31 | 0.1429 | 0.0257 | 0.460 |
| 37 | 0.0110 | 0.0045 | 0.163 |
| 44 | 1.3110 | 0.0351 | >1.00 |
| 46 | 0.0043 | 0.0024 | 0.150 |
| 47 | 0.0074 | 0.0052 | 0.041 |
| 48 | 0.4167 | 0.1058 | 0.460 |
| 56 | 0.1548 | 0.0359 | 0.482 |
| 57 | 0.3097 | 0.0582 | 0.521 |
| 58 | 0.0122 | 0.0022 | 0.098 |
| 64 | 0.0120 | 0.0010 | 0.048 |
| 66 | 6.0640 | 0.7784 | >2.50 |
| 71 | 0.2612 | 0.0156 | 0.945 |
| 73 | 4.6040 | 0.7379 | 2.243 |
| 80 | 4.6580 | 1.4930 | >1.00 |
| 81 | 0.5125 | 0.1149 | >1.00 |
| 82 | 0.4792 | 0.1258 | 0.127 |
| 89 | 6.6690 | 0.9400 | >1.00 |
| 93 | 0.7120 | 0.0684 | >1.00 |
| 95 | 0.0065 | 0.0030 | 0.022 |
| 111 | 0.1164 | 0.0240 | 0.034 |
| 160 | 0.0197 | 0.0046 | 0.045 |
| 167 | 0.1031 | 0.0125 | >1.00 |
| 168 | 0.0119 | 0.0049 | 0.128 |
| 196 | 0.0122 | 0.0034 | 0.065 |
| 214 | 0.5957 | 0.1189 | >10.00 |
| 224 | 0.7938 | 0.1261 | >10.00 |
| 225 | 0.0082 | 0.0011 | 0.035 |
| 228 | 0.0090 | 0.0017 | 0.327 |
| 233 | 0.0071 | 0.0023 | 0.128 |
| 235 | 0.0250 | 0.0064 | 0.433 |
| 244 | 0.1023 | 0.0228 | 1.111 |

Compounds of the present invention exhibit enhanced CK2 inhibitory activity over the compounds disclosed in U.S. Publication No. 2008/0045536. Comparing the data in Table 1 and Table 2, compounds of the invention herein, e.g., compounds of Formula (I) (including Formulae (II), (III), (IV), (V), (V), (VII), (VIII), (IX), and (X)), are surprisingly advantageous for their CK2 enzyme inhibition activity and/or other drugability properties.

TABLE 2

| Example No. in US 2008/0045536 | Structure | CK2A1 $IC_{50}$ (μM) | CK2A2 $IC_{50}$ (μM) |
|---|---|---|---|
| I(1) Page 27 | 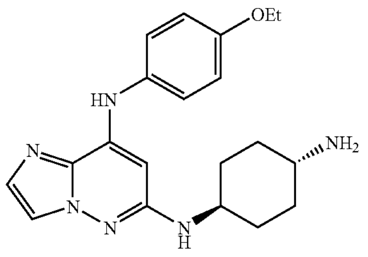 | >50 | 10.35 |
| I(7) Page 29 | 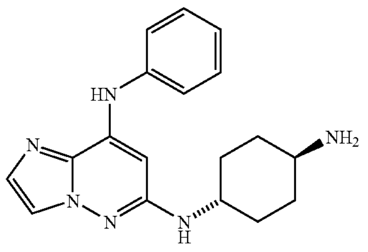 | >50 | >50 |
| II(16) Page 46 | 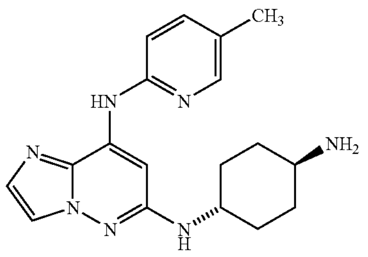 | >50 | 31.77 |
| XXV(1) Page 70 | 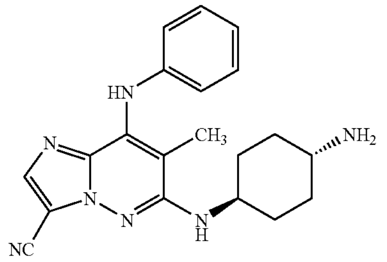 | 2.69 | 8.09 |

Methods of Preparation

The compounds of the present invention may be prepared by methods such as those illustrated in the following schemes. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). All documents cited herein are incorporated herein by reference in their entirety.

In general, the time taken to complete a reaction procedure will be judged by the person performing the procedure, preferably with the aid of information obtained by monitoring the reaction by methods such as HPLC or TLC. A reaction does not have to go to completion to be useful to this invention. The methods for the preparation of various heterocycles used to this invention can be found in standard organic reference books, for example, Katritzky, A. R. et al., eds., *Comprehensive Heterocyclic Chemistry, The Structure, Reactions, Synthesis and Uses, of Heterocyclic Compounds*, First Edition, Pergamon Press, New York (1984), and Katritzky, A. R. et al., eds., *Comprehensive Heterocyclic Chemistry II, A Review of the Literature* 1982-1995*: The Structure, Reactions, Synthesis and Uses, of Heterocyclic Compounds*, Pergamon Press, New York (1996).

Unless otherwise specified, the various substituents of the compounds are defined in the same manner as the Formula (I) compound of the invention.

Scheme 1

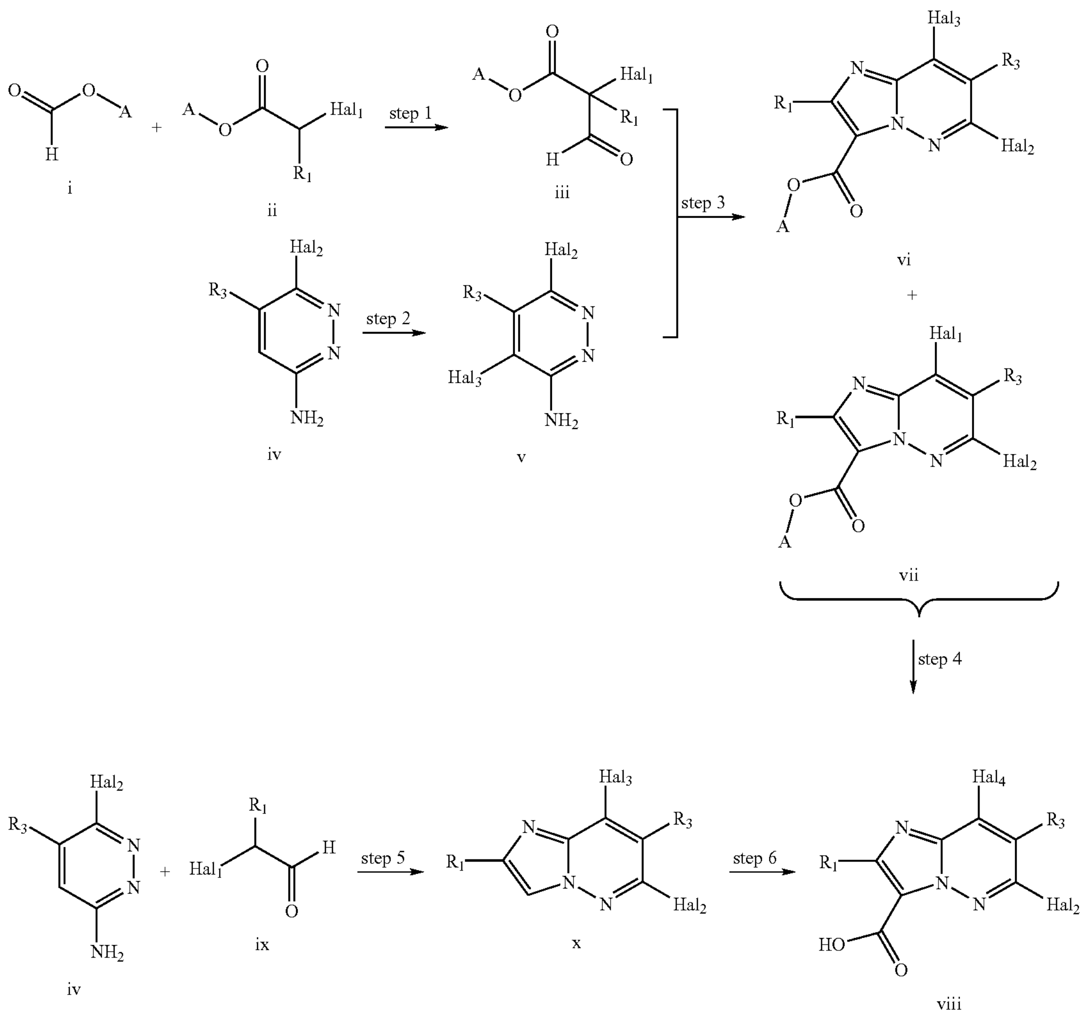

i, ii, iii, iv, v, vi, vii, iv, ix, x, viii

Step 1

The first step in Scheme 1 is accomplished by treating an appropriately substituted α-haloester (ii, A=$C_{1-4}$ lower alkyl, $Hal_1$-$Hal_5$=Cl, Br, I, F) with a formate ester (i) such as ethyl formate in the presence of a base such as sodium ethoxide in a suitable solvent such as ethanol to afford a compound of Formula iii.

Step 2

Halogenation of a suitably substituted pyridazine-3-amine (iv) such as 6-chloropyridazine-3-amine using a reagent such as bromine in an appropriate solvent such as ethanol or methanol provides compounds of Formula v.

Step 3

The reaction of compounds iii and v at elevated temperature, for example above 80° C., in an appropriate solvent such as ethanol, results in formation of a mixture of esters vi and vii ($Hal_4$=$Hal_1$ or $Hal_3$) that may be used in subsequent steps without separation.

Step 4

The acid catalyzed hydrolysis of vi/vii using, for example, aqueous HCl in a solvent such as methanol at elevated temperature affords compounds of Formula viii.

Step 5

Alternatively, compounds of Formula iv may be reacted with an α-haloaldehyde at elevated temperature, for example above 80° C., in an appropriate solvent such as ethanol to afford compounds of Formula x.

Step 6

Treatment of compounds with general Formula x with a base such as lithium diisopropylamide in an aprotic solvent, such as tetrahydrofuran, followed by quenching with carbon dioxide may also afford compounds of general Formula viii.

Scheme 2

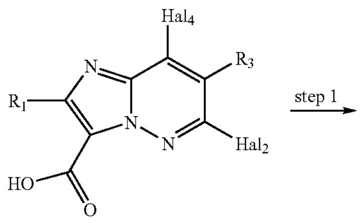

viii

-continued

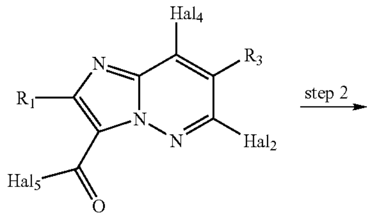

xi

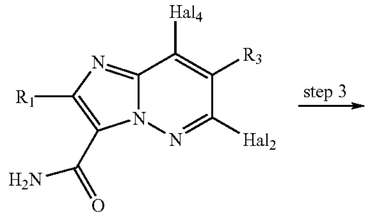

xii

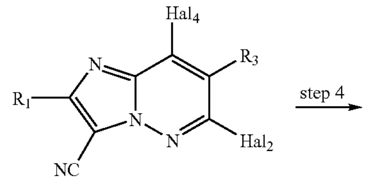

xiii

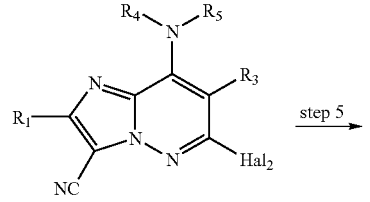

ivx

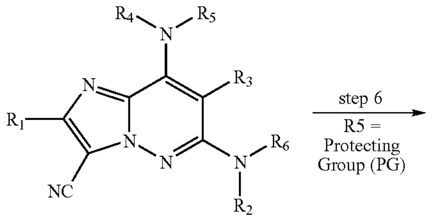

xv

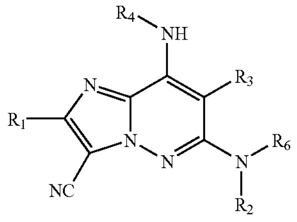

xvi

Step 1

Further modifications may be made according to Scheme 2. Activation of the carboxylic acid of compound viii through, for example, formation of the acid chloride with thionyl chloride in a suitable solvent such as dichloromethane affords compounds of Formula xi.

Step 2

Reaction of xi with ammonia or a suitable equivalent in a solvent such as 1,4-dioxane or THF affords amides of Formula xii. Alternatively, steps 1-2 may be accomplished in a single step through use of a coupling reagent such as BOP or DCC in the presence of ammonia or a suitable equivalent in an appropriate solvent such as DMF.

Step 3

Dehydration of compounds of Formula xii may be accomplished through reaction with a suitable dehydrating reagent such as $POCl_3$ in an appropriate solvent such as chloroform to afford compounds of Formula xiii Step 4

Treatment of compound xiii with an amine ($R_4R_5NH$) such as N-(4-methoxybenzyl)cyclopropanamine or N-(4-methoxybenzyl)pyridin-2-amine in the presence of a base such as diisopropylethylamine or sodium tert-butoxide in an aprotic solvent such as THF or DMF affords compounds of Formula ivx.

Step 5

Compounds of Formula xv may be formed through the direct displacement of $Hal_2$ with a suitable amine at elevated temperature, for example above 100° C., in an appropriate solvent such as NMP. Alternatively, treatment of ivx with a palladium catalyst, such as $Pd_2(dba)_3$, in the presence of a ligand, such as 4,5-bis(diphenyl-phosphino)-9,9-dimethylxanthene (Xantphos) (Guari, Y. et al., *Chem. Eur. J.,* 7:475-482 (2001)), and a base, such as cesium carbonate, and an additive, such as copper (I) iodide, may be used with an appropriately substituted amine with a suitable solvent such as NMP to afford compounds of general Formula xv. Alternatively, treatment of ivx with a palladium catalyst, such as allyl palladium (II) chloride dimer, in the presence of a ligand, such as di-tert-butyl(1-methyl-2,2-diphenylcyclopropyl)phosphine (Suzuki, K. et al., *Adv. Synth. Catal.,* 350:652 (2008)), and a base, such as sodium t-butoxide, may be used with an appropriately substituted amine with a suitable solvent such as toluene to afford compounds of general Formula xv.

Step 6

In cases where $R_5$ is an amine protecting group, such as p-methoxybenzyl, removal of the protecting group can be effected through known methods. For example, treatment with trifluoroacetic acid with or without an appropriate solvent, such as dichloromethane in the presence of a cation trap such as triethylsilane affords compounds of Formula xvi.

Scheme 3

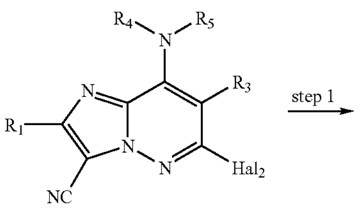

ivx

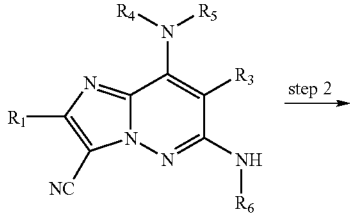

xvii

-continued

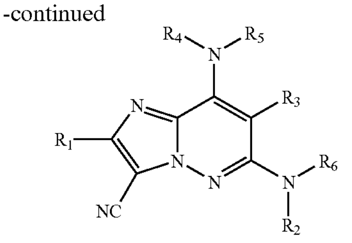

xv

Step 1

Alternatively, compounds of Formula xv may be prepared according to Scheme 3. Treatment of compounds of Formula ivx with an amine ($R_6NH_2$) at elevated temperatures, for example above 100° C., in an appropriate solvent such as DMF or DMA may afford compounds of Formula xvii. Alternatively, treatment of ivx with a palladium catalyst, such as $Pd_2(dba)_3$, in the presence of a ligand, such as 4,5-bis(diphenyl-phosphino)-9,9-dimethylxanthene (Xantphos) (Guari, Y. et al., *Chem. Eur. J.,* 7:475-482 (2001)), and a base, such as cesium carbonate, and an additive, such as copper (I) iodide, may be used with an appropriately substituted amine with a suitable solvent such as NMP to afford compounds of general Formula xvii. Alternatively, treatment of ivx with a palladium catalyst, such as allyl palladium (II) chloride dimer, in the presence of a ligand, such as di-tert-butyl (1-methyl-2,2-diphenylcyclopropyl)phosphine (Suzuki, K. et al., *Adv. Synth. Catal.,* 350:652 (2008)), and a base, such as sodium t-butoxide, may be used with an appropriately substituted amine with a suitable solvent such as toluene to afford compounds of general Formula xvii.

Step 2

Compounds of Formula xvii may then be further modified through reactions known to one skilled in art to afford compounds of Formula xv. Such reactions may include treatment of xvii with an aryl halide in the presence of a palladium catalyst, such as $Pd_2(dba)_3$ with an appropriate ligand, such as Xantphos, and a base, such as cesium carbonate or sodium t-butoxide, and an additive, such as copper (I) iodide.

Scheme 4

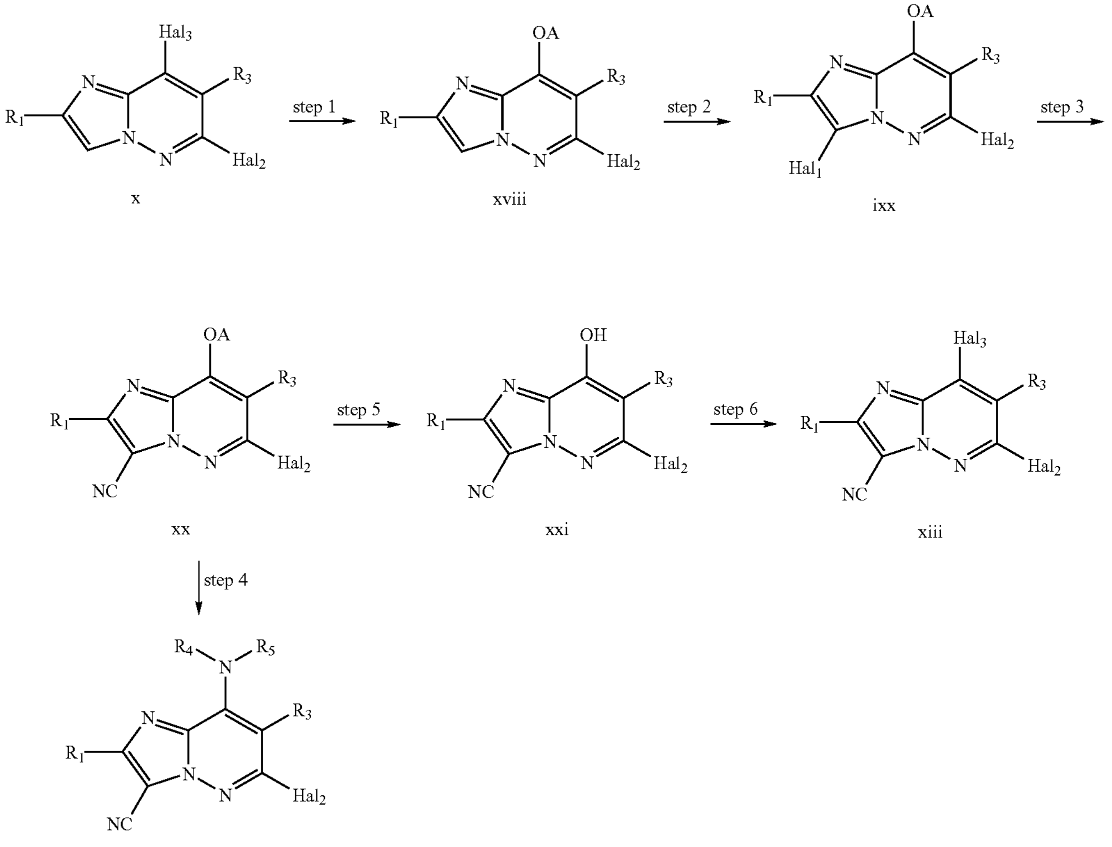

x, xviii, ixx, xx, xxi, xiii, ivx

Step 1

An alternative route towards intermediates of general Formula ivx is shown in Scheme 4. Compounds of Formula x may be treated with an alcohol or phenol (A=$C_{1-4}$ alkyl or Ph) in the presence of a base, such as $K_2CO_3$ or NaH, in an appropriate solvent, such as THF to afford compounds of Formula xviii.

Step 2

Treatment of xviii with a suitable halogenating reagent such as N-bromosuccinimide or N-chlorosuccinimide in an appropriate solvent such as chloroform affords compounds of Formula ixx.

Step 3

A cyano group may be introduced either directly through displacement of $Hal_1$ with a reagent such as sodium cyanide in an appropriate solvent such as DMSO or alternatively, through palladium mediated coupling with a reagent such as $Zn(CN)_2$ in the presence of $Pd(PPh_3)_4$ in a solvent such as toluene or DMF to afford compounds of Formula xx.

Step 4

Direct displacement of the alkoxy group (—OA) of compound xx with an amine ($R_4R_5NH$) at elevated temperatures, for example above 100° C., with or without an appropriate solvent such as DMF or DMA may afford compounds of Formula ivx.

Step 5

Alternatively, treatment of xx with an acid, such as aqueous HCl affords compounds of Formula xxi.

Step 6

Compounds of Formula xxi may be converted to compounds of Formula xiii by treatment with a halogenating reagent such as $POBr_3$ or $POCl_3$, either neat or in an appropriate solvent such as toluene.

It is anticipated that, where possible, the products of the reaction schemes described above may be further elaborated by one of ordinary skill in the art. For example, in instances where $R_2$ contains suitable functional groups, such as amino or carboxy groups, further modifications may be made according to methods well known to those skilled in the art (See e.g., March, J., *Advanced Organic Chemistry: Reactions, Mechanisms and Structure,* 4th Ed., John Wiley and Sons, New York (1992).)

EXAMPLES

The invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

For ease of reference, the following abbreviations are used herein:

BOC=tert-butoxycarbonyl
bp=boiling point
BOP=(Benzotriazol-1-yloxy)tris(dimethylamino)phosphonium hexafluorophosphate
DMAP=4-dimethylaminopyridine
DCC=Dicyclohexyl carbodiimide
DCM=Dichloromethane
DIPEA or DIEA=N,N-diisopropylethylamine
DMA=dimethyl acetamide
DME=1,2-dimethoxyethane
DMF=dimethyl formamide
EDCI=N-(3-Dimethylaminopropyl)-N'-ethylcarbodiimide hydrochloride
Et=ethyl
$Et_2O$=diethyl ether
HOBT=1-hydroxybenzotriazole
EtOAc=ethyl acetate
EtOH=ethanol
g=gram(s)
h=hr(s)=hour(s)
H=hydrogen
l=liter
mCPBA—meta chloro perbenzoic acid
Me=methyl
MeCN=acetonitrile
MeOH=methanol
min(s)=minute(s)
NMP=1-methyl-2-pyrrolidinone
$Pd_2(dba)_3$=$Pd_2dba_3$=Tris(dibenzylineneacetone)dipalladium(0)
Pd/C=palladium on carbon
Rt=retention time
THF=tetrahydrofuran
TEA=triethylamine
TFA=trifluoroacetic acid
Xantphos=4,5-bis(diphenyl-phosphino)-9,9-dimethylxanthene
mg=milligram(s)
ml or mL=milliliter
μl=microliter
mmol=millimole
μmol=micromole
mol=mole
PSI=$lbs/in^2$

Synthesis of Intermediates

Intermediate 1

3-(1H-1,2,4-Triazol-1-yl)-5-(trifluoromethyl)aniline

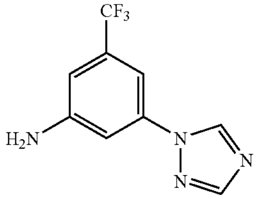

3-Bromo-5-(trifluoromethyl)aniline (3.5 g, 14.6 mmol), copper(I) iodide (1.39 g, 7.3 mmol), potassium carbonate (6.0 g, 43.7 mmol) and 1H-1,2,4-triazole (3.0 g, 43.7 mmol) in NMP (10 mL) were heated at 195° C. for 2 hours. The reaction mixture was filtered through a plug of silica gel, washed with ethyl acetate, and concentrated. The crude residue was purified by silica gel column chromatography (stepwise gradient, from hexanes to 75% ethyl acetate/hexanes). The fractions were concentrated, dissolved in diethyl ether (150 mL), washed with water (4×50 mL), dried over $Na_2SO_4$, filtered and concentrated to afford Intermediate 1 (1.95 g, 58.6% yield) as a tan solid. HPLC: Rt=1.193 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=229.01

[M+H]$^+$. $^1$H NMR (500 MHz, DMSO-$d_6$) δ ppm 8.27 (1H, s), 7.34 (1H, s), 6.47 (2H, d, J=2.29), 6.14 (1H, s). Intermediate 1 was used in the synthesis of Examples 13, 104, 165, 169, and 175.

Intermediate 2

3-Methoxy-5-(1H-1,2,4-triazol-1-yl)aniline

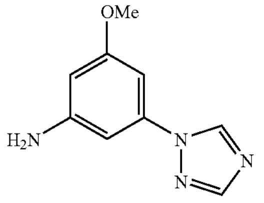

Intermediate 2A: Preparation of 1-(3-methoxy-5-nitrophenyl)-1H-1,2,4-triazole

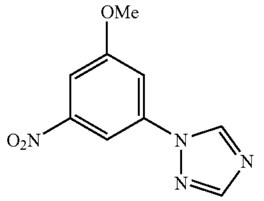

1-Bromo-3-methoxy-5-nitrobenzene (500 mg, 2.16 mmol), copper(I) iodide (205 mg, 1.08 mmol), potassium carbonate (893 mg, 6.5 mmol) and 1H-1,2,4-triazole (446 mg, 6.5 mmol) in NMP (2 mL) were heated at 100° C. for 12 hours. The reaction mixture was diluted with DCM, filtered through a plug of silica gel and washed with ethyl acetate. The filtrate was concentrated, and the residue was purified by reverse phase HPLC to obtain Intermediate 2 (251 mg, 52.9% yield) as a yellow solid. HPLC: Rt=1.235 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=221.0 [M+H]$^+$.

Preparation of 3-methoxy-5-(1H-1,2,4-triazol-1-yl)aniline

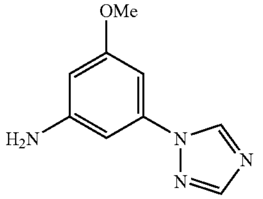

A solution of Intermediate 2A (197 mg, 0.895 mmol) in ethyl acetate (30 m) was passed through a 10% Pd/C cartridge of a H-Cube hydrogenator (ThalesNano, 20 bar of hydrogen at 25° C.). After a second passage, the reaction mixture was concentrated to give Intermediate 2 (131 mg, 77% yield) as a light yellow solid. HPLC: Rt=0.298 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=191.09 [M+H]$^+$. Intermediate 2 was used in the synthesis of Example 2.

The following intermediates in Table 3 were prepared using the procedures described in the preparation of Intermediate 1 and Intermediate 2.

TABLE 3

| Intermediate No. | Structure | Used for Example | Name | [M + H] | HPLC Retention Time (min.)* |
|---|---|---|---|---|---|
| 3 | 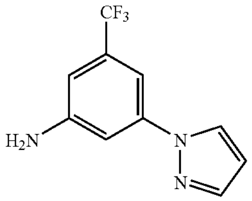 | 103 | 3-(1H-Pyrazol-1-yl)-5-(trifluoromethyl) aniline | 228.17 | 1.38[a] |
| 4 | 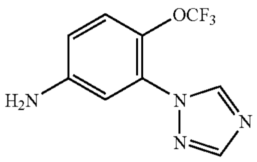 | 137 | 3-(1H-1,2,4-Triazol-1-yl)-4-(trifluoromethoxy) aniline | 245.02 | 1.01[a] |
| 5 | 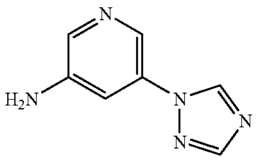 | 145 | 5-(1H-1,2,4-Triazol-1-yl)pyridin-3-amine | 162.09 | 0.17[a] |

TABLE 3-continued
| Intermediate No. | Structure | Used for Example | Name | [M + H] | HPLC Retention Time (min.)* |
|---|---|---|---|---|---|
| 6 | 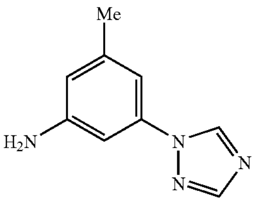 | 155 | 3-Methyl-5-(1H-1,2,4-triazol-1-yl)aniline | 175.20 | 0.63[a] |
| 7 | 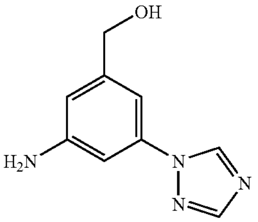 | 159 | 3-Amino-5-(1H-1,2,4-triazol-1-yl)phenyl) methanol | 191.17 | 0.27[a] |
| 8 | 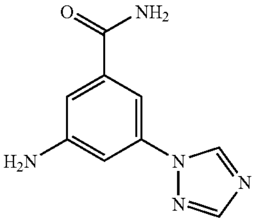 | 192 | 3-Amino-5-(1H-1,2,4-triazol-1-yl) benzamide | 203.9 | 0.41[a] |
| 9 | 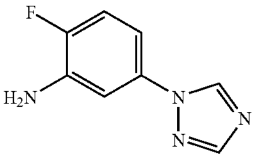 | 170 | 2-Fluoro-5-(1H-1,2,4-triazol-1-yl)aniline | 179.25 | 0.78[a] |
| 10 | 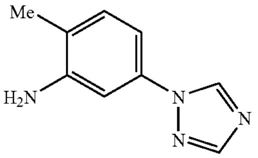 | 162 | 2-Methyl-5-(1H-1,2,4-triazol-1-yl)aniline | 175.14 | 1.01[c] |
| 11 | 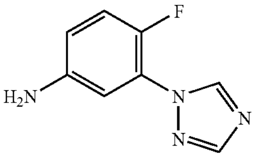 | 163 | 4-Fluoro-3-(1H-1,2,4-triazol-1-yl)aniline | 179.07 | 0.21[a] |
| 12 | 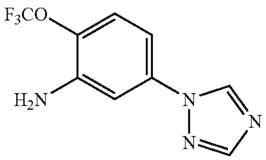 | 167 | 5-(1H-1,2,4-Triazol-1-yl)-2-(trifluoromethoxy) aniline | 245.11 | 2.5[c] |
| 13 | 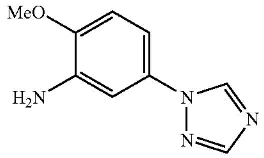 | 160 | 2-Methoxy-5-(1H-1,2,4-triazol-1-yl) aniline | 191.14 | 0.66[b] |

TABLE 3-continued

| Inter-mediate No. | Structure | Used for Example | Name | [M + H] | HPLC Retention Time (min.)* |
|---|---|---|---|---|---|
| 14 | 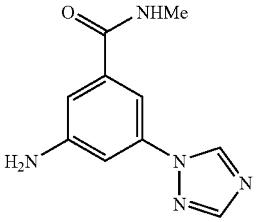 | 194 | 3-Amino-N-methyl-5-(1H-1,2,4-triazol-1-yl) benzamide | 218.17 | 0.15[a] |
| 15 | 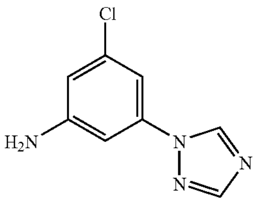 | 156 | 3-Chloro-5-(1H-1,2,4-triazol-1-yl)aniline | 195.12 | 1.03[a] |

*HPLC conditions

[a]PHENOMENEX® Luna 5 micron C18 4.6 x 30 mm, 0 to 100 B in 2 min. with 1 min. hold time, flow rate = 5 mL/min., detection at 254 nm, Solvent A: 10% methanol/90% water/0.1% TFA; Solvent B: 10% water/90% methanol/0.1% TFA

[b]CHROMOLITH® column 4.6 x 50 mm eluting with 10-90% aqueous methanol over 4 min. containing 0.1% TFA, 4 mL/min, monitoring at 220 nm.

[g]Waters Sunfire C18 4.6 x 150 mm 5 micron. 1 mL/min., 0-100% Water-Methanol 0.2% $H_3PO_4$, gradient over 4 min.

Intermediate 16

3-(2-(Dimethylamino)ethoxy)-5-(1H-1,2,4-triazol-1-yl)aniline

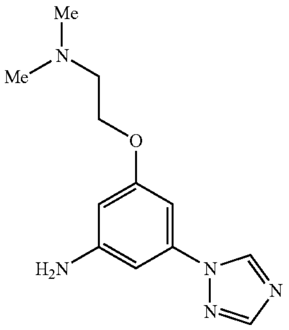

Intermediate 16A: Preparation of 2-(3-bromo-5-nitrophenoxy)-N,N-dimethylethanamine

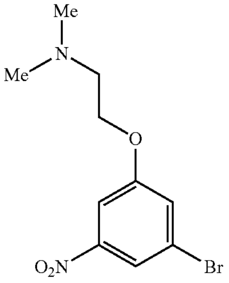

1-Bromo-3,5-dinitrobenzene (1 g, 4.1 mmol), 2-(dimethylamino)ethanol (0.54 g, 6.1 mmol), potassium hydroxide (0.45 g, 8.1 mmol), and water (0.5 mL) in DMF (5 mL) were heated at 80° C. After 20 hours, the reaction mixture was diluted with cold water and extracted with dichloromethane (2×100 mL). The organic phase was washed with brine, dried over sodium sulfate, filtered and concentrated. The crude product was purified by silica gel chromatography (stepwise gradient, 2% ethyl acetate in hexanes to ethyl acetate) to give 2-(3-bromo-5-nitrophenoxy)-N,N-dimethylethanamine (669 mg, 57.2% yield) as a brown oil. HPLC: Rt=1.04 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=290.93 $[M+H]^+$.

Intermediate 16B: Preparation of N,N-dimethyl-2-(3-nitro-5-(1H-1,2,4-triazol-1-yl)phenoxy)ethanamine

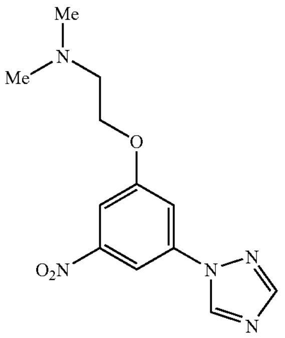

Intermediate 16A (200 mg, 0.69 mmol), copper(I) iodide (65.9 mg, 0.35 mmol), potassium carbonate (287 mg, 2.1 mmol) and 1H-1,2,4-triazole (143 mg, 2.075 mmol) in NMP (2 mL) were heated at 120° C. for 6 hours. The reaction mixture was diluted with dichloromethane, and filtered through a plug of silica gel and washed with ethyl acetate. The filtrate was concentrated, and the residue was purified by reverse phase HPLC to obtain Intermediate 16B (109 mg, 56.8% yield) as a yellow solid. HPLC: Rt=0.74 min. (PHENOMENEX® Luna 5 micron C18 4.6×30 mm, 10-90% aqueous methanol containing 0.1% TFA, 2 min. gradient, flow rate=5 mL/min, detection at 254 nm). MS (ES): m/z=278.08 $[M+H]^+$.

Preparation of 3-(2-(dimethylamino)ethoxy)-5-(1H-1,2,4-triazol-1-yl)aniline

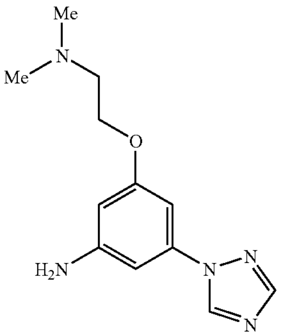

Intermediate 16 B (97 mg, 0.35 mmol) and 10% Pd/C (22.3 mg, 0.21 mmol) in MeOH (10 mL) were stirred under a hydrogen atmosphere (balloon) for 8 hours. The reaction mixture was filtered though a pad of silica gel. The filtrate was concentrated to give Intermediate 16 (81 mg, 94% yield) as a yellow solid. HPLC: Rt=0.26 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=248.15 $[M+H]^+$. Intermediate 16 was used in the synthesis of Examples 146 and 147.

The following intermediates in Table 4 were prepared using the procedures described in the preparation of Intermediate 16.

TABLE 4

| Intermediate No. | Structure | Used for Example | Name | [M + H] | HPLC Retention Time (min)* |
|---|---|---|---|---|---|
| 17 | 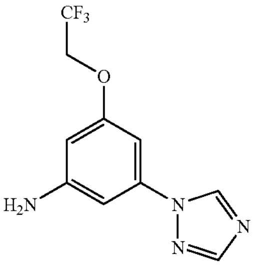 | 157 | 3-(1H-1,2,4-Triazol-1-yl)-5-(2,2,2-trifluoroethoxy)aniline | 259.15 | 1.10[a] |
| 18 | 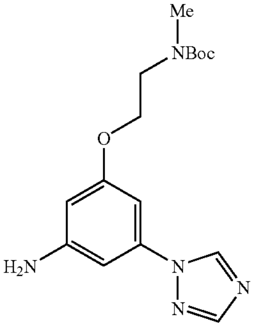 | 174 | tert-Butyl 2-(3-amino-5-(1H-1,2,4-triazol-1-yl)phenoxy)ethyl(methyl)carbamate | 334.15 | 1.35[a] |

*= HPLC conditions

[a]= PHENOMENEX® Luna 5 micron C18 4.6 x 30 mm, 0 to 100 B in 2 min. with 1 min. hold time, flow rate = 5 mL/min., detection at 254 nm, Solvent A: 10% methanol/90% water/0.1% TFA; Solvent B: 10% water/90% methanol/0.1% TFA.

Intermediate 19

N[1]-(2-Morpholinoethyl)-2-(1H-1,2,4-triazol-1-yl)benzene-1,4-diamine

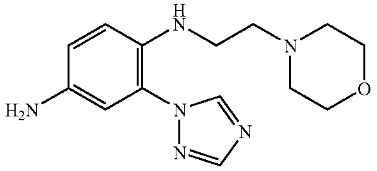

Intermediate 19A: Preparation of 2-bromo-N-(2-morpholinoethyl)-4-nitroaniline

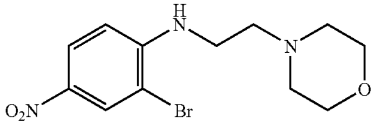

2-Bromo-1-fluoro-4-nitrobenzene (1.0 g, 4.5 mmol), 2-morpholinoethanamine (0.77 g, 5.9 mmol) and potassium carbonate (1.571 g, 11.4 mmol) in DMSO (5 mL) were stirred at room temperature for 1.5 hours. The mixture was triturated with water, and 2-bromo-N-(2-morpholinoethyl)-4-nitroaniline (1.1 g, 72.8% yield) was collected via filtration. HPLC: Rt=0.61 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=332.06 $[M+H]^+$.

Preparation of N[1]-(2-morpholinoethyl)-2-(1H-1,2,4-triazol-1-yl)benzene-1,4-diamine

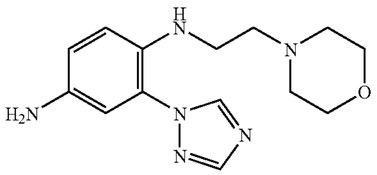

Intermediate 19 was prepared from Intermediate 19A following the procedure in Intermediate 2. HPLC: Rt=0.10 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=289.12 $[M+H]^+$. Intermediate 19 was used in the synthesis of Example 148.

Intermediate 20

N[1]-(Tetrahydro-2H-pyran-4-yl)-2-(1H-1,2,4-triazol-1-yl)benzene-1,4-diamine

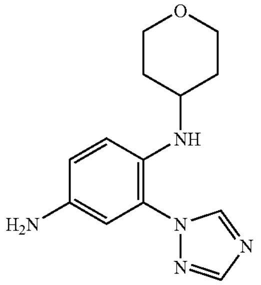

Intermediate 20 was prepared from 2-bromo-1-fluoro-4-nitrobenzene following the procedure in Intermediate 16. HPLC: Rt=0.63 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=260.08 $[M+H]^+$. Intermediate 20 was used in the synthesis of Example 158.

Intermediate 21

3-Fluoro-5-(1H-1,2,4-triazol-1-yl)aniline and 3,5-di(1H-1,2,4-triazol-1-yl)aniline

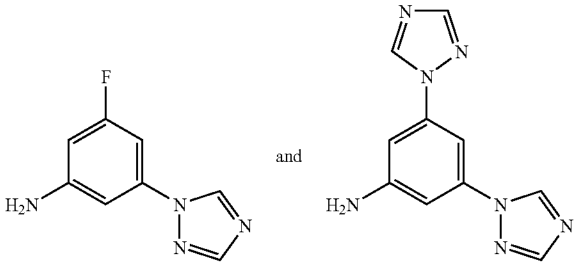

1,3-Difluoro-5-nitrobenzene (1 g, 6.29 mmol), 1H-1,2,4-triazole (0.43 g, 6.29 mmol), and potassium carbonate (2.17 g, 15.7 mmol) in DMSO (5 mL) were stirred at room temperature for 15 hours. The reaction mixture was triturated with water, and the solid was collected via filtration. The solid was dissolved in methanol (40 mL), and treated with 10% Pd/C (100 mg, 0.94 mmol) and stirred under a hydrogen atmosphere at room temperature for 8 hours. The reaction mixture was filtered though a pad of silica gel. The filtrate was concentrated to give Intermediate 21 as a mixture of 3-fluoro-5-(1H-1,2,4-triazol-1-yl)aniline and 3,5-di(1H-1,2,4-triazol-1-yl)aniline (825 mg, 65% yield).

HPLC: Rt=0.78 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=179.07 $[M+H]^+$. HPLC: Rt=0.82 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES):

m/z=228.10 [M+H]+. Intermediate 21 was used in the synthesis of the compounds of Examples 172, 173 and 207.

Intermediate 22

3-Amino-N-(tetrahydro-2H-pyran-4-yl)-5-(1H-1,2,4-triazol-1-yl)benzamide

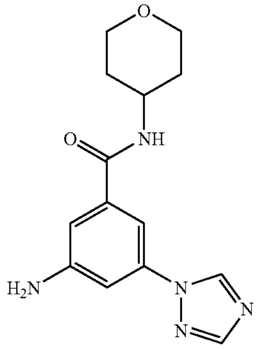

Intermediate 22A: Preparation of 3-nitro-5-(1H-1,2,4-triazol-1-yl)benzoic acid

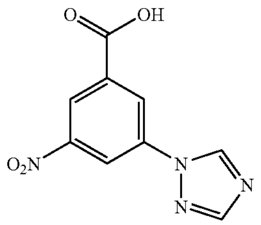

3-Nitro-5-(1H-1,2,4-triazol-1-yl)benzoic acid was prepared from 3-bromo-5-nitrobenzoic acid following the procedure in Intermediate 2A. HPLC: Rt=1.12 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=235.07 [M+H]+.

Preparation of 3-amino-N-(tetrahydro-2H-pyran-4-yl)-5-(1H-1,2,4-triazol-1-yl)benzamide

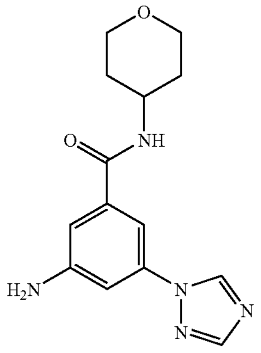

To a solution of Intermediate 22A (400 mg, 1.71 mmol), tetrahydro-2H-pyran-4-amine (207 mg, 2.05 mmol) and TEA (0.36 mL, 2.56 mmol) in DMF (4 mL) was added BOP (1133 mg, 2.56 mmol), and the reaction solution was stirred at room temperature for 2 hours. The reaction mixture was filtered though a pad of silica gel. The filtrate was concentrated and purified with reverse phase HPLC. The fractions were concentrated, dissolved in methanol (30 mL), and treated with 10% Pd/C (27.3 mg, 0.26 mmol) and stirred under a hydrogen atmosphere at room temperature for 8 hours. The reaction mixture was filtered though a pad of silica gel. The filtrate was concentrated to give Intermediate 22 (276 mg, 56.2% yield) as a yellow solid. HPLC: Rt=0.75 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=288.09 [M+H]+. Intermediate 22 was used in the synthesis of Example 171.

Intermediate 23

3-Amino-N-(2-(diethylamino)ethyl)-5-(1H-1,2,4-triazol-1-yl)benzamide

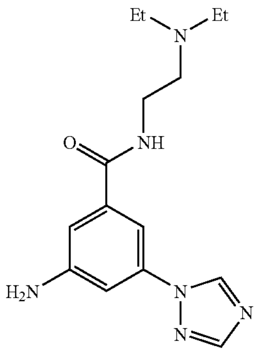

Intermediate 23 was prepared from Intermediate 22A and $N^1$,$N^1$-diethylethane-1,2-diamine following the procedure in Intermediate 22. HPLC: Rt=0.65 min. (PHENOMENEX® S5 4.6×30 mm, 10-90% aqueous methanol containing 0.1% TFA, 4 min. gradient, flow rate=5 mL/min., detection at 254 nm). MS (ES): m/z=303.15 [M+H]+. Intermediate 23 was used in the synthesis of Example 183.

Intermediate 24

3-Amino-4-(trifluoromethyl)benzonitrile

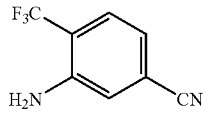

Intermediate 24A: Preparation of 3-(4-methoxybenzylamino)-4-(trifluoromethyl)benzonitrile

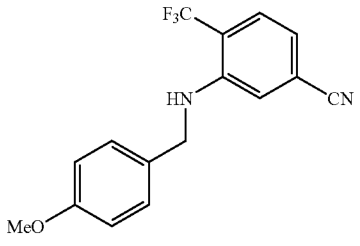

3-Fluoro-4(trifluoromethyl)benzonitrile (1 g, 5.29 mmol), (4-methoxyphenyl)methanamine (0.73 g, 5.29 mmol) and potassium carbonate (1.46 g, 10.6 mmol) in DMSO (2 mL) were heated at 75° C. for 6 hours. The reaction mixture was triturated with water, and the solid was collected via filtration to isolate 24A (1.14 g, 70.6% yield) as a yellow solid. HPLC: Rt=2.64 min. (PHENOMENEX® S5 4.6×30 mm, 10-90% aqueous methanol containing 0.1% TFA, 4 min. gradient, flow rate=5 mL/min., detection at 254 nm). MS (ES): m/z=329.09 $[M+H]^+$.

Preparation of 3-amino-4-(trifluoromethyl)benzonitrile

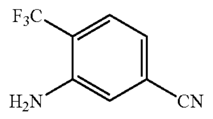

A solution of 3-(4-methoxybenzylamino)-4-(trifluoromethyl)benzonitrile (500 mg, 1.63 mmol) and triethylsilane (0.2 mL) in dichloroethane (2 mL) was treated with TFA (1 mL) and stirred at room temperature for 30 min. The reaction mixture was concentrated to obtain Intermediate 24 (284 mg, 93% yield) as an orange solid. HPLC: Rt=1.24 min. (PHENOMENEX® S5 4.6×30 mm, 10-90% aqueous methanol containing 0.1% TFA, 4 min. gradient, flow rate=5 mL/min., detection at 254 nm). MS (ES): m/z=187.1 $[M+H]^+$. Intermediate 24 was used in the synthesis Examples 229, 230 and 241.

Intermediate 25

3-Amino-5-fluoro-4-methoxybenzonitrile

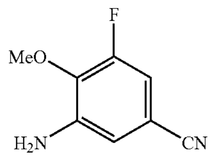

Intermediate 25A: Preparation of 5-bromo-3-fluoro-2-methoxyaniline

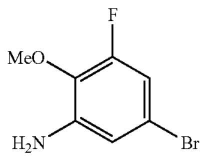

5-Bromo-1-fluoro-2-methoxy-3-nitrobenzene (1.0 g, 4.0 mmol), zinc (2.62 g, 40.0 mmol) and ammonium chloride (2.14 g, 40.0 mmol) in EtOH (20 mL) and water (12 mL) were heated at 80° C. for 10 minutes and then stirred at room temperature for 2 hours. The reaction mixture was diluted with dichloromethane (100 mL) and water (60 mL), and filtered through CELITE®. The organic phase was dried over sodium sulfate and filtered and then concentrated to afford Intermediate 25A (723 mg, 82% yield) as a gray solid. HPLC: Rt=1.3 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=222.0 $[M+H]^+$.

Preparation of 3-amino-5-fluoro-4-methoxybenzonitrile

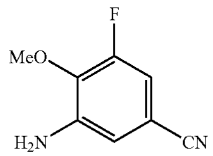

A mixture of 5-bromo-3-fluoro-2-methoxyaniline (500 mg, 2.27 mmol), potassium ferrocyanide (II) hydrate (240 mg, 0.57 mmol), sodium carbonate (241 mg, 2.27 mmol) and palladium(II) acetate (25.5 mg, 0.11 mmol) in DMA (2 mL) was purged with nitrogen and heated at 120° C. for 6 hours. The reaction mixture was diluted with ethyl acetate (20 mL) and filtered through CELITE®. The filtrate was washed with water (20 mL), 5% $NH_4OH$ (10 mL), dried over $MgSO_4$, filtered and concentrated to isolate Intermediate 25 (213 mg, 56.4% yield). HPLC: Rt=0.73 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=167.2 $[M+H]^+$. Intermediate 25 was used in the synthesis of Examples 234 and 239.

Intermediate 26

3-Amino-4-(trifluoromethoxy)benzonitrile

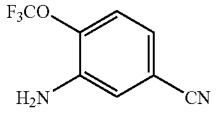

3-Amino-4-(trifluoromethoxy)benzonitrile was prepared from 4-bromo-2-nitro-1-(trifluoromethoxy)benzene following the procedure in Intermediate 25. HPLC: Rt=1.29 min (PHENOMENEX® S5 4.6×30 mm, 10-90% aqueous methanol containing 0.1% TFA, 4 min. gradient, flow rate=5 mL/min., detection at 254 nm). MS (ES): m/z=203.1 $[M+H]^+$. Intermediate 26 was used in the synthesis of Example 237.

Intermediate 27

3-Amino-4-(2-morpholinoethoxy)benzonitrile

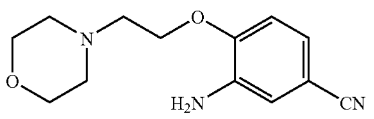

Intermediate 27A: Preparation of 4-(2-morpholinoethoxy)-3-nitrobenzonitrile

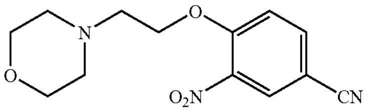

4-Fluoro-3-nitrobenzonitrile (0.5 g, 3.0 mmol), 2-morpholinoethanol (0.37 mL, 3.0 mmol), and potassium carbonate (0.42 g, 3.0 mmol) in DMSO (2 mL) were heated at 50° C. for 16 hours. Water (10 mL) was added to the reaction mixture, and the solid was collected via filtration. The solid was washed with water (3×2 mL) to afford Intermediate 27A (422 mg, 50.6% yield) as a tan solid. HPLC: Rt=0.78 min. (PHENOMENEX® S5 4.6×30 mm, 10-90% aqueous methanol containing 0.1% TFA, 4 min. gradient, flow rate=5 mL/min., detection at 254 nm). MS (ES): m/z=278.16 $[M+H]^+$.

Preparation of 3-amino-4-(2-morpholinoethoxy)benzonitrile

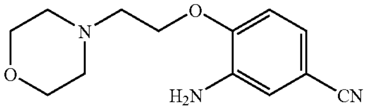

To 4-(2-morpholinoethoxy)-3-nitrobenzonitrile (422 mg, 1.52 mmol) suspended in MeOH (20 mL) was added 10% Pd/C (100 mg), and the reaction mixture stirred under hydrogen atmosphere (balloon). After 30 min., the reaction mixture was filtered through CELITE®. The filtrate was concentrated to give Intermediate 27 (322 mg, 86% yield) as a tan solid. HPLC: Rt=0.5 min. (PHENOMENEX® S5 4.6×30 mm, 10-90% aqueous methanol containing 0.1% TFA, 4 min. gradient, flow rate=5 mL/min., detection at 254 nm). MS (ES): m/z=248.18 $[M+H]^+$. Intermediate 27 was used in the synthesis of Example 238.

Intermediate 28

4-Fluoro-3-(4H-1,2,4-triazol-4-yl)aniline

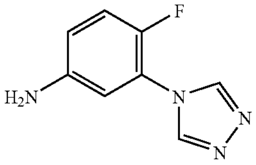

Intermediate 28A: Preparation of 4-(2-fluoro-5-nitrophenyl)-4H-1,2,4-triazole

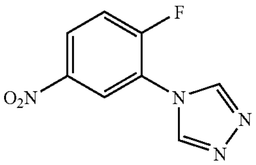

A solution of 2-fluoro-5-nitroaniline (415 mg, 2.7 mmol) in pyridine (15 mL) was treated with N'-formylformohydrazide (703 mg, 7.98 mmol), and TMS-Cl (5.10 mL, 39.9 mmol) was then added dropwise. After the addition, $Et_3N$ (2.60 mL, 18.6 mmol) was added, and the reaction mixture was heated to 100° C. for 4 hours. The reaction mixture was then cooled to room temperature and concentrated to dryness. The resulting solid was suspended in $H_2O$ (25 mL) and filtered. The filtrate was extracted with EtOAc (4×20 mL), and the organics were dried ($Na_2SO_4$), filtered and concentrated. The crude product was dissolved in a small amount of DCM and purified by flash chromatography ($SiO_2$, hexanes to 100% EtOAc, 40 g column, 40 min. gradient) to afford Intermediate 28A (210 mg, 37.9%). HPLC: Rt=1.497 min. (YMC S5 ODS 4.6×50 mm, 10-90% aqueous methanol containing 0.2% $H_3PO_4$, 4 min. gradient, monitored at 220 nm). MS (ES): m/z=209.1 $[M+H]^+$. $^1H$ NMR (400 MHz, DMSO-$d_6$) δ ppm 9.05 (1H, s), 9.05 (1H, s), 8.72 (1H, dd, J=6.55, 2.77 Hz), 8.39-8.45 (1H, m), 7.85 (1H, t, J=9.57 Hz).

Preparation of 4-fluoro-3-(4H-1,2,4-triazol-4-yl)aniline

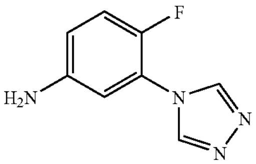

A solution of 4-(2-fluoro-5-nitrophenyl)-4H-1,2,4-triazole (210 mg, 1.009 mmol) in MeOH (4 mL) was treated with 10% Pd/C (20 mg, 0.19 mmol) and stirred under a hydrogen atmosphere at room temperature for 16 hours. The reaction mixture was filtered, and the filtrate was concentrated to dryness to afford Intermediate 28 (155 mg, 86%). HPLC: Rt=0.343 min. (YMC S5 ODS 4.6×50 mm, 10-90% aqueous methanol containing 0.2% $H_3PO_4$, 4 min. gradient, monitored at 220 nm). MS (ES): m/z=179.1 $[M+H]^+$. $^1H$ NMR (400 MHz, DMSO-$d_6$) δ ppm 8.85 (1H, s), 8.85 (1H, s), 7.15 (1H, dd, J=10.45, 8.94 Hz), 6.68 (1H, dd, J=6.55, 2.77 Hz), 6.61-6.66 (1H, m), 5.35 (2H, s). Intermediate 28 was used in the synthesis of Examples 46 and 114.

The following intermediates in Table 5 were prepared using the procedures described in the preparation of Intermediate 28.

TABLE 5

| Intermediate No. | Structure | Used for Example | Name | [M + H] | HPLC Retention Time (min.)* |
|---|---|---|---|---|---|
| 29 | 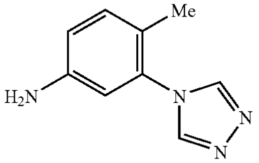 | 106 | 4-Methyl-3-(4H-1,2,4-triazol-4-yl)aniline | 175.1 | 0.28[a] |
| 30 | 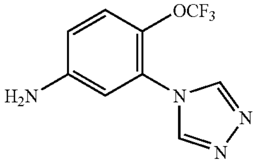 | 17, 52, 111 | 3-(4H-1,2,4-Triazol-4-yl)-4-(trifluoromethoxy) aniline | 245.1 | 2.20[a] |
| 31 | 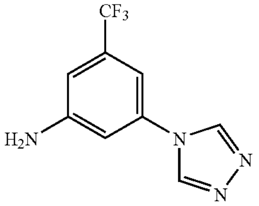 | 169, 236 | 3-(4H-1,2,4-Triazol-4-yl)-5-(trifluoromethyl) aniline | 229 | 1.28[b] |

*= HPLC conditions
[a]= YMC S5 ODS 4.6 x 50 mm, 10-90% aqueous methanol containing 0.2% $H_3PO_4$, 4 min. gradient, monitored at 220 nm
[b]= CHROMOLITH® column 4.6 x 50 mm eluting with 10-90% aqueous methanol over 4 min. containing 0.1% TFA, 4 mL/min, monitoring at 220 nm.

Intermediate 32

1-(3-Amino-5-(4H-1,2,4-triazol-4-yl)phenyl)piperidin-4-ol

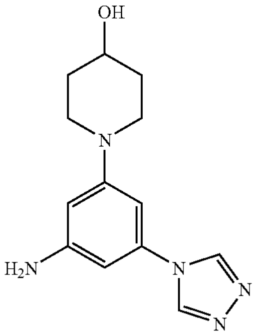

A mixture of 4-(3-fluoro-5-nitrophenyl)-4H-1,2,4-triazole (200 mg, 0.96 mmol) and piperidin-4-ol (486 mg, 4.80 mmol) in DMSO (1 mL) was heated at 100° C. overnight. The reaction mixture was extracted with EtOAc five times. The combined extracts were washed with brine, dried and concentrated to give an orange solid. The solid was dissolved in MeOH (25 mL), and 10% Pd/C (55 mg) was added. The mixture was degassed and stirred under a hydrogen atmosphere for 1 hour. The catalyst was filtered off, and the filtrate was concentrated to give Intermediate 32 (233 mg, 84%) as a brown solid. HPLC: Rt=0.227 min. (CHROMOLITH® column 4.6×50 mm eluting with 10-90% aqueous methanol over 4 min. containing 0.1% TFA, 4 mL/min., monitoring at 220 nm). MS (ES): m/z=260 $[M+H]^+$. Intermediate 32 was used in the synthesis of Example 141.

Intermediate 33 tert-Butyl (3R,4S)-1-(3-amino-5-(4H-1,2,4-triazol-4-yl)phenyl)-3-hydroxypiperidin-4-ylcarbamate

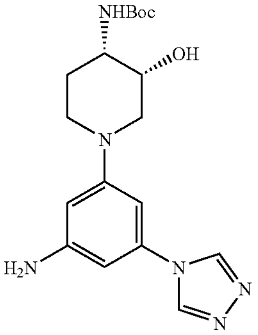

Intermediate 33A. Preparation of (3R,4S)-4-azido-1-(3-nitro-5-(4H-1,2,4-triazol-4-yl)phenyl)piperidin-3-ol

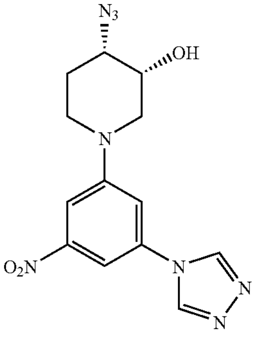

A mixture of 4-(3-fluoro-5-nitrophenyl)-4H-1,2,4-triazole (200 mg, 0.96 mmol), 4-azidopiperidin-3-ol (164 mg, 1.15 mmol) and $K_2CO_3$ (199 mg, 1.44 mmol) in DMSO was heated at 100° C. for 4 hours. The reaction mixture was poured into water and extracted with EtOAc (two times). The combined extracts were washed with water and brine, dried over $MgSO_4$, filtered and concentrated. The crude material was purified by flash chromatography, ($SiO_2$, 24 g column, 0-12% MeOH/DCM) to give Intermediate 33A (135 mg, 43%) as a yellow solid. HPLC: Rt=1.722 min. (CHROMOLITH® column 4.6×50 mm eluting with 10-90% aqueous methanol over 4 min. containing 0.1% TFA, 4 mL/min., monitoring at 220 nm). MS (ES): m/z=331 $[M+H]^+$.

Preparation of tert-butyl (3R,4S)-1-(3-amino-5-(4H-1,2,4-triazol-4-yl)phenyl)-3-hydroxypiperidin-4-ylcarbamate

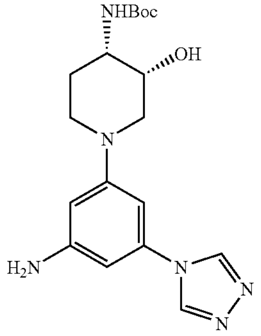

To a solution of Intermediate 33A (135 mg, 0.41 mmol) in THF (5 mL) was added trimethylphosphine (1.0 M solution in toluene, 3 mL, 3.00 mmol). The reaction mixture was stirred for 1 hour, and MeOH (2 mL) and 1N NaOH (2 mL) were added and stirred for an additional 30 min. The reaction mixture was extracted with EtOAc (three times). The combined extracts were dried over $MgSO_4$, filtered and concentrated. The residue was dissolved in THF (30 mL) with TEA (0.171 mL, 1.23 mmol) and $Boc_2O$ (0.190 mL, 0.82 mmol) and stirred at room temperature for 2 hours. The reaction mixture was diluted with water and extracted with EtOAc (three times). The combined organic layers were washed with brine, dried over $MgSO_4$, filtered and concentrated. The crude was purified by flash chromatography, ($SiO_2$, 12 g column, MeOH/DCM=0-8%) to give a yellow solid. The solid was dissolved in MeOH (20 mL), and 10% Pd/C (50 mg) was added. The mixture was stirred under hydrogen atmosphere overnight. The reaction mixture was filtered and concentrated to give Intermediate 33A (84 mg, 19%). HPLC: Rt=1.573 min. (CHROMOLITH® column 4.6×50 mm eluting with 10-90% aqueous methanol over 4 min. containing 0.1% TFA, 4 mL/min., monitoring at 220 nm). MS (ES): m/z=375 $[M+H]^+$. Intermediate 33 was used in the synthesis of Example 142.

Intermediate 34

4-Morpholino-3-(4H-1,2,4-triazol-4-yl)aniline

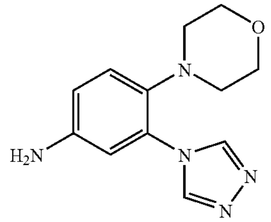

To a solution containing 4-(2-fluoro-5-nitrophenyl)-4H-1,2,4-triazole (0.500 g, 2.402 mmol) and morpholine (0.251 g, 2.88 mmol) in DMSO (6 mL) at room temperature was added potassium carbonate (0.498 g, 3.60 mmol). The dark brown mixture was stirred for 30 min. The solution was then diluted with water, and a precipitate formed. Filtration of the suspension afforded a brown solid. The solid was then suspended in MeOH (15 mL), and 10% Pd/C (0.051 g, 0.480 mmol) was added. An atmosphere of $H_2$ (balloon) was introduced, and the black suspension was stirred for 30 minutes at ambient temperature. The catalyst was removed via filtration. The filtrate was concentrated and dried overnight to afford Intermediate 34 (0.250 g, 42.4% yield) as an orange solid. HPLC: Rt=0.327 min. (YMC S5 ODS 4.6×50 mm, 10-90% aqueous methanol containing 0.2% $H_3PO_4$, 4 min. gradient, monitored at 220 nm). MS (ES): m/z=246.1 $[M+H]^+$. $^1H$ NMR (400 MHz, DMSO-$d_6$) δ ppm 8.79 (2H, s), 7.06 (1H, d, J=8.81 Hz), 6.64 (1H, dd, J=8.56, 2.52 Hz), 6.55 (1H, d, J=2.52 Hz), 5.25 (2H, br. s.), 3.43-3.54 (4H, m), 2.51-2.57 (4H, m). Intermediate 34 was used in the synthesis of Examples 116, 118 and 119.

The following intermediates in Table 6 were prepared using the procedures described in the preparation of Intermediate 34.

TABLE 6

| Intermediate No. | Structure | Used for Example | Name | M + H | HPLC Retention Time (min.)* |
|---|---|---|---|---|---|
| 35 | 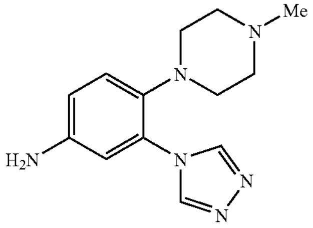 | 121 | 4-(4-Methylpiperazin-1-yl)-3-(4H-1,2,4-triazol-4-yl)aniline | 259.2 | 0.160[a] |

TABLE 6-continued
| Intermediate No. | Structure | Used for Example | Name | M + H | HPLC Retention Time (min.)* |
|---|---|---|---|---|---|
| 36 | 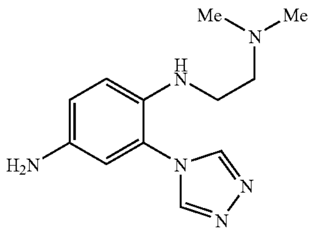 | 4, 122, 166 | N1-(2-(Dimethylamino)ethyl)-2-(4H-1,2,4-triazol-4-yl)benzene-1,4-diamine | 247.2 | 0.152[a] |
| 37 | 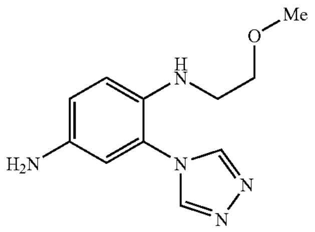 | 123 | N1-(2-Methoxyethyl)-2-(4H-1,2,4-triazol-4-yl)benzene-1,4-diamine | 234.1 | 0.173[a] |
| 38 | 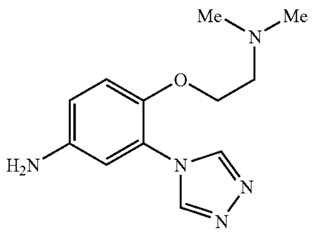 | 127 | 4-(2-(Dimethylamino)ethoxy)-3-(4H-1,2,4-triazol-4-yl)aniline | 248.1 | 0.27[b] |
| 39 | 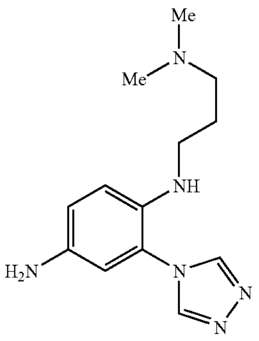 | 129 | N1-(3-(Dimethylamino)propyl)-2-(4H-1,2,4-triazol-4-yl)benzene-1,4-diamine | 261.2 | 0.158[a] |
| 40 | 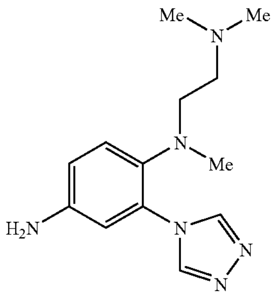 | 132 | N1-(2-(Dimethylamino)ethyl)-N1-methyl-2-(4H-1,2,4-triazol-4-yl)benzene-1,4-diamine | 261.2 | 0.175[a] |

TABLE 6-continued
| Intermediate No. | Structure | Used for Example | Name | M + H | HPLC Retention Time (min.)* |
|---|---|---|---|---|---|
| 41 | 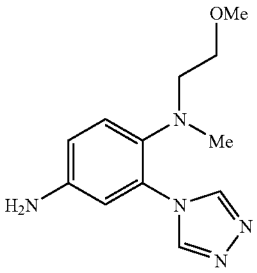 | 135 | N1-(2-Methoxyethyl)-N1-methyl-2-(4H-1,2,4-triazol-4-yl) benzene-1,4-diamine | 248.2 | 0.663[a] |
| 42 | 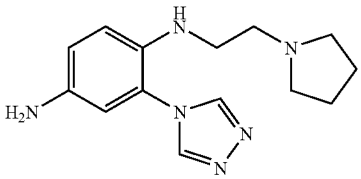 | 139 | N1-(2-(Pyrrolidin-1-yl)ethyl)-2-(4H-1,2,4-triazol-4-yl)benzene-1,4-diamine | 273.1 | 0.158[a] |
| 43 | 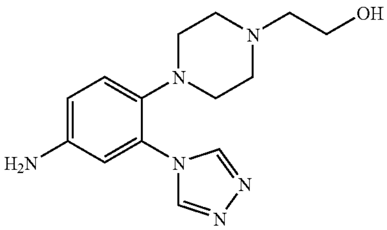 | 149 | 2-(4-(4-Amino-2-(4H-1,2,4-triazol-4-yl) phenyl)piperazin-1-yl) ethanol | 289.1 | 0.157[a] |
| 44 | 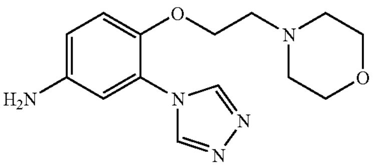 | 150 | 4-(2-Morpholino-ethoxy)-3-(4H-1,2,4-triazol-4-yl)aniline | 290.1 | 0.163[a] |
| 45 | 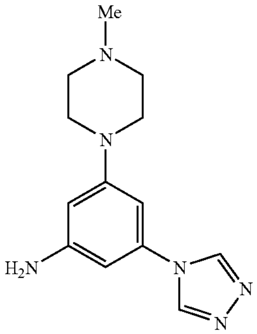 | 130, 152 | 3-(4-Methylpiperazin-1-yl)-5-(4H-1,2,4-triazol-4-yl)aniline | 259 | 0.233[b] |

TABLE 6-continued

| Inter-mediate No. | Structure | Used for Example | Name | M + H | HPLC Retention Time (min.)* |
|---|---|---|---|---|---|
| 46 | 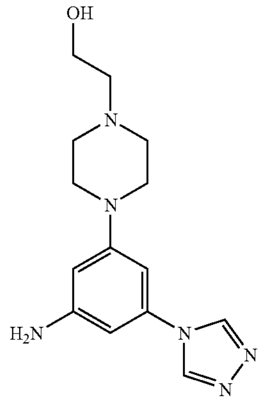 | 133 | 2-(4-(3-Amino-5-(4H-1,2,4-triazol-4-yl) phenyl)piperazin-1-yl) ethanol | 289 | 0.215[b] |
| 47 | 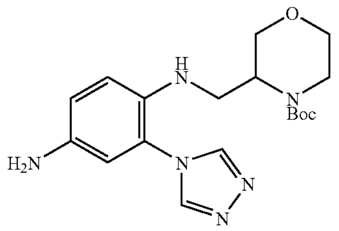 | 151 | tert-Butyl 3-((4-amino-2-(4H-1,2,4-triazol-4-yl)phenylamino) methyl)morpholine-4-carboxylate | 375.2 | 3.260[a] |
| 48 | 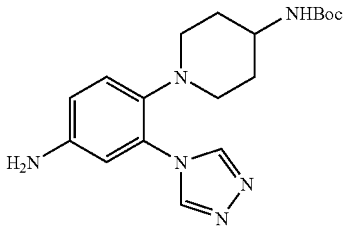 | 144 | tert-Butyl 1-(4-amino-2-(4H-1,2,4-triazol-4-yl)phenyl)piperidin-4-ylcarbamate | 259.1 | 2.527[a] |

*HPLC conditions

[a]YMC S5 ODS 4.6 x 50 mm, 10-90% aqueous methanol containing 0.2% $H_3PO_4$, 4 min. gradient, monitored at 220 nm

[b]CHROMOLITH® column 4.6 x 50 mm eluting with 10-90% aqueous methanol over 4 min. containing 0.1% TFA, 4 mL/min, monitoring at 220 nm.

Intermediate 49

4-(Trifluoromethoxy)benzene-1,3-diamine

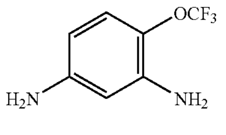

A mixture of 3-nitro-4-(trifluoromethoxy)aniline (500 mg, 2.25 mmol) and 10% Pd/C (240 mg, 0.225 mmol) in ethyl acetate (20 mL) was degassed with nitrogen. The mixture was stirred under a hydrogen atmosphere overnight. The catalyst was filtered off, and the filtrate was concentrated to give Intermediate 49 (433 mg, 100%) as a brown solid. HPLC: Rt=0.707 min. (YMC S5 ODS 4.6×50 mm, 10-90% aqueous methanol containing 0.2% $H_3PO_4$, 4 min. gradient, monitored at 220 nm). MS (ES): m/z=193.1 $[M+H]^+$. $^1H$ NMR (400 MHz, DMSO-$d_6$) δ ppm 6.69 (1H, dd, J=8.56, 1.26 Hz), 5.95 (1H, d, J=2.52 Hz), 5.75 (1H, dd, J=8.69, 2.64 Hz), 4.91 (2H, s), 4.89 (2H, s). Intermediate 49 was used in the synthesis of Examples 90 and 91.

Intermediate 50

4-(2-Methoxyethoxy)-3-(4H-1,2,4-triazol-4-yl) aniline

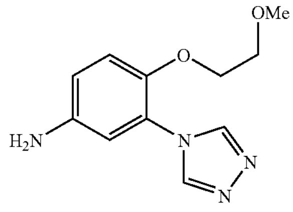

To a solution containing 2-methoxyethanol (0.136 mL, 1.730 mmol) in anhydrous DMF (15 mL) at 0° C. was added NaH (0.063 g, 1.585 mmol) as a 60% dispersion in mineral oil. A solution of 4-(2-fluoro-5-nitrophenyl)-4H-1,2,4-triazole (0.300 g, 1.441 mmol) in DMF (2.0 mL) was added via syringe. After 30 minutes, the reaction mixture was quenched with water. A brown precipitate was collected by filtration and washed with water. The solid was suspended in MeOH (10 mL) and treated with Pd/C (0.031 g, 0.29 mmol), and the reaction was stirred under a hydrogen atmosphere. The dark suspension was stirred for 1 hour at ambient temperature. The catalyst was removed via filtration, and the filtrate was concentrated to dryness to give Intermediate 50 (0.073 g, 21.4% yield) as a brown oil. HPLC: Rt=0.187 min. (YMC S5 ODS 4.6×50 mm, 10-90% aqueous methanol containing 0.2% $H_3PO_4$, 4 min. gradient, monitored at 220 nm). MS (ES): m/z=235.1 $[M+H]^+$. $^1H$ NMR (400 MHz, DMSO-$d_6$) δ ppm 8.75 (2H, s), 7.01 (1H, d, J=9.57 Hz), 6.59-6.66 (2H, m), 5.04 (2H, s), 3.98-4.06 (2H, m), 3.50-3.57 (2H, m), 3.22 (3H, s). Intermediate 50 was used in the synthesis of Example 126.

Intermediate 51

4-(1-Methylpiperidin-4-yloxy)-3-(4H-1,2,4-triazol-4-yl)aniline

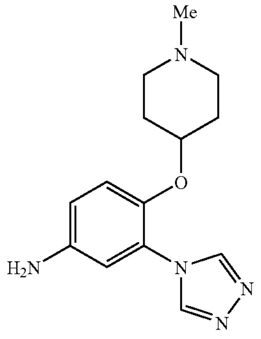

To a solution of 4-(2-fluoro-5-nitrophenyl)-4H-1,2,4-triazole (0.150 g, 0.721 mmol) in anhydrous DMF (0.721 mL) at room temperature was added cesium carbonate (0.49 g, 1.5 mmol) and 1-methylpiperidin-4-ol (0.108 g, 0.94 mmol). The resulting solution was heated to 75° C. After 2 hours, the reaction was cooled and diluted with water. The solution was extracted three times with 20 mL DCM, and the organics were combined, washed with water and brine, and dried over anhydrous sodium sulfate. The reaction mixture was filtered and concentrated, and the solid was suspended in MeOH (10 mL) at ambient temperature. To the mixture was added 10% Pd/C (0.015 g, 0.144 mmol), and the reaction was stirred under a hydrogen atmosphere. The dark suspension was stirred for 1 hour. The catalyst was removed via filtration, and the filtrate was concentrated to give Intermediate 51 (0.064 g, 0.222 mmol, 30.9% yield) as a beige solid. HPLC: Rt=0.160 min. (YMC S5 ODS 4.6×50 mm, 10-90% aqueous methanol containing 0.2% $H_3PO_4$, 4 min. gradient, monitored at 220 nm). MS (ES): m/z=274.1 $[M+H]^+$. $^1H$ NMR (400 MHz, DMSO-$d_6$) δ ppm 8.70 (2H, s), 7.01 (1H, d, J=8.81 Hz), 6.57-6.66 (2H, m), 5.04-5.12 (2H, m), 4.04 (1H, br. s.), 2.20-2.36 (2H, m), 2.07 (3H, s), 1.66-1.78 (2H, m), 1.39-1.50 (2H, m). Intermediate 51 was used in the synthesis of Example 128.

The following intermediates in Table 7 were prepared using the procedures described in the preparation of Intermediate 50 and Intermediate 51.

TABLE 7

| Intermediate No. | Structure | Used for Example | Name | M + H | HPLC Retention Time (min.)* |
|---|---|---|---|---|---|
| 52 | 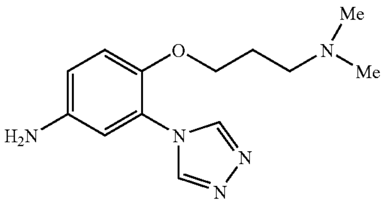 | 140 | 4-(3-(Dimethylamino)propoxy)-3-(4H-1,2,4-triazol-4-yl)aniline | 262.1 | 0.173[a] |
| 53 | 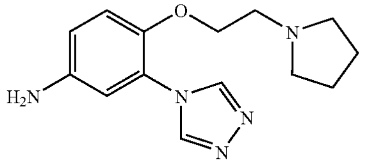 | 143 | 4-(2-(Pyrrolidin-1-yl)ethoxy)-3-(4H-1,2,4-triazol-4-yl)aniline | 274.1 | 0.162[a] |
| 54 | 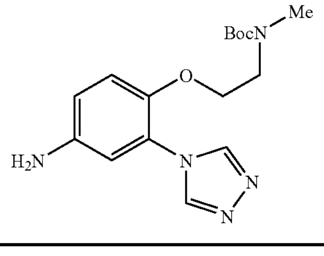 | 153 | tert-Butyl 2-(4-amino-2-(4H-1,2,4-triazol-4-yl)phenoxy)ethyl (methyl)carbamate | 334.1 | 2.158[a] |

*HPLC conditions

[a]YMC S5 ODS 4.6 × 50 mm, 10-90% aqueous methanol containing 0.2% $H_3PO_4$, 4 min. gradient, monitored at 220 nm.

Intermediate 55

4-Chloro-3-(oxazol-5-yl)aniline

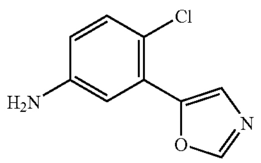

To a solution of 2-chloro-5-nitrobenzaldehyde (2.5 g, 13.5 mmol) in DME (27 mL) at room temperature was added tosylmethyl isocyanide (2.76 g, 14.15 mmol) and potassium carbonate (3.72 g, 26.9 mmol). The mixture was heated to reflux overnight. The mixture was cooled and poured into EtOAc. The resulting suspension was washed with $H_2O$ (2×100 mL) and brine (2×100 mL). The organics were combined, dried over anhydrous magnesium sulfate, filtered, and concentrated in vacuo. The crude intermediate was dissolved in DCM and charged to a 80 g silica gel cartridge which was eluted at 60 mL/min. with a 25 min. gradient from 100% hexanes to 40% EtOAc/hexanes (monitoring at 254 nm). The appropriate fractions were concentrated, and the resulting solid was dissolved in THF (40 mL). Acetic acid (54.0 mL, 943 mmol) and iron powder (1.88 g, 33.7 mmol) were then added, and the resulting mixture was heated overnight at 50° C. The reaction mixture was cooled and poured into 500 mL of saturated aqueous sodium carbonate and extracted with ethyl acetate (3×100 mL). The organics were combined, washed with water and brine, and dried over anhydrous magnesium sulfate, and concentrated. The crude product was dissolved in a small amount of DCM and charged to a 80 g silica gel cartridge which was eluted at 60 mL/min. with a 25 min. gradient from 100% hexanes to 50% EtOAc/hexanes (monitoring at 254 nm). The appropriate fractions were concentrated to afford Intermediate 55 (0.40 g, 15% yield) as a light yellow solid. HPLC: Rt=1.837 min. (YMC S5 ODS 4.6×50 mm, 10-90% aqueous methanol containing 0.2% $H_3PO_4$, 4 min. gradient, monitored at 220 nm). MS (ES): m/z=195.1 $[M+H]^+$. $^1H$ NMR (400 MHz, DMSO-$d_6$) δ ppm 8.49 (1H, s), 7.67 (1H, s), 7.18 (1H, d, J=8.56 Hz), 7.01 (1H, d, J=2.77 Hz), 6.58 (1H, dd, J=8.56, 2.77 Hz), 5.49 (2H, s). Intermediate 55 was used in the synthesis of Example 79.

Intermediate 56

4-Chloro-3-(oxazol-2-yl)aniline

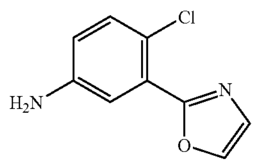

Intermediate 56A: Preparation of 2-(2-Chloro-5-nitrophenyl)oxazole

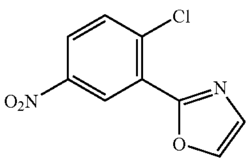

To a cloudy suspension of 2-chloro-5-nitrobenzoic acid (1.0 g, 4.96 mmol) and DMF (0.019 mL, 0.25 mmol) in DCM (12.4 mL) at 0° C. was added a 2M solution of oxalyl chloride in DCM (2.98 mL, 5.95 mmol). The resulting suspension was stirred for 1 hour at room temperature. The reaction mixture was concentrated in vacuo and azeotroped with toluene to remove HCl and oxalyl chloride. The residue was dissolved in tetramethylenesulfone (12.4 mL), to which potassium carbonate (1.37 g, 9.92 mmol) and 1H-1,2,3-triazole (0.29 mL, 4.96 mmol) were added. The mixture was heated to 150° C. under nitrogen for 1 hour. The mixture was cooled and diluted with EtOAc and water. The layers were separated, and the aqueous phase extracted three times with EtOAc (50 mL). The organics were combined, washed with water and brine, and then dried over anhydrous magnesium sulfate. Filtration and concentration afforded a dark brown oil which was dissolved in a small amount of DCM and charged to a 80 g silica gel cartridge which was eluted at 65 mL/min. with a 25 min. gradient from 100% to 50% EtOAc/hexanes (monitoring at 254 nm). Concentration of the appropriate fractions afforded Intermediate 56A (0.431 g, 39% yield) as a light yellow solid. HPLC: Rt=3.246 min. (YMC S5 ODS 4.6×50 mm, 10-90% aqueous methanol containing 0.2% $H_3PO_4$, 4 min. gradient, monitored at 220 nm). MS (ES): m/z=225.0 $[M+H]^+$. $^1H$ NMR (400 MHz, DMSO-$d_6$) δ ppm 8.71 (1H, d, J=2.77 Hz), 8.42 (1H, s), 8.33 (1H, dd, J=8.81, 2.77 Hz), 7.95 (1H, d, J=8.81 Hz), 7.56 (1H, s).

Preparation of 4-chloro-3-(oxazol-2-yl)aniline

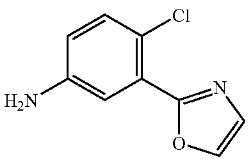

To a solution of Intermediate 56A (0.431 g, 1.92 mmol) and acetic acid (7.69 mL, 134 mmol) in THF (19.2 mL) was added iron powder (0.268 g, 4.80 mmol). The mixture was heated to 50° C. overnight. The reaction mixture was cooled and poured into 300 mL of saturated aqueous $Na_2CO_3$ and extracted with EtOAc (3×75 mL), and washed with water and brine. The organic phase was dried over anhydrous magnesium sulfate, filtered, and concentrated. The dark brown oil was dissolved in a small amount of DCM and charged to a 40 g silica gel cartridge which was eluted at 40 mL/min. with a 25 min. gradient from 100% hexanes to 70% EtOAc/hexanes. Concentration of the appropriate fractions afforded Intermediate 56 (0.301 g, 80% yield) as an orange oil. HPLC: Rt=1.923 min. (YMC S5 ODS 4.6×50 mm, 10-90% aqueous methanol containing 0.2% $H_3PO_4$, 4 min. gradient, monitored at 220 nm). MS (ES): m/z=195.1 $[M+H]^+$. $^1H$ NMR (400 MHz, DMSO-$d_6$) δ ppm 8.24 (1H, s), 7.38 (1H, s), 7.19 (1H, d, J=8.56 Hz), 7.13 (1H, d, J=2.77 Hz), 6.67 (1H, dd, J=8.56, 2.77 Hz), 5.53 (2H, s). Intermediate 56 was used in the synthesis of Example 81.

Intermediate 57

3-(Thiazol-2-yl)aniline

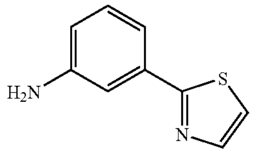

Intermediate 57A: Preparation of 2-(3-Nitrophenyl)thiazole

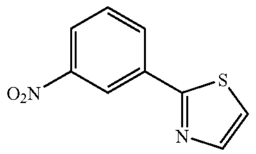

A yellow suspension of 3-nitrobenzothioamide (2.0 g, 10.98 mmol), 2-chloroacetaldehyde (45% in $H_2O$) (2.01 g, 11.53 mmol), and acetic acid (7.32 mL) was heated to reflux for 1 hour. The mixture was cooled to room temperature, poured into ice water, and rendered alkaline using 30 mL of 12 N NaOH solution. Ethyl acetate was then added, and the resulting emulsion was filtered through CELITE®. The aqueous layer was extracted twice with ethyl acetate, and the combined organic layers were dried over magnesium sulfate. Filtration and concentration under reduced pressure afforded Intermediate 57A (2.107 g, 91% yield) as a brown solid. HPLC: Rt=3.331 min. (YMC S5 ODS 4.6×50 mm, 10-90% aqueous methanol containing 0.2% H3PO4, 4 min. gradient, monitored at 220 nm). MS (ES): m/z=207.0 $[M+H]^+$. $^1H$ NMR (400 MHz, DMSO-$d_6$) δ ppm 8.68 (1H, t, J=1.89 Hz), 8.34-8.41 (1H, m), 8.28-8.34 (1H, m), 8.00-8.05 (1H, m), 7.94 (1H, d, J=3.27 Hz), 7.80 (1H, t, J=8.06 Hz).

Preparation of 3-(thiazol-2-yl) aniline

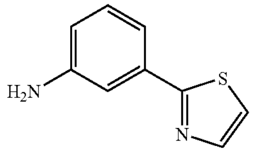

To a suspension of Intermediate 57A (500 mg, 2.425 mmol) in absolute ethanol (12 mL) at ambient temperature was added Raney nickel (60 mg, 2.425 mmol). An atmosphere of hydrogen was then introduced, and the mixture was stirred for 5 hours at ambient temperature. The suspension was filtered through CELITE®, concentrated under reduced pressure and dried in vacuo, furnishing Intermediate 57 (0.32 g, 73.0% yield) as a yellow oil. HPLC: Rt=1.433 min. (YMC S5 ODS 4.6×50 mm, 10-90% aqueous methanol containing 0.2% $H_3PO_4$, 4 min. gradient, monitored at 220 nm). MS (ES): m/z=177.1 $[M+H]^+$. $^1H$ NMR (400 MHz, DMSO-$d_6$) δ ppm 7.85 (1H, d, J=3.02 Hz), 7.70 (1H, t, J=3.40 Hz), 7.17 (1H, t, J=1.89 Hz), 7.02-7.15 (2H, m), 6.60-6.67 (1H, m), 5.34 (2H, s). Intermediate 57 was used in the synthesis of Example 107.

Intermediate 58

Methyl 6-aminoindoline-1-carboxylate

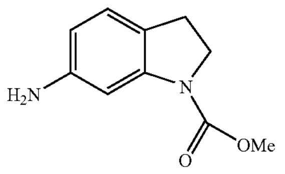

A suspension of methyl 6-nitroindoline-1-carboxylate (187 mg, 0.84 mmol) in MeOH (15 mL) was purged with nitrogen and treated with 10% Pd/C (20 mg, 0.19 mmol). The reaction mixture was stirred at room temperature under a hydrogen atmosphere for 5 hours. The suspension was then purged with nitrogen, filtered and concentrated to dryness to afford Intermediate 58 (93 mg, 57.5%). HPLC: Rt=1.54 min. (YMC S5 ODS 4.6×50 mm, 10-90% aqueous methanol containing 0.2% $H_3PO_4$, 4 min. gradient, monitored at 220 nm). MS (ES): m/z=193.1 $[M+H]^+$. $^1H$ NMR (400 MHz, DMSO-$d_6$) δ ppm 7.08 (1H, s), 6.80 (1H, d, J=7.81 Hz), 6.15 (1H, dd, J=7.93, 2.14 Hz), 4.97 (2H, s), 3.81-3.91 (2H, m), 3.70 (3H, s), 2.88 (2H, t, J=8.44 Hz). Intermediate 58 was used in the synthesis of Example 43.

Intermediate 59

Methyl 5-amino-2-fluorophenylcarbamate

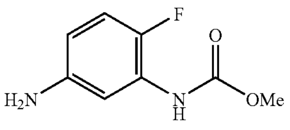

Intermediate 59A: Preparation of methyl 2-fluoro-5-nitrophenylcarbamate

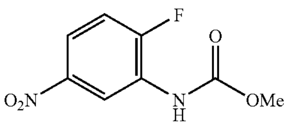

A solution of 2-fluoro-5-nitroaniline (500 mg, 3.20 mmol) in THF (20 mL) was treated with DIEA (0.84 mL, 4.8 mmol) followed by methyl chloroformate (0.25 mL, 3.20 mmol). The reaction mixture was stirred at room temperature overnight and concentrated to dryness. The crude product was dissolved in a small amount of DCM and purified by flash chromatography ($SiO_2$, 20% ethyl acetate/hexanes to 50% ethyl acetate/hexanes, 40 g column, 30 min. gradient) to afford Intermediate 59A (450 mg, 65.6%). HPLC: Rt=2.868 min. (YMC S5 ODS 4.6×50 mm, 10-90% aqueous methanol containing 0.2% $H_3PO_4$, 4 min. gradient, monitored at 220 nm). $^1H$ NMR (400 MHz, DMSO-$d_6$) δ ppm 9.94 (1H, s), 8.72 (1H, dd, J=6.80, 2.77 Hz), 7.87-8.09 (1H, m), 7.52 (1H, t), 3.72 (3H, s).

Preparation of methyl 5-amino-2-fluorophenylcarbamate

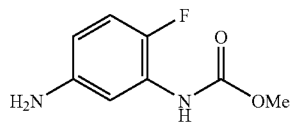

A solution of Intermediate 59A (450 mg, 2.10 mmol) in MeOH (20 mL) was treated with 10% Pd/C (40 mg, 0.38 mmol) and stirred at room temperature under a hydrogen atmosphere for 3 hours. The reaction mixture was filtered and concentrated to a white solid to afford Intermediate 59 (375 mg, 97%). HPLC: Rt=0.403 min. (YMC S5 ODS 4.6×50 mm, 10-90% aqueous methanol containing 0.2% $H_3PO_4$, 4 min. gradient, monitored at 220 nm). MS (ES): m/z=185.0 $[M+H]^+$. $^1H$ NMR (400 MHz, DMSO-$d_6$) δ ppm 8.97 (1H, s), 6.76-6.86 (2H, m), 6.20-6.29 (1H, m), 4.94 (2H, s), 3.62 (3H, s). Intermediate 59 was used in the synthesis of Examples 8, 68, and 39.

Intermediate 60

Methyl 6-amino-3,3-dimethylindoline-1-carboxylate

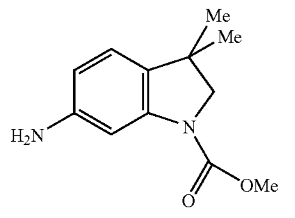

Intermediate 60A: Preparation of methyl 2-bromo-5-nitrophenylcarbamate

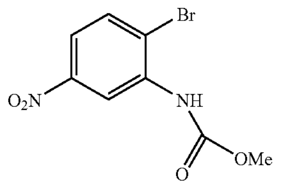

A solution of 2-bromo-5-nitroaniline (500 mg, 2.30 mmol) in THF (40 mL) was treated with pyridine (0.19 mL, 2.3 mmol) and methyl chloroformate (0.27 mL, 3.5 mmol) at room temperature. After 4 hours, additional methyl chloroformate (0.27 mL, 3.5 mmol) was added, and the reaction mixture was stirred at room temperature for an additional 3 hours. The reaction mixture was concentrated to dryness and then taken up in EtOAc (30 mL) and washed with 1 N HCl (3×25 mL), dried ($Na_2SO_4$), filtered and concentrated. The crude product was dissolved in a small amount of DCM and purified by flash chromatography ($SiO_2$, 0% ethyl acetate/hexanes to 30% ethyl acetate/hexanes, 40 g column, 30 min. gradient) to afford Intermediate 60A (390 mg, 61.5%). HPLC: Rt=3.215 min. (YMC S5 ODS 4.6×50 mm, 10-90% aqueous methanol containing 0.2% $H_3PO_4$, 4 min gradient, monitored at 220 nm). MS (ES): m/z=274.9 $[M+H]^+$. $^1H$ NMR (400 MHz, DMSO-$d_6$) δ ppm 9.39 (1H, s), 8.44 (1H, d, J=2.52 Hz), 7.92-7.96 (1H, m), 7.88-7.92 (1H, m), 3.71 (3H, s).

Intermediate 60B: Preparation of methyl 2-bromo-5-nitrophenyl (2-methylallyl)carbamate

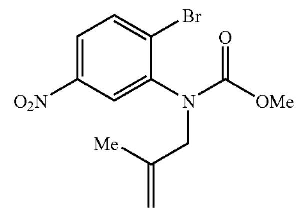

A solution of Intermediate 60B (250 mg, 0.91 mmol) in DMF (25 mL) was treated with sodium hydride (43.6 mg, 1.1 mmol) at 0° C. The mixture was warmed to room temperature for 10 min. and then cooled back to 0° C. The mixture was treated with 3-bromo-2-methylpropene (0.092 mL, 0.91 mmol), and the reaction was warmed to room temperature for 4 hours. The mixture was poured into EtOAc (50 mL) and washed with 10% aq. LiCl (3×25 mL). The organics were dried ($Na_2SO_4$), filtered and concentrated to dryness. The crude product was dissolved in a small amount of DCM and purified by flash chromatography ($SiO_2$, hexanes to 30% ethyl acetate/hexanes, 40 g column, 30 min. gradient) to afford Intermediate 60A (248 mg 83%). HPLC: Rt=3.835 min. (YMC S5 ODS 4.6×50 mm, 10-90% aqueous methanol containing 0.2% $H_3PO_4$, 4 min. gradient, monitored at 220 nm). MS (ES): m/z=331.0 $[M+H]^+$. $^1H$ NMR (400 MHz, DMSO-$d_6$) δ ppm 8.14 (1H, d, J=2.52 Hz), 8.06-8.11 (1H, m), 8.00-8.05 (1H, m), 4.70-4.88 (1H, m), 4.41 (1H, d, J=15.36 Hz), 3.88 (1H, d, J=15.36 Hz), 3.57 (3H, s), 1.75 (3H, s).

Intermediate 60C: Preparation of methyl 3,3-dimethyl-6-nitroindoline-1-carboxylate

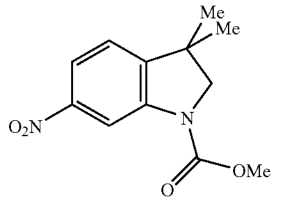

A solution of Intermediate 60B (248 mg, 0.75 mmol) in degassed DMF (3 mL) was treated with palladium(II) acetate (16.9 mg, 0.075 mmol), sodium formate (64.6 mg, 0.95 mmol), sodium acetate (161 mg, 1.96 mmol), and tetraethylammonium chloride (0.146 mL, 0.95 mmol). The reaction mixture was purged with argon and heated to 90° C. for one hour, then cooled to room temperature. The reaction mixture was filtered and diluted with EtOAc (25 mL). The solution was washed with 10% aq. LiCl (3×25 mL), dried ($Na_2SO_4$), filtered and concentrated to dryness. The crude product was dissolved in a small amount of DCM and purified by flash chromatography ($SiO_2$, 0% ethyl acetate/hexanes to 30% ethyl acetate/hexanes, 40 g column, 30 min. gradient) to afford 60C (196.1 mg, 99%). HPLC: Rt=3.831 min. (YMC S5 ODS 4.6×50 mm, 10-90% aqueous methanol containing 0.2% $H_3PO_4$, 4 min. gradient, monitored at 220 nm). MS (ES): m/z=251.1 $[M+H]^+$. $^1$H NMR (400 MHz, DMSO-$d_6$) δ ppm 8.43 (1H, s), 7.90 (1H, dd, J=8.31, 2.27 Hz), 7.52 (1H, d, J=8.31 Hz), 3.82 (2H, s), 3.78 (3H, s), 1.32 (6H, s).

Preparation of methyl 6-amino-3,3-dimethylindoline-1-carboxylate

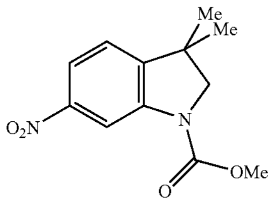

A suspension of Intermediate 60C (196 mg, 0.783 mmol) in MeOH (10 mL) was treated with 10% Pd/C (20 mg, 0.19 mmol) and stirred at room temperature under a hydrogen atmosphere for three hours, then filtered and concentrated to dryness. The crude product was dissolved in a small amount of DCM and purified by flash chromatography ($SiO_2$, hexanes to 40% ethyl acetate/hexanes, 40 g column, 30 min. gradient) to afford Intermediate 60 (112 mg, 64.9%). HPLC: Rt=2.308 min. (YMC S5 ODS 4.6×50 mm, 10-90% aqueous methanol containing 0.2% $H_3PO_4$, 4 min. gradient, monitored at 220 nm). MS (ES): m/z=221.1 $[M+H]^+$. $^1$H NMR (400 MHz, DMSO-$d_6$) δ ppm 7.01 (1H, s), 6.81 (1H, d, J=8.06 Hz), 6.17 (1H, dd, J=7.93, 2.14 Hz), 4.98 (2H, s), 3.70 (3H, s), 3.61 (2H, s), 1.18 (6H, s). Intermediate 60 was used in the synthesis of Example 45.

Intermediate 61

7-Amino-1,4-dimethylquinolin-2(1H)-one

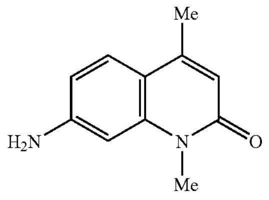

A solution of 7-amino-4-methylquinolin-2(1H)-one (530 mg, 3.04 mmol) in DMF (40 mL) was treated with sodium hydride (146 mg, 3.65 mmol), followed by methyl iodide (0.23 mL, 3.65 mmol). The reaction was stirred at room temperature for 2 hours. The reaction was quenched with water (60 mL), and extracted with EtOAc (3×50 mL). The combined organics were washed with 10% aq LiCl solution, dried ($Na_2SO_4$), filtered and concentrated to dryness. The crude product was dissolved in a small amount of DCM and purified by flash chromatography ($SiO_2$, 0-10% MeOH/$CH_2Cl_2$, 24 g column, 30 min. gradient) to afford Intermediate 61 (124 mg, 21.7%). HPLC: Rt=1.93 min. (YMC S5 ODS 4.6×50 mm, 10-90% aqueous methanol containing 0.2% $H_3PO_4$, 4 min. gradient, monitored at 220 nm). MS (ES): m/z=189.1 $[M+H]^+$. $^1$H NMR (400 MHz, DMSO-$d_6$) δ ppm 7.42 (1H, d, J=9.03 Hz), 6.53 (1H, d, J=6.27 Hz), 6.52 (1H, s), 6.09 (1H, d, J=1.00 Hz), 5.87 (2H, s), 3.45 (3H, s), 2.30 (3H, d, J=0.75 Hz). Intermediate 61 was used in the synthesis of Example 164.

Intermediate 62

N-(4-Aminopyridin-2-yl)acetamide

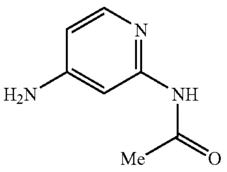

Intermediate 62A: Preparation of methyl 2-acetamidoisonicotinate

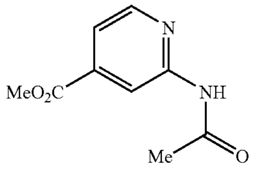

To a solution of methyl 2-aminoisonicotinate (0.5 g, 3.29 mmol) in AcOH (6.6 mL) at room temperature was added acetic anhydride (0.37 mL, 3.94 mmol), and the mixture was refluxed for 1 hour. The mixture was cooled and transferred to a 100 mL round-bottom, where the product was precipitated out of solution by slowly adding water (~6 mL). The suspension was then filtered and washed with water. The solid was dried in vacuo overnight, furnishing Intermediate 62A (0.491 g, 76% yield) as a light yellow solid. HPLC: Rt=1.927 min. (YMC S5 ODS 4.6×50 mm, 10-90% aqueous methanol containing 0.2% $H_3PO_4$, 4 min. gradient, monitored at 220 nm). MS (ES): m/z=195.1 $[M+H]^+$. $^1$H NMR (400 MHz, DMSO-$d_6$) δ ppm 10.76 (1H, s), 8.57 (1H, s), 8.48 (1H, d, J=5.04 Hz), 7.51 (1H, dd, J=5.04, 1.51 Hz), 3.88 (3H, s), 2.11 (3H, s).

Intermediate 62B: Preparation of 2-acetamidoisonicotinoyl azide

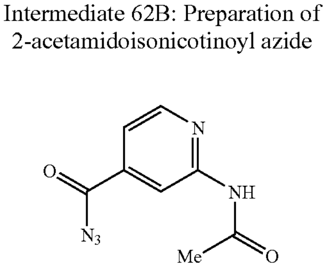

To a suspension of Intermediate 62A (0.250 g, 1.29 mmol) in MeOH (2 mL) at room temperature was added anhydrous hydrazine (0.048 mL, 1.55 mmol), and the mixture was heated to reflux for 1 hour. The suspension was cooled and filtered, washing the solid with MeOH. The solid was dried in vacuo and used immediately. The acyl hydrazide was suspended in 2N HCl (5 mL) and cooled to 0° C., whereupon sodium nitrite (0.533 g, 7.72 mmol) was added slowly in portions with vigorous stirring. The resulting solution stirred for 1 hour at 0° C. The reaction was then quenched by carefully adding solid sodium bicarbonate to pH 6, whereupon a precipitate formed. The solid was filtered, washed with cold water, and dried in vacuo overnight to provide Intermediate 62B (0.182 g, 68% yield) as a white solid. HPLC: Rt=2.345 min. (YMC S5 ODS 4.6×50 mm, 10-90% aqueous methanol containing 0.2% $H_3PO_4$, 4 min. gradient, monitored at 220 nm). $^1$H NMR (400 MHz, DMSO-$d_6$) δ ppm 10.82 (1H, s), 8.58 (1H, s), 8.52 (1H, d, J=5.29 Hz), 7.51 (1H, dd, J=5.16, 1.64 Hz), 2.11 (3H, s).

Preparation of N-(4-Aminopyridin-2-yl)acetamide

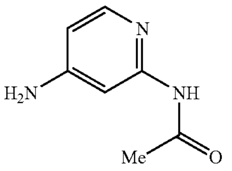

A suspension of 2-acetamidoisonicotinoyl azide (0.180 g, 0.877 mmol) in AcOH (2 mL) and water (2 mL) was heated to 100° C. for 30 min. The mixture was cooled and azeotroped multiple times with toluene to remove water and AcOH. The resulting white solid was dried in vacuo overnight, furnishing Intermediate 62 (0.178 g, 134% yield—residual toluene, acetic acid by NMR) as a light tan solid. HPLC: Rt=0.183 min. (YMC S5 ODS 4.6×50 mm, 10-90% aqueous methanol containing 0.2% $H_3PO_4$, 4 min. gradient, monitored at 220 nm). MS (ES): m/z=152.1 $[M+H]^+$. $^1$H NMR (400 MHz, DMSO-$d_6$) δ ppm 9.94 (1H, s), 7.69 (1H, d, J=5.79 Hz), 7.28 (1H, s), 6.18 (1H, dd, J=5.67, 2.14 Hz), 6.03 (2H, s), 1.90 (3H, s). Intermediate 62 was used in the synthesis of Example 69.

Intermediate 63

1-(3-Aminophenyl)pyrrolidin-2-one

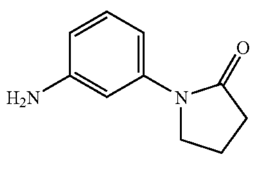

A 25 mL round-bottomed flask was charged with cesium carbonate (1.38 g, 4.2 mmol), copper(I) bromide (0.029 g, 0.20 mmol), and ethyl 2-oxocyclohexanecarboxylate (0.064 mL, 0.40 mmol). The mixture was pump/purged with argon three times, and then DMSO (1.0 mL) was added. The mixture was stirred 30 min. at room temperature under argon. A solution of 1-iodo-3-nitrobenzene (0.5 g, 2.0 mmol) and pyrrolidin-2-one (0.20 g, 2.4 mmol) in DMSO (1.0 mL) was then added, and the mixture was stirred for 2 days at room temperature. The blue suspension was filtered through CELITE®, and the filter cake was washed with EtOAc. The filtrate was washed with brine, dried over $Na_2SO_4$, and then filtered and concentrated. The solid was dissolved in a small amount of DCM and charged to a 40 g silica gel cartridge which was eluted at 40 mL/min. with a 20 min. gradient from 100% to 30% EtOAc/DCM, monitoring at 254 nm. The appropriate fractions were collected and concentrated to provide 0.22 g of product as a light yellow solid. The material was dissolved in EtOAc and charged with 10% Pd/C (0.043 g, 0.402 mmol), and a hydrogen balloon was introduced at room temperature. The dark suspension was stirred for 1 hour. The catalyst was removed via filtration and the filtrate was concentrated in vacuo, affording Intermediate 63 (0.190 g, 53% yield) as a light yellow viscous oil. HPLC: Rt=0.543 min. (YMC S5 ODS 4.6×50 mm, 10-90% aqueous methanol containing 0.2% $H_3PO_4$, 4 min. gradient, monitored at 220 nm). MS (ES): m/z=177.1 $[M+H]^+$. $^1$H NMR (400 MHz, DMSO-$d_6$) δ ppm 6.89-7.00 (2H, m), 6.70 (1H, dd, J=8.06, 1.26 Hz), 6.31 (1H, dd, J=8.06, 1.26 Hz), 5.08 (2H, s), 3.72 (2H, t, J=6.92 Hz), 2.39-2.47 (2H, m), 1.95-2.07 (2H, m). Intermediate 63 was used in the synthesis of Example 73.

Intermediate 64

1-(Methylsulfonyl)-1H-indol-6-amine

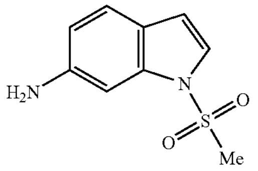

Intermediate 64A: Preparation of 1-(methylsulfonyl)-6-nitro-1H-indole

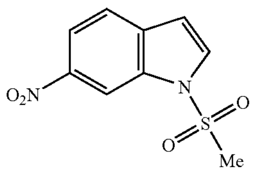

To a solution of 6-nitro-1H-indole (0.250 g, 1.54 mmol) in dry THF (15.4 mL) at −78° C. under nitrogen was added sodium bis(trimethylsilyl)amide (1.850 mL, 1.850 mmol) dropwise via syringe. The resulting solution was stirred for 20 minutes at −78° C., followed by addition of methanesulfonyl chloride (0.14 mL, 1.85 mmol) dropwise via syringe. Following the addition, the cooling bath was removed, and the mixture was allowed to warm to room temperature. After 1 hour, the suspension was filtered, and the resulting solid was taken up in 10 mL of aqueous MeOH and heated to reflux. The hot mixture was filtered to afford a light yellow solid which was dried in vacuo, furnishing Intermediate 64A (0.208 g, 56% yield) as a light yellow solid. HPLC: Rt=3.160 min. (YMC S5

ODS 4.6×50 mm, 10-90% aqueous methanol containing 0.2% $H_3PO_4$, 4 min. gradient, monitored at 220 nm). MS (ES): m/z=241.0 $[M+H]^+$. $^1H$ NMR (400 MHz, DMSO-$d_6$) δ ppm 8.70 (1H, d, J=2.01 Hz), 8.18 (1H, dd, J=8.81, 2.01 Hz), 7.98 (1H, d, J=3.78 Hz), 7.92 (1H, d, J=8.81 Hz), 7.05 (1H, d, J=3.78 Hz), 3.55-3.66 (3H, m).

Preparation of 1-(Methylsulfonyl)-1H-indol-6-amine

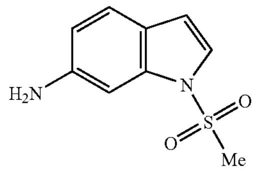

A suspension of Intermediate 64A (0.100 g, 0.42 mmol) and platinum(IV) oxide (4.73 mg, 0.021 mmol) in MeOH (4.16 mL) was hydrogenated at 40 PSI in a hydrogenation pressure vessel at room temperature for 1 hour. The suspension was filtered, concentrated in vacuo, and dried to give Intermediate 64 (0.095 g, 103% yield) as a light yellow solid. HPLC: Rt=1.167 min. (YMC S5 ODS 4.6×50 mm, 10-90% aqueous methanol containing 0.2% $H_3PO_4$, 4 min. gradient, monitored at 220 nm). MS (ES): m/z=211.0 $[M+H]^+$. $^1H$ NMR (400 MHz, DMSO-$d_6$) δ ppm 7.27 (1H, d, J=8.31 Hz), 7.16 (1H, d, J=3.53 Hz), 7.03 (1H, s), 6.54-6.63 (2H, m), 5.26 (2H, s), 3.24 (3H, s). Intermediate 64 was used in the synthesis of Example 64.

Intermediate 65

N-(5-Amino-2,4-difluorophenyl)acetamide

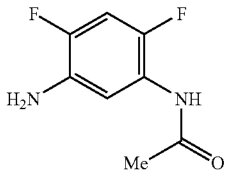

Hydrogen was introduced via a balloon to a suspension of N-(2,4-difluoro-5-nitrophenyl)acetamide (0.300 g, 1.39 mmol) and 10% Pd/C (0.052 g, 0.49 mmol) in ethyl acetate (5 mL) at room temperature. The suspension was stirred for 1.5 hours. The catalyst was removed via filtration, and the filtrate was concentrated in vacuo to give Intermediate 65 (0.240 g, 93% yield) as an off-white solid. HPLC: Rt=0.442 min. (YMC S5 ODS 4.6×50 mm, 10-90% aqueous methanol containing 0.2% $H_3PO_4$, 4 min. gradient, monitored at 220 nm). MS (ES): m/z=187.1 $[M+H]^+$. $^1H$ NMR (400 MHz, DMSO-$d_6$) δ ppm 9.45 (1H, s), 7.23 (1H, dd, J=9.44, 8.44 Hz), 7.04 (1H, t, J=10.83 Hz), 5.02 (2H, s), 1.96-2.07 (3H, m). Intermediate 65 was used in the synthesis of Example 76.

Intermediate 66

Methyl 3-amino-4-fluorophenylcarbamate

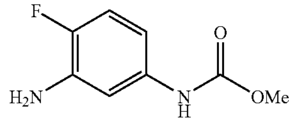

To a solution of 4-fluoro-3-nitroaniline (0.500 g, 3.20 mmol) in THF (30 mL) was added DIEA (0.839 mL, 4.80 mmol) and methyl chloroformate (0.248 mL, 3.20 mmol). The brown solution was stirred overnight at room temperature. The solution was diluted with water and EtOAc, and the layers were separated. The aqueous phase was extracted twice with EtOAc, and the organics were combined, washed with water and brine, and then dried over anhydrous sodium sulfate. Filtration and concentration afforded a light tan solid, which was taken up in EtOAc (30 mL) and treated with 10% Pd/C (0.102 g, 0.961 mmol) and hydrogen (balloon) was introduced. The resulting black suspension was stirred vigorously for 2 hours at room temperature. The mixture was then filtered and subjected to the same reaction conditions. After 1.5 hours, the suspension was filtered, and the brown filtrate concentrated in vacuo and azeotroped with toluene to remove residual MeOH. The crude residue was dissolved in a small amount of DCM and charged to a 24 g silica gel cartridge which was eluted at 30 mL/min. with a 20 min. gradient from 100% to 30% EtOAc/DCM (monitoring at 254 nm). Appropriate fractions were concentrated, affording Intermediate 66 (0.44 g, 74% yield) as a light yellow solid. HPLC: Rt=185.1 min. (YMC S5 ODS 4.6×50 mm, 10-90% aqueous methanol containing 0.2% $H_3PO_4$, 4 min. gradient, monitored at 220 nm). MS (ES): m/z=0.837 $[M+H]^+$. $^1H$ NMR (400 MHz, $CDCl_3$) δ ppm 7.02 (1H, s), 6.87 (1H, dd, J=10.58, 8.81 Hz), 6.47-6.53 (1H, m), 6.41-6.47 (1H, m), 3.67-3.81 (3H, m). Intermediate 66 was used in the synthesis of Example 78.

Intermediate 67

Methyl 3-amino-5-(tetrahydro-2H-pyran-4-ylcarbamoyl)phenylcarbamate

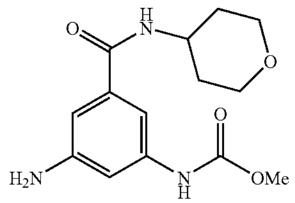

To a solution of BOP (0.911 g, 2.06 mmol) and 3-amino-5-nitrobenzoic acid (0.25 g, 1.37 mmol) in DMF (6.5 mL) at room temperature was added tetrahydro-2H-pyran-4-amine (0.17 g, 1.65 mmol). The solution was stirred overnight at ambient temperature and then concentrated. The crude coupling product was suspended in DCM (6.50 mL) and treated with pyridine (0.22 mL, 2.75 mmol), and methyl chloroformate (0.128 mL, 1.647 mmol). The solid was isolated via filtration and dried overnight. To a suspension of methyl 3-nitro-5-(tetrahydro-2H-pyran-4-ylcarbamoyl)phenylcarbamate (0.140 g, 0.433 mmol) in MeOH (5 mL) at room temperature was added 10% Pd/C (9 mg, 0.085 mmol). An atmosphere of hydrogen was introduced. The reaction mixture was stirred for 30 minutes. The catalyst was removed via filtration, and the filtrate was concentrated under reduced pressure to give Intermediate 67 (0.134 g, 104% yield) as a light gray solid. HPLC: Rt=1.583 min. (YMC S5 ODS 4.6×50 mm, 10-90% aqueous methanol containing 0.2% $H_3PO_4$, 4 min. gradient, monitored at 220 nm). MS (ES): m/z=294.1 $[M+H]^+$. Intermediate 67 was used in the synthesis of Example 177.

Intermediate 68

Methyl 3-amino-5-(methylsulfonyl)phenylcarbamate

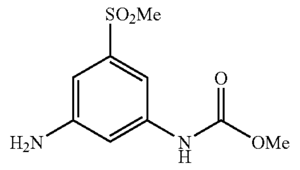

To a suspension of 3-(methylsulfonyl)-5-nitroaniline (0.026 g, 0.120 mmol) and pyridine (0.016 mL, 0.192 mmol) in DCM (3.00 mL) at room temperature was added methyl chloroformate (0.010 mL, 0.129 mmol). The reaction mixture was stirred at room temperature for 30 min. The reaction mixture was quenched with water, and the layers were separated. The aqueous phase was washed once with 5 mL DCM. The organics were combined, washed with water and brine, then dried over anhydrous sodium sulfate. Filtration and concentration afforded a dark yellow solid. The crude solid was dissolved in MeOH (3 mL) at ambient temperature, and 10% Pd/C (2.56 mg, 0.024 mmol) was added. An atmosphere of hydrogen (balloon) was introduced, and the suspension stirred for 1 hour. The catalyst was removed via filtration, and the filtrate was concentrated under reduced pressure and dried to afford Intermediate 68 (0.025 g, 85% yield) as a light green solid. HPLC: Rt=1.370 min. (YMC S5 ODS 4.6×50 mm, 10-90% aqueous methanol containing 0.2% H3PO4, 4 min. gradient, monitored at 220 nm). MS (ES): m/z=245.0 $[M+H]^+$. $^1$H NMR (400 MHz, DMSO-$d_6$) δ ppm 9.73 (1H, s), 7.14 (1H, t, J=1.76 Hz), 6.98 (1H, t, J=1.88 Hz), 6.70 (1H, t, J=1.88 Hz), 5.70 (2H, s), 3.65 (3H, s), 3.06 (3H, s). Intermediate 68 was used in the synthesis of Example 182.

Intermediate 69

(2,4-Diaminophenyl)(4-methylpiperazin-1-yl)methanone

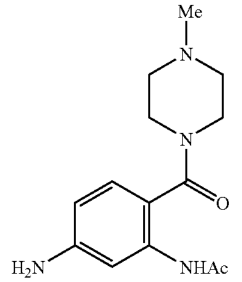

Intermediate 69A: Preparation of 2-Amino-4-nitrobenzoyl chloride

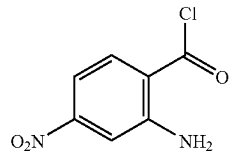

2-Amino-4-nitrobenzoic acid (15 g, 82 mmol) was refluxed with sulfurous dichloride (40 mL, 82 mmol) for 2.5 hours. The reaction mixture was cooled to room temperature and concentrated to give Intermediate 69A (19.7 g, 119%) as a brown oil. HPLC: Rt=2.323 (as methyl ester) min. (CHROMOLITH® column 4.6×50 mm eluting with 10-90% aqueous methanol over 4 min. containing 0.1% TFA, 4 mL/min., monitoring at 220 nm.). MS (ES): m/z=197 (as methyl ester) $[M+H]^+$.

Intermediate 69B: Preparation of (2-amino-4-nitrophenyl)(4-methylpiperazin-1-yl)methanone

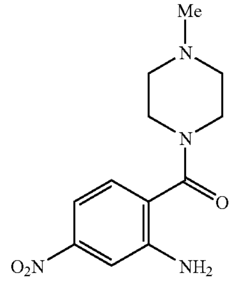

To a solution of 1-methylpiperazine (2.5 g, 24.96 mmol) in DCM (30 mL) at 0° C. was added a solution of Intermediate 69A (1.13 g, 5.63 mmol) in DCM (10 mL) slowly. The reaction was stirred at room temperature for 1 hour. The reaction mixture was washed with saturated aqueous $NaHCO_3$, dried over $MgSO_4$, filtered and concentrated. The crude material was purified by flash chromatography, ($SiO_2$, 24 g, 0-10% MeOH/DCM) to give Intermediate 69B (0.77 g, 52%) as a yellow oil. HPLC: Rt=0.360 min. (CHROMOLITH® column 4.6×50 mm eluting with 10-90% aqueous methanol over 4 min. containing 0.1% TFA, 4 mL/min., monitoring at 220 nm). MS (ES): m/z=265 $[M+H]^+$.

Intermediate 69C: Preparation of methyl 2-(4-methylpiperazine-1-carbonyl)-5-nitrophenylcarbamate

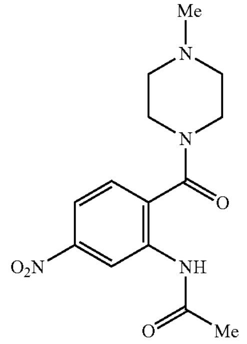

To a solution of Intermediate 69B (540 mg, 2.04 mmol) in DCM (20 mL) was added TEA (0.570 mL, 4.09 mmol), acetic anhydride (0.289 mL, 3.06 mmol), and DMAP (2 mg, 0.016 mmol). The reaction mixture was stirred overnight, then washed with saturated aqueous $NaHCO_3$, dried, and concentrated. The reaction mixture was purified by flash chromatography, ($SiO_2$, 24 g, 0-10% MeOH/DCM) to give Intermediate 69C (600 mg, 96%) as a yellow solid. HPLC: Rt=0.517 min. (CHROMOLITH® column 4.6×50 mm eluting with 10-90% aqueous methanol over 4 min. containing 0.1% TFA, 4 mL/min., monitoring at 220 nm). MS (ES): m/z=307 $[M+H]^+$.

Preparation of N-(5-amino-2-(4-methylpiperazine-1-carbonyl)phenyl)acetamide

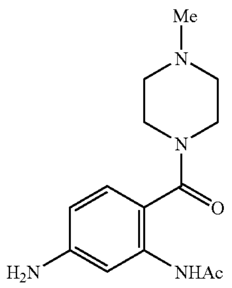

To a solution of Intermediate 69C (600 mg, 1.96 mmol) in EtOAc (25 mL) and MeOH (5.0 mL) was added 10% Pd/C (208 mg, 0.196 mmol). The mixture was degassed and stirred under a hydrogen atmosphere (balloon) overnight. The catalyst was filtered off, and the filtrate was concentrated to give Intermediate 69 (505 mg, 93%) as white solid. HPLC: Rt=0.243 min. (CHROMOLITH® column 4.6×50 mm eluting with 10-90% aqueous methanol over 4 min. containing 0.1% TFA, 4 mL/min., monitoring at 220 nm). MS (ES): m/z=277 $[M+H]^+$. Intermediate 69 was used in the synthesis of Example 93 and Example 89.

Intermediate 70

1-(3-Aminophenyl)piperidin-4-ol

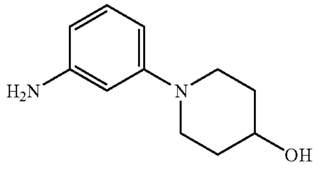

A solution of 1-fluoro-3-nitrobenzene (200 mg, 1.42 mmol), and piperidin-4-ol (430 mg, 4.25 mmol) in DMSO (1 mL) was heated at 80° C. for two days. The reaction mixture was diluted with water, extracted with EtOAc (two times), and the combined extracts were washed with brine, dried and concentrated. The residue was purified by flash chromatography ($SiO_2$, 12 g column, 0-100% EtOAc/DCM) to give an oil. The residue was dissolved in MeOH, and 10% Pd/C was added. The mixture was stirred under a hydrogen atmosphere (balloon) overnight. The catalyst was filtered off, and the filtrate was concentrated to give Intermediate 70 (400 mg, 146%) as a yellow oil. HPLC: Rt=0.228 min. (CHROMOLITH® column 4.6×50 mm eluting with 10-90% aqueous methanol over 4 min. containing 0.1% TFA, 4 mL/min., monitoring at 220 nm). MS (ES): m/z=193 $[M+H]^+$. Intermediate 70 was used in the synthesis of Example 154.

Intermediate 71

3-Amino-5-cyano-N-methylbenzenesulfonamide

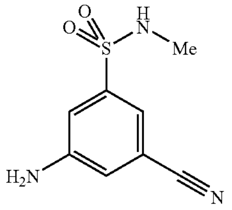

Intermediate 71A: Preparation of 3-amino-5-nitrobenzonitrile

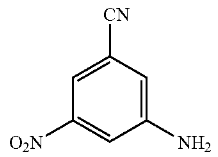

To a suspension of 3,5-dinitrobenzonitrile (4.5 g, 23.30 mmol) in MeOH (100 mL) was added concentrated HCl (15 mL), followed by iron powder (3.90 g, 69.9 mmol). The mixture was stirred at room temperature for 30 min. and then concentrated. The residue was treated with water and the resulting solid product was collected by filtration to give Intermediate 71A (2.3 g, 61%). HPLC: Rt=1.245 min. (CHROMOLITH® column 4.6×50 mm eluting with 10-90% aqueous methanol over 4 min. containing 0.1% TFA, 4 mL/min., monitoring at 220 nm). $^1H$ NMR (500 MHz, DMSO-$d_6$) δ ppm 7.68 (1H, s), 7.64 (1H, s), 7.24 (1H, s), 6.33 (2H, s).

Intermediate 71B: Preparation of 3-cyano-5-nitrobenzene-1-sulfonyl chloride

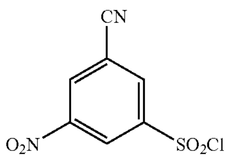

To a solution of acetic acid (7.5 mL) and hydrochloric acid, 37% (1.5 mL) was added Intermediate 71A (1.49 g, 9.13 mmol). The suspension was cooled to −5° C. A solution of sodium nitrite (0.882 g, 12.79 mmol) in water (2 mL) was added dropwise. The resulting mixture was stirred at 0° C. for 2 hours. A mixture of copper (II) chloride (0.31 g, 2.28 mmol) in acetic acid (15 mL) was saturated with sulfur dioxide by bubbling for 40 min. The reaction mixture containing the diazonium salt was slowly poured into the copper (II) chloride-$SO_2$ mixture. The resulting mixture was stirred at 0° C. for 30 minutes, diluted with ice-water, and extracted with DCM (three times). The combined organic layers were dried over $MgSO_4$, filtered and concentrated to give Intermediate 71B (1.9 g, 84%) as yellow oil. HPLC: Rt=1.622 min. (CHROMOLITH® column 4.6×50 mm eluting with 10-90% aqueous methanol over 4 min. containing 0.1% TFA, 4 mL/min., monitoring at 220 nm).

Intermediate 71C: Preparation of 3-cyano-N-methyl-5-nitrobenzenesulfonamide

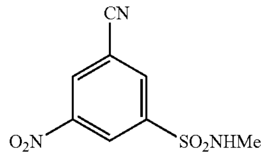

To a solution of Intermediate 71B (150 mg, 0.61 mmol) in DCM (4 mL) was added methylamine (2.0 M solution in THF, 1.5 mL, 3.0 mmol) and TEA (0.424 mL, 3.04 mmol). The reaction mixture was stirred at room temperature for 1 hour, diluted with DCM, washed with water, dried over $MgSO_4$ and concentrated. The residue was purified by silica gel chromatography (flash chromatography, 12 g, EtOAC/hexane=0-100%) to give Intermediate 71C (45 mg, 31%) as a white solid. HPLC: Rt=1.112 min. (CHROMOLITH® column 4.6×50 mm eluting with 10-90% aqueous methanol over 4 min. containing 0.1% TFA, 4 mL/min., monitoring at 220 nm). $^1H$ NMR (500 MHz, $CDCl_3$) δ ppm 8.90 (1H, s), 8.71 (1H, s), 8.46 (1H, s), 4.76 (1H, br. s.), 2.81 (3H, d, J=4.95 Hz).

Preparation of 3-amino-5-cyano-N-methylbenzenesulfonamide

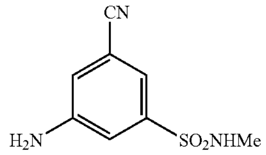

Intermediate 71 was prepared from Intermediate 71C following hydrogenation condition employed in the preparation of Intermediate 70. HPLC: Rt=0.84 min. (CHROMOLITH® column 4.6×50 mm eluting with 10-90% aqueous methanol over 4 minutes containing 0.1% TFA, 4 mL/min., monitoring at 220 nm). MS (ES): m/z=212 $[M+H]^+$. Intermediate 71 was used in the synthesis of Example 178.

Intermediate 72

3-Amino-5-cyano-N-(4-methoxybenzyl)benzenesulfonamide

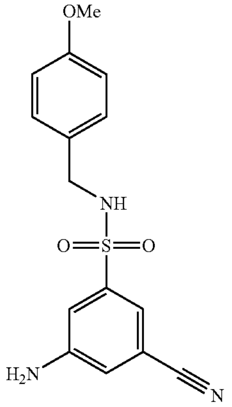

Intermediate 72 was prepared from Intermediate 71B and (4-methoxyphenyl)methanamine following the procedure described in the preparation of Intermediate 71. HPLC: Rt=1.932 min. (CHROMOLITH® column 4.6×50 mm eluting with 10-90% aqueous methanol over 4 min. containing 0.1% TFA, 4 mL/min., monitoring at 220 nm). $^1H$ NMR (500 MHz, DMSO-$d_6$) δ ppm 8.13 (1H, br. s.), 7.22 (1H, s), 7.08-7.16 (3H, m), 7.01 (1H, s), 6.83 (2H, d, J=8.80 Hz), 6.12 (2H, s), 3.93 (2H, s), 3.72 (3H, s). Intermediate 72 was used in the synthesis of Example 187.

Intermediate 73

3-Amino-5-cyano-N-(tetrahydro-2H-pyran-4-yl)benzenesulfonamide

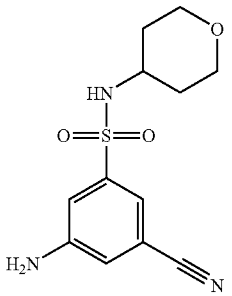

Intermediate 73 was prepared from Intermediate 71B and tetrahydro-2H-pyran-4-amine following a procedure employed for the preparation of Intermediate 71. HPLC: Rt=1.180 min. (CHROMOLITH® column 4.6×50 mm eluting with 10-90% aqueous methanol over 4 min. containing 0.1% TFA, 4 mL/min., monitoring at 220 nm). $^1H$ NMR (500 MHz, DMSO-$d_6$) δ ppm 7.86 (1H, br. s.), 7.26 (1H, s), 7.22 (1H, s), 7.03 (1H, s), 6.15 (2H, s), 3.73 (2H, d, J=11.55 Hz), 3.06-3.28 (3H, m), 1.53 (2H, d, J=10.45 Hz), 1.25-1.42 (2H, m). Intermediate 73 was used in the synthesis of Example 185.

The following intermediates in Table 8 were prepared using the procedures described in the preparation of Intermediate 71.

TABLE 8

| Intermediate No. | Structure | Used for Example | Name | M + H | HPLC Retention Time (min.)* |
|---|---|---|---|---|---|
| 74 | 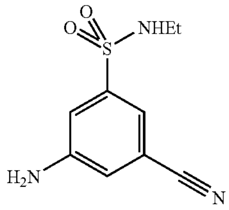 | 180 | 3-Amino-5-cyano-N-ethylbenzenesulfonamide | 226 | 1.1[a] |
| 75 | 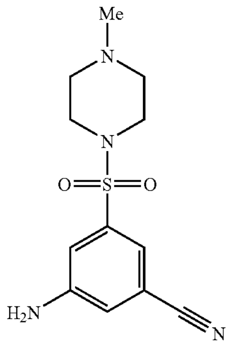 | 186 | 3-Amino-5-(4-methylpiperazin-1-ylsulfonyl)benzonitrile | 281 | 0.83[a] |

*HPLC conditions

[a]CHROMOLITH® column 4.6 x 50 mm eluting with 10-90% aqueous methanol over 4 min. containing 0.1% TFA, 4 mL/min, monitoring at 220 nm.

Intermediate 76

N-(3-Amino-5-cyanophenyl)-N-(methylsulfonyl) methanesulfonamide

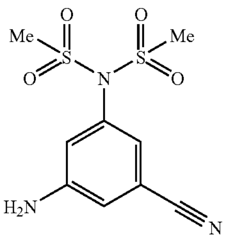

Intermediate 76A: Preparation of N-(3-cyano-5-nitrophenyl)-N-(methylsulfonyl)methanesulfonamide

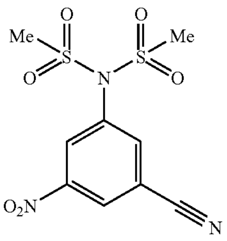

To a suspension of 3-amino-5-nitrobenzonitrile (161 mg, 0.987 mmol) in DCM (8 mL) was added TEA (0.55 mL, 3.95 mmol), followed by methanesulfonyl chloride (0.165 mL, 2.12 mmol). The reaction mixture was stirred at room temperature for 60 min., then diluted with DCM, washed with $H_2O$, dried over $Na_2SO_4$, and concentrated. The crude solid was triturated with DCM and isolated by filtration to give Intermediate 76A (242 mg, 76%) as a white solid. HPLC: Rt=1.198 min. (CHROMOLITH® column 4.6×50 mm eluting with 10-90% aqueous methanol over 4 min. containing 0.1% TFA, 4 mL/min, monitoring at 220 nm). $^1$H NMR (500 MHz, $CDCl_3$) δ ppm 8.65 (1H, s), 8.45 (1H, s), 7.98 (1H, s), 3.48 (6H, s).

Intermediate 76: Preparation of N-(3-Amino-5-cyanophenyl)-N-(methylsulfonyl)methanesulfonamide

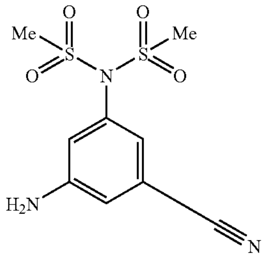

A suspension of Intermediate 76A (240 mg, 0.752 mmol) and 10% Pd/C (105 mg, 0.099 mmol) in MeOH (30 mL) and EtOAc (15 mL) was degassed and then stirred under a hydrogen atmosphere (balloon) for 1.5 hours. The catalyst was filtered off, and the filtrate was concentrated to give Intermediate 76 (215 mg, 99%). HPLC: Rt=0.847 min. (CHROMOLITH® column 4.6×50 mm eluting with 10-90% aqueous methanol over 4 min. containing 0.1% TFA, 4 mL/min., monitoring at 220 nm). $^1$H NMR (400 MHz, DMSO-$d_6$) δ ppm 8.93 (1H, s), 8.82 (1H, d, J=1.76 Hz), 7.43 (1H, t, J=1.63 Hz), 7.23 (1H, s), 7.14 (1H, t, J=2.01 Hz), 3.55 (6H, s). Intermediate 76 was used in the synthesis of Example 179.

Intermediate 77

3-Amino-5-(methylsulfonyl)benzoic acid

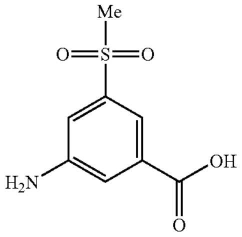

Intermediate 77A: Preparation of 3-(methylsulfonyl)-5-nitrobenzoic acid

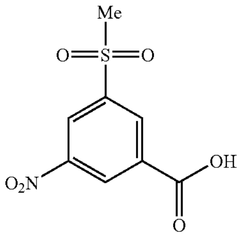

A mixture of 3-(methylsulfonyl)benzonitrile (1.2 g, 6.62 mmol) in 30% oleum (fuming $H_2SO_4$, 6 mL) was cooled to 0° C., and fuming $HNO_3$ acid (5 mL) was added dropwise. The resulting mixture was heated at 70° C. for 30 min. The reaction mixture was poured over ice water. The solid was collected by filtration, rinsed with water, and dried to give Intermediate 77A (832 mg, 51%) as a yellow solid. HPLC: Rt=1.088 min. (CHROMOLITH® column 4.6x50 mm eluting with 10-90% aqueous methanol over 4 min. containing 0.1% TFA, 4 mL/min., monitoring at 220 nm). $^1$H NMR (500 MHz, DMSO-$d_6$) δ ppm 14.24 (1H, br. s.), 8.85 (1H, s), 8.82 (1H, s), 8.84 (1H, d, J=11.55 Hz), 8.73 (1H, s), 3.41 (3H, s).

Intermediate 77: Preparation of 3-amino-5-(methylsulfonyl)benzoic acid

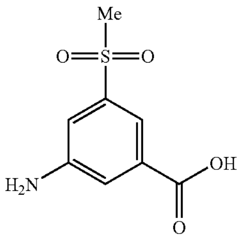

Intermediate 77 was prepared from Intermediate 77A following hydrogenation conditions employed in the preparation of Intermediate 70. HPLC: Rt=0.465 min. (CHROMOLITH® column 4.6x50 mm eluting with 10-90% aqueous methanol over 4 min. containing 0.1% TFA, 4 mL/min., monitoring at 220 nm). MS (ES): m/z=216 $[M+H]^+$. Intermediate 77 was used in the synthesis of Example 188.

Intermediate 78

N-(5-Amino-2-ethylphenyl)methanesulfonamide

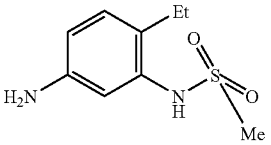

Intermediate 78A: Preparation of N-(2-ethyl-5-nitrophenyl)methanesulfonamide

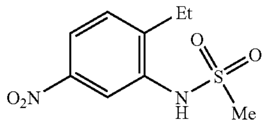

To a solution of 2-ethyl-5-nitroaniline (200 mg, 1.20 mmol) in DCM (5 mL) was added pyridine (0.195 mL, 2.41 mmol) and methanesulfonyl chloride (0.11 mL, 1.44 mmol). The reaction mixture was stirred at room temperature overnight. The mixture was diluted with DCM, washed with water and brine and dried to give Intermediate 78A (290 mg, 99%) as a yellow solid. $^1$H NMR (400 MHz, $CDCl_3$) δ ppm 8.35 (1H, d, J=2.26 Hz), 8.04 (1H, dd, J=8.53, 2.26 Hz), 7.44 (1H, d, J=8.53 Hz), 6.59 (1H, br. s.), 3.15 (3H, s), 2.76 (2H, q, J=7.53 Hz), 1.32 (3H, t, J=7.53 Hz).

Intermediate 78: Preparation of N-(5-amino-2-ethylphenyl)methanesulfonamide

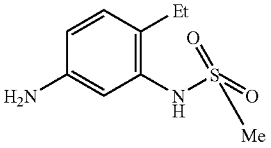

Intermediate 78 was prepared from Intermediate 78A following hydrogenation conditions employed in the preparation of Intermediate 70. HPLC: Rt=0.230 min. (CHROMOLITH® column 4.6x50 mm eluting with 10-90% aqueous methanol over 4 min. containing 0.1% TFA, 4 mL/min., monitoring at 220 nm). MS (ES): m/z=215 $[M+H]^+$. Intermediate 78 was used in the synthesis of Example 235.

Intermediate 79

N-(5-Amino-4-chloro-2-methylphenyl)methane-sulfonamide

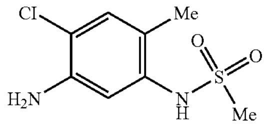

Intermediate 79A: Preparation of N-(4-chloro-2-methyl-5-nitrophenyl)methanesulfonamide

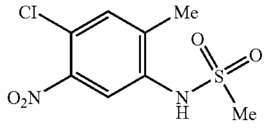

Intermediate 79A was prepared from 4-chloro-2-methyl-5-nitroaniline following the procedure employed in the preparation of Intermediate 78A. HPLC: Rt=1.618 min. (CHROMOLITH® column 4.6×50 mm eluting with 10-90% aqueous methanol over 4 min. containing 0.1% TFA, 4 mL/min., monitoring at 220 nm). MS (ES): m/z=265 $[M+H]^+$.

Intermediate 79: Preparation of N-(5-amino-4-chloro-2-methylphenyl)methanesulfonamide

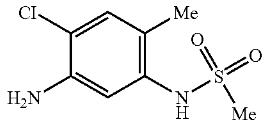

A mixture of Intermediate 79A (175 mg, 0.66 mmol), zinc (432 mg, 6.61 mmol), ammonium chloride (354 mg, 6.61 mmol) in ethanol (10 mL) and water (5.0 mL) was heated to reflux for 30 min. The reaction mixture was concentrated, suspended in ethyl acetate and filtered. The filtrate was washed with water, aqueous $NaHCO_3$ and brine, dried over $MgSO_4$ and concentrated to give Intermediate 79 (149 mg, 96%) as a white solid. HPLC: Rt=0.453 min. (CHROMOLITH® column 4.6×50 mm eluting with 10-90% aqueous methanol over 4 min. containing 0.1% TFA, 4 mL/min., monitoring at 220 nm). MS (ES): m/z=235 $[M+H]^+$. Intermediate 79 was used in the synthesis of Example 243.

Intermediate 80

2-(5-Amino-2-methylphenyl)acetic acid

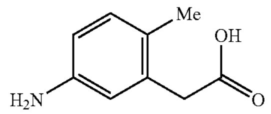

Intermediate 80A: Preparation of 2-(2-methyl-5-nitrophenyl)acetic acid

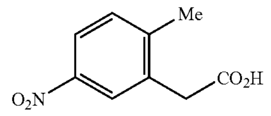

A solution of 2-o-tolylacetic acid (3.54 g, 23.6 mmol) in DCM (12 mL) was added to a pre-cooled mixture of concentrated sulfuric acid (10 mL, 188 mmol) and 90% nitric acid (1 mL, 22.4 mmol) at −20° C. The reaction mixture was stirred at −20° C. for 30 minutes, then slowly warmed to room temperature and stirred overnight. The reaction mixture was poured into ice-water. The white solid was collected by filtration, rinsed with water, and concentrated. The solid was triturated with ether and filtered to obtain Intermediate 80A (2.4 g, 42%) as a white solid. $^1H$ NMR (400 MHz, DMSO-$d_6$) δ ppm 12.62 (1H, br. s.), 8.13 (1H, d, J=2.51 Hz), 8.04 (1H, dd, J=8.28, 2.51 Hz), 7.47 (1H, d, J=8.53 Hz), 3.80 (2H, s), 2.34 (3H, s).

Intermediate 80: Preparation of 2-(5-amino-2-methylphenyl)acetic acid

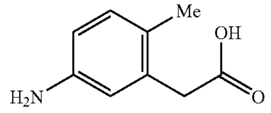

Intermediate 80 was prepared from Intermediate 80A following the hydrogenation conditions employed in the preparation of Intermediate 70. HPLC: Rt=0.705 min. (CHROMOLITH® column 4.6×50 mm eluting with 10-90% aqueous methanol over 4 min. containing 0.1% TFA, 4 mL/min., monitoring at 220 nm). MS (ES): m/z=166 $[M+H]^+$. Intermediate 80 was used in the synthesis of Example 224.

Intermediate 81

4-(4-Methylpiperazin-1-yl)benzene-1,3-diamine

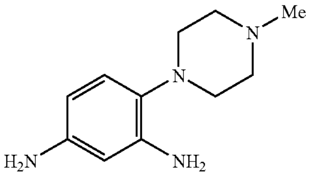

Intermediate 81A: 1-(2,4-Dinitrophenyl)-4-methylpiperazine

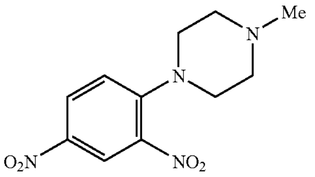

To 1-fluoro-2,4-dinitrobenzene (1 g, 5.37 mmol) was added 1-methylpiperazine (1.615 g, 16.12 mmol) slowly. Dilute aqueous $NaHCO_3$ was added, and the mixture was extracted with EtOAc. The combined extracts were dried, concentrated and purified by ISCO silica gel chromatography (24 g, stepwise gradient from DCM to 10% MeOH/DCM) to give Intermediate 81 (1.4 g, 98%) as a yellow oil. HPLC: Rt=1.032 min. (CHROMOLITH® column 4.6×50 mm eluting with 10-90% aqueous methanol over 4 min. containing 0.1% TFA, 4 mL/min., monitoring at 220 nm). MS (ES): m/z=267 $[M+H]^+$.

Intermediate 81: 4-(4-Methylpiperazin-1-yl)benzene-1,3-diamine

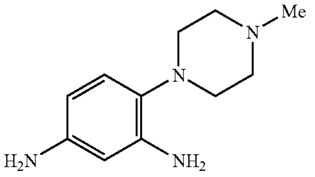

Compound 81 was prepared from 81A in a similar way as Intermediate 70. HPLC: Rt=0.228 min. (CHROMOLITH® column 4.6×50 mm eluting with 10-90% aqueous methanol over 4 min. containing 0.1% TFA, 4 mL/min., monitoring at 220 nm). MS (ES): m/z=207 $[M+H]^+$. Intermediate 81 was used in the synthesis of Examples 92 and 94.

Example 1

N-(5-((3-Cyano-8-(cyclopropylamino)imidazo[1,2-b]pyridazin-6-yl)amino)-2-methylphenyl)acetamide

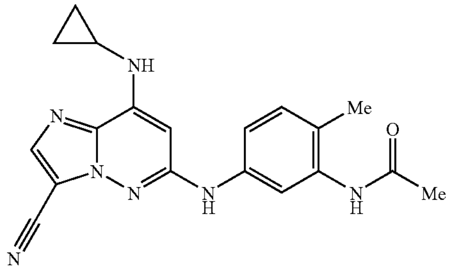

1A: Preparation of 4-bromo-6-chloropyridazin-3-amine

1A

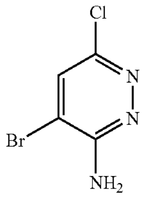

To a 250 mL round-bottomed flask was added 6-chloropyridazin-3-amine (3.92 g, 30.3 mmol), sodium bicarbonate (5.08 g, 60.5 mmol) and ethanol (20 mL). To the resulting solution, bromine (1.559 mL, 30.3 mmol) was added dropwise. The resulting mixture was stirred at room temperature for 16 hours. The solution was filtered and then concentrated in vacuo. The residue was dissolved in water, and the product extracted with ethyl acetate (3 times). The organic layers were combined, dried over anhydrous sodium sulfate and concentrated in vacuo to give 1A (4.5 g, 71.3% yield). HPLC: Rt=1.25 min (Waters Sunfire C18 column (4.6×50 mm). 10-90% aqueous methanol containing 0.1% TFA, 4 min gradient, flow rate=4 mL/min, detection at 254 nm). MS (ES): m/z=207.88 $[M+H]^+$.

1B: Preparation of ethyl 2-chloro-3-oxopropanoate

1B

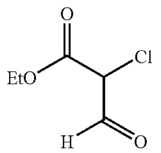

To a flask was added sodium (4.45 g, 194 mmol) and ethanol (56.5 mL, 968 mmol) and the mixture was stirred at room temperature for 4 hours until all of the metal had dissolved. Diethyl ether (100 mL) was added, followed by the slow addition of ethyl formate (17.2 mL, 213 mmol) and ethyl chloroacetate (22.79 mL, 213 mmol) as a solution in diethyl ether (100 mL). The reaction solution was stirred at room temperature for 16 hours. The resulting precipitate that formed was filtered and washed with ether, and dissolved in water. The aqueous layer was acidified with HCl (1N) to pH 4, and the product was extracted with diethyl ether (3 times). The organic layers were combined, dried over anhydrous sodium sulfate and concentrated to give 1B (4.5 g, 15.4% yield).

1C: Preparation of ethyl 8-bromo-6-chloroimidazo[1,2-b]pyridazine-3-carboxylate and ethyl 6,8-dichloroimidazo[1,2-b]pyridazine-3-carboxylate 1C-1

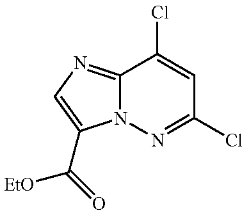

and 1C-2

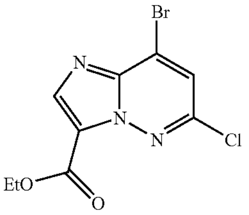

To a 250 mL round-bottomed flask was added 1B (4.33 g, 28.8 mmol) and 1A (5 g, 24.0 mmol). The solution was heated to 90° C. for 16 hours. The solution was quenched with ethyl acetate and washed with water. The organic layer was dried over anhydrous sodium sulfate and concentrated in vacuo. The crude was purified by flash chromatography ($SiO_2$, 10% ethyl acetate/DCM; 80 g column) to give a mixture of 1C-1 and 1C-2 (2.1 g, 29% yield).

1C-1: HPLC: Rt=2.54 min (Waters Sunfire C18 column (4.6×50 mm). 10-90% aqueous methanol containing 0.1% TFA, 4 min gradient, flow rate=4 mL/min, detection at 254 nm). MS (ES): m/z=256.96 $[M+H]^+$.

1C-2: HPLC: Rt=2.63 min (Waters Sunfire C18 column (4.6×50 mm). 10-90% aqueous methanol containing 0.1% TFA, 4 min gradient, flow rate=4 mL/min, detection at 254 nm). MS (ES): m/z=303.92 $[M+H]^+$.

1D: Preparation of 8-bromo-6-chloroimidazo[1,2-b]pyridazine-3-carboxylic acid and 6,8-dichloroimidazo[1,2-b]pyridazine-3-carboxylic acid 1D-1

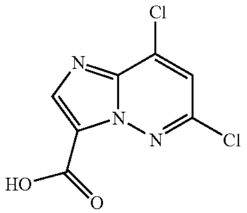

and

-continued 1D-2

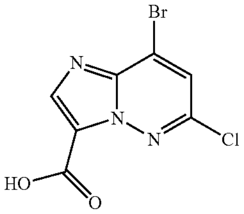

To a vial was added the mixture of 1C (300 mg, 0.98 mmol) in methanol (10 mL). To this mixture was added 6 N HCl (1.64 mL, 9.85 mmol). The solution was heated at 90° C. for 16 hours. The solution was diluted with ethyl acetate, and the product extracted with saturated aqueous sodium bicarbonate solution. The combined aqueous layer was acidified with HCl (1N) to pH 4 and extracted with ethyl acetate (3 times). The ethyl acetate extracts were combined, dried over anhydrous sodium sulfate and concentrated in vacuo to give a mixture of 1D-1 and 1D-2 (150 mg, 55%).

1D-1: HPLC: Rt=1.67 min (Waters Sunfire C18 column (4.6×50 mm). 10-90% aqueous methanol containing 0.1% TFA, 4 min gradient, flow rate=4 mL/min, detection at 254 nm). MS (ES): m/z=231.87 $[M+H]^+$.

1D-2: HPLC: Rt=1.81 min (Waters Sunfire C18 column (4.6×50 mm). 10-90% aqueous methanol containing 0.1% TFA, 4 min gradient, flow rate=4 mL/min, detection at 254 nm). MS (ES): m/z=275.79 $[M+H]^+$.

1E: Preparation of 8-bromo-6-chloroimidazo[1,2-b]pyridazine-3-carboxamide and 6,8-dichloroimidazo[1,2-b]pyridazine-3-carboxamide 1E-1

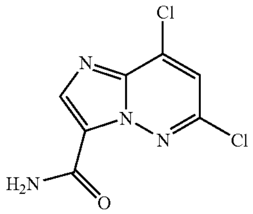

and 1E-2

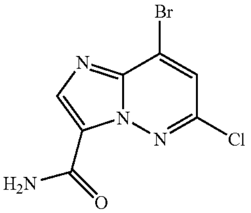

A 1 L flask was charged with a mixture of 1D-1 and 1D-2 (10 g, 36.2 mmol) and DCM (100 mL). DMF (0.280 mL, 3.62 mmol) was added, followed by the dropwise addition of oxalyl chloride (72.3 mL, 145 mmol). The resulting reaction was heated to 45° C. for 2 hours and then concentrated to dryness. The crude acid chloride was taken up in 1,4-dioxane (100 mL) and treated with ammonia (0.5 N ammonia in THF) in THF (72.3 mL, 36.2 mmol). The reaction mixture was stirred at room temperature for 1 hour, and more ammonia in THF (72.3 mL, 36.2 mmol) was added. The resulting suspension was stirred for 1 hour and then concentrated to dryness. The crude material was suspended in water (100 mL) and stirred for 2 hours. The solid was collected by filtration, and dried under reduced pressure to afford a mixture of 1E-1 and 1E-2 (8.7 g, 87%).

1E-1: HPLC: Rt=2.08 min. (YMC S5 ODS 4.6×50 mm, 10-90% aqueous methanol containing 0.2% $H_3PO_4$, 4 min gradient, monitored at 220 nm); MS (ES): m/z=231 $[M+H]^+$.

1E-2: HPLC: Rt=2.20 min. (YMC S5 ODS 4.6×50 mm, 10-90% aqueous methanol containing 0.2% $H_3PO_4$, 4 min gradient, monitored at 220 nm); MS (ES): m/z=275 $[M+H]^+$.

1F: Preparation of 8-bromo-6-chloroimidazo[1,2-b]pyridazine-3-carbonitrile and 6,8-dichloroimidazo[1,2-b]pyridazine-3-carbonitrile 1F-1

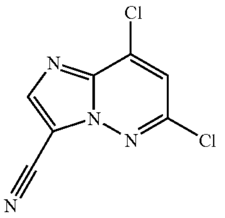

and 1F-2

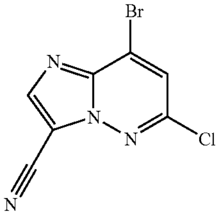

A suspension of 1D-1 and 1D-2 (8.7 g, 31.6 mmol) in $CHCl_3$ (500 mL) was treated with $POCl_3$ (35.3 mL, 380 mmol) and heated to reflux for 3 days. The resulting solution was cooled to room temperature and poured into cold saturated aqueous $NaHCO_3$ (1 L). Solid $Na_2CO_3$ was added until neutral pH was achieved. The resulting layers were separated and the aqueous layer was extracted with $CHCl_3$ (1 L). The combined organics were dried with $Na_2SO_4$, filtered and concentrated to dryness to afford a mixture of 1F-1 and 1F-2 as a yellow powder (5.6 g, 68.9%).

1F-1: HPLC: Rt=2.53 min. (YMC S5 ODS 4.6×50 mm, 10-90% aqueous methanol containing 0.2% $H_3PO_4$, 4 min gradient, monitored at 220 nm); MS (ES): m/z=213 $[M+H]^+$.

1F-2: HPLC: Rt=2.67 min. (YMC S5 ODS 4.6×50 mm, 10-90% aqueous methanol containing 0.2% $H_3PO_4$, 4 min gradient, monitored at 220 nm); MS (ES): m/z=258.9 $[M+H]^+$.

1G: Preparation of 6-chloro-8-(cyclopropyl(4-methoxybenzyl)amino) imidazo[1,2-b]pyridazine-3-carbonitrile

1G

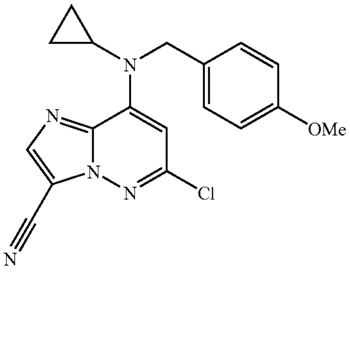

To a solution of 1F-1 and 1F-2 and N-(4-methoxybenzyl) cyclopropanamine (1, 4.13 g, 23.30 mmol) in THF (155 mL) at room temperature was added DIEA (4.1 mL, 23.3 mmol). The resulting solution was heated to reflux for 5 hours, and then cooled to room temperature and concentrated. The crude solid was dried under reduced pressure overnight. The crude solid was stirred in MeOH for 1 hour at room temperature, filtered, and washed with MeOH. The solid was dried under reduced pressure to afford 1G (5.17 g, 14.03 mmol, 90% yield) as an off-white solid. HPLC: Rt=4.26 min (YMC S5 ODS 4.6×50 mm, 10-90% aqueous methanol containing 0.2% $H_3PO_4$, 4 min gradient, monitored at 220 nm). MS (ES): m/z=354.0 $[M+H]^+$.

Example 1

Preparation of N-(5-((3-cyano-8-(cyclopropylamino)imidazo[1,2-b]pyridazin-6-yl)amino)-2-methylphenyl)acetamide

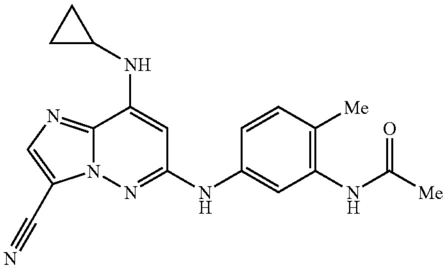

DMA (1.5 mL) was placed in a 1-dram vial with a teflon-lined septum cap, and the solvent was degassed by bubbling argon through it for 10 minutes. 1G (0.15 g, 0.42 mmol), N-(5-amino-2-methylphenyl)acetamide (0.104 g, 0.636 mmol), copper(I) iodide (0.040 g, 0.212 mmol), xantphos (0.049 g, 0.085 mmol), and $Pd_2(dba)_3$ (0.039 g, 0.042 mmol) were added in one portion, and the suspension was pump/purged three times with argon. The vessel was then heated to 125° C. for 45 min. and then cooled to room temperature. The solids were removed via filtration through CELITE®, washing with THF. The filtrate was then diluted with water and EtOAc. The layers were separated, and the aqueous phase extracted EtOAc (3×10 mL). The organics were combined, washed with water and brine, and dried over anhydrous sodium sulfate. Filtration and concentration afforded a tan solid, which was triturated in DCM and cooled to 0° C. The resulting precipitate was filtered and washed with cold DCM. The filtrate was dissolved in a small amount of DCM and purified by flash chromatography ($SiO_2$, 0% EtOAc/DCM to 60% EtOAc/DCM, 24 g column, 30 mL/min, 20 min gradient, monitoring at 254 nm). The appropriate fractions were pooled and concentrated under reduced pressure. The material isolated from chromatography, and the solid were combined, suspended in DCM (3 mL) and treated with triethylsilane (0.68 mL, 4.24 mmol) and TFA (0.3 mL). After 30 minutes, the suspension was cooled in an ice bath and filtered. The solid was suspended in EtOAc (20 mL) and stirred with saturated aqueous sodium bicarbonate (15 mL). After 30 minutes, the solid was isolated via filtration, washed with water and EtOAc, and dried overnight in vacuo to afford Example 1 (0.154 g, 0.422 mmol, 100%) as a white solid. HPLC: Rt=3.496 min (YMC S5 ODS 4.6×50 mm, 10-90% aqueous methanol containing 0.2% $H_3PO_4$, 4 min gradient, monitored at 220 nm). MS (ES): m/z=362.0 $[M+H]^+$. $^1$H NMR (400 MHz, DMSO-$d_6$) δ ppm 9.24 (1H, s), 9.21 (1H, s), 8.10 (1H, s), 7.81 (1H, s), 7.64 (2H, s), 7.11 (1H, d, J=8.03 Hz), 6.25 (1H, s), 2.52-2.55 (1H, m), 2.15 (3H, s), 2.06 (3H, s), 0.75-0.82 (2H, m), 0.61-0.68 (2H, m).

Example 2

N-(6-(3-Cyano-8-(cyclopropylamino)imidazo[1,2-b]pyridazin-6-ylamino)pyridin-2-yl)acetamide

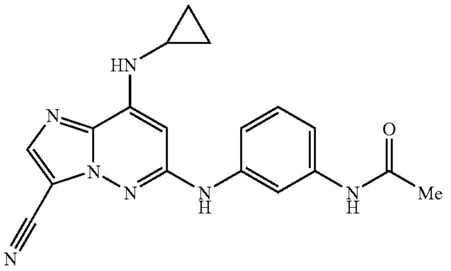

2A: Preparation of 6-(6-aminopyridin-2-ylamino)-8-(cyclopropyl (4-methoxybenzyl)amino)imidazo[1,2-b]pyridazine-3-carbonitrile

2A

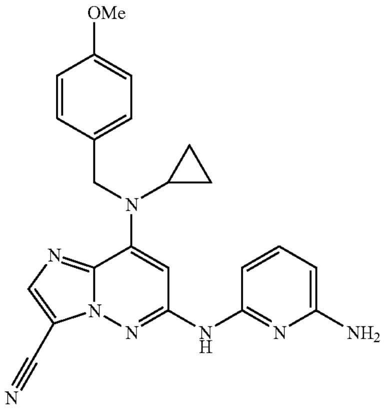

A sealed tube was charged with DME (1.5 mL) and purged with argon. The vessel was then charged with 1G (0.050 g, 0.14 mmol), pyridine-2,6-diamine (0.039 g, 0.35 mmol), cesium carbonate (0.184 g, 0.57 mmol), copper(I) iodide (0.013 g, 0.071 mmol), Xantphos (0.016 g, 0.028 mmol), and $Pd_2(dba)_3$ (0.013 g, 0.014 mmol), in one portion. The resulting suspension was pump/purged with argon three times. The cap was placed on the vessel, and the suspension heated to 125° C. overnight. The solids were filtered off, and the filtrate was concentrated in vacuo. The crude product was dissolved in a small amount of DCM and charged to a 24 g silica gel cartridge which was eluted at 30 mL/min with a 20 min gradient from 100% DCM to 60% EtOAc/DCM, monitoring at 254 nm, affording 2A (0.014 g, 23% yield) as a tan solid. HPLC: Rt=3.62 min (YMC S5 ODS 4.6×50 mm, 10-90% aqueous methanol containing 0.2% $H_3PO_4$, 4 min gradient, monitored at 220 nm). MS (ES): m/z=427.1 $[M+H]^+$. $^1$H NMR (400 MHz, DMSO-$d_6$) δ ppm 8.19-8.28 (1 H, m), 7.41

(1H, s), 7.03-7.12 (3H, m), 6.96-7.03 (1H, m), 6.79-6.86 (2H, m), 6.13 (1H, s), 5.49 (2H, s), 3.68 (3H, s), 3.49-3.65 (3H, m), 2.45 (1H, d, J=3.78 Hz), 0.91-0.98 (2H, m), 0.74 (2H, m).

Example 2

Preparation of N-(6-(3-cyano-8-(cyclopropylamino)imidazo[1,2-b]pyridazin-6-ylamino)pyridin-2-yl)acetamide

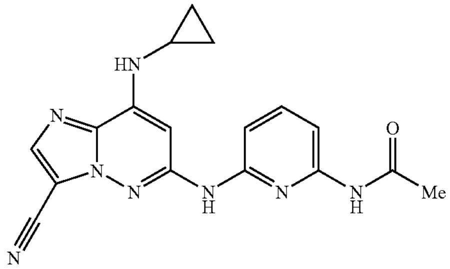

2A (0.014 g, 0.033 mmol) was suspended in acetic acid (3 mL) at room temperature, and acetic anhydride (3.72 μL, 0.039 mmol) was added. The resulting clear yellow solution was refluxed for 30 min. The solution was cooled to room temperature, and water was added slowly until a precipitate formed. The resulting solid was filtered and washed with water, then dissolved in THF and azeotroped three times with toluene to remove residual AcOH/$H_2O$. The resulting intermediate was dried in vacuo for 1 hour, and then dissolved in TFA (0.4 mL) and triethylsilane (0.021 mL, 0.13 mmol) was added immediately. The mixture was stirred for 30 min. at room temperature. The volatiles were removed via a stream of nitrogen, and the solid was dissolved in DMF and purified via preparatory HPLC using a YMC ODS C-18 column (30×250 mm), 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 30 min (total run time: 37 min), flow rate 25 mL/min, monitoring at 254 nm. Rt=27.582 min. Fractions were concentrated and lyophilized overnight, affording Example 2 (0.005 g, 32% yield) as a white solid. HPLC: Rt=3.14 min (YMC S5 ODS 4.6×50 mm, 10-90% aqueous methanol containing 0.2% $H_3PO_4$, 4 min gradient, monitored at 220 nm). MS (ES): m/z=349.1 $[M+H]^+$. $^1$H NMR (400 MHz, DMSO-$d_6$) δ ppm 10.00 (1H, s), 9.65 (1H, s), 8.16 (1H, s), 7.96 (1H, d, J=1.51 Hz), 7.68 (1H, d, J=7.81 Hz), 7.58 (2H, d, J=8.06 Hz), 6.93 (1H, s), 2.55-2.64 (1H, m), 2.10 (3H, s), 0.74-0.82 (2H, m), 0.60-0.70 (2H, m).

Example 3

N-(3-(3-Cyano-8-(cyclopropylamino)imidazo[1,2-b]pyridazin-6-ylamino)phenyl)methanesulfonamide

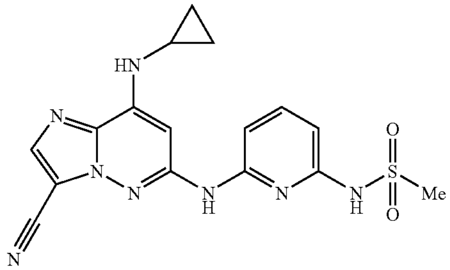

3A: Preparation of 6-(3-aminophenylamino)-8-(cyclopropyl (4-methoxybenzyl)amino) imidazo[1,2-b] pyridazine-3-carbonitrile

3A

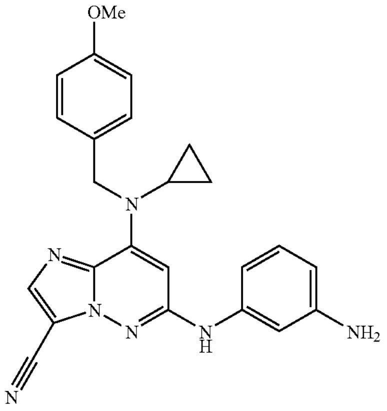

A 1-dram vial was charged with 1-methoxy-2-(2-methoxyethoxy)ethane (1.5 mL) and purged for 10 min with argon. The vessel was then charged with 1G (0.100 g, 0.28 mmol), benzene-1,3-diamine (0.037 g, 0.34 mmol), cesium carbonate (0.368 g, 1.13 mmol), copper(I) iodide (0.027 g, 0.14 mmol), Xantphos (0.033 g, 0.057 mmol), and $Pd_2(dba)_3$ (0.026 g, 0.028 mmol) in one portion. The resulting suspension was heated to 125° C. overnight. The suspension was filtered through a medium-porosity frit, and the solid was washed with THF. The filtrate was diluted with EtOAc and water, and the layers were separated. The aqueous phase was extracted three times with EtOAc. The organics were then combined, dried over anhydrous sodium sulfate, filtered and concentrated in vacuo. The crude residue was dissolved in DMF and purified via preparatory HPLC using a YMC ODS C-18 column (30×250 mm), 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 60 min, flow rate 25 mL/min, monitoring at 220 nm. Rt=53.697 min. The appropriate fractions were concentrated and lyophilized to dryness, affording 3A (11 mg, 9% yield). HPLC: Rt=3.68 min (YMC S5 ODS 4.6×50 mm, 10-90% aqueous methanol containing 0.2% $H_3PO_4$, 4 min gradient, monitored at 220 nm). MS (ES): m/z=426.0 $[M+H]^+$.

Example 3

Preparation of N-(3-(3-cyano-8-(cyclopropylamino) imidazo[1,2-b]pyridazin-6-ylamino)phenyl)methanesulfonamide

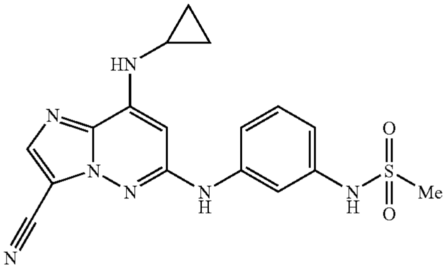

To a solution of 3A (0.011 g, 0.026 mmol) in THF (0.5 mL) at 0° C. was added pyridine (6.27 μL, 0.078 mmol) and methanesulfonyl chloride (2.2 μL, 0.028 mmol). The reaction was stirred overnight at room temperature. The reaction mixture was diluted with water and EtOAc, and the aqueous layer was extracted twice with EtOAc. The organic extracts were combined, dried over anhydrous sodium sulfate, filtered, and concentrated in vacuo. The crude material was dissolved in TFA (0.5 mL) and triethylsilane (0.041 mL, 0.26 mmol) was added. The reaction was stirred for 30 min. at room temperature. The volatiles were removed under a stream of nitrogen, and the crude material was dissolved in DCM/EtOAc (1:1) and charged to a 12 g silica gel cartridge which was eluted at 30 mL/min with a 15 min gradient from 100% DCM to 40% EtOAc/DCM. Example 3 was isolated as a light yellow solid (5 mg, 52% yield). HPLC: Rt=3.52 min (YMC S5 ODS 4.6×50 mm, 10-90% aqueous methanol containing 0.2% $H_3PO_4$, 4 min gradient, monitored at 220 nm). MS (ES): m/z=383.9 $[M+H]^+$. $^1H$ NMR (400 MHz, DMSO-$d_6$) δ ppm 9.71 (1H, s), 9.35 (1H, s), 8.12 (1H, s), 7.86 (1H, d, J=1.76 Hz), 7.69 (1H, dd, J=8.18, 1.38 Hz), 7.33 (1H, t, J=2.01 Hz), 7.24 (1H, t, J=8.06 Hz), 6.77 (1H, dd, J=7.55, 1.76 Hz), 6.26 (1H, s), 3.00 (3H, s), 2.51-2.56 (1H, m), 0.75-0.83 (2H, m), 0.62-0.68 (2H, m).

Example 4

8-(Cyclobutylamino)-6-((4-((2-(dimethylamino) ethyl)amino)-3-(4H-1,2,4-triazol-4-yl)phenyl)amino) imidazo[1,2-b]pyridazine-3-carbonitrile

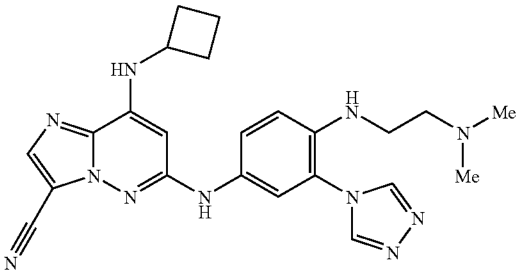

4A: Preparation of N-(4-methoxybenzyl)cyclobutanamine

4A

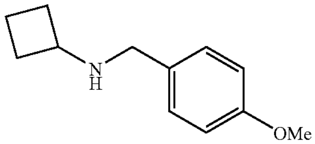

4-Methoxybenzaldehyde (5.63 mL, 46.4 mmol) and cyclobutanamine (3.3 g, 46.4 mmol) in dichloromethane (40 mL) were stirred at room temperature. After 45 min., magnesium perchlorate (0.231 g, 2.320 mmol) was added, and the reaction mixture was stirred at room temperature. After 16 hours, the reaction mixture was treated with $Na_2SO_4$ (2 g) and stirred at room temperature for 2 hours, filtered and concentrated to dryness. The reaction mixture was dissolved in methanol (40 mL), cooled to 0° C., and $NaBH_4$ (1.6 g, 69.6 mmol) was added. After 15 min., the reaction mixture was warmed to room temperature. After 2 hours, the reaction mixture was diluted with 1N NaOH (100 mL) and extracted with ethyl acetate (3×100 mL). The combined organic layers were dried over $Na_2SO_4$, filtered and concentrated to isolate 4A (8.5 g, 82% yield) as a clear oil. HPLC: Rt=0.82 min (PHENOMENEX® Luna 5 micron C18 4.6×30 mm, 10-90% aqueous methanol containing 0.1% TFA, 2 min gradient, flow rate=5 mL/min, detection at 254 nm). MS (ES): m/z=192.6 $[M+H]^+$.

4B: Preparation of 6-chloro-8-(cyclobutyl(4-methoxybenzyl)amino) imidazo[1,2-b]pyridazine-3-carbonitrile

4B

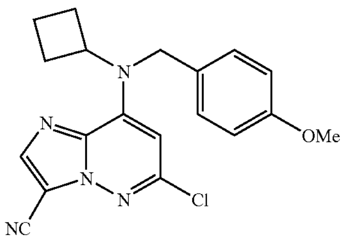

A mixture of 1F (500 mg, 1.94 mmol), 4A (464 mg, 2.43 mmol), and DIEA (0.509 mL, 2.91 mmol) in DMF (0.5 mL) was heated to 80° C. After 1 hour, the reaction mixture was concentrated to dryness, and triturated with methanol to isolate 4B (582 mg, 77% yield) as a yellow solid. HPLC: Rt=2.02 min (PHENOMENEX® Luna 5 micron C18 4.6×30 mm, 10-90% aqueous methanol containing 0.1% TFA, 2 min gradient, flow rate=5 mL/min, detection at 254 nm). MS (ES): m/z=367.98 $[M+H]^+$.

Example 4

Preparation of 8-(cyclobutylamino)-6-((4-((2-(dimethylamino)ethyl)amino)-3-(4H-1,2,4-triazol-4-yl) phenyl)amino)imidazo[1,2-b]pyridazine-3-carbonitrile

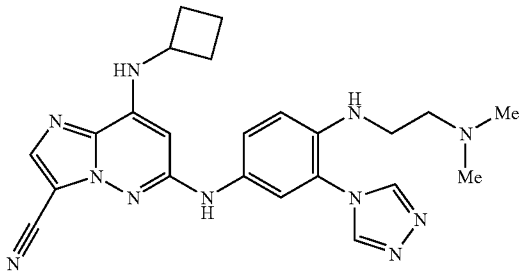

A suspension of 4B (79 mg, 0.22 mmol), Intermediate 36 (50 mg, 0.20 mmol) and di-tert-butyl (1-methyl-2,2-diphenylcyclopropyl)phosphine (14.3 mg, 0.041 mmol) in toluene (1 mL) were purged with nitrogen, and allylpalladium (II) chloride dimer (7.4 mg, 0.020 mmol) and sodium tert-butoxide (23.4 mg, 0.244 mmol) were added. The reaction mixture was heated at 100° C. for 45 min. The reaction mixture was concentrated, and then taken up in water (50 mL) and extracted with DCM (3×25 mL), dried over $Na_2SO_4$, filtered and concentrated. The reaction mixture was dissolved in dichloroethane (4 mL) and treated with triethylsilane (0.5 ml) and TFA (1 mL). After 15 min., the reaction mixture was concentrated, and then purified using reverse phase HPLC and lyophilized from 1N HCl to isolate Example 4 (8 mg, 7.1% yield) as a yellow solid. HPLC: Rt=1.38 min (PHENOMENEX® Luna 5 micron C18 4.6×30 mm, 10-90% aqueous methanol containing 0.1% TFA, 2 min gradient, flow rate=5 mL/min, detection at 254 nm). MS (ES): m/z=458.17 $[M+H]^+$. $^1H$ NMR (500 MHz, $CD_3OD$) δ ppm 9.77 (2H, s), 8.26 (1H, d, J=2.75 Hz), 8.10 (1H, s), 7.56 (1H, dd, J=8.94, 2.52 Hz), 7.10 (1H, d, J=8.71 Hz), 5.91 (1H, s), 4.11 (1H, t, J=7.79 Hz), 3.58 (2H, t, J=5.96 Hz), 3.41 (2H, t, J=5.96 Hz), 2.87-3.01 (6H, m), 2.39-2.65 (2H, m), 2.02-2.21 (2H, m), 1.84-2.00 (2H, m).

Example 5

N-(5-(3-Cyano-8-(5-methoxypyridin-2-ylamino) imidazo[1,2-b]pyridazin-6-ylamino)-2-methylphenyl)acetamide

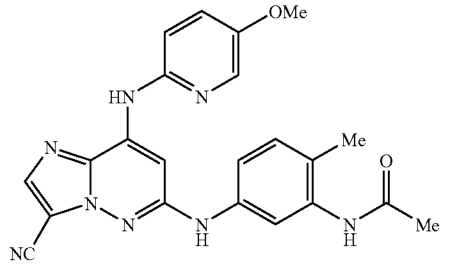

5A: Preparation of 5-methoxy-N-(4-methoxybenzyl)pyridine-2-amine

5A

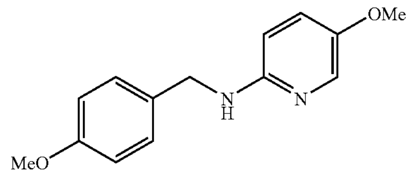

5A was prepared from 4-methoxybenzaldehyde and 5-methoxypyridin-2-amine following the procedure employed for the preparation of 4A. HPLC: Rt=1.30 min (PHENOMENEX® Luna C18 4.6×30 mm 3 u, A10-90% aqueous methanol containing 0.1% TFA in 2 min; 4 mL/min flow). MS (ES): m/z=244.9 $[M+H]^+$.

5B: Preparation of 6-chloro-8-((5-methoxypyridin-2-yl)(4-methoxybenzyl)amino)imidazo[1,2-b]pyridazine-3-carbonitrile

5B

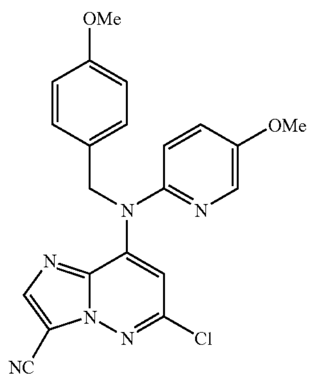

To a mixture of 1F (100 mg, 0.47 mmol) and 5A (138 mg, 0.56 mmol) in DMF (3 mL) was added KHMDS (1.13 mL, 0.5 molar solution) dropwise at 0° C. After 10 minutes, the reaction was quenched with saturated aqueous ammonia chloride, extracted with ethyl acetate (3×15 mL), dried over $Na_2SO_4$, filtered and concentrated. The resulting residue was dissolved in DCM and purified by silica chromatography (gradient=0% to 100%, hexanes to ethyl acetate in 12 min.) to give 5B (156 mg, 63.2% yield). HPLC: Rt=1.13 min (PHENOMENEX® Luna C18 4.6×30 mm 3 u, 10-90% aqueous methanol containing 0.1% TFA in 2 min; 4 mL/min flow). MS (ES): m/z=421.0 $[M+H]^+$.

5C: Preparation of N-(5-(3-cyano-8-((5-methoxypyridin-2-yl)(4-methoxybenzyl)amino)imidazo[1,2-b]pyridazin-6-ylamino)-2-methylphenyl)acetamide

5C

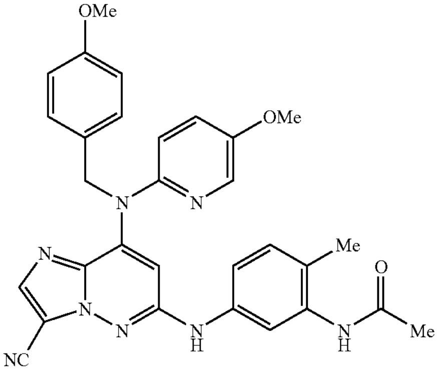

A mixture of 5B (60 mg, 0.14 mmol), N-(5-amino-2-methylphenyl)acetamide (46.8 mg, 0.29 mmol), $Pd_2(dba)_3$ (13.1 mg, 0.014 mmol), Xantphos (18.2 mg, 0.031 mmol), copper (I) iodide (13.6 mg, 0.071 mmol) and $Cs_2CO_3$ (186 mg, 0.57 mmol) in DMA (1 mL) was purged with nitrogen and heated at 125° C. After 1.5 hours, the reaction mixture was diluted with ethyl acetate, washed with 15% $NH_4OH$, dried over $Na_2SO_4$, and concentrated to dryness under reduced pressure. The resulting oil was purified by silica column chromatography (gradient=0%-100% hexanes to ethyl acetate in 12 min.) to isolate 5C (47.5 mg, 60.7% yield). HPLC: Rt=3.805 min (YMC S5 ODS 4.6×50 mm, 10-90% aqueous methanol containing 0.2% $H_3PO_4$, 4 min gradient, monitored at 220 nm). MS (ES): m/z=549.2 $[M+H]^+$.

Example 5

Preparation of N-(5-(3-cyano-8-(5-methoxypyridin-2-ylamino)imidazo[1,2-b]pyridazin-6-ylamino)-2-methylphenyl)acetamide

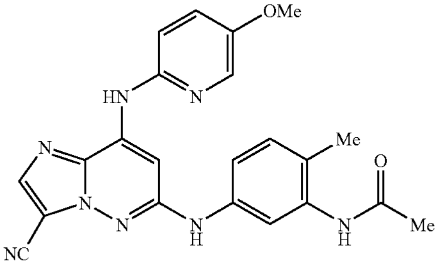

A solution of 5C (60 mg, 0.11 mmol) in DCM (0.5 mL) was treated with triethylsilane (0.03 mL, 0.19 mmol) followed by TFA (0.06 mL, 0.78 mmol). The reaction mixture was stirred at 45° C. for 1.5 hours, concentrated, purified with reverse phase HPLC, and lyophilized with 1.0 N HCl to yield Example 5 (21.9 mg, 37.1% yield). MS (ES): m/z=429.1 $[M+H]^+$. $^1$H NMR (400 MHz, DMSO-$d_6$) δ ppm 9.88 (1H, s), 9.42 (1H, s), 9.22 (1H, s), 8.19 (1H, s), 8.04 (1H, s), 8.02 (1H, dd, J=2.38, 1.13 Hz), 7.60-7.69 (2H, m), 7.44-7.47 (2H, m), 7.10 (1H, d, J=8.28 Hz), 3.80 (3H, s), 2.12 (3H, s), 2.03 (3H, s).

Example 6

N-(5-((8-(3-Azetidinylamino)-3-cyanoimidazo[1,2-b]pyridazin-6-yl)amino)-2-methylphenyl)acetamide

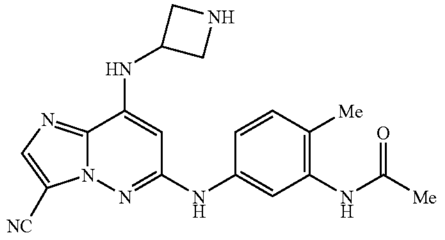

6A: Preparation of tert-butyl 3-(4-methoxybenzylamino)azetidine-1-carboxylate

6A

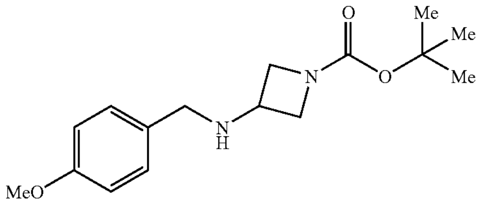

6A was prepared from 4-methoxybenzaldehyde and tert-butyl 3-aminoazetidine-1-carboxylate following the procedure employed for the preparation of 4A. HPLC: Rt=3.0 min (PHENOMENEX® Luna C18 4.6×30 mm 3 u, 10-90% aqueous methanol containing 0.1% TFA in 2 min; 4 mL/min flow). MS (ES): m/z=293.9 $[M+H]^+$.

6B: Preparation of tert-butyl 3-((6-chloro-3-cyanoimidazo[1,2-b]pyridazin-8-yl)(4-methoxybenzyl)amino)azetidine-1-carboxylate

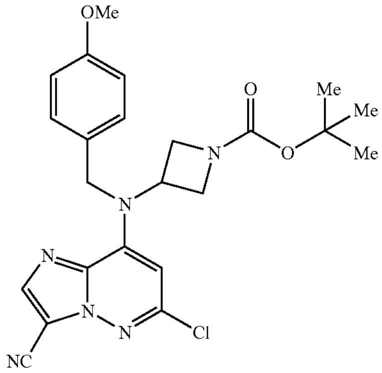

A solution of 1F (100 mg, 0.47 mmol) in THF (5 mL) was treated with 6A (274 mg, 0.94 mmol) and DIEA (0.246 mL, 1.41 mmol) and heated at 70° C. After 18 hours, the reaction mixture was diluted with water, extracted with ethyl acetate (3×15 mL), dried over $Na_2SO_4$, filtered and concentrated. The residue was purified by flash chromatography, silica column (12 g, gradient=12 min, 100% hexanes to 70% ethyl acetate/hexanes) to provide 6B (142.8 mg, 0.305 mmol, 64.9.0% yield) as a tan solid. HPLC: Rt=4.55 min (PHENOMENEX® Luna C18 4.6×30 mm 3 u, 10-90% aqueous methanol containing 0.1% TFA in 5 min; 4 mL/min flow). MS (ES): m/z=469.0 $[M+H]^+$.

Example 6

Preparation of N-(5-(8-(azetidin-3-ylamino-3-cyanoimidazo[1,2-b]pyridazin-6-ylamino)-2-methylphenyl)acetamide

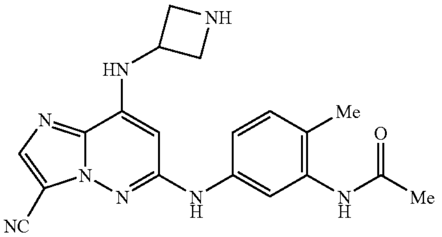

A mixture of 6B (50 mg, 0.11 mmol), N-(5-amino-2-methylphenyl)acetamide (35.0 mg, 0.213 mmol), $Pd_2(dba)_3$ (9.76 mg, 10.7 μmol), xantphos (13.6 mg, 0.023 mmol), copper (I) iodide (10.2 mg, 0.053 mmol) and $Cs_2CO_3$ (139 mg, 0.43 mmol) in DMA (1 mL) was purged with nitrogen and heated at 125° C. After 2 hours, the reaction mixture was diluted with ethyl acetate, washed with 15% $NH_4OH$, dried over $Na_2SO_4$, filtered and concentrated. The resulting oil was dissolved in DCM (1 mL), treated with $Et_3SiH$ (0.1 mL) and TFA (0.1 mL), and heated at 60° C. After 10 min., the reaction mixture was concentrated, purified by reverse phase HPLC, lyophilized with 1.0 N HCl to isolate Example 6 (18.0 mg, 37.6%). HPLC: Rt=9.610 min (YMC S5 ODS 4.6×50 mm, 10-90% aqueous methanol containing 0.2% $H_3PO_4$, 15 min gradient, monitored at 220 nm). MS (ES): m/z=377.1 $[M+H]^+$. $^1H$ NMR (500 MHz, DMSO-$d_6$) δ ppm 9.25 (1H, s), 9.24 (1H, s), 9.10 (1H, br. s.), 8.89 (1H, br. s.), 8.17 (1H, s), 7.57-7.63 (2H, m), 7.11 (1H, d), 5.91 (1H, s), 4.56 (1H, br. s.), 4.19-4.27 (2H, m), 4.09-4.18 (2H, m), 2.14 (3H, s), 2.05 (3H, s).

Example 7

N-(3-(3-Cyano-8-(phenylamino)imidazo[1,2-b]pyridazin-6-ylamino)phenyl)acetamide

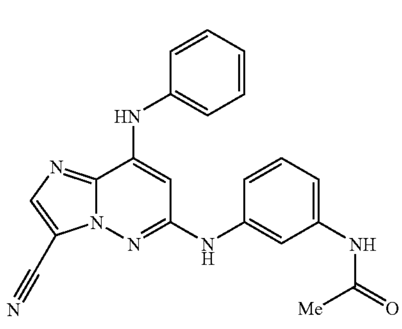

7A: Preparation of 6-chloro-8-((4-methoxybenzyl)(phenyl)amino)imidazo[1,2-b]pyridazine-3-carbonitrile

7A

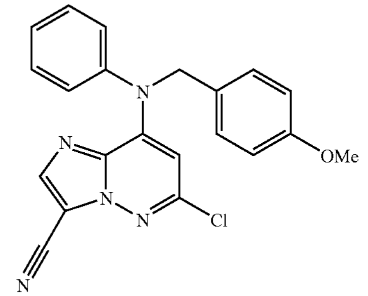

A solution of 1F (0.200 g, 0.94 mmol) and N-(4-methoxybenzyl)aniline (0.210 g, 0.99 mmol) in THF (9.4 mL) was cooled to 0° C. Potassium tert-butoxide (1.0 M solution, 1.03 mL, 1.03 mmol) was then added dropwise via syringe. The resulting solution was stirred for 10 min. at 0° C., and then warmed to room temperature. The reaction was quenched with water and diluted with EtOAc. The aqueous phase was extracted twice with EtOAc, and the organics were combined, dried over sodium sulfate, filtered, and concentrated. The crude product was dissolved in a small amount of DCM and charged to a 24 g silica gel flash chromatography ($SiO_2$) which was eluted at 30 mL/min. with a 20 min. gradient from 100% hexanes to 15% EtOAc/hexanes (monitoring at 254 nm). Concentration of the appropriate fractions afforded 7A (0.13 g, 33% yield) as a light brown solid. HPLC: Rt=4.5 min. (YMC S5 ODS 4.6×50 mm, 10-90% aqueous methanol containing 0.2% $H_3PO_4$, 4 min. gradient, monitored at 220 nm). MS (ES): m/z=390.0 $[M+H]^+$. $^1H$ NMR (400 MHz, DMSO-$d_6$) δ ppm 8.41 (1H, s), 7.45 (2H, t, J=7.68 Hz), 7.36 (1H, t, J=7.43 Hz), 7.22-7.30 (2H, m), 7.17 (2H, d, J=8.81 Hz), 6.77-6.84 (2H, m), 5.91 (1H, s), 5.78 (2H, s), 3.68 (3H, s).

Example 7

Preparation of N-(3-(3-cyano-8-(phenylamino)imidazo[1,2-b]pyridazin-6-ylamino)phenyl)acetamide

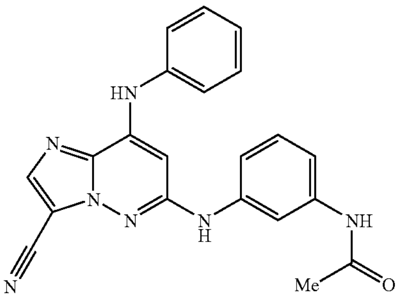

A sealed tube was charged with DME (1.5 mL) and purged with argon for 10 min. 7A (0.046 g, 0.31 mmol), cesium carbonate (0.209 g, 0.641 mmol), copper(I) iodide (0.012 g, 0.064 mmol), Xantphos (0.015 g, 0.026 mmol), and $Pd_2(dba)_3$ (0.012 g, 0.013 mmol) were all added in one portion, and the vessel was pump/purged three times with argon. The vessel was then sealed and heated to 125° C. overnight. The solids were filtered off, and the filtrate was concentrated in vacuo. The crude product was dissolved in a small amount of DCM and charged to a 12 g silica gel cartridge which was eluted at 30 mL/min. with a 15 min. gradient from 100% DCM to 50% EtOAc/DCM (monitoring at 254 nm). The fractions were concentrated, dissolved in TFA (0.4 mL), and triethylsilane (0.082 mL, 0.513 mmol) was immediately added. The mixture was stirred for 20 min. at room temperature. A gray precipitate formed after 20 minutes, and the reaction was filtered, affording Example 7 (0.047 g, 73% yield) as a gray solid. HPLC: Rt=3.928 min. (YMC S5 ODS 4.6×50 mm, 10-90% aqueous methanol containing 0.2% $H_3PO_4$, 4 min. gradient, monitored at 220 nm). MS (ES): m/z=384.0 $[M+H]^+$. $^1H$ NMR (400 MHz, DMSO-$d_6$) δ ppm 9.88 (1H, s), 9.49 (1H, s), 9.28 (1H, s), 8.23 (1H, s), 7.81 (1H, d, J=6.29 Hz), 7.73 (1H, s), 7.40-7.47 (4H, m), 7.15-7.25 (2H, m), 6.97 (1H, s), 6.57 (1H, s), 2.04 (3H, s).

Example 8

Methyl (5-((3-cyano-8-(2-pyridinylamino)imidazo[1,2-b]pyridazin-6-yl)amino)-2-fluorophenyl)carbamate

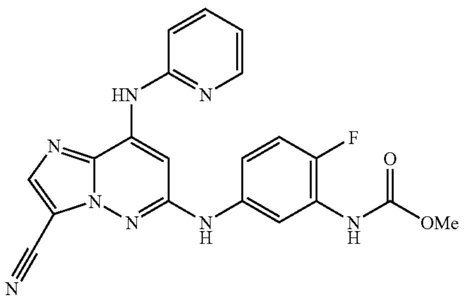

8A: Preparation of 6-chloro-8-((4-methoxybenzyl)(2-pyridinyl)amino)imidazo[1,2-b]pyridazine-3-carbonitrile

8A

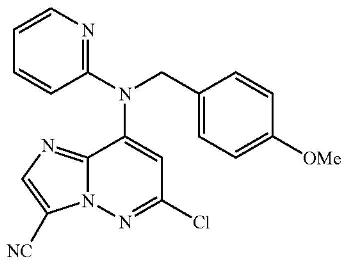

8A was prepared from a mixture of 1F and N-(4-methoxybenzyl)pyridin-2-amine following the procedure employed for the preparation of 5B. HPLC: Rt=3.881 min. (YMC S5 ODS 4.6×50 mm, 10-90% aqueous methanol containing 0.2% $H_3PO_4$, 4 min gradient, monitored at 220 nm). MS (ES): m/z=391.0 $[M+H]^+$.

8B: Preparation of 6-(3-amino-4-fluorophenylamino)-8-((4-methoxybenzyl)(pyridin-2-yl)amino)imidazo[1,2-b]pyridazine-3-carbonitrile

8B

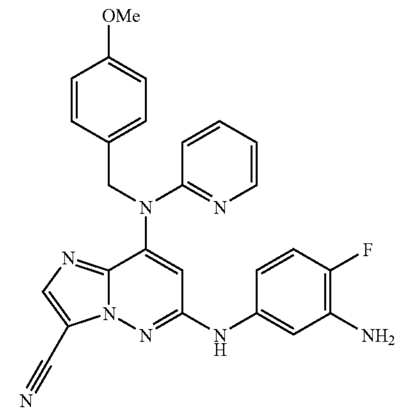

A solution of Intermediate 59 (70.7 mg, 0.384 mmol) in degassed DME (5 mL) was treated with 8A (75 mg, 0.192 mmol), Xantphos (24.4 mg, 0.042 mmol), bis(dibenzylideneacetone)palladium (11.03 mg, 0.019 mmol), cesium carbonate (250 mg, 0.768 mmol), and copper (I) iodide (18.3 mg, 0.096 mmol). The reaction mixture was purged with argon and heated in a sealed tube to 125° C. for 8 hours. The reaction was cooled to room temperature and filtered. The filtrate was concentrated to dryness. The crude product was dissolved in a small amount of DCM and purified by flash chromatography ($SiO_2$, DCM to 50% ethyl acetate/DCM, 40 g column, 40 min. gradient) to afford 8B (82 mg, 89% yield).

HPLC: Rt=3.71 min. (YMC S5 ODS 4.6×50 mm, 10-90% aqueous methanol containing 0.2% $H_3PO_4$, 4 min. gradient, monitored at 220 nm); MS (ES): m/z=481.1 $[M+H]^+$.

8C: Preparation of methyl 5-(3-cyano-8-((4-methoxybenzyl)(pyridin-2-yl)amino)imidazo[1,2-b]pyridazin-6-ylamino)-2-fluorophenylcarbamate

8C

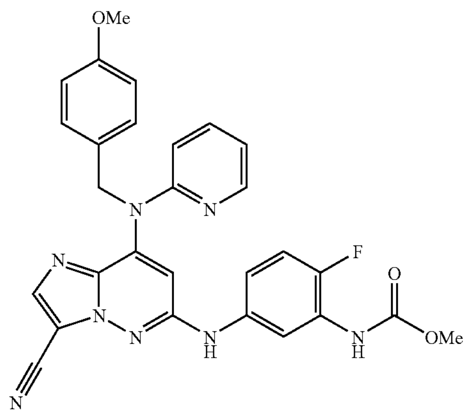

A solution of 8B (82 mg, 0.17 mmol) in THF (3 mL) was treated with DIEA (0.039 mL, 0.22 mmol), followed by methyl chloroformate (0.048 mL, 0.62 mmol). The resulting solution was stirred at room temperature for 12 hours and then concentrated to dryness. The crude product was dissolved in a small amount of DCM and purified by flash chromatography ($SiO_2$, DCM to 20% ethyl acetate/DCM, 24 g column, 40 min. gradient) to afford 8C (15 mg, 16.3%). HPLC: Rt=3.98 min. (YMC S5 ODS 4.6×50 mm, 10-90% aqueous methanol containing 0.2% $H_3PO_4$, 4 min. gradient, monitored at 220 nm). MS (ES): m/z=539.2 $[M+H]^+$.

Example 8

Preparation of methyl 5-(3-cyano-8-(pyridin-2-ylamino)imidazo[1,2-b]pyridazin-6-ylamino)-2-fluorophenylcarbamate

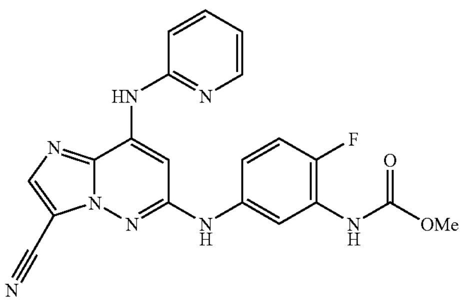

A solution of 8C (15 mg, 0.028 mmol) in triethylsilane (0.044 mL, 0.279 mmol) and TFA (0.5 mL, 0.028 mmol) was heated at 45° C. for 2 hours. The reaction mixture was concentrated to dryness. The crude reaction product was dissolved in a small amount of MeOH and purified by reversed phase HPLC (YMC ODS-A 5 um 30×250 mm, 10-90% aqueous methanol containing 0.1% TFA, 25 mL/min., 40 min. gradient, monitored at 254 nm) to afford Example 8 (3.2 mg, 20.3%). HPLC: Rt=4.04 min. (YMC S5 ODS 4.6×50 mm, 10-90% aqueous methanol containing 0.2% $H_3PO_4$, 4 min. gradient, monitored at 220 nm); MS (ES): m/z=419.1 $[M+H]^+$.

Example 9

6-((5-Cyano-2-methoxyphenyl)amino)-8-((2,2,2-trifluoroethyl)amino)imidazo[1,2-b]pyridazine-3-carbonitrile

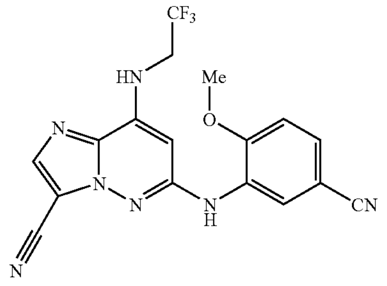

9A: Preparation of 6-chloro-8-((2,2,2-trifluoroethyl)amino)imidazo[1,2-b]pyridazine-3-carbonitrile

9A

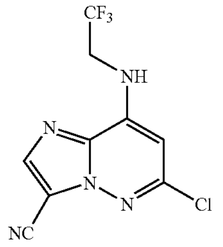

9A was prepared from a mixture of 1F and 2,2,2-trifluoroethanamine following the procedure employed for the preparation of 4A. HPLC: Rt=0.88 min. (BEH C18 2.1×50 mm, 1.7 u, 0 to 100 B in 1 min. with 0.5 min. hold time, flow rate=1 mL/min., detection at 254 nm, Solvent A: 100% water/0.1% TFA; Solvent B: 100% ACN1/0.1% TFA). MS (ES): m/z=276.1 $[M+H]^+$.

Example 9

Preparation of 6-((5-cyano-2-methoxyphenyl)amino)-8-((2,2,2-trifluoroethyl)amino)imidazo[1,2-b]pyridazine-3-carbonitrile

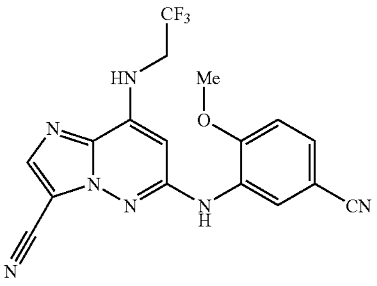

A mixture of 9A (100 mg, 0.36 mmol), 3-amino-4-methoxybenzonitrile (108 mg, 0.73 mmol) and di-tert-butyl(1-methyl-2,2-diphenylcyclopropyl)phosphine (25.6 mg, 0.073 mmol) in toluene (1 mL) was purged with nitrogen. Allylpalladium (II) chloride dimer (13.3 mg, 0.036 mmol) and sodium tert-butoxide (41.8 mg, 0.435 mmol) were added, and the reaction mixture was purged with nitrogen and heated at 100° C. After 20 minutes, the reaction mixture was cooled to room temperature, diluted with DCM, and filtered through CELITE®. The filtrate was concentrated under reduced pressure, dissolved in DMSO/methanol, and purified by reverse phase HPLC (PHENOMENEX® Luna Axia 5 micron 30×250 mm) 20% B (Solvent B=90% MeOH-10% $H_2O$-0.1% TFA) to 100% B in (Solvent A=10% MeOH-90% $H_2O$-0.1% TFA) in 15 min.) to obtain Example 9, (9.9 mg, 0.020 mmol, 5.4% yield) as a light yellow solid. HPLC: Rt=0.95 min. (BEH C18 2.1×50 mm, 1.7 u, 0 to 100 B in 1 min. with 0.5 min. hold time, flow rate=1 mL/min., detection at 254 nm, Solvent A: 100% water/0.1% TFA; Solvent B: 100% ACN1/0.1% TFA). MS (ES): m/z=388.3 $[M+H]^+$. $^1H$ NMR (500 MHz, DMSO-$d_6$) δ ppm 8.76 (1H, d, J=1.94 Hz), 8.67 (1H, s), 8.23 (1H, s), 8.03-8.12 (1H, m), 7.41-7.55 (1H, m), 7.24 (1H, d, J=8.32 Hz), 6.75 (1H, s), 4.06-4.17 (2H, m), 4.00 (3H, s).

Example 10

6-(3-Cyano-5-(trifluoromethyl)phenylamino)-8-(isopropylamino)imidazo[1,2-b]pyridazine-3-carbonitrile

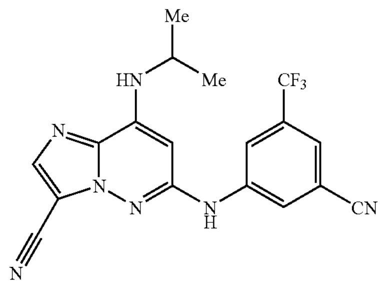

10A: Preparation of 6-chloro-8-(isopropyl (4-methoxybenzyl)amino)imidazo[1,2-b]pyridazine-3-carbonitrile

10A

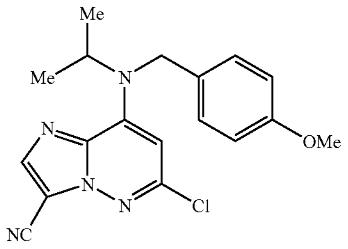

10A was prepared from a mixture of 1F and N-(4-methoxybenzyl)propan-2-amine following the procedure employed for the preparation of 1G. HPLC: Rt=4.27 min. (YMC S5 ODS 4.6×50 mm, 10-90% aqueous methanol containing 0.2% $H_3PO_4$, 4 min. gradient, monitored at 220 nm). MS (ES): m/z=356.1 $[M+H]^+$.

Example 10

Preparation of 6-(3-cyano-5-(trifluoromethyl)phenylamino)-8-(isopropylamino)imidazo[1,2-b]pyridazine-3-carbonitrile

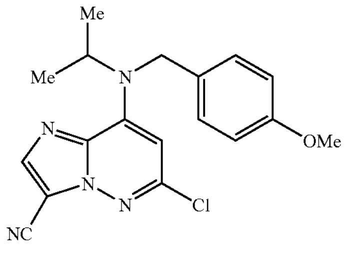

A solution of 3-amino-5-(trifluoromethyl)benzonitrile (0.078 g, 0.42 mmol) in DMA (1 mL) was placed in a 1-dram vial with a teflon-lined septum cap, and the solvent was purged with argon. 10A (0.100 g, 0.281 mmol), cesium carbonate (0.366 g, 1.124 mmol), copper(I) iodide (0.027 g, 0.141 mmol), Xantphos (0.033 g, 0.056 mmol), and $Pd_2(dba)_3$ (0.026 g, 0.028 mmol) were added in one portion, and the suspension was pump/purged three times with argon. The vessel was then heated to 125° C. for 45 min. The solids were removed via filtration through CELITE® and washed with THF. The dark brown filtrate was concentrated under reduced pressure and then diluted with water and ethyl acetate. The layers were separated, and the aqueous phase extracted with ethyl acetate (2×10 mL). The organics were combined, washed with water and brine, dried over sodium sulfate, filtered, concentrated, and the residue was purified by flash chromatography ($SiO_2$, hexanes to 40% EtOAc/hexanes, 12 g column, 30 mL/min., 20 min. gradient, monitoring at 254 nm). The fractions were concentrated, dissolved in DCM (1 mL), and treated with triethylsilane (0.45 mL, 2.8 mmol), and TFA (0.3 mL) at room temperature. After 20 min., the volatiles were removed via a stream of nitrogen. The residue was triturated with MeOH, forming a white precipitate. The solid was isolated via filtration, washed with MeOH, and suspended in 1:1 1N HCl/MeCN and lyophilized, affording Example 10, (0.081 g, 68.3% yield) as a white solid. HPLC: Rt=4.35 min. (YMC S5 ODS 4.6×50 mm, 10-90% aqueous methanol containing 0.2% $H_3PO_4$, 4 min. gradient, monitored at 220 nm). MS (ES): m/z=386.0 $[M+H]^+$. $^1H$ NMR (400 MHz, DMSO-$d_6$) δ ppm 9.98 (1H, s), 8.52 (1H, s), 8.24 (1H, s), 8.19 (1H, s), 7.82 (1H, s), 7.48 (1H, d, J=8.03 Hz), 5.94 (1H, s), 2.52-2.55 (1H, m), 1.28 (6H, d, J=6.27 Hz).

Example 11

N-(5-(3-Cyano-8-(2-hydroxyethylamino)imidazo[1,2-b]pyridazin-6-ylamino)-2-methylphenyl)acetamide

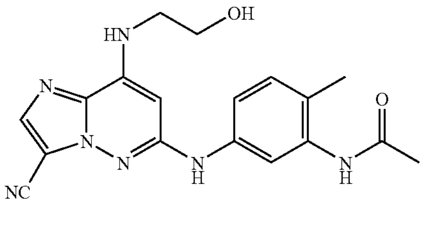

11A: Preparation of 6-chloro-8-((2-hydroxyethyl)(4-methoxybenzyl)amino)imidazo[1,2-b]pyridazine-3-carbonitrile

11A

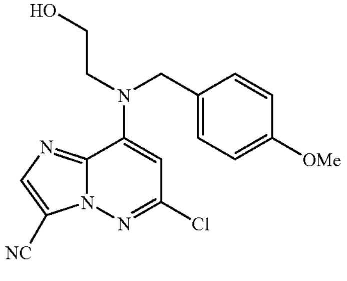

11A was prepared from 2-((4-methoxybenzyl)amino)ethanol and a mixture of 1F following the procedure employed in the preparation of 4A. HPLC: Rt=3.64 min. (YMC S5 ODS 4.6×50 mm, 10-90% aqueous methanol containing 0.2% $H_3PO_4$, 4 min. gradient, monitored at 220 nm). MS (ES): m/z=358.0 $[M+H]^+$.

Example 11

Preparation of N-(5-(3-cyano-8-(2-hydroxyethylamino)imidazo[1,2-b]pyridazin-6-ylamino)-2-methylphenyl)acetamide

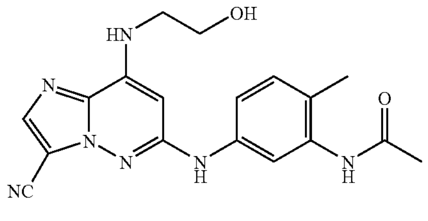

A mixture of 11A (50 mg, 0.14 mmol), N-(5-amino-2-methylphenyl)acetamide (45.9 mg, 0.28 mmol), $Pd_2(dba)_3$ (12.80 mg, 0.014 mmol), Xantphos (17.79 mg, 0.031 mmol), copper (I) iodide (13.31 mg, 0.070 mmol) and cesium carbonate (182 mg, 0.56 mmol) in DMA (1.0 mL) was purged with nitrogen, cooled to room temperature and then reaction mixture was stirred at 125° C. in a sealed vial for 2 hours, and then diluted with ethyl acetate. The reaction mixture was washed with 20% $NH_4OH$, dried over $Na_2SO_4$, filtered and concentrated under reduced pressure. The resulting solid was triturated with ether and isolated by filtration. The solid obtained was suspended in DCM (2 mL), and treated with triethylsilane (0.1 mL, 0.63 mmol) and TFA (0.1 mL, 1.3 mmol), and stirred for 20 min. at room temperature. The reaction mixture was concentrated and purified by reverse phase HPLC, lyophilized with 1.0 N HCl to yield Example 11 (15.0 mg, 26.7% yield). HPLC: Rt=11.424 min. (YMC S5 ODS 4.6×50 mm, 10-90% aqueous methanol containing 0.2% $H_3PO_4$, 15 min. Gradient, monitored at 220 nm). MS (ES): m/z=366.0 $[M+H]^+$. $^1H$ NMR (400 MHz, DMSO-$d_6$) δ ppm 9.24 (1H, s), 9.15 (1H, s), 8.13 (1H, s), 7.62 (2H, s), 7.26-7.37 (1H, m), 7.12 (1H, d, J=8.03 Hz), 5.99 (1H, s), 4.92 (1H, t, J=5.40 Hz), 3.65 (2H, q, J=5.77 Hz), 3.22-3.42 (2H, m), 2.15 (3H, s), 2.01-2.13 (3H, m).

Example 12

8-((1-(2-Hydroxyethyl)-1H-pyrazol-3-yl)amino)-6-((3-methoxy-5-(5-methyl-1H-tetrazol-1-yl)phenyl)amino)imidazo[1,2-b]pyridazine-3-carbonitrile

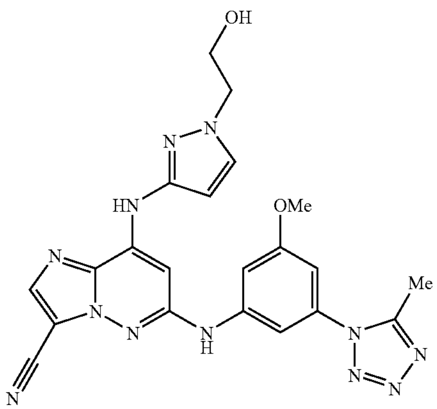

12A: Preparation of 8-((1-(2-((tert-butyl(dimethyl)silyl)oxy)ethyl)-1H-pyrazol-3-yl)amino)-6-chloroimidazo[1,2-b]pyridazine-3-carbonitrile

12A

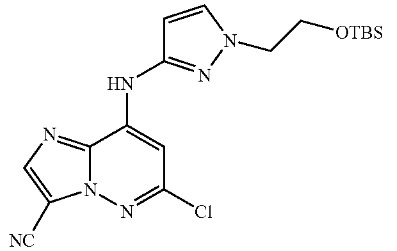

12A was prepared from a mixture of 1F and 1-(2-(tert-butyldimethylsilyloxy)ethyl)-1H-pyrazol-3-amine following the procedure employed in the preparation of 4A. HPLC: Rt=4.26 min. (Waters Sunfire C18 column (4.6×50 mm). 10-90% aqueous methanol containing 0.1% TFA, 4 min. gradient, flow rate=4 mL/min., detection at 254 nm). MS (ES): m/z=418.2 $[M+H]^+$.

Example 12

Preparation of 8-((1-(2-hydroxyethyl)-1H-pyrazol-3-yl)amino)-6-((3-methoxy-5-(5-methyl-1H-tetrazol-1-yl)phenyl)amino)imidazo[1,2-b]pyridazine-3-carbonitrile

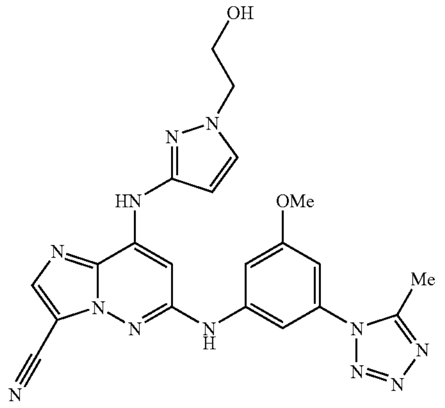

A suspension of 12A (39 mg, 0.093 mmol), 3-methoxy-5-(5-methyl-1H-tetrazol-1-yl)aniline (28.7 mg, 0.14 mmol), and di-tert-butyl (1-methyl-2,2-diphenylcyclopropyl) phosphine (6.58 mg, 0.019 mmol) in toluene (0.75 mL) was purged with nitrogen. Allylpalladium (II) chloride dimer (3.41 mg, 9.3 μmol) and sodium tert-butoxide (10.76 mg, 0.11 mmol) were added, and the reaction mixture was purged with nitrogen and heated at 100° C. After 15 minutes, the reaction mixture was concentrated, suspended in water (50 mL), extracted with 10% isopropanol/dichloromethane (3×25 mL), dried over $Na_2SO_4$, and concentrated. The crude was purified with silica gel chromatography (stepwise gradient, 20 to 50% ethyl acetate/hexanes to neat ethyl acetate). The fractions were concentrated, dissolved in dichloromethane (2 mL) and treated with TFA (2 mL). After 3 hours, the reaction mixture was concentrated, purified using reverse phase HPLC, and lyophilized with 1.0 N HCl to isolate Example 12, (2.1 mg, 3.84% yield) as a tan solid. HPLC: Rt=1.65 min.

(PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=473.06 $[M+H]^+$. $^1H$ NMR (500 MHz, methanol-$d_3$) δ ppm 8.03 (1H, s), 7.86 (1H, s), 7.61 (1H, d, J=1.83 Hz), 7.51 (1H, s), 7.47 (1H, s), 6.68-6.89 (1H, m), 6.13 (1H, d, J=2.29 Hz), 4.23 (2H, t, J=5.27 Hz), 3.97 (2H, t, J=5.27 Hz), 3.94 (3H, s), 2.69 (3H, s).

Example 13

8-(Ethylamino)-6-((3-(1H-1,2,4-triazol-1-yl)-5-(trifluoromethyl)phenyl)amino)imidazo[1,2-b]pyridazine-3-carbonitrile

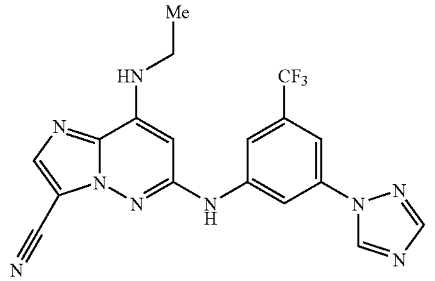

13A: Preparation of 6-chloro-8-(ethyl(4-methoxybenzyl)amino)imidazo[1,2-b]pyridazine-3-carbonitrile

13A

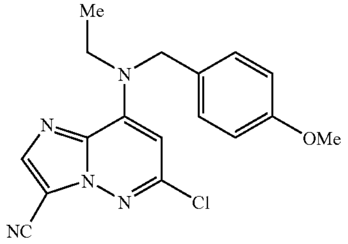

13A was prepared from N-(4-methoxybenzyl)ethanamine and a mixture of 1F following the procedure employed in the preparation of 4A. HPLC: Rt=1.88 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=341.9 $[M+H]^+$.

Example 13

Preparation of 8-(ethylamino)-6-((3-(1H-1,2,4-triazol-1-yl)-5-(trifluoromethyl)phenyl)amino)imidazo[1,2-b]pyridazine-3-carbonitrile

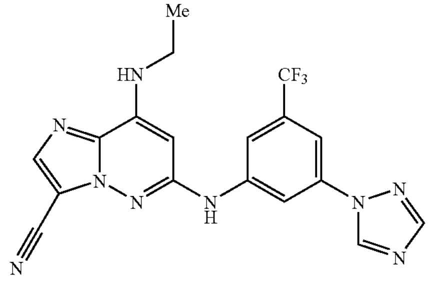

A mixture of 13A (100 mg, 0.29 mmol), Intermediate 1 (100 mg, 0.44 mmol), $Pd_2(dba)_3$ (26.8 mg, 0.029 mmol), cesium carbonate (381 mg, 1.17 mmol), copper (I) iodide (27.9 mg, 0.15 mmol), and Xantphos (33.9 mg, 0.059 mmol) in DMA (2 mL) was purged with nitrogen and heated at 125° C. for 1 hour. The reaction mixture was filtered through a pad of silica gel and washed with 30% methanol/chloroform. The filtrate was concentrated and dissolved in dichloroethane (4 mL), and treated with triethylsilane (0.3 mL) and TFA (1 mL). After 30 min., the reaction mixture was concentrated to dryness, dissolved in DMSO (1 mL) and methanol (1 mL), purified using reverse phase HPLC, and lyophilized with 1.0 N HCl to isolate Example 13, as a tan solid (20 mg, 15.2% yield). HPLC: Rt=1.9 min. (PHENOMENEX® Luna 5 micron C18 4.6×30 mm, 10-90% aqueous methanol containing 0.1% TFA, 2 min. gradient, flow rate=5 mL/min., detection at 254 nm). MS (ES): m/z=414.98 $[M+H]^+$. $^1H$ NMR (500 MHz, DMSO-$d_6$) δ ppm 9.26 (1H, s), 8.71 (1H, s), 7.41-7.87 (4H, m), 7.14 (1H, s), 5.27 (1H, s), 2.87-3.50 (2H, m), 2.57-2.79 (1H, m), 0.58 (3H, t, J=7.10 Hz).

Example 14

8-Amino-6-((3-chloro-5-cyanophenyl)amino)imidazo[1,2-b]pyridazine-3-carbonitrile

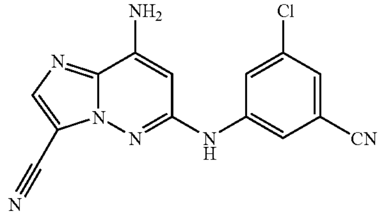

14A: Preparation of 8-(bis(4-methoxybenzyl)amino)-6-chloroimidazo[1,2-b]pyridazine-3-carbonitrile

14A

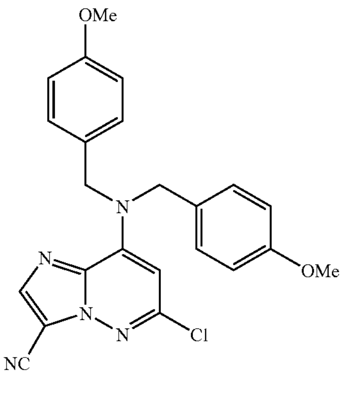

14A was prepared from a mixture of 1F and N-(4-methoxybenzyl)-1-(4-methoxyphenyl)methanamine following the procedure employed in the preparation of 4A. HPLC: Rt=1.13 min. (BEH C18 2.1×50 mm, 1.7 u, 0 to 100 B in 1 min. with 0.5 min. hold time, flow rate=1 mL/min., detection at 254 nm, Solvent A: 100% water/0.1% TFA; Solvent B: 100% ACN1/0.1% TFA). MS (ES): m/z=434.2 $[M+H]^+$.

Example 14

Preparation of 8-amino-6-((3-chloro-5-cyanophenyl)amino)imidazo[1,2-b]pyridazine-3-carbonitrile

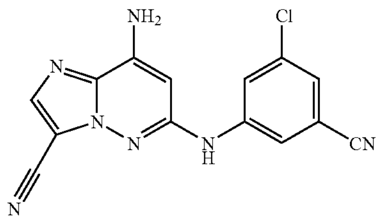

A mixture of 14A (100 mg, 0.23 mmol), cesium carbonate (225 mg, 0.69 mmol), copper(I) iodide (21.95 mg, 0.12 mmol), 3-amino-5-chlorobenzonitrile (38.7 mg, 0.25 mmol), $Pd_2(dba)_3$ (21.10 mg, 0.023 mmol) and Xantphos (29.3 mg, 0.051 mmol) in DMA (2 mL) was purged with nitrogen and heated at 125° C. After 13 hours, the reaction mixture was diluted with DCM, filtered through a silica gel plug (20 g) and washed with 10% MeOH in DCM. The filtrate was concentrated, triturated with water, and the solid was collected via filtration. The solid was dried under reduced pressure, dissolved in DCM (2 mL), and treated with triethylsilane (0.64 mL) and TFA (1.3 mL). After 1 hour, the reaction mixture was concentrated, re-dissolved in MeOH/DMSO and purified by HPLC (PHENOMENEX® Luna Axia 5 micron 30×100 mm) 30% B (Solvent B=90% MeOH-10% $H_2O$-0.1% TFA) to 100% B in A (Solvent A=10% MeOH-90% $H_2O$-0.1% TFA) in 15 min.) to isolate Example 14 (9 mg, 0.029 mmol, 12.61% yield) as a light brown solid. HPLC: Rt=0.88 min. (PHENOMENEX® Luna 5 micron C18 4.6x30 mm, 10-90% aqueous methanol containing 0.1% TFA, 2 min. gradient, flow rate=5 mL/min., detection at 254 nm). MS (ES): m/z=310.0 $[M+H]^+$. $^1H$ NMR (400 MHz, DMSO-$d_6$) δ ppm 9.71 (1H, s), 8.19 (1H, s), 8.14 (1H, t, J=2.01 Hz), 7.97-8.07 (1H, m), 7.46-7.57 (1H, m), 7.28 (2H, br. s.), 6.04 (1H, s).

Example 15

6-((3-Cyano-5-(trifluoromethyl)phenyl)amino)-8-((2-methoxyethyl)amino)imidazo[1,2-b]pyridazine-3-carbonitrile

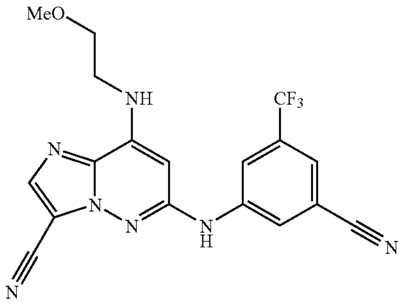

15A: Preparation of 6-chloro-8-((4-methoxybenzyl)(2-methoxyethyl)amino)imidazo[1,2-b]pyridazine-3-carbonitrile

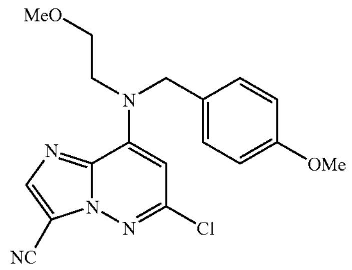

15A 15A was prepared from 2-methoxy-N-(4-methoxybenzyl)ethanamine and 1F following the procedure employed in the preparation of 1G. HPLC: Rt=3.20 min. (CHROMOLITH® column 4.6x50 mm eluting with 10-90% aqueous methanol over 4 min. containing 0.1% TFA, 4 mL/min., monitoring at 220 nm). MS (ES): m/z=372.1 $[M+H]^+$.

Example 15

Preparation of 6-((3-cyano-5-(trifluoromethyl)phenyl)amino)-8-((2-methoxyethyl)amino)imidazo[1,2-b]pyridazine-3-carbonitrile

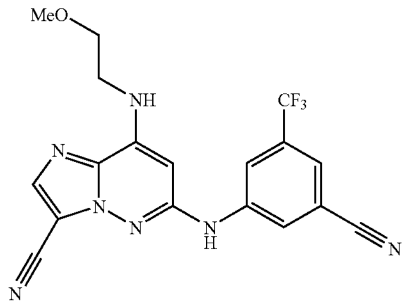

A solution of 3-amino-5-(trifluoromethyl)benzonitrile (0.075 g, 0.40 mmol) in DMA (1 mL) was placed in a 1-dram vial with a teflon-lined septum cap, and the solvent was purged with argon. 15A (0.100 g, 0.269 mmol), cesium carbonate (0.351 g, 1.076 mmol), copper (I) iodide (0.026 g, 0.134 mmol), Xantphos (0.031 g, 0.054 mmol), and $Pd_2(dba)_3$ (0.025 g, 0.027 mmol) were added in one portion, and the suspension was pump/purged three times with argon. The vessel was heated to 125° C. for 45 min. and then cooled to room temperature. The solids were removed via filtration through CELITE® and washed with THF. The filtrate was concentrated under reduced pressure and diluted with water and EtOAc. The layers were separated, and the aqueous phase extracted with EtOAc (3×10 mL). The organics were combined, washed with water and brine, dried over anhydrous sodium sulfate, filtered and concentrated. The crude product was dissolved in DCM and purified by flash chromatography ($SiO_2$, hexanes to 40% EtOAc/hexanes, 12 g column, 30 mL/min., 20 min. gradient, monitoring at 254 nm). The fractions were concentrated, dissolved in DCM (1 mL) and treated with triethylsilane (0.430 mL, 2.7 mmol) and TFA (0.3 mL) at room temperature. After 20 minutes, the volatiles were removed via a stream of nitrogen, and the residue was triturated with MeOH. The solid was isolated via filtration, suspended in 1:1 1N HCl/MeCN, and lyophilized overnight, furnishing Example 15, (0.080 g, 0.181 mmol, 67.3% yield) as a gray solid. HPLC: Rt=4.160 min. (YMC S5 ODS 4.6×50 mm, 10-90% aqueous methanol containing 0.2% $H_3PO_4$, 4 min. gradient, monitored at 220 nm). MS (ES): m/z=402.0 $[M+H]^+$. $^1H$ NMR (400 MHz, DMSO-$d_6$) δ ppm 9.98 (1H, s), 8.52 (1H, s), 8.25 (1H, s), 8.20 (1H, s), 7.82 (1H, s), 7.68 (1H, s), 5.99 (1H, s), 3.54-3.62 (2H, m), 3.40-3.52 (2H, m), 3.30 (3H, s).

Example 16

6-((3-Cyano-5-(trifluoromethyl)phenyl)amino)-8-(methylamino)imidazo[1,2-b]pyridazine-3-carbonitrile

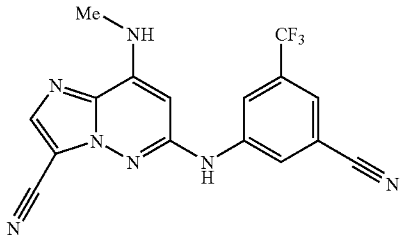

16A: Preparation of 6-chloro-8-((4-methoxybenzyl)(methyl)amino)imidazo[1,2-b]pyridazine-3-carbonitrile

16A

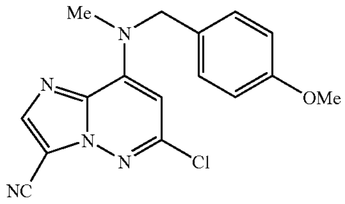

16A was prepared from 1F and 1-(4-methoxyphenyl)-N-methylmethanamine following the procedure employed in the preparation of 1G. HPLC: Rt=3.12 min. (CHROMOLITH® column 4.6×50 mm eluting with 10-90% aqueous methanol over 4 min. containing 0.1% TFA, 4 mL/min., monitoring at 220 nm). MS (ES): m/z=328.1 $[M+H]^+$.

Example 16

Preparation of 6-((3-cyano-5-(trifluoromethyl)phenyl)amino)-8-(methylamino)imidazo[1,2-b]pyridazine-3-carbonitrile

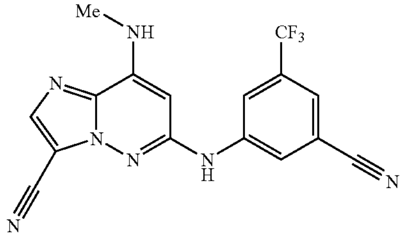

A mixture of 16A (80 mg, 0.24 mmol), 3-amino-5-(trifluoromethyl)benzonitrile (68.1 mg, 0.37 mmol), $Pd_2(dba)_3$ (22.35 mg, 0.024 mmol), xantphos (28.2 mg, 0.049 mmol), copper (I) iodide (23.2 mg, 0.12 mmol) and cesium carbonate (318 mg, 0.976 mmol) in DMA (0.8 mL) was purged with $N_2$ and then heated at 120° C. for 6 hours. The reaction mixture was cooled to room temperature and diluted with DCM (5 mL). The mixture was loaded onto a short silica gel pad and eluted with 10% MeOH/DCM. The filtrate was concentrated and purified by reverse phase preparative HPLC (XTERRA® C-8 20×100 mm, 40-90% aqueous acetonitrile containing 0.1% TFA, 15 min. gradient, monitored at 254 nm). The desired fraction was concentrated. The residue was dissolved in DCM (2 mL) and treated with $Et_3SiH$ (200 μL) and TFA (2 mL). The reaction mixture was stirred at room temperature for 30 min. and then concentrated. The residue was triturated with DMF and methanol, filtered and washed with a mixed solvent of DCM and 2N ammonia in MeOH. The solid was dissolved in ethyl acetate and filtered through silica gel. The filtrate was concentrated to afford Example 16 (47 mg, 53%). HPLC: Rt=3.268 min. (CHROMOLITH® column 4.6×50 mm eluting with 10-90% aqueous methanol over 4 min. containing 0.1% TFA, 4 mL/min., monitoring at 220 nm). MS (ES): m/z=358 $[M+H]^+$.

Example 17

8-((2-(4-Morpholinyl)ethyl)amino)-6-((3-(4H-1,2,4-triazol-4-yl)-4-(trifluoromethoxy)phenyl)amino)imidazo[1,2-b]pyridazine-3-carbonitrile

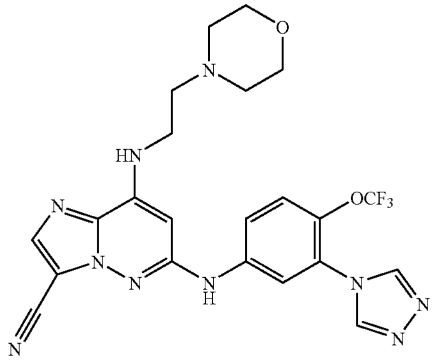

17A: Preparation of 6-chloro-8-((4-methoxybenzyl)(2-(4-morpholinyl)ethyl)amino)imidazo[1,2-b]pyridazine-3-carbonitrile

17A

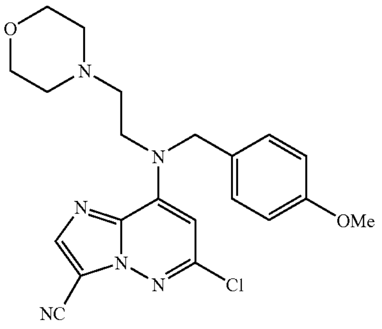

17A was prepared from 1F and N-(4-methoxybenzyl)-2-(4-morpholinyl)ethanamine following the procedure employed in the preparation of 1G. HPLC: Rt=2.95 min. (YMC S5 ODS 4.6×50 mm, 10-90% aqueous methanol containing 0.2% $H_3PO_4$, 4 min. gradient, monitored at 220 nm). MS (ES): m/z=427.1 $[M+H]^+$.

17B: Preparation of 6-(3-(4H-1,2,4-triazol-4-yl)-4-(trifluoromethoxy)phenylamino)-8-((4-methoxybenzyl)(2-morpholinoethyl)amino)imidazo[1,2-b]pyridazine-3-carbonitrile

17B

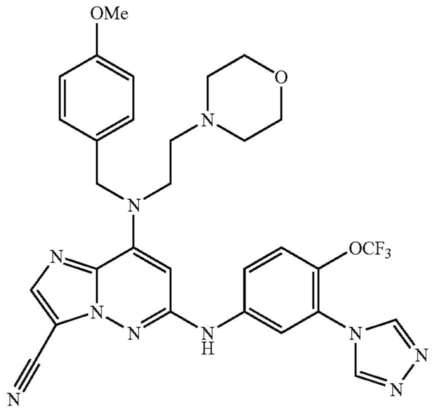

A solution of 17A (56 mg, 0.131 mmol) in DMA (2 mL) was treated with Intermediate 30 (64.1 mg, 0.26 mmol), $Pd_2(dba)_3$ (12.0 mg, 0.013 mmol), copper (I) iodide (12.49 mg, 0.066 mmol), xantphos (15.2 mg, 0.026 mmol), and cesium carbonate (214 mg, 0.66 mmol). The reaction mixture was purged with argon and heated to 125° C. for 2 hours, and then cooled to room temperature. The reaction mixture was filtered and concentrated. The residue was taken up in EtOAc (10 mL) and washed with 10% LiCl solution (2×10 mL). The organic layer was dried ($Na_2SO_4$), filtered and concentrated to dryness. The crude product was dissolved in a small amount of $CH_2Cl_2$ and purified by flash chromatography ($SiO_2$, DCM to 10% MeOH/DCM, 24 g column, 30 min. gradient) to afford 17B (73 mg, 88% yield). HPLC: Rt=3.441 min. (YMC S5 ODS 4.6×50 mm, 10-90% aqueous methanol containing 0.2% $H_3PO_4$, 4 min. gradient, monitored at 220 nm). MS (ES): m/z=635.2 $[M+H]^+$.

Example 17

Preparation of 8-((2-(4-morpholinyl)ethyl)amino)-6-((3-(4H-1,2,4-triazol-4-yl)-4-(trifluoromethoxy)phenyl)amino)imidazo[1,2-b]pyridazine-3-carbonitrile

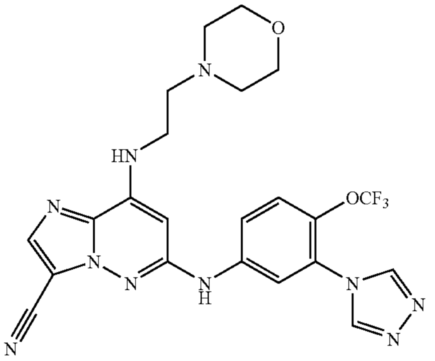

A suspension of 17B (73 mg, 0.12 mmol) in DCM (3 mL) was treated with triethylsilane (0.092 mL, 0.58 mmol), followed by TFA (0.1 mL, 1.298 mmol). The resulting solution was stirred at room temperature for 2 hours and concentrated. The crude reaction product was dissolved in a small amount of MeOH and DMF, purified by reversed phase HPLC (YMC ODS-A 5 um 30×250 mm, 10-90% aqueous methanol containing 0.1% TFA, 25 mL/min., 30 min. gradient, monitored at 254 nm), and lyophilized with 1:1 1N HCl:ACN to afford Example 17 (8 mg, 11.3%). HPLC: Rt=2.995 min. (YMC S5 ODS 4.6×50 mm, 10-90% aqueous methanol containing 0.2% $H_3PO_4$, 4 min. gradient, monitored at 220 nm). MS (ES): m/z=515.2 $[M+H]^+$.

The compounds listed below were prepared by the similar synthetic procedure used for Examples 1 through 17.

TABLE 9

| Example No. | Structure | Name | $[M + H]^+$ | HPLC Retention Time (min.)* |
|---|---|---|---|---|
| 18 | 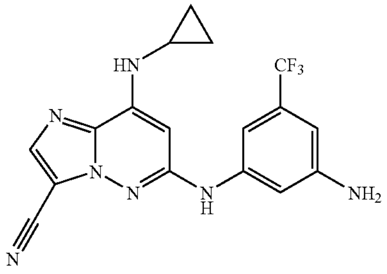 | 6-((3-Amino-5-(trifluoromethyl)phenyl)amino)-8-(cyclopropylamino)imidazo[1,2-b]pyridazine-3-carbonitrile | 374.1 | $1.57^c$ |

TABLE 9-continued

| Example No. | Structure | Name | [M + H]+ | HPLC Retention Time (min.)* |
|---|---|---|---|---|
| 19 | 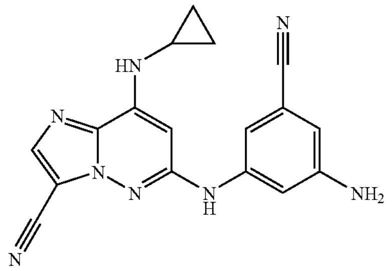 | 6-((3-Amino-5-cyanophenyl)amino)-8-(cyclopropylamino)imidazo[1,2-b]pyridazine-3-carbonitrile | 331.1 | 1.48[c] |
| 20 | 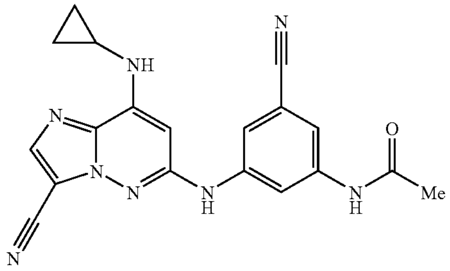 | N-(3-Cyano-5-((3-cyano-8-(cyclopropylamino)imidazo[1,2-b]pyridazin-6-yl)amino)phenyl)acetamide | 373.1 | 1.64[c] |
| 21 | 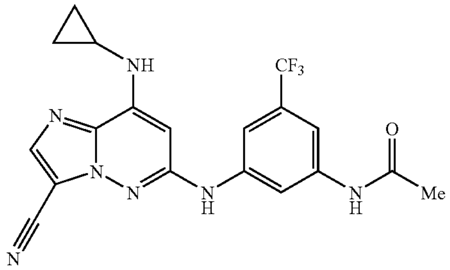 | N-(3-((3-Cyano-8-(cyclopropylamino)imidazo[1,2-b]pyridazin-6-yl)amino)-5-(trifluoromethyl)phenyl)acetamide | 416.1 | 1.8[c] |
| 22 | 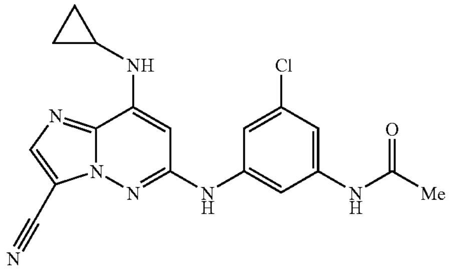 | N-(3-Chloro-5-((3-cyano-8-(cyclopropylamino)imidazo[1,2-b]pyridazin-6-yl)amino)phenyl)acetamide | 382.1 | 1.72[c] |
| 23 | 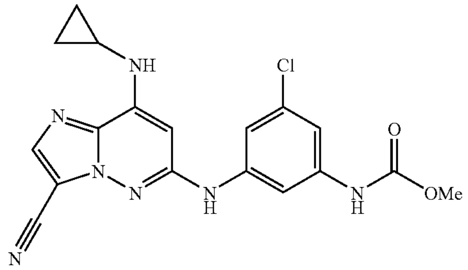 | Methyl (3-chloro-5-((3-cyano-8-(cyclopropylamino)imidazo[1,2-b]pyridazin-6-yl)amino)phenyl)carbamate | 398.1 | 1.79[c] |

TABLE 9-continued

| Example No. | Structure | Name | [M + H]+ | HPLC Retention Time (min.)* |
|---|---|---|---|---|
| 24 | 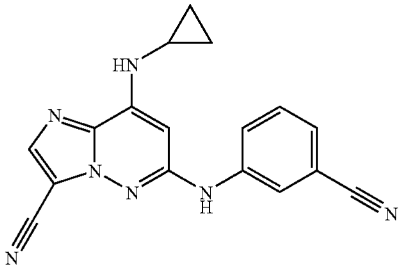 | 6-((3-Cyanophenyl)amino)-8-(cyclopropylamino) imidazo[1,2-b]pyridazine-3-carbonitrile | 316.1 | 1.74[c] |
| 25 | 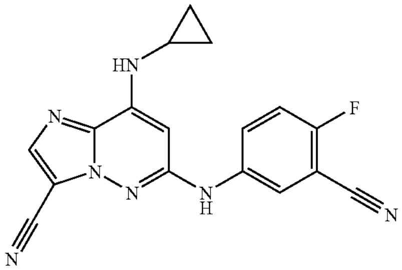 | 6-((3-Cyano-4-fluorophenyl) amino)-8-(cyclopropylamino)imidazo [1,2-b]pyridazine-3-carbonitrile | 334.1 | 1.81[c] |
| 26 | 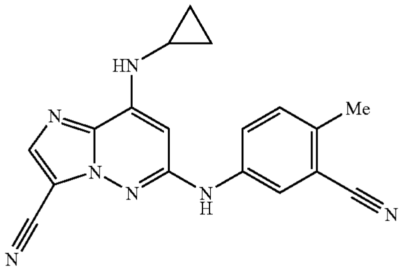 | 6-((3-Cyano-4-methylphenyl)amino)-8-(cyclopropylamino)imidazo [1,2-b]pyridazine-3-carbonitrile | 330.2 | 1.83[c] |
| 27 | 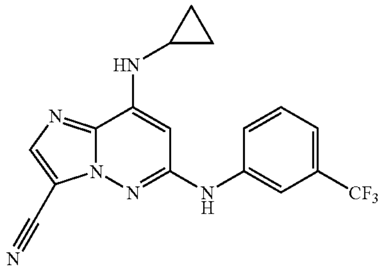 | 8-(Cyclopropylamino)-6-((3-(trifluoromethyl)phenyl) amino)imidazo[1,2-b] pyridazine-3-carbonitrile | 359.1 | 1.93[c] |
| 28 | 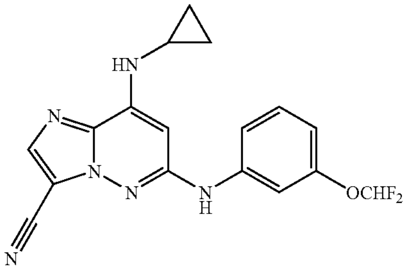 | 8-(Cyclopropylamino)-6-((3-(difluoromethoxy)phenyl) amino)imidazo[1,2-b] pyridazine-3-carbonitrile | 357.1 | 1.83[c] |

TABLE 9-continued

| Example No. | Structure | Name | [M + H]+ | HPLC Retention Time (min.)* |
|---|---|---|---|---|
| 29 | 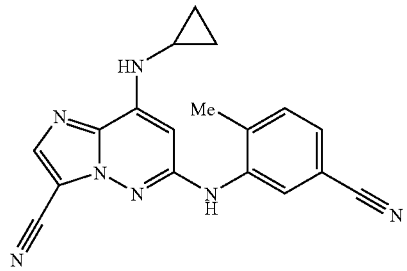 | 6-((5-Cyano-2-methylphenyl)amino)-8-(cyclopropylamino)imidazo[1,2-b]pyridazine-3-carbonitrile | 330.2 | 1.69[c] |
| 30 | 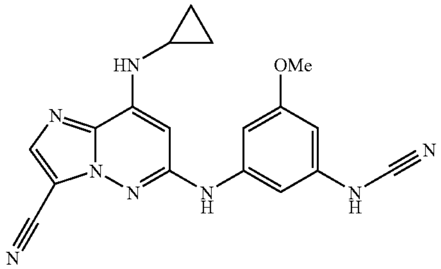 | (3-((3-Cyano-8-(cyclopropylamino)imidazo[1,2-b]pyridazin-6-yl)amino)-5-methoxyphenyl)cyanamide | 361.2 | 1.7[c] |
| 31 | 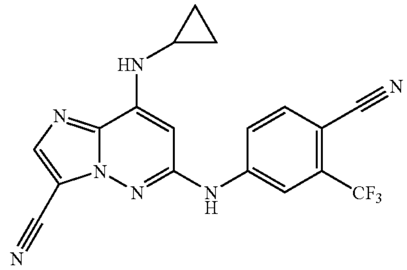 | 6-((4-Cyano-3-(trifluoromethyl)phenyl)amino)-8-(cyclopropylamino)imidazo[1,2-b]pyridazine-3-carbonitrile | 384.2 | 1.86[c] |
| 32 | 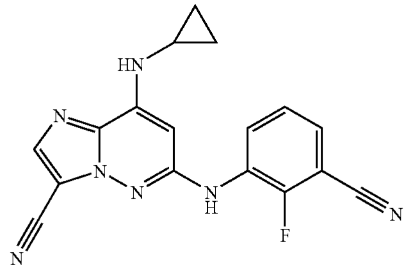 | 6-((3-Cyano-2-fluorophenyl)amino)-8-(cyclopropylamino)imidazo[1,2-b]pyridazine-3-carbonitrile | 334.1 | 1.76[c] |
| 33 | 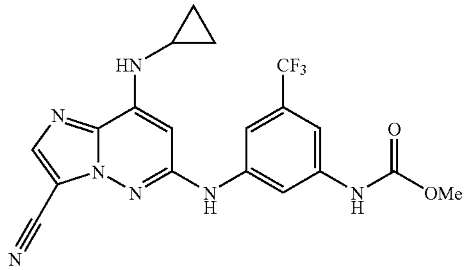 | Methyl (3-((3-cyano-8-(cyclopropylamino)imidazo[1,2-b]pyridazin-6-yl)amino)-5-(trifluoromethyl)phenyl)carbamate | 432.1 | 1.76[c] |

TABLE 9-continued

| Example No. | Structure | Name | [M + H]$^+$ | HPLC Retention Time (min.)* |
|---|---|---|---|---|
| 34 | 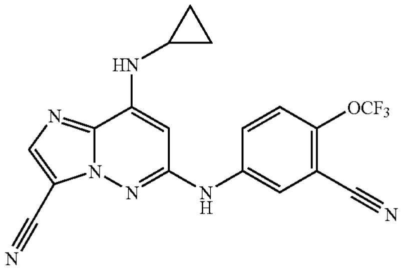 | 6-((3-Cyano-4-(trifluoromethoxy)phenyl)amino)-8-(cyclopropylamino)imidazo[1,2-b]pyridazine-3-carbonitrile | 400.1 | 1.97[c] |
| 35 | 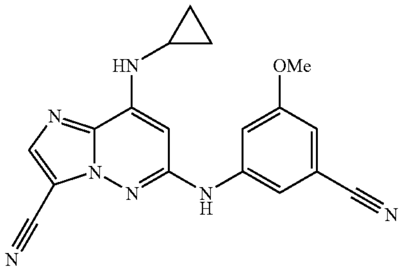 | 6-((3-Cyano-5-methoxyphenyl)amino)-8-(cyclopropylamino)imidazo[1,2-b]pyridazine-3-carbonitrile | 346.2 | 1.93[c] |
| 36 | 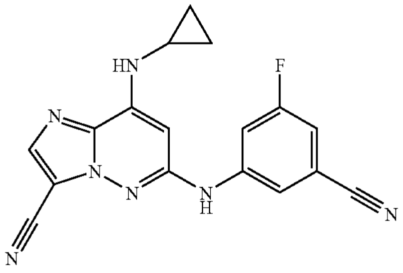 | 6-((3-Cyano-5-fluorophenyl)amino)-8-(cyclopropylamino)imidazo[1,2-b]pyridazine-3-carbonitrile | 334.1 | 1.86[c] |
| 37 | 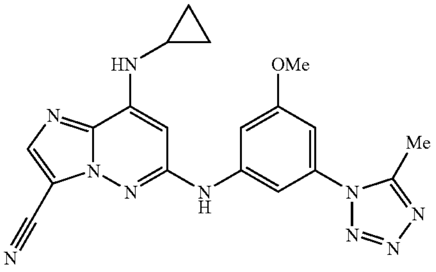 | 8-(Cyclopropylamino)-6-((3-methoxy-5-(5-methyl-1H-tetrazol-1-yl)phenyl)amino)imidazo[1,2-b]pyridazine-3-carbonitrile | 403.2 | 1.5[c] |
| 38 | 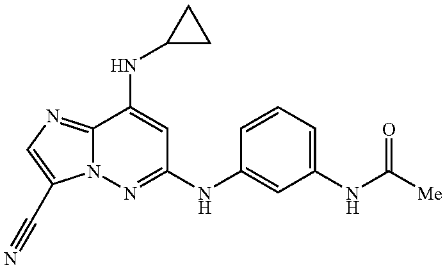 | N-(3-((3-Cyano-8-(cyclopropylamino)imidazo[1,2-b]pyridazin-6-yl)amino)phenyl)acetamide | 348.0 | 3.62[a] |

TABLE 9-continued

| Example No. | Structure | Name | [M + H]+ | HPLC Retention Time (min.)* |
|---|---|---|---|---|
| 39 | 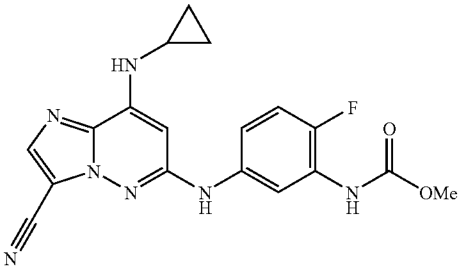 | Methyl (5-((3-cyano-8-(cyclopropylamino)imidazo[1,2-b]pyridazin-6-yl)amino)-2-fluorophenyl)carbamate | 382.1 | 3.856[a] |
| 40 | 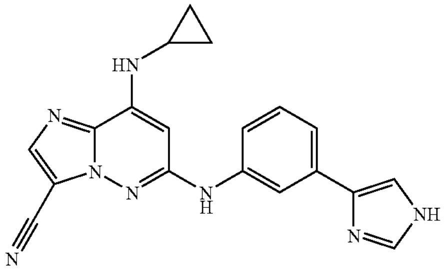 | 8-(Cyclopropylamino)-6-((3-(1H-imidazol-4-yl)phenyl)amino)imidazo[1,2-b]pyridazine-3-carbonitrile | 357.1 | 3.313[a] |
| 41 | 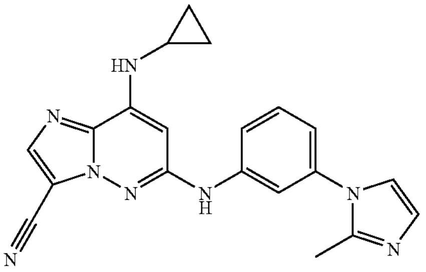 | 8-(Cyclopropylamino)-6-((3-(2-methyl-1H-imidazol-1-yl)phenyl)amino)imidazo[1,2-b]pyridazine-3-carbonitrile | 371.1 | 3.116[a] |
| 42 | 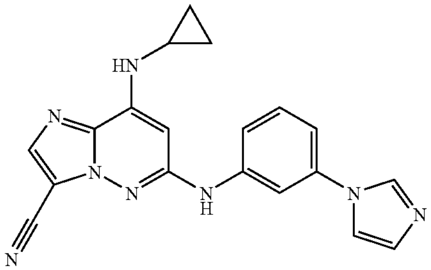 | 8-(Cyclopropylamino)-6-((3-(1H-imidazol-1-yl)phenyl)amino)imidazo[1,2-b]pyridazine-3-carbonitrile | 357.1 | 3.186[a] |
| 43 | 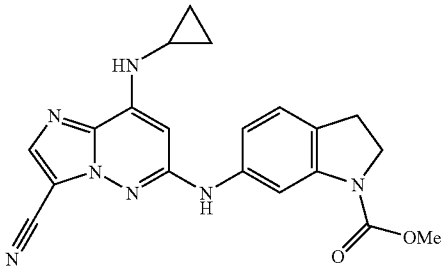 | Methyl 6-((3-cyano-8-(cyclopropylamino)imidazo[1,2-b]pyridazin-6-yl)amino)-1-indolinecarboxylate | 390.1 | 4.185[a] |

TABLE 9-continued

| Example No. | Structure | Name | [M + H]+ | HPLC Retention Time (min.)* |
|---|---|---|---|---|
| 44 | 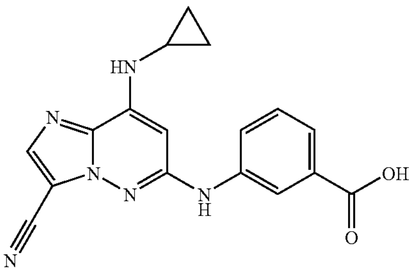 | 3-((3-Cyano-8-(cyclopropylamino)imidazo[1,2-b]pyridazin-6-yl)amino)benzoic acid | 335.2 | 3.816[a] |
| 45 | 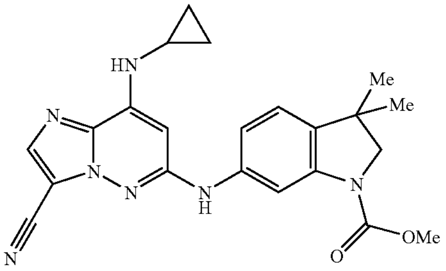 | Methyl 6-((3-cyano-8-(cyclopropylamino)imidazo[1,2-b]pyridazin-6-yl)amino)-3,3-dimethyl-1-indolinecarboxylate | 418.1 | 4.41[a] |
| 46 | 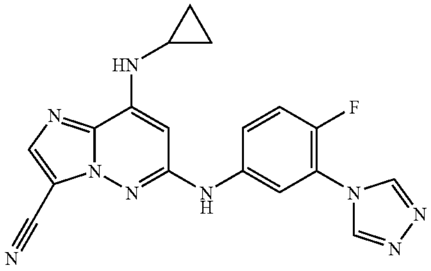 | 8-(Cyclopropylamino)-6-((4-fluoro-3-(4H-1,2,4-triazol-4-yl)phenyl)amino)imidazo[1,2-b]pyridazine-3-carbonitrile | 376.1 | 3.715[a] |
| 47 | 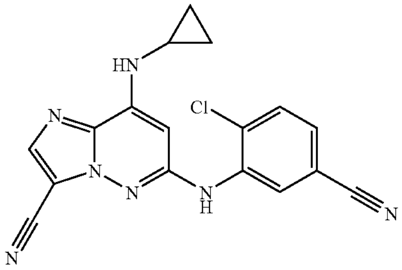 | 6-((2-Chloro-5-cyanophenyl)amino)-8-(cyclopropylamino)imidazo[1,2-b]pyridazine-3-carbonitrile | 350.1 | 3.996[a] |
| 48 | 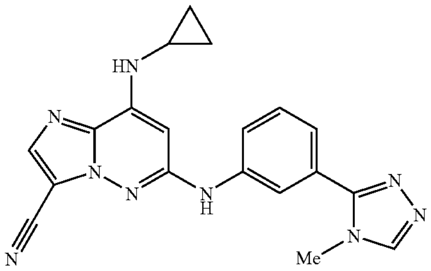 | 8-(Cyclopropylamino)-6-((3-(4-methyl-4H-1,2,4-triazol-3-yl)phenyl)amino)imidazo[1,2-b]pyridazine-3-carbonitrile | 372.1 | 3.341[a] |

TABLE 9-continued

| Example No. | Structure | Name | [M + H]+ | HPLC Retention Time (min.)* |
|---|---|---|---|---|
| 49 | 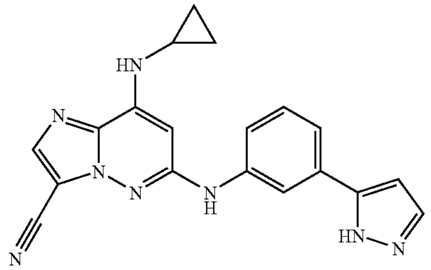 | 8-(Cyclopropylamino)-6-((3-(1H-pyrazol-5-yl)phenyl) amino)imidazo[1,2-b] pyridazine-3-carbonitrile | 357.2 | 3.286[a] |
| 50 | 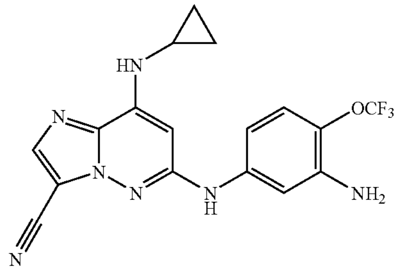 | 6-((3-Amino-4-(trifluoromethoxy)phenyl) amino)-8-(cyclopropylamino) imidazo[1,2-b]pyridazine-3-carbonitrile | 390.1 | 3.973[a] |
| 51 | 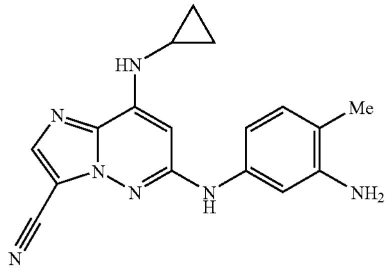 | 6-((3-Amino-4-methylphenyl)amino)-8-(cyclopropylamino)imidazo [1,2-b]pyridazine-3-carbonitrile | 320.2 | 2.988[a] |
| 52 | 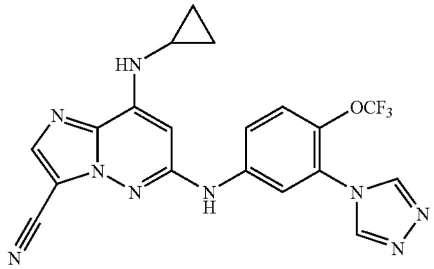 | 8-(Cyclopropylamino)-6-((3-(4H-1,2,4-triazol-4-yl)-4-(trifluoromethoxy)phenyl) amino)imidazo[1,2-b] pyridazine-3-carbonitrile | 442.1 | 3.915[a] |
| 53 | 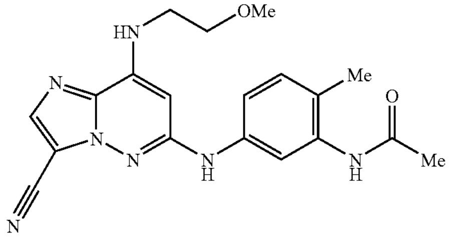 | N-(5-((3-Cyano-8-((2-methoxyethyl)amino) imidazo[1,2-b]pyridazin-6-yl)amino)-2-methylphenyl) acetamide | 380 | 12.43[b] |

TABLE 9-continued

| Example No. | Structure | Name | [M + H]+ | HPLC Retention Time (min.)* |
|---|---|---|---|---|
| 54 | 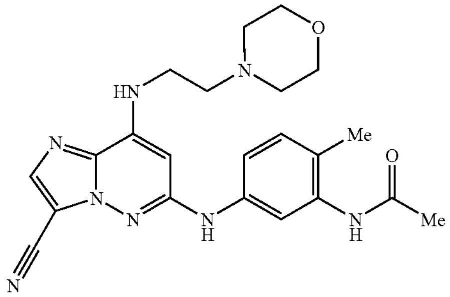 | N-(5-((3-Cyano-8-((2-(4-morpholinyl)ethyl)amino) imidazo[1,2-b]pyridazin-6-yl)amino)-2-methylphenyl) acetamide | 435.1 | 9.673[d] |
| 55 | 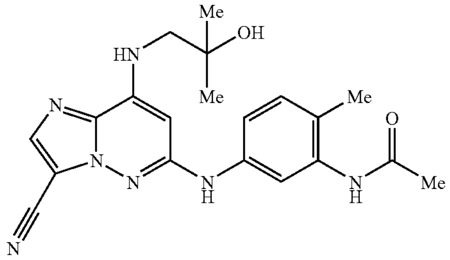 | N-(5-((3-Cyano-8-((2-hydroxy-2-methylpropyl) amino)imidazo[1,2-b] pyridazin-6-yl)amino)-2-methylphenyl)acetamide | 394.1 | 3.263[a] |
| 56 | 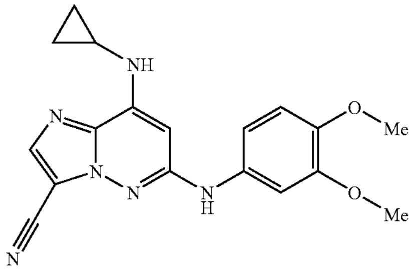 | 8-(Cyclopropylamino)-6-((3,4-dimethoxyphenyl) amino)imidazo[1,2-b] pyridazine-3-carbonitrile | 351.2 | 1.69[c] |
| 57 | 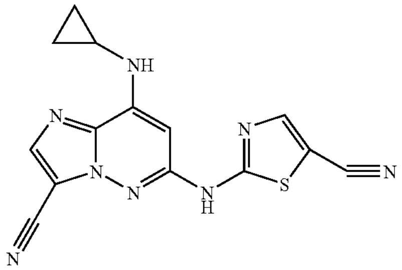 | 6-((5-Cyano-1,3-thiazol-2-yl)amino)-8-(cyclopropylamino) imidazo[1,2-b]pyridazine-3-carbonitrile | 323.1 | 1.67[c] |
| 58 | 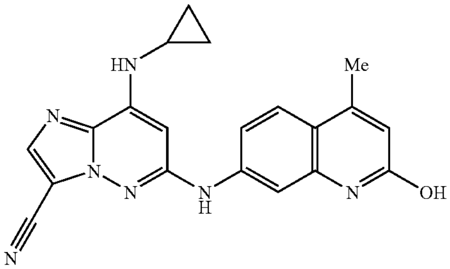 | 8-(Cyclopropylamino)-6-((4-methyl-2-oxo-1,2-dihydro-7-quinolinyl)amino)imidazo[1,2-b]pyridazine-3-carbonitrile | 372.0 | 3.961[a] |

TABLE 9-continued

| Example No. | Structure | Name | [M + H]$^+$ | HPLC Retention Time (min.)* |
|---|---|---|---|---|
| 59 | 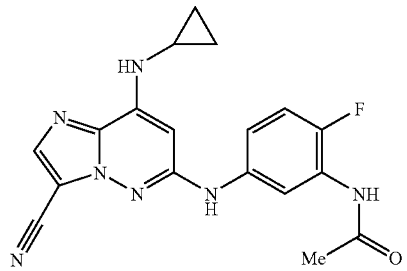 | N-(5-((3-Cyano-8-(cyclopropylamino)imidazo[1,2-b]pyridazin-6-yl)amino)-2-fluorophenyl acetamide | 366.0 | 3.595[a] |
| 60 | 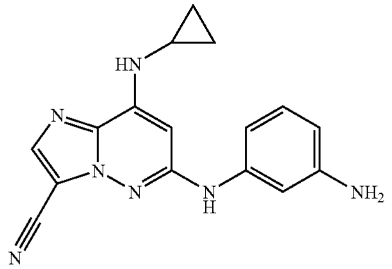 | 6-((3-Aminophenyl)amino)-8-(cyclopropylamino)imidazo[1,2-b]pyridazine-3-carbonitrile | 306.1 | 2.82[a] |
| 61 | 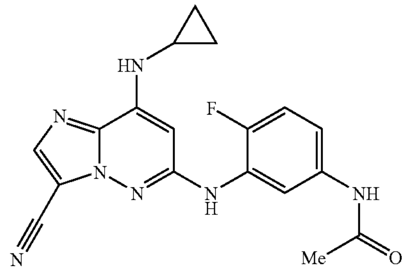 | N-(3-((3-Cyano-8-(cyclopropylamino)imidazo[1,2-b]pyridazin-6-yl)amino)-4-fluorophenyl) acetamide | 366.0 | 3.483[a] |
| 62 | 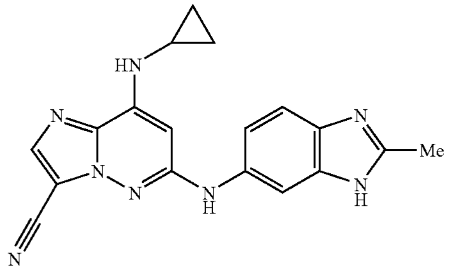 | 8-(Cyclopropylamino)-6-((2-methyl-1H-benzimidazol-5-yl)amino)imidazo[1,2-b]pyridazine-3-carbonitrile | 345.0 | 3.131[a] |
| 63 | 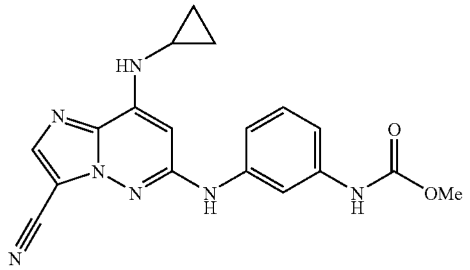 | Methyl (3-((3-cyano-8-(cyclopropylamino)imidazo[1,2-b]pyridazin-6-yl)amino)phenyl)carbamate | 364.1 | 3.788[a] |

TABLE 9-continued

| Example No. | Structure | Name | [M + H]+ | HPLC Retention Time (min.)* |
|---|---|---|---|---|
| 64 | 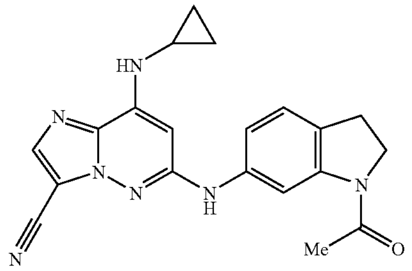 | 6-((1-Acetyl-2,3-dihydro-1H-indol-6-yl)amino)-8-(cyclopropylamino)imidazo[1,2-b]pyridazine-3-carbonitrile | 374.1 | 3.931[a] |
| 65 | 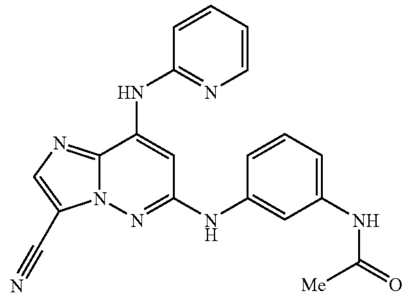 | N-(3-((3-Cyano-8-(2-pyridinylamino)imidazo[1,2-b]pyridazin-6-yl)amino)phenyl)acetamide | 385.0 | 3.761[a] |
| 66 | 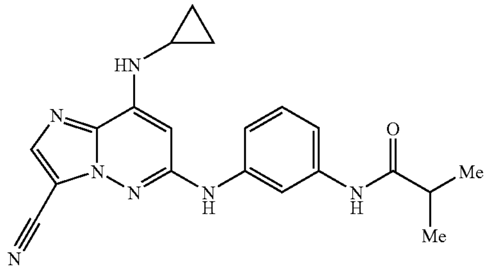 | N-(3-((3-Cyano-8-(cyclopropylamino)imidazo[1,2-b]pyridazin-6-yl)amino)phenyl)-2-methylpropanamide | 376.1 | 3.863[a] |
| 67 | 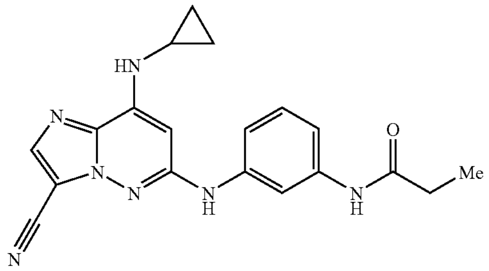 | N-(3-((3-Cyano-8-(cyclopropylamino)imidazo[1,2-b]pyridazin-6-yl)amino)phenyl)propanamide | 362.1 | 3.769[a] |
| 68 | 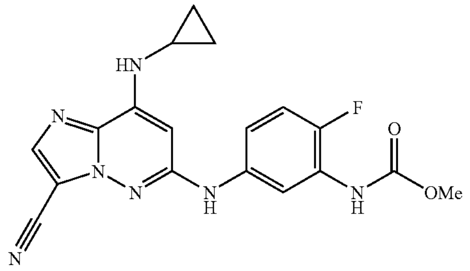 | Methyl (5-((3-cyano-8-(cyclopropylamino)imidazo[1,2-b]pyridazin-6-yl)amino)-2-fluorophenyl)carbamate | 382.0 | 3.841[a] |

TABLE 9-continued

| Example No. | Structure | Name | [M + H]+ | HPLC Retention Time (min.)* |
|---|---|---|---|---|
| 69 | 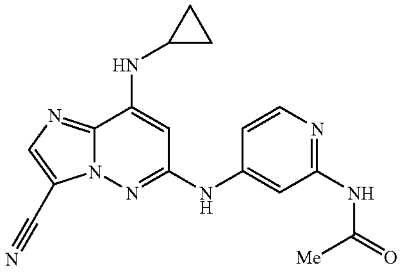 | N-(4-((3-Cyano-8-(cyclopropylamino)imidazo[1,2-b]pyridazin-6-yl)amino)-2-pyridinyl)acetamide | 349.1 | 2.965[a] |
| 70 | 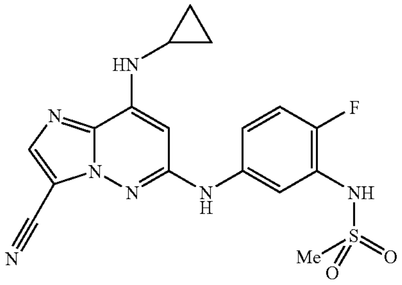 | N-(5-((3-Cyano-8-(cyclopropylamino)imidazo[1,2-b]pyridazin-6-yl)amino)-2-fluorophenyl)methanesulfonamide | 402.0 | 3.56[a] |
| 71 | 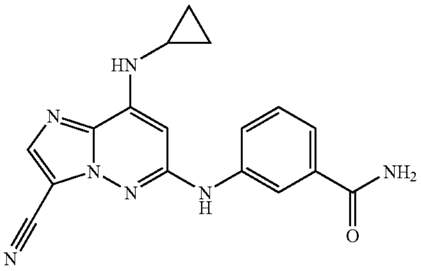 | 3-((3-Cyano-8-(cyclopropylamino)imidazo[1,2-b]pyridazin-6-yl)amino)benzamide | 334.1 | 3.496[a] |
| 72 | 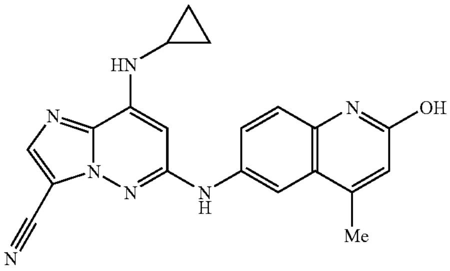 | 8-(Cyclopropylamino)-6-((4-methyl-2-oxo-1,2-dihydro-6-quinolinyl)amino)imidazo[1,2-b]pyridazine-3-carbonitrile | 372.1 | 4.093[a] |
| 73 | 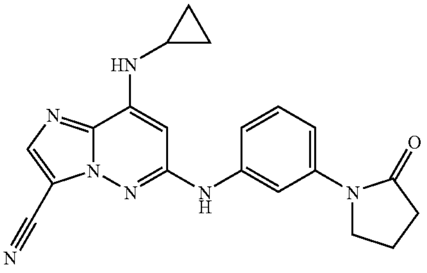 | 8-(Cyclopropylamino)-6-((3-(2-oxo-1-pyrrolidinyl)phenyl)amino)imidazo[1,2-b]pyridazine-3-carbonitrile | 374.1 | 3.978[a] |

TABLE 9-continued

| Example No. | Structure | Name | [M + H]+ | HPLC Retention Time (min.)* |
| --- | --- | --- | --- | --- |
| 74 | 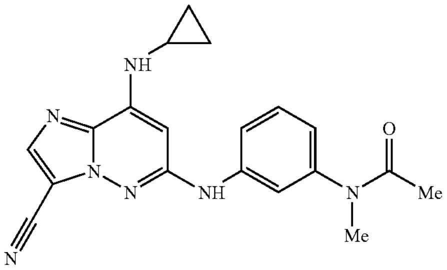 | N-(3-((3-Cyano-8-(cyclopropylamino)imidazo[1,2-b]pyridazin-6-yl)amino)phenyl)-N-methylacetamide | 362.1 | 3.858[a] |
| 75 | 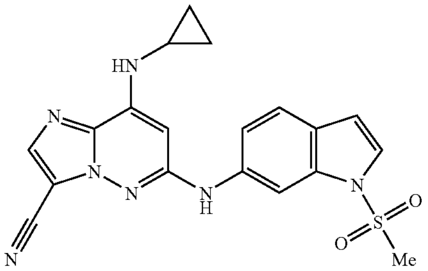 | 8-(Cyclopropylamino)-6-((1-(methylsulfonyl)-1H-indol-6-yl)amino)imidazo[1,2-b]pyridazine-3-carbonitrile | 408.1 | 3.956[a] |
| 76 | 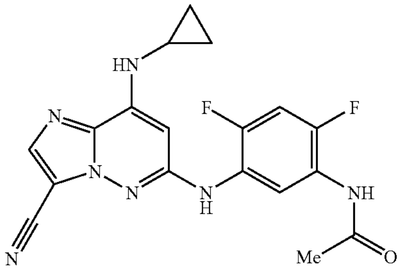 | N-(5-((3-Cyano-8-(cyclopropylamino)imidazo[1,2-b]pyridazin-6-yl)amino)-2,4-difluorophenyl)acetamide | 384.1 | 3.481[a] |
| 77 | 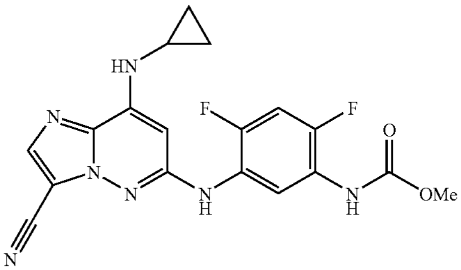 | Methyl (5-((3-cyano-8-(cyclopropylamino)imidazo[1,2-b]pyridazin-6-yl)amino)-2,4-difluorophenyl)carbamate | 462 | 2.395[a] |
| 78 | 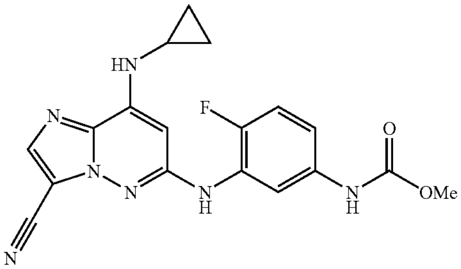 | Methyl (3-((3-cyano-8-(cyclopropylamino)imidazo[1,2-b]pyridazin-6-yl)amino)-4-fluorophenyl)carbamate | 382.1 | 3.673[a] |

TABLE 9-continued

| Example No. | Structure | Name | [M + H]+ | HPLC Retention Time (min.)* |
|---|---|---|---|---|
| 79 | 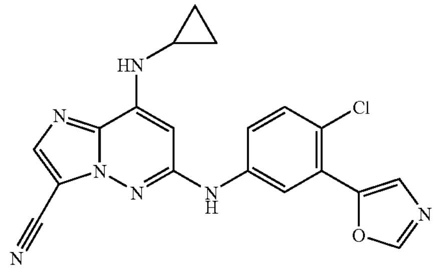 | 6-((4-Chloro-3-(1,3-oxazol-5-yl)phenyl)amino)-8-(cyclopropylamino)imidazo[1,2-b]pyridazine-3-carbonitrile | 392.1 | 4.368[a] |
| 80 | 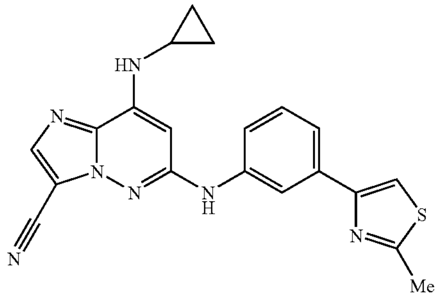 | 8-(Cyclopropylamino)-6-((3-(2-methyl-1,3-thiazol-4-yl)phenyl)amino)imidazo[1,2-b]pyridazine-3-carbonitrile | 388.1 | 4.271[a] |
| 81 | 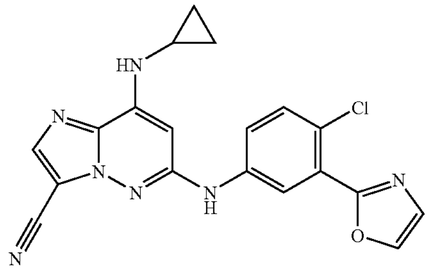 | 6-((4-Chloro-3-(1,3-oxazol-2-yl)phenyl)amino)-8-(cyclopropylamino)imidazo[1,2-b]pyridazine-3-carbonitrile | 392.1 | 4.201[a] |
| 82 | 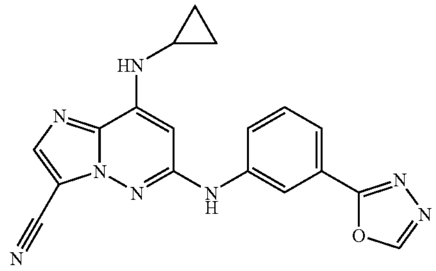 | 8-(Cyclopropylamino)-6-((3-(1,3,4-oxadiazol-2-yl)phenyl)amino)imidazo[1,2-b]pyridazine-3-carbonitrile | 359.2 | 3.4[a] |
| 83 | 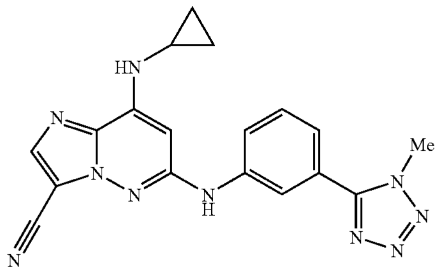 | 8-(Cyclopropylamino)-6-((3-(1-methyl-1H-tetrazol-5-yl)phenyl)amino)imidazo[1,2-b]pyridazine-3-carbonitrile | 373.2 | 3.688[a] |

TABLE 9-continued

| Example No. | Structure | Name | [M + H]+ | HPLC Retention Time (min.)* |
|---|---|---|---|---|
| 84 | 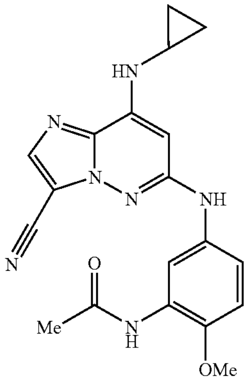 | N-(5-((3-Cyano-8-(cyclopropylamino)imidazo[1,2-b]pyridazin-6-yl)amino)-2-methoxyphenyl)acetamide | 378 | 2.492$^b$ |
| 85 | 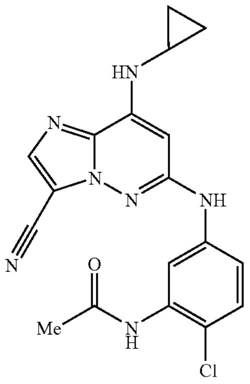 | N-(2-Chloro-5-((3-cyano-8-(cyclopropylamino)imidazo[1,2-b]pyridazin-6-yl)amino)phenyl)acetamide | 382 | 2.643$^b$ |
| 86 | 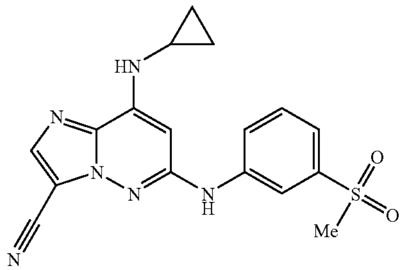 | 8-(Cyclopropylamino)-6-((3-(methylsulfonyl)phenyl)amino)imidazo[1,2-b]pyridazine-3-carbonitrile | 401 | 2.675$^b$ |
| 87 | 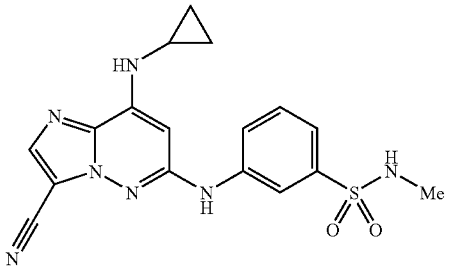 | 3-((3-Cyano-8-(cyclopropylamino)imidazo[1,2-b]pyridazin-6-yl)amino)-N-methylbenzenesulfonamide | 384 | 2.405$^b$ |

TABLE 9-continued

| Example No. | Structure | Name | [M + H]+ | HPLC Retention Time (min.)* |
|---|---|---|---|---|
| 88 | 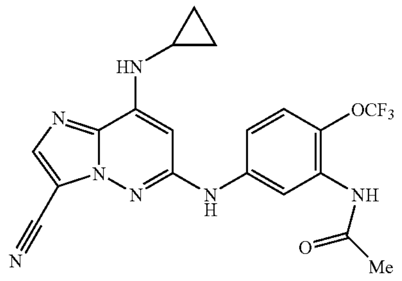 | N-(5-((3-Cyano-8-(cyclopropylamino)imidazo[1,2-b]pyridazin-6-yl)amino)-2-(trifluoromethoxy)phenyl)acetamide | 432 | 3.098[b] |
| 89 | 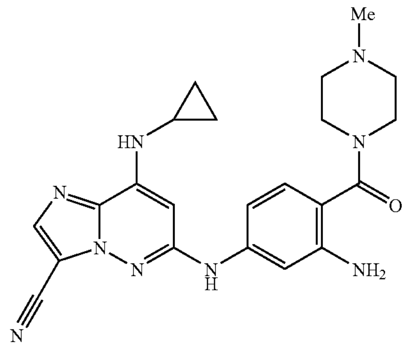 | 6-((3-Amino-4-((4-methyl-1-piperazinyl)carbonyl)phenyl)amino)-8-(cyclopropylamino)imidazo[1,2-b]pyridazine-3-carbonitrile | 432.1 | 2.008[b] |
| 90 | 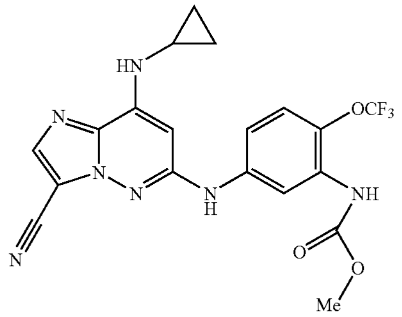 | Methyl (5-((3-cyano-8-(cyclopropylamino)imidazo[1,2-b]pyridazin-6-yl)amino)-2-(trifluoromethoxy)phenyl)carbamate | 448 | 3.298[b] |
| 91 | 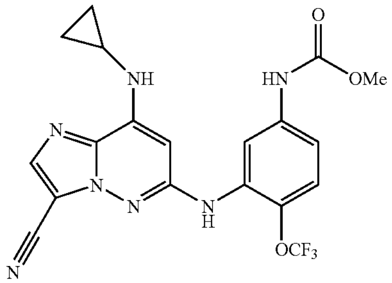 | Methyl (3-((3-cyano-8-(cyclopropylamino)imidazo[1,2-b]pyridazin-6-yl)amino)-4-(trifluoromethoxy)phenyl)carbamate | 448 | 3.136[b] |
| 92 | 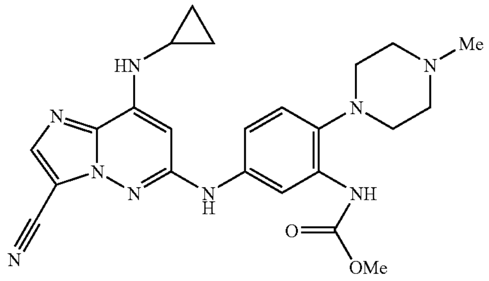 | Methyl (5-((3-cyano-8-(cyclopropylamino)imidazo[1,2-b]pyridazin-6-yl)amino)-2-(4-methyl-1-piperazinyl)phenyl)carbamate | 462 | 2.395[b] |

TABLE 9-continued

| Example No. | Structure | Name | [M + H]+ | HPLC Retention Time (min.)* |
|---|---|---|---|---|
| 93 | 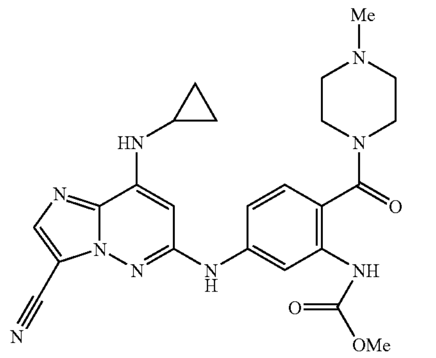 | Methyl (5-((3-cyano-8-(cyclopropylamino)imidazo[1,2-b]pyridazin-6-yl)amino)-2-((4-methyl-1-piperazinyl)carbonyl)phenyl)carbamate | 490 | 2.272[b] |
| 94 | 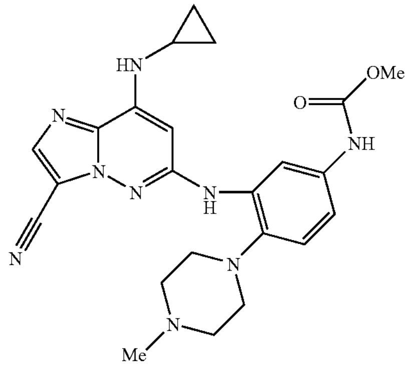 | Methyl (3-((3-cyano-8-(cyclopropylamino)imidazo[1,2-b]pyridazin-6-yl)amino)-4-(4-methyl-1-piperazinyl)phenyl)carbamate | 462 | 2.283[b] |
| 95 | 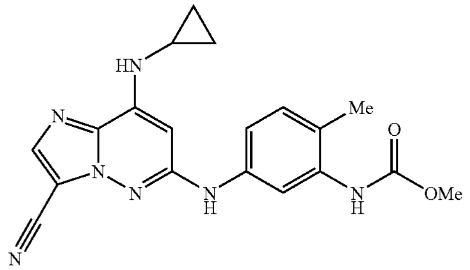 | Methyl (5-((3-cyano-8-(cyclopropylamino)imidazo[1,2-b]pyridazin-6-yl)amino)-2-methylphenyl)carbamate | 378 | 2.916[b] |
| 96 | 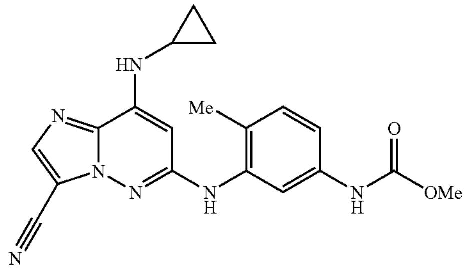 | Methyl (3-((3-cyano-8-(cyclopropylamino)imidazo[1,2-b]pyridazin-6-yl)amino)-4-methylphenyl)carbamate | 378 | 2.891[b] |
| 97 | 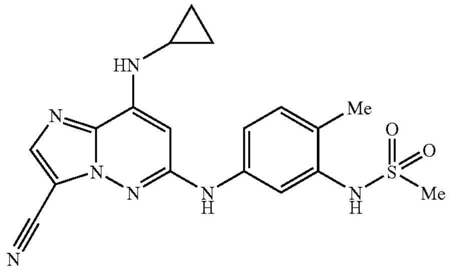 | N-(5-((3-Cyano-8-(cyclopropylamino)imidazo[1,2-b]pyridazin-6-yl)amino)-2-methylphenyl)methanesulfonamide | 398 | 2.838[b] |

TABLE 9-continued

| Example No. | Structure | Name | [M + H]+ | HPLC Retention Time (min.)* |
|---|---|---|---|---|
| 98 | 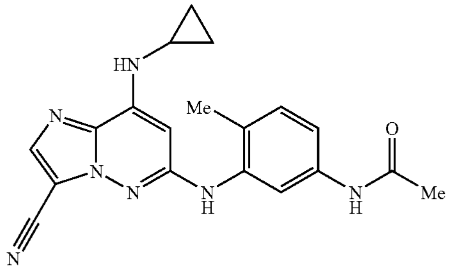 | N-(3-((3-Cyano-8-(cyclopropylamino)imidazo[1,2-b]pyridazin-6-yl)amino)-4-methylphenyl)acetamide | 362.20 | 2.66[c] |
| 99 | 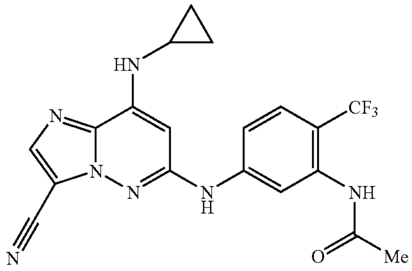 | N-(5-((3-Cyano-8-(cyclopropylamino)imidazo[1,2-b]pyridazin-6-yl)amino)-2-(trifluoromethyl)phenyl)acetamide | 416.10 | 2.94[c] |
| 100 | 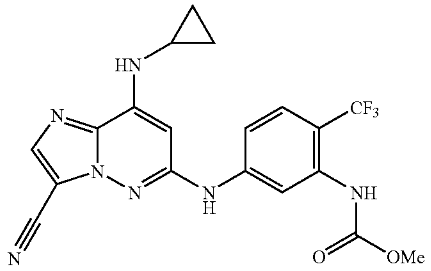 | Methyl (5-((3-cyano-8-(cyclopropylamino)imidazo[1,2-b]pyridazin-6-yl)amino)-2-(trifluoromethyl)phenyl)carbamate | 432.10 | 3.22[c] |
| 101 | 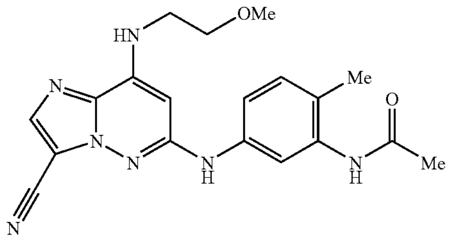 | N-(5-((3-Cyano-8-((2-methoxyethyl)amino)imidazo[1,2-b]pyridazin-6-yl)amino)-2-methylphenyl)acetamide | 380.00 | 12.434[d] |
| 102 | 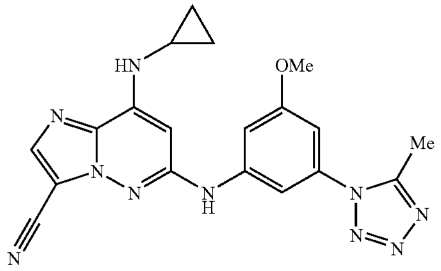 | 8-(Cyclopropylamino)-6-((3-methoxy-5-(5-methyl-1H-tetrazol-1-yl)phenyl)amino)imidazo[1,2-b]pyridazine-3-carbonitrile | 403.17 | 1.5[c] |

TABLE 9-continued

| Example No. | Structure | Name | [M + H]+ | HPLC Retention Time (min.)* |
|---|---|---|---|---|
| 103 | 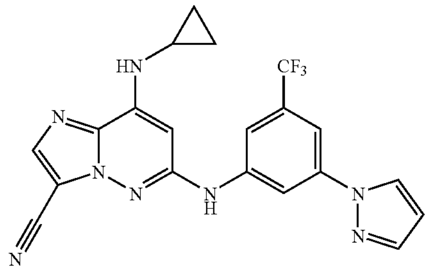 | 8-(Cyclopropylamino)-6-((3-(1H-pyrazol-1-yl)-5-(trifluoromethyl)phenyl) amino)imidazo[1,2-b] pyridazine-3-carbonitrile | 425.12 | 2.045[c] |
| 104 | 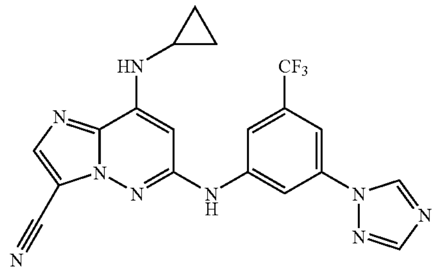 | 8-(Cyclopropylamino)-6-((3-(1H-1,2,4-triazol-1-yl)-5-(trifluoromethyl)phenyl) amino)imidazo[1,2-b] pyridazine-3-carbonitrile | 426.11 | 1.958[c] |
| 105 | 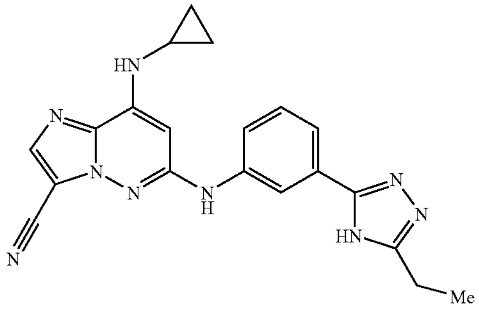 | 8-(Cyclopropylamino)-6-((3-(3-ethyl-1H-1,2,4-triazol-5-yl)phenyl)amino)imidazo [1,2-b]pyridazine-3-carbonitrile | 386.10 | 3.370[a] |
| 106 | 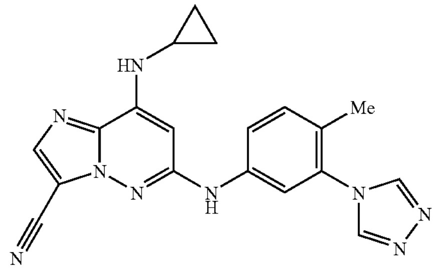 | 8-(Cyclopropylamino)-6-((4-methyl-3-(4H-1,2,4-triazol-4-yl)phenyl)amino) imidazo[1,2-b]pyridazine-3-carbonitrile | 372.10 | 3.606[a] |
| 107 | 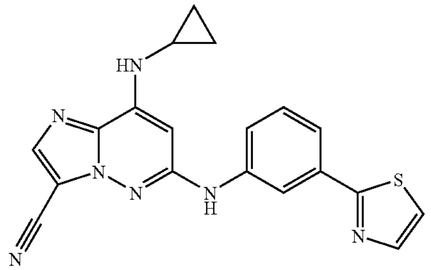 | 8-(Cyclopropylamino)-6-((3-(1,3-thiazol-2-yl)phenyl) amino)imidazo[1,2-b] pyridazine-3-carbonitrile | 374.10 | 4.216[a] |

TABLE 9-continued

| Example No. | Structure | Name | [M + H]+ | HPLC Retention Time (min.)* |
|---|---|---|---|---|
| 108 | 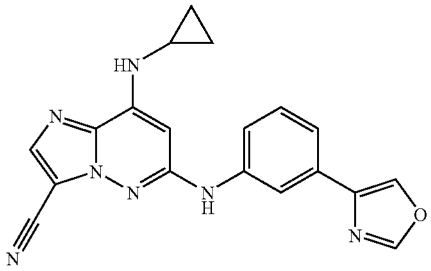 | 8-(Cyclopropylamino)-6-((3-(1,3-oxazol-4-yl)phenyl)amino)imidazo[1,2-b]pyridazine-3-carbonitrile | 358.10 | 4.115[a] |
| 109 | 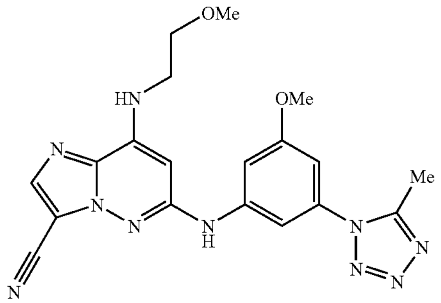 | 8-((2-Methoxyethyl)amino)-6-((3-methoxy-5-(5-methyl-1H-tetrazol-1-yl)phenyl)amino)imidazo[1,2-b]pyridazine-3-carbonitrile | 421.20 | 1.675[c] |
| 110 | 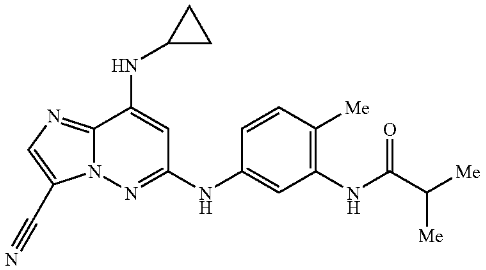 | N-(5-((3-Cyano-8-(cyclopropylamino)imidazo[1,2-b]pyridazin-6-yl)amino)-2-methylphenyl)-2-methylpropanamide | 390.30 | 3.753[a] |
| 111 | 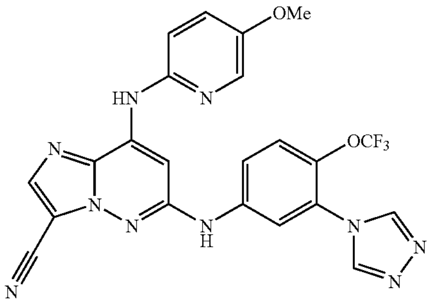 | 8-((5-Methoxy-2-pyridinyl)amino)-6-((3-(4H-1,2,4-triazol-4-yl)-4-(trifluoromethoxy)phenyl)amino)imidazo[1,2-b]pyridazine-3-carbonitrile | 509.10 | 4.160[a] |
| 112 | 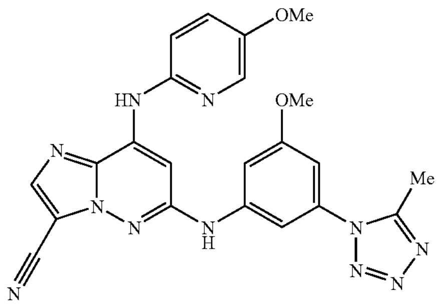 | 6-((3-Methoxy-5-(5-methyl-1H-tetrazol-1-yl)phenyl)amino)-8-((5-methoxy-2-pyridinyl)amino)imidazo[1,2-b]pyridazine-3-carbonitrile | 470.06 | 1.918[c] |

TABLE 9-continued

| Example No. | Structure | Name | [M + H]+ | HPLC Retention Time (min.)* |
|---|---|---|---|---|
| 113 | 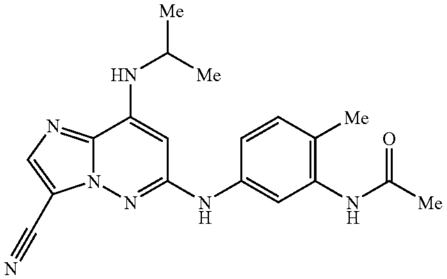 | N-(5-((3-Cyano-8-(isopropylamino)imidazo[1,2-b]pyridazin-6-yl)amino)-2-methylphenyl)acetamide | 364.20 | 3.556[a] |
| 114 | 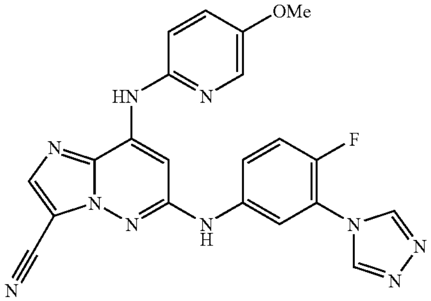 | 6-((4-Fluoro-3-(4H-1,2,4-triazol-4-yl)phenyl)amino)-8-((5-methoxy-2-pyridinyl)amino)imidazo[1,2-b]pyridazine-3-carbonitrile | 443.04 | 1.755[c] |
| 115 | 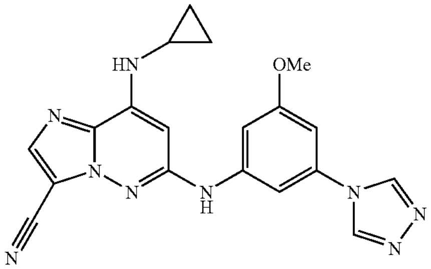 | 8-(Cyclopropylamino)-6-((3-methoxy-5-(4H-1,2,4-triazol-4-yl)phenyl)amino)imidazo[1,2-b]pyridazine-3-carbonitrile | 388.10 | 3.815[a] |
| 116 | 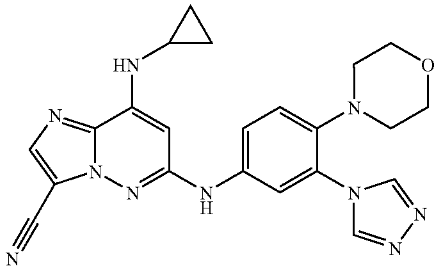 | 8-(Cyclopropylamino)-6-((4-(4-morpholinyl)-3-(4H-1,2,4-triazol-4-yl)phenyl)amino)imidazo[1,2-b]pyridazine-3-carbonitrile | 443.00 | 3.638[a] |
| 117 | 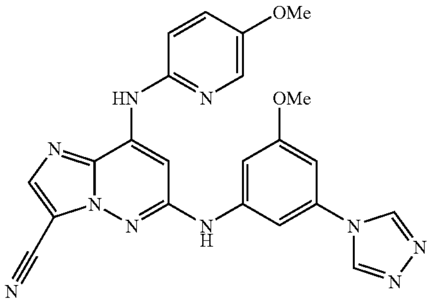 | 8-((5-Methoxy-2-pyridinyl)amino)-6-((3-methoxy-5-(4H-1,2,4-triazol-4-yl)phenyl)amino)imidazo[1,2-b]pyridazine-3-carbonitrile | 455.10 | 4.118[a] |

TABLE 9-continued

| Example No. | Structure | Name | [M + H]+ | HPLC Retention Time (min.)* |
|---|---|---|---|---|
| 118 | 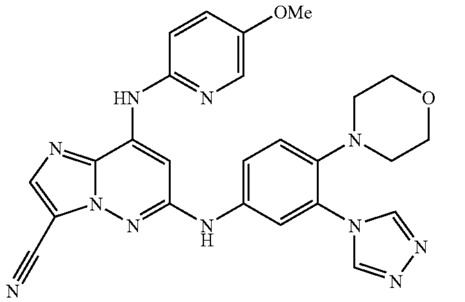 | 8-((5-Methoxy-2-pyridinyl) amino)-6-((4-(4-morpholinyl)-3-(4H-1,2,4-triazol-4-yl)phenyl)amino) imidazo[1,2-b]pyridazine-3-carbonitrile | 510.20 | 3.951[a] |
| 119 | 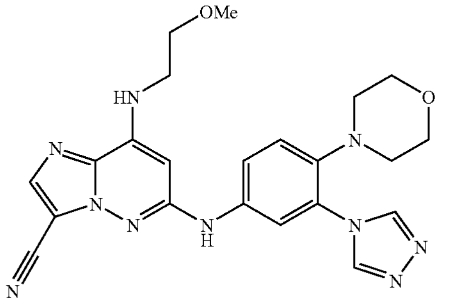 | 8-((2-Methoxyethyl)amino)-6-((4-(4-morpholinyl)-3-(4H-1,2,4-triazol-4-yl)phenyl) amino)imidazo[1,2-b]pyridazine-3-carbonitrile | 461.20 | 3.445[a] |
| 120 | 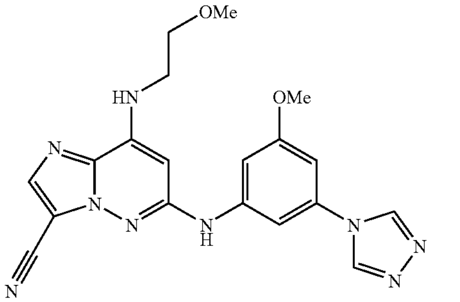 | 8-((2-Methoxyethyl)amino)-6-((3-methoxy-5-(4H-1,2,4-triazol-4-yl)phenyl)amino) imidazo[1,2-b]pyridazine-3-carbonitrile | 406.10 | 3.628[a] |
| 121 | 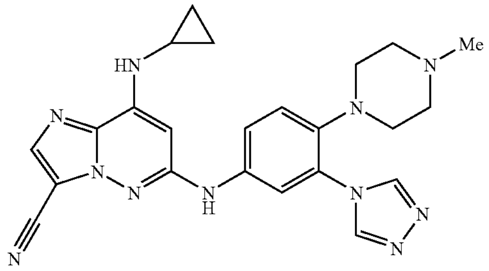 | 8-(Cyclopropylamino)-6-((4-(4-methyl-1-piperazinyl)-3-(4H-1,2,4-triazol-4-yl) phenyl)amino)imidazo[1,2-b]pyridazine-3-carbonitrile | 456.10 | 2.883[a] |
| 122 | 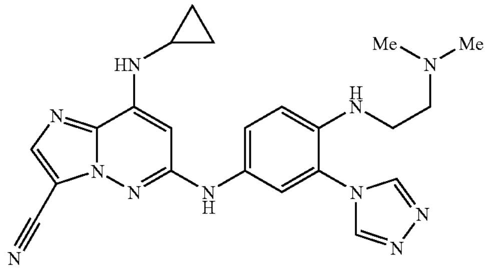 | 8-(Cyclopropylamino)-6-((4-((2-(dimethylamino)ethyl) amino)-3-(4H-1,2,4-triazol-4-yl)phenyl)amino)imidazo [1,2-b]pyridazine-3-carbonitrile | 444.10 | 2.800[a] |

TABLE 9-continued

| Example No. | Structure | Name | [M + H]+ | HPLC Retention Time (min.)* |
|---|---|---|---|---|
| 123 | 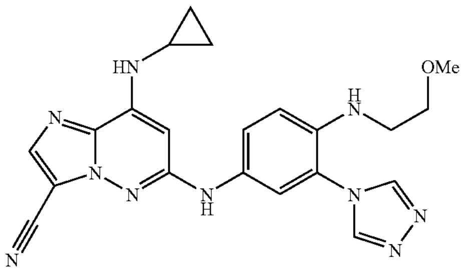 | 8-(Cyclopropylamino)-6-((4-((2-methoxyethyl)amino)-3-(4H-1,2,4-triazol-4-yl) phenyl)amino)imidazo[1,2-b]pyridazine-3-carbonitrile | 431.10 | 3.561[a] |
| 124 | 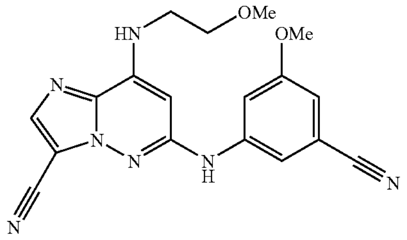 | 6-((3-Cyano-5-methoxyphenyl)amino)-8-((2-methoxyethyl)amino) imidazo[1,2-b]pyridazine-3-carbonitrile | 364.01 | 1.783[c] |
| 125 | 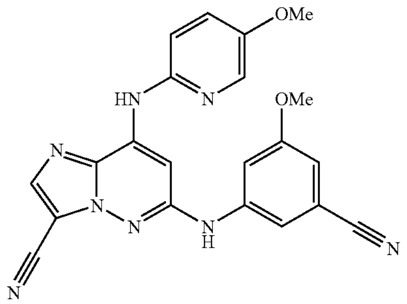 | 6-((3-Cyano-5-methoxyphenyl)amino)-8-((5-methoxy-2-pyridinyl) amino)imidazo[1,2-b]pyridazine-3-carbonitrile | 413.02 | 1.983[c] |
| 126 | 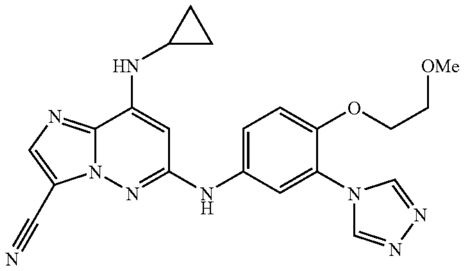 | 8-(Cyclopropylamino)-6-((4-(2-methoxyethoxy)-3-(4H-1,2,4-triazol-4-yl)phenyl) amino)imidazo[1,2-b]pyridazine-3-carbonitrile | 432.00 | 3.666[a] |
| 127 | 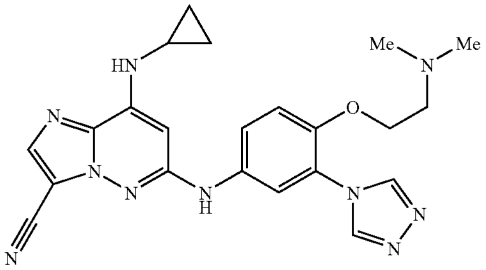 | 8-(Cyclopropylamino)-6-((4-(2-(dimethylamino)ethoxy)-3-(4H-1,2,4-triazol-4-yl) phenyl)amino)imidazo[1,2-b]pyridazine-3-carbonitrile | 445.10 | 2.905[a] |

TABLE 9-continued

| Example No. | Structure | Name | [M + H]+ | HPLC Retention Time (min.)* |
|---|---|---|---|---|
| 128 | 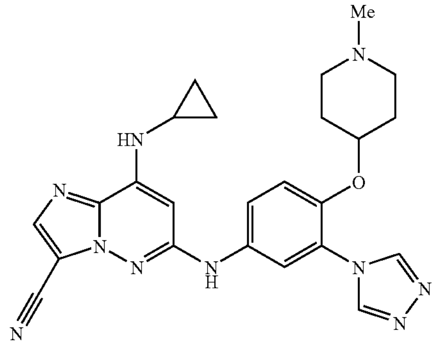 | 8-(Cyclopropylamino)-6-((4-((1-methyl-4-piperidinyl)oxy)-3-(4H-1,2,4-triazol-4-yl)phenyl)amino)imidazo[1,2-b]pyridazine-3-carbonitrile | 471.10 | 3.040[a] |
| 129 | 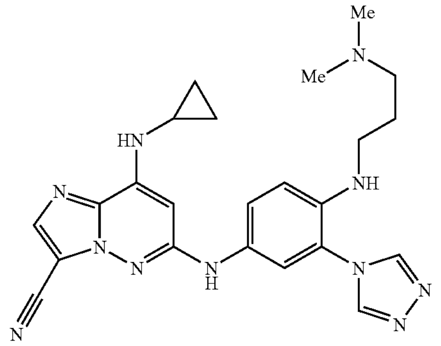 | 8-(Cyclopropylamino)-6-((4-((3-(dimethylamino)propyl)amino)-3-(4H-1,2,4-triazol-4-yl)phenyl)amino)imidazo[1,2-b]pyridazine-3-carbonitrile | 458.10 | 2.938[a] |
| 130 | 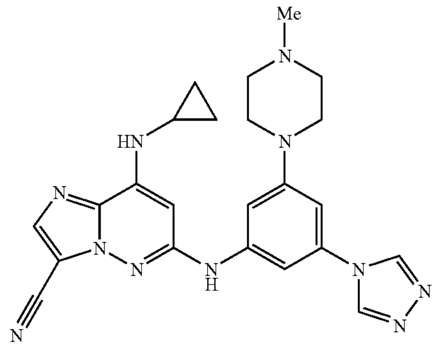 | 8-(Cyclopropylamino)-6-((3-(4-methyl-1-piperazinyl)-5-(4H-1,2,4-triazol-4-yl)phenyl)amino)imidazo[1,2-b]pyridazine-3-carbonitrile | 456.10 | 2.405[b] |
| 131 | 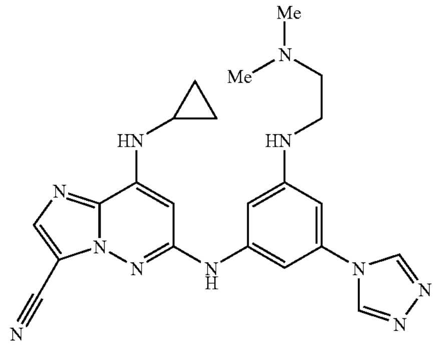 | 8-(Cyclopropylamino)-6-((3-((2-(dimethylamino)ethyl)amino)-5-(4H-1,2,4-triazol-4-yl)phenyl)amino)imidazo[1,2-b]pyridazine-3-carbonitrile | 444.10 | 2.440[b] |

TABLE 9-continued

| Example No. | Structure | Name | [M + H]$^+$ | HPLC Retention Time (min.)* |
|---|---|---|---|---|
| 132 | 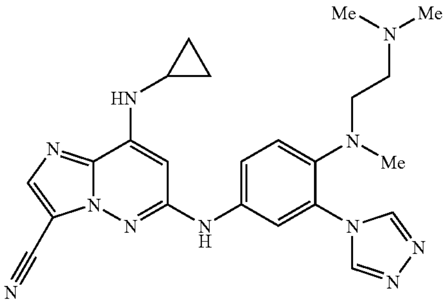 | 8-(Cyclopropylamino)-6-((4-((2-(dimethylamino)ethyl)(methyl)amino)-3-(4H-1,2,4-triazol-4-yl)phenyl)amino)imidazo[1,2-b]pyridazine-3-carbonitrile | 458.10 | 3.041[a] |
| 133 | 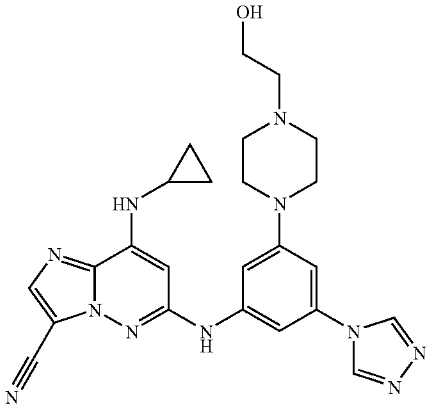 | 8-(Cyclopropylamino)-6-((3-(4-(2-hydroxyethyl)-1-piperazinyl)-5-(4H-1,2,4-triazol-4-yl)phenyl)amino)imidazo[1,2-b]pyridazine-3-carbonitrile | 486.10 | 2.437[b] |
| 134 | 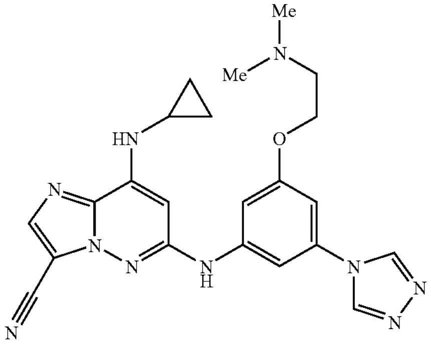 | 8-(Cyclopropylamino)-6-((3-(2-(dimethylamino)ethoxy)-5-(4H-1,2,4-triazol-4-yl)phenyl)amino)imidazo[1,2-b]pyridazine-3-carbonitrile | 445.10 | 2.468[b] |
| 135 | 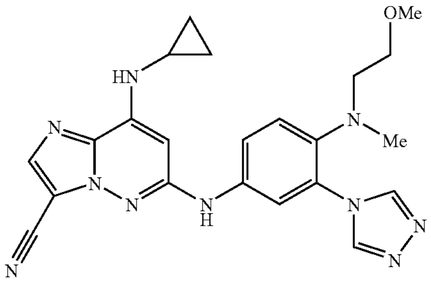 | 8-(Cyclopropylamino)-6-((4-((2-methoxyethyl)(methyl)amino)-3-(4H-1,2,4-triazol-4-yl)phenyl)amino)imidazo[1,2-b]pyridazine-3-carbonitrile | 445.10 | 3.791[a] |

TABLE 9-continued

| Example No. | Structure | Name | [M + H]+ | HPLC Retention Time (min.)* |
|---|---|---|---|---|
| 136 | 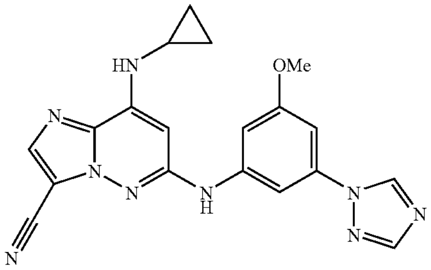 | 8-(Cyclopropylamino)-6-((3-methoxy-5-(1H-1,2,4-triazol-1-yl)phenyl)amino)imidazo [1,2-b]pyridazine-3-carbonitrile | 387.98 | 1.803[c] |
| 137 | 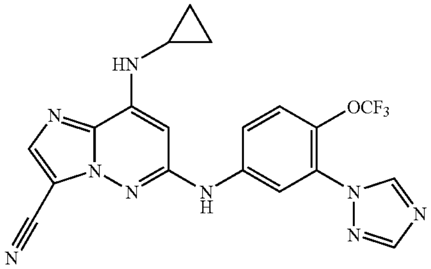 | 8-(Cyclopropylamino)-6-((3-(1H-1,2,4-triazol-1-yl)-4-(trifluoromethoxy)phenyl) amino)imidazo[1,2-b]pyridazine-3-carbonitrile | 441.91 | 1.793[c] |
| 138 | 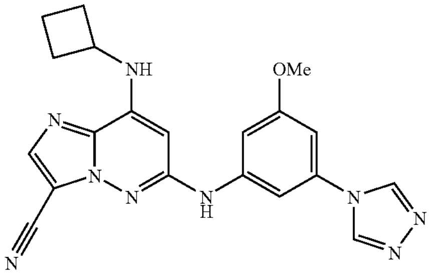 | 8-(Cyclobutylamino)-6-((3-methoxy-5-(4H-1,2,4-triazol-4-yl)phenyl)amino)imidazo [1,2-b]pyridazine-3-carbonitrile | 402.1 | 1.76[c] |
| 139 | 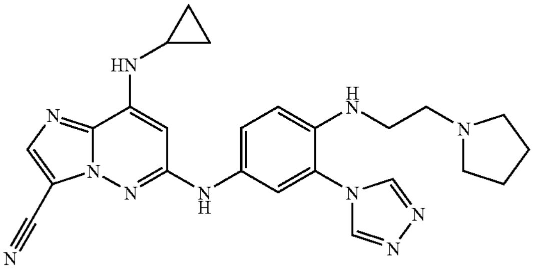 | 8-(Cyclopropylamino)-6-((4-((2-(1-pyrrolidinyl)ethyl) amino)-3-(4H-1,2,4-triazol-4-yl)phenyl)amino)imidazo [1,2-b]pyridazine-3-carbonitrile | 470.10 | 2.851[a] |
| 140 | 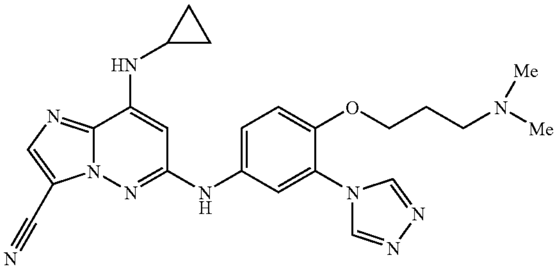 | 8-(Cyclopropylamino)-6-((4-(3-(dimethylamino) propoxy)-3-(4H-1,2,4-triazol-4-yl)phenyl)amino) imidazo[1,2-b]pyridazine-3-carbonitrile | 459.00 | 2.920[a] |

TABLE 9-continued

| Example No. | Structure | Name | [M + H]$^+$ | HPLC Retention Time (min.)* |
|---|---|---|---|---|
| 141 | 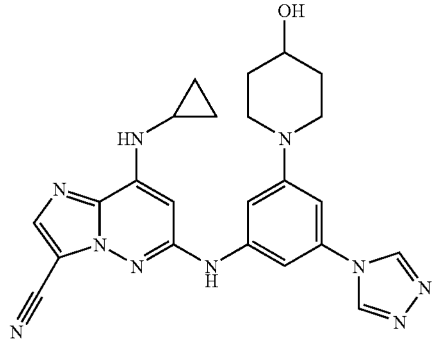 | 8-(Cyclopropylamino)-6-((3-(4-hydroxy-1-piperidinyl)-5-(4H-1,2,4-triazol-4-yl) phenyl)amino)imidazo[1,2-b]pyridazine-3-carbonitrile | 457.00 | 2.545[b] |
| 142 | 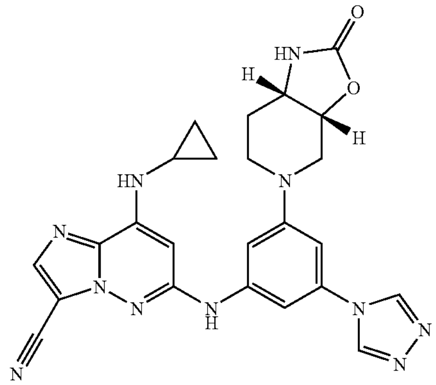 | 8-(Cyclopropylamino)-6-((3-((3aR,7aS)-2-oxohexahydro [1,3]oxazolo[5,4-c]pyridin-5(2H)-yl)-5-(4H-1,2,4-triazol-4-yl)phenyl)amino) imidazo[1,2-b]pyridazine-3-carbonitrile | 498.00 | 2.753[b] |
| 143 | 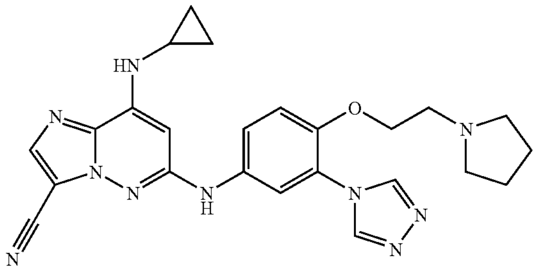 | 8-(Cyclopropylamino)-6-((4-(2-(1-pyrrolidinyl)ethoxy)-3-(4H-1,2,4-triazol-4-yl) phenyl)amino)imidazo[1,2-b]pyridazine-3-carbonitrile | 471.00 | 2.846[a] |
| 144 | 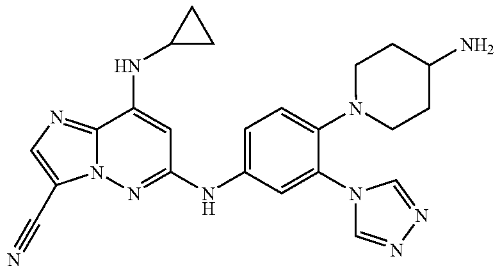 | 6-((4-(4-Amino-1-piperidinyl)-3-(4H-1,2,4-triazol-4-yl)phenyl)amino)-8-(cyclopropylamino) imidazo[1,2-b]pyridazine-3-carbonitrile | 456.10 | 3.053[c] |
| 145 | 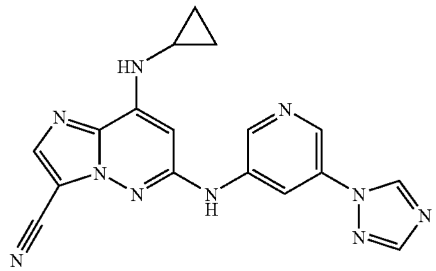 | 8-(Cyclopropylamino)-6-((5-(1H-1,2,4-triazol-1-yl)-3-pyridinyl)amino)imidazo [1,2-b]pyridazine-3-carbonitrile | 358.92 | 1.533[c] |

TABLE 9-continued

| Example No. | Structure | Name | [M + H]+ | HPLC Retention Time (min.)* |
|---|---|---|---|---|
| 146 | 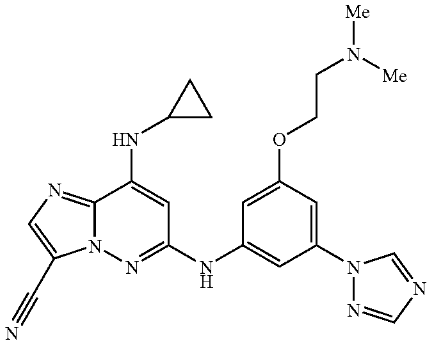 | 8-(Cyclopropylamino)-6-((3-(2-(dimethylamino)ethoxy)-5-(1H-1,2,4-triazol-1-yl) phenyl)amino)imidazo[1,2-b]pyridazine-3-carbonitrile | 444.98 | 1.420[c] |
| 147 | 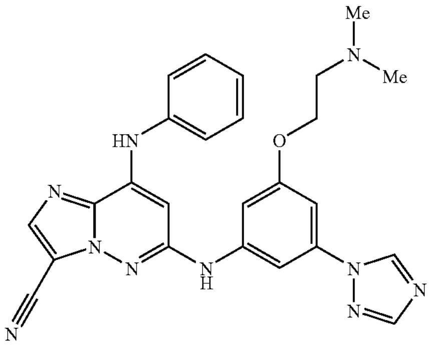 | 8-Anilino-6-((3-(2-(dimethylamino)ethoxy)-5-(1H-1,2,4-triazol-1-yl) phenyl)amino)imidazo[1,2-b]pyridazine-3-carbonitrile | 481.22 | 1.532[c] |
| 148 | 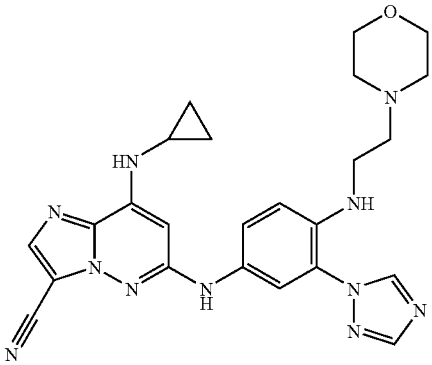 | 8-(Cyclopropylamino)-6-((4-((2-(4-morpholinyl)ethyl) amino)-3-(1H-1,2,4-triazol-1-yl)phenyl)amino)imidazo [1,2-b]pyridazine-3-carbonitrile | 486.22 | 1.310[c] |
| 149 | 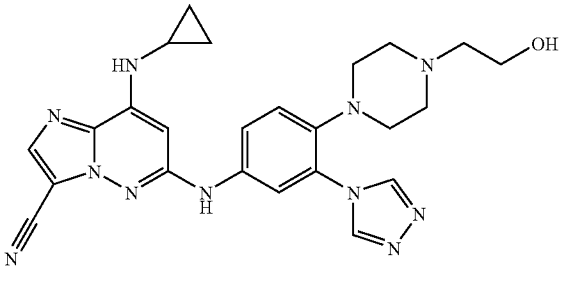 | 8-(Cyclopropylamino)-6-((4-(4-(2-hydroxyethyl)-1-piperazinyl)-3-(4H-1,2,4-triazol-4-yl)phenyl)amino) imidazo[1,2-b]pyridazine-3-carbonitrile | 486.10 | 2.825[a] |

TABLE 9-continued

| Example No. | Structure | Name | [M + H]+ | HPLC Retention Time (min.)* |
|---|---|---|---|---|
| 150 | 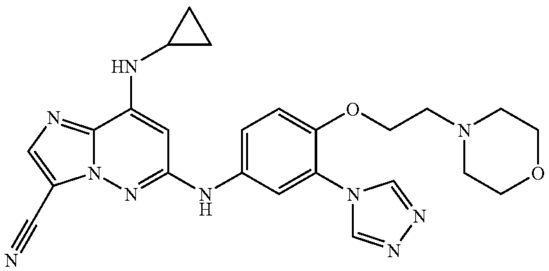 | 8-(Cyclopropylamino)-6-((4-(2-(4-morpholinyl)ethoxy)-3-(4H-1,2,4-triazol-4-yl)phenyl)amino)imidazo[1,2-b]pyridazine-3-carbonitrile | 487.10 | 2.836[a] |
| 151 | 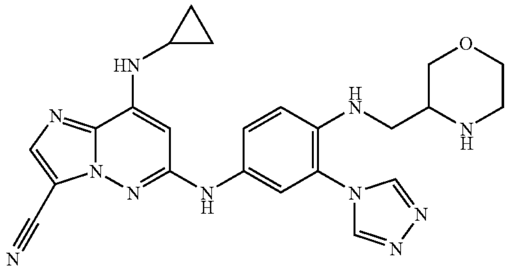 | 8-(Cyclopropylamino)-6-((4-((3-morpholinylmethyl)amino)-3-(4H-1,2,4-triazol-4-yl)phenyl)amino)imidazo[1,2-b]pyridazine-3-carbonitrile | 472.00 | 2.910[a] |
| 152 | 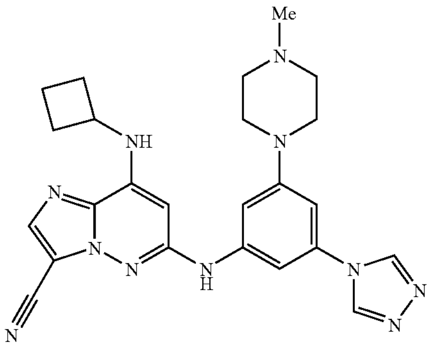 | 8-(Cyclobutylamino)-6-((3-(4-methyl-1-piperazinyl)-5-(4H-1,2,4-triazol-4-yl)phenyl)amino)imidazo[1,2-b]pyridazine-3-carbonitrile | 470.3 | 1.45[c] |
| 153 | 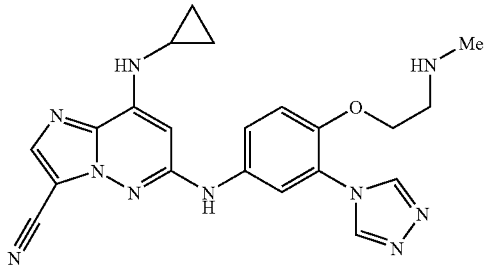 | 8-(Cyclopropylamino)-6-((4-(2-(methylamino)ethoxy)-3-(4H-1,2,4-triazol-4-yl)phenyl)amino)imidazo[1,2-b]pyridazine-3-carbonitrile | 431.00 | 2.798[a] |
| 154 | 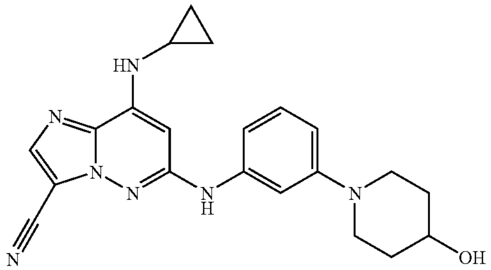 | 8-(Cyclopropylamino)-6-((3-(4-hydroxy-1-piperidinyl)phenyl)amino)imidazo[1,2-b]pyridazine-3-carbonitrile | 390.10 | 2.243[b] |

TABLE 9-continued

| Example No. | Structure | Name | [M + H]+ | HPLC Retention Time (min.)* |
|---|---|---|---|---|
| 155 | 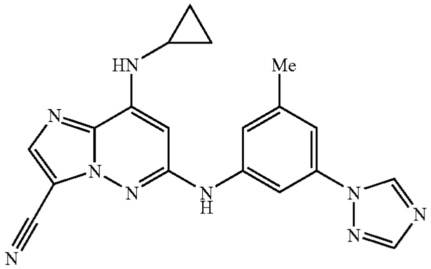 | 8-(Cyclopropylamino)-6-((3-methyl-5-(1H-1,2,4-triazol-1-yl)phenyl)amino)imidazo[1,2-b]pyridazine-3-carbonitrile | 372.14 | 1.808[c] |
| 156 | 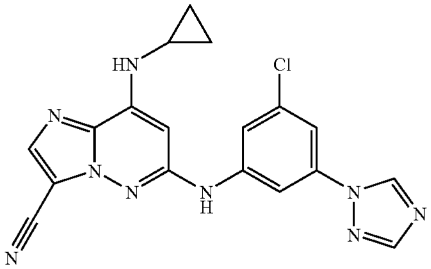 | 6-((3-Chloro-5-(1H-1,2,4-triazol-1-yl)phenyl)amino)-8-(cyclopropylamino)imidazo[1,2-b]pyridazine-3-carbonitrile | 392.05 | 1.910[c] |
| 157 | 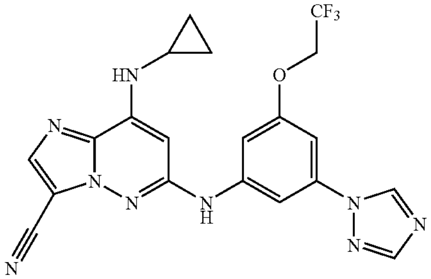 | 8-(Cyclopropylamino)-6-((3-(1H-1,2,4-triazol-1-yl)-5-(2,2,2-trifluoroethoxy)phenyl)amino)imidazo[1,2-b]pyridazine-3-carbonitrile | 456.12 | 1.928[c] |
| 158 | 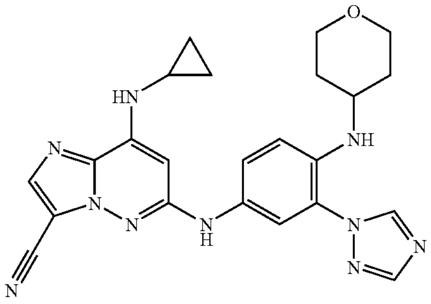 | 8-(Cyclopropylamino)-6-((4-(tetrahydro-2H-pyran-4-ylamino)-3-(1H-1,2,4-triazol-1-yl)phenyl)amino)imidazo[1,2-b]pyridazine-3-carbonitrile | 457.15 | 1.623[c] |
| 159 | 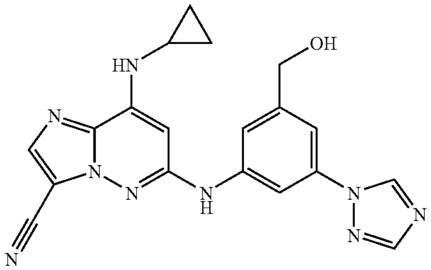 | 8-(Cyclopropylamino)-6-((3-(hydroxymethyl)-5-(1H-1,2,4-triazol-1-yl)phenyl)amino)imidazo[1,2-b]pyridazine-3-carbonitrile | 388.13 | 1.533[c] |

TABLE 9-continued

| Example No. | Structure | Name | [M + H]$^+$ | HPLC Retention Time (min.)* |
|---|---|---|---|---|
| 160 | 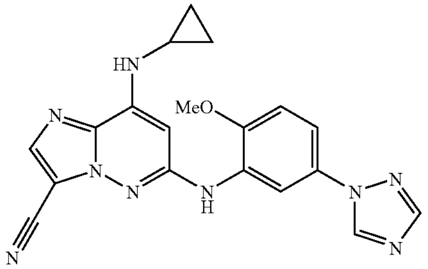 | 8-(Cyclopropylamino)-6-((2-methoxy-5-(1H-1,2,4-triazol-1-yl)phenyl)amino)imidazo[1,2-b]pyridazine-3-carbonitrile | 388.00 | 3.083[b] |
| 161 | 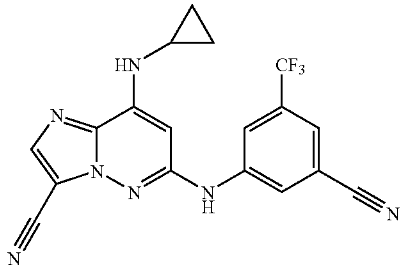 | 6-((3-Cyano-5-(trifluoromethyl)phenyl)amino)-8-(cyclopropylamino)imidazo[1,2-b]pyridazine-3-carbonitrile | 384 | 3.430[b] |
| 162 | 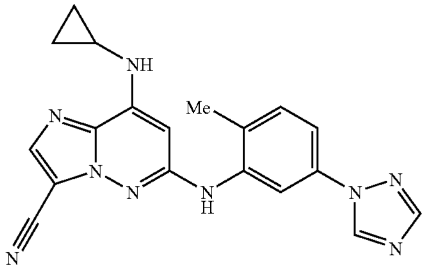 | 8-(Cyclopropylamino)-6-((2-methyl-5-(1H-1,2,4-triazol-1-yl)phenyl)amino)imidazo[1,2-b]pyridazine-3-carbonitrile | 372.20 | 1.72[c] |
| 163 | 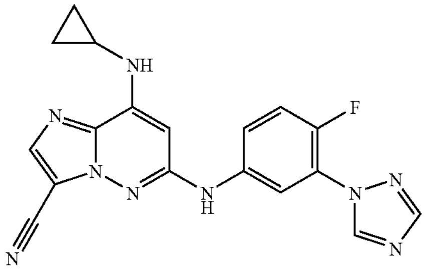 | 8-(Cyclopropylamino)-6-((4-fluoro-3-(1H-1,2,4-triazol-1-yl)phenyl)amino)imidazo[1,2-b]pyridazine-3-carbonitrile | 376.09 | 1.68[c] |
| 164 | 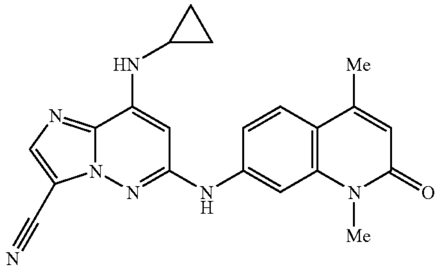 | 8-(Cyclopropylamino)-6-((1,4-dimethyl-2-oxo-1,2-dihydro-7-quinolinyl)amino)imidazo[1,2-b]pyridazine-3-carbonitrile | 386.00 | 4.170[a] |

TABLE 9-continued

| Example No. | Structure | Name | [M + H]+ | HPLC Retention Time (min.)* |
|---|---|---|---|---|
| 165 | 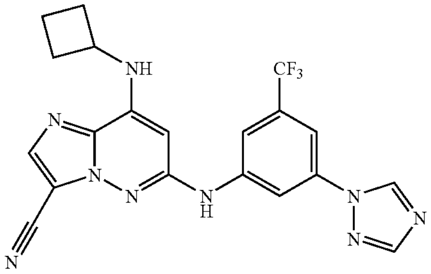 | 8-(Cyclobutylamino)-6-((3-(1H-1,2,4-triazol-1-yl)-5-(trifluoromethyl)phenyl) amino)imidazo[1,2-b]pyridazine-3-carbonitrile | 440.09 | 1.983[c] |
| 166 | 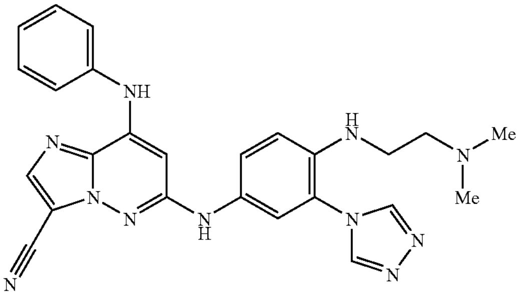 | 8-Anilino-6-((4-((2-(dimethylamino)ethyl) amino)-3-(4H-1,2,4-triazol-4-yl)phenyl)amino)imidazo [1,2-b]pyridazine-3-carbonitrile | 480.19 | 1.46[c] |
| 167 | 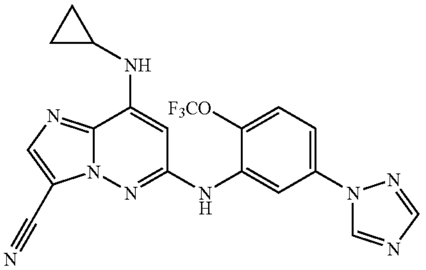 | 8-(Cyclopropylamino)-6-((5-(1H-1,2,4-triazol-1-yl)-2-(trifluoromethoxy)phenyl) amino)imidazo[1,2-b]pyridazine-3-carbonitrile | 441.99 | 1.91[c] |
| 168 | 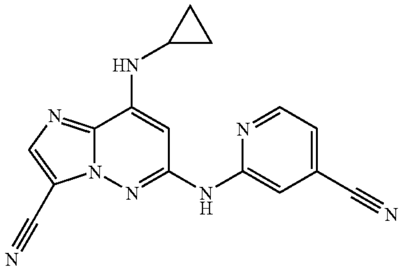 | 6-((4-Cyano-2-pyridinyl) amino)-8-(cyclopropylamino) imidazo[1,2-b]pyridazine-3-carbonitrile | 317.00 | 2.796[b] |
| 169 | 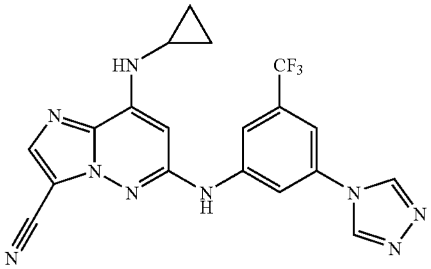 | 8-(Cyclopropylamino)-6-((3-(4H-1,2,4-triazol-4-yl)-5-(trifluoromethyl)phenyl) amino)imidazo[1,2-b]pyridazine-3-carbonitrile | 425.90 | 3.073[b] |

TABLE 9-continued

| Example No. | Structure | Name | [M + H]+ | HPLC Retention Time (min.)* |
|---|---|---|---|---|
| 170 | 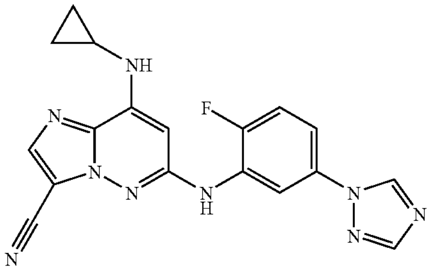 | 8-(Cyclopropylamino)-6-((2-fluoro-5-(1H-1,2,4-triazol-1-yl)phenyl)amino)imidazo[1,2-b]pyridazine-3-carbonitrile | 376.02 | 1.760[c] |
| 171 | 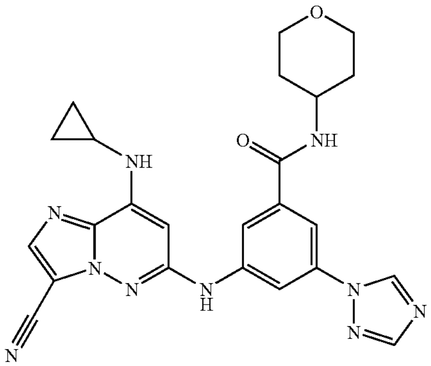 | 3-((3-Cyano-8-(cyclopropylamino)imidazo[1,2-b]pyridazin-6-yl)amino)-N-(tetrahydro-2H-pyran-4-yl)-5-(1H-1,2,4-triazol-1-yl)benzamide | 485.14 | 1.705[c] |
| 172 | 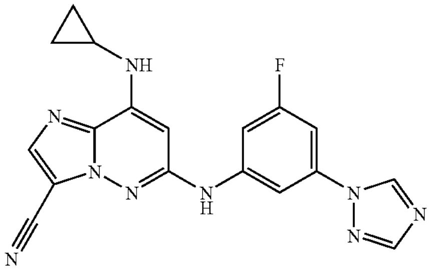 | 8-(Cyclopropylamino)-6-((3-fluoro-5-(1H-1,2,4-triazol-1-yl)phenyl)amino)imidazo[1,2-b]pyridazine-3-carbonitrile | 376.03 | 1.832[c] |
| 173 | 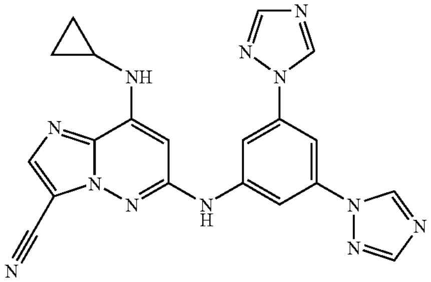 | 8-(Cyclopropylamino)-6-((3,5-di-1H-1,2,4-triazol-1-ylphenyl)amino)imidazo[1,2-b]pyridazine-3-carbonitrile | 425.05 | 1.757[c] |
| 174 | 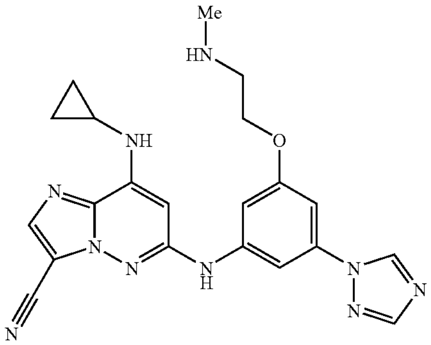 | 8-(Cyclopropylamino)-6-((3-(2-(methylamino)ethoxy)-5-(1H-1,2,4-triazol-1-yl)phenyl)amino)imidazo[1,2-b]pyridazine-3-carbonitrile | 431.13 | 1.377[c] |

TABLE 9-continued

| Example No. | Structure | Name | [M + H]+ | HPLC Retention Time (min.)* |
|---|---|---|---|---|
| 175 | 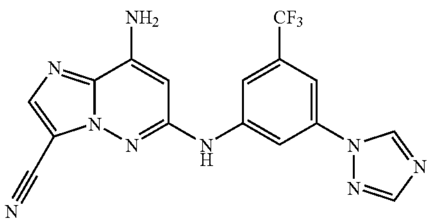 | 8-Amino-6-((3-(1H-1,2,4-triazol-1-yl)-5-(trifluoromethyl)phenyl) amino)imidazo[1,2-b]pyridazine-3-carbonitrile | 385.99 | 1.75[c] |
| 176 | 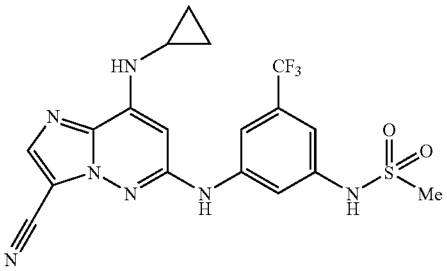 | N-(3-((3-Cyano-8-(cyclopropylamino)imidazo [1,2-b]pyridazin-6-yl) amino)-5-(trifluoromethyl) phenyl)methanesulfonamide | 451.90 | 9.139[h] |
| 177 | 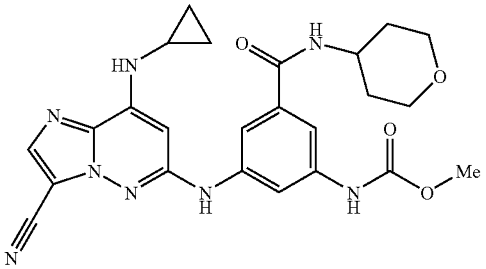 | Methyl (3-((3-cyano-8-(cyclopropylamino)imidazo [1,2-b]pyridazin-6-yl) amino)-5-(tetrahydro-2H-pyran-4-ylcarbamoyl)phenyl) carbamate | 491.00 | 3.690[a] |
| 178 | 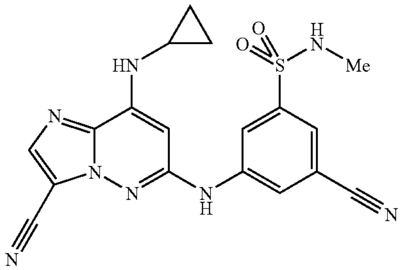 | 3-Cyano-5-((3-cyano-8-(cyclopropylamino)imidazo [1,2-b]pyridazin-6-yl) amino)-N-methylbenzenesulfonamide | 408.90 | 2.800[b] |
| 179 | 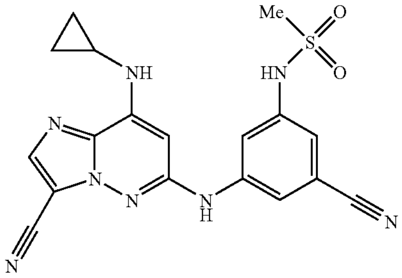 | N-(3-Cyano-5-((3-cyano-8-(cyclopropylamino)imidazo [1,2-b]pyridazin-6-yl)amino) phenyl)methanesulfonamide | 409.00 | 2.773[b] |

TABLE 9-continued

| Example No. | Structure | Name | [M + H]+ | HPLC Retention Time (min.)* |
|---|---|---|---|---|
| 180 | 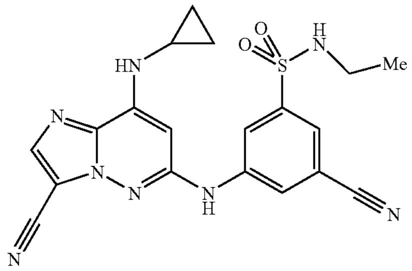 | 3-Cyano-5-((3-cyano-8-(cyclopropylamino)imidazo[1,2-b]pyridazin-6-yl)amino)-N-ethylbenzenesulfonamide | 422.90 | 2.925[b] |
| 181 | 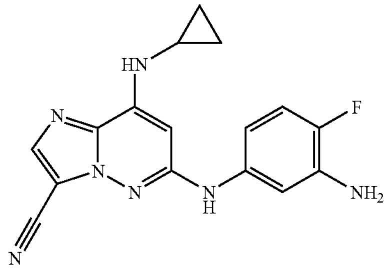 | 6-((3-Amino-4-fluorophenyl)amino)-8-(cyclopropylamino)imidazo[1,2-b]pyridazine-3-carbonitrile | 324.00 | 3.386[a] |
| 182 | 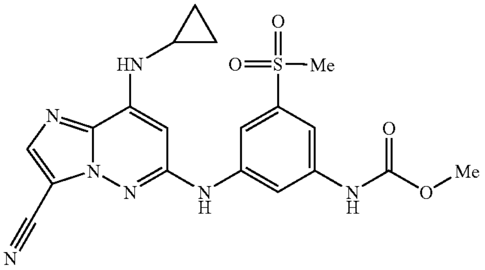 | Methyl (3-((3-cyano-8-(cyclopropylamino)imidazo[1,2-b]pyridazin-6-yl)amino)-5-(methylsulfonyl)phenyl)carbamate | 442.00 | 3.561[a] |
| 183 | 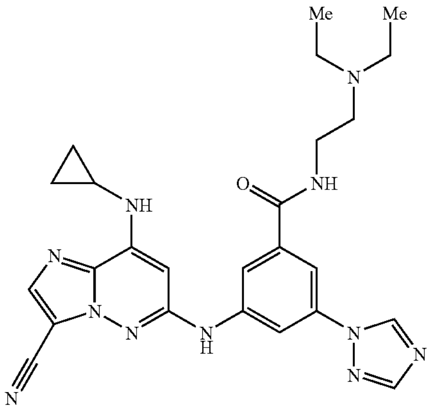 | 3-((3-Cyano-8-(cyclopropylamino)imidazo[1,2-b]pyridazin-6-yl)amino)-N-(2-(diethylamino)ethyl)-5-(1H-1,2,4-triazol-1-yl)benzamide | 500.19 | 1.410[c] |
| 184 | 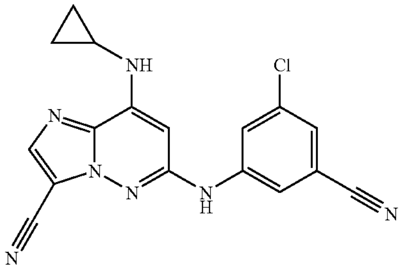 | 6-((3-Chloro-5-cyanophenyl)amino)-8-(cyclopropylamino)imidazo[1,2-b]pyridazine-3-carbonitrile | 350.08 | 1.967[c] |

TABLE 9-continued

| Example No. | Structure | Name | [M + H]+ | HPLC Retention Time (min.)* |
|---|---|---|---|---|
| 185 | 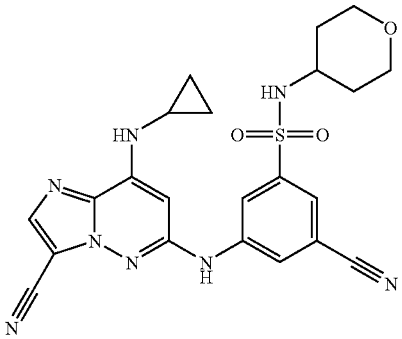 | 3-Cyano-5-((3-cyano-8-(cyclopropylamino)imidazo[1,2-b]pyridazin-6-yl)amino)-N-(tetrahydro-2H-pyran-4-yl)benzenesulfonamide | 479.00 | 2.850[b] |
| 186 | 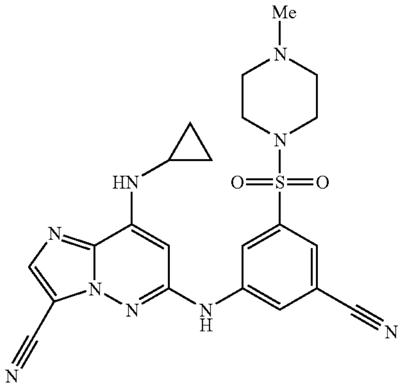 | 6-((3-Cyano-5-((4-methyl-1-piperazinyl)sulfonyl)phenyl)amino)-8-(cyclopropylamino)imidazo[1,2-b]pyridazine-3-carbonitrile | 478.00 | 2.661[b] |
| 187 | 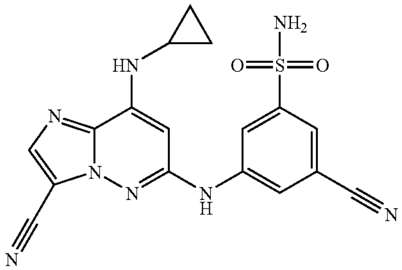 | 3-Cyano-5-((3-cyano-8-(cyclopropylamino)imidazo[1,2-b]pyridazin-6-yl)amino)benzenesulfonamide | 395.00 | 2.562[b] |
| 188 | 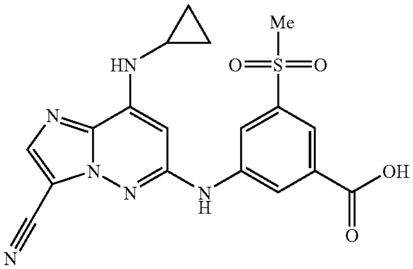 | 3-((3-Cyano-8-(cyclopropylamino)imidazo[1,2-b]pyridazin-6-yl)amino)-5-(methylsulfonyl)benzoic acid | 413 | 2.626[b] |
| 189 | 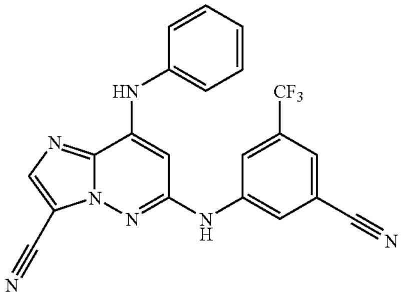 | 8-Anilino-6-((3-cyano-5-(trifluoromethyl)phenyl)amino)imidazo[1,2-b]pyridazine-3-carbonitrile | 420.00 | 4.460[a] |

TABLE 9-continued

| Example No. | Structure | Name | [M + H]+ | HPLC Retention Time (min.)* |
|---|---|---|---|---|
| 190 | 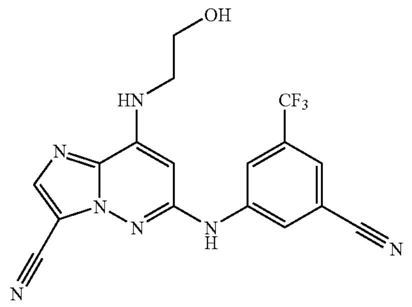 | 6-((3-Cyano-5-(trifluoromethyl)phenyl)amino)-8-((2-hydroxyethyl)amino)imidazo[1,2-b]pyridazine-3-carbonitrile | 388.00 | 3.958[a] |
| 191 | 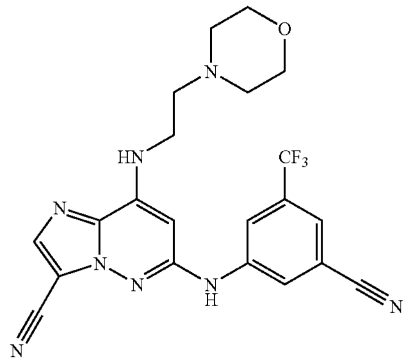 | 6-((3-Cyano-5-(trifluoromethyl)phenyl)amino)-8-((2-(4-morpholinyl)ethyl)amino)imidazo[1,2-b]pyridazine-3-carbonitrile | 457.00 | 3.376[a] |
| 192 | 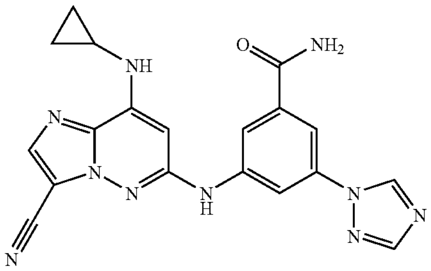 | 3-((3-Cyano-8-(cyclopropylamino)imidazo[1,2-b]pyridazin-6-yl)amino)-5-(1H-1,2,4-triazol-1-yl)benzamide | 401.14 | 1.700[c] |
| 193 | 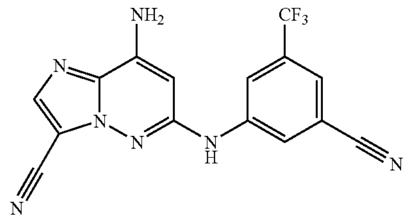 | 8-Amino-6-((3-cyano-5-(trifluoromethyl)phenyl)amino)imidazo[1,2-b]pyridazine-3-carbonitrile | 344.00 | 0.900[c] |
| 194 | 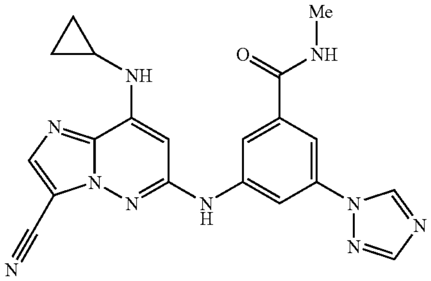 | 3-((3-Cyano-8-(cyclopropylamino)imidazo[1,2-b]pyridazin-6-yl)amino)-N-methyl-5-(1H-1,2,4-triazol-1-yl)benzamide | 415.13 | 1.975[c] |

TABLE 9-continued

| Example No. | Structure | Name | [M + H]+ | HPLC Retention Time (min.)* |
|---|---|---|---|---|
| 195 | 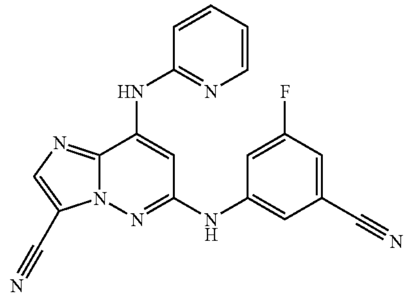 | 6-((3-Cyano-5-fluorophenyl) amino)-8-(2-pyridinylamino) imidazo[1,2-b]pyridazine-3-carbonitrile | 371 | 3.423[b] |
| 196 | 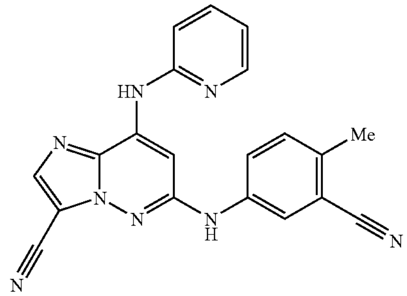 | 6-((3-Cyano-4-methylphenyl)amino)-8-(2-pyridinylamino)imidazo[1,2-b]pyridazine-3-carbonitrile | 367 | 3.396[b] |
| 197 | 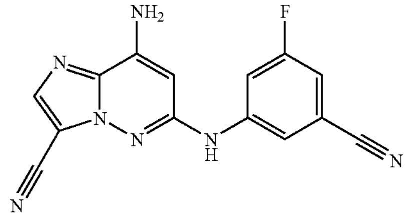 | 8-Amino-6-((3-cyano-5-fluorophenyl)amino)imidazo [1,2-b]pyridazine-3-carbonitrile | 294 | 2.831[b] |
| 198 | 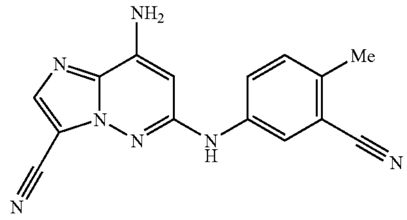 | 8-Amino-6-((3-cyano-4-methylphenyl)amino) imidazo[1,2-b]pyridazine-3-carbonitrile | 290 | 2.813[b] |
| 199 | 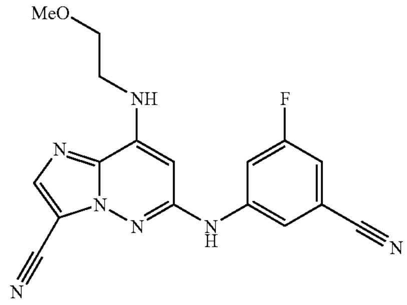 | 6-((3-Cyano-5-fluorophenyl) amino)-8-((2-methoxyethyl) amino)imidazo[1,2-b]pyridazine-3-carbonitrile | 352 | 3.068[b] |

TABLE 9-continued

| Example No. | Structure | Name | [M + H]+ | HPLC Retention Time (min.)* |
|---|---|---|---|---|
| 200 | 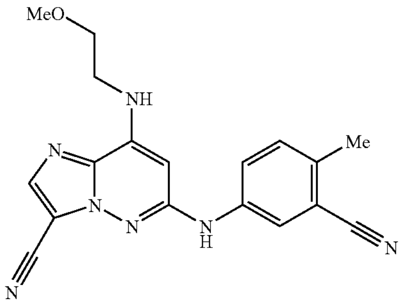 | 6-((3-Cyano-4-methylphenyl)amino)-8-((2-methoxyethyl)amino) imidazo[1,2-b]pyridazine-3-carbonitrile | 348 | 3.06[b] |
| 201 | 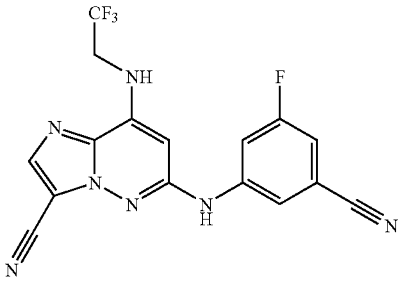 | 6-((3-Cyano-5-fluorophenyl) amino)-8-((2,2,2-trifluoroethyl)amino)imidazo [1,2-b]pyridazine-3-carbonitrile | 376.00 | 2.100[c] |
| 202 | 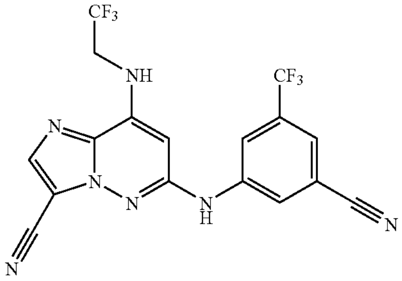 | 6-((3-Cyano-5-(trifluoromethyl)phenyl) amino)-8-((2,2,2-trifluoroethyl)amino)imidazo [1,2-b]pyridazine-3-carbonitrile | 426.20 | 1.000[e] |
| 203 | 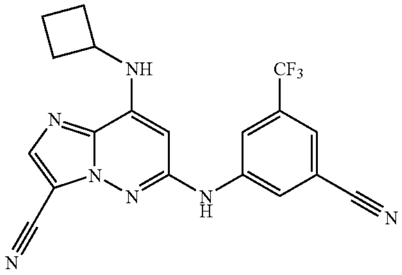 | 6-((3-Cyano-5-(trifluoromethyl)phenyl) amino)-8-(cyclobutylamino) imidazo[1,2-b]pyridazine-3-carbonitrile | 398.10 | 2.270[c] |
| 204 | 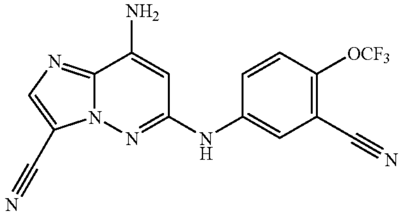 | 8-Amino-6-((3-cyano-4-(trifluoromethoxy)phenyl) amino)imidazo[1,2-b]pyridazine-3-carbonitrile | 360 | 3.135[b] |

TABLE 9-continued

| Example No. | Structure | Name | [M + H]+ | HPLC Retention Time (min.)* |
| --- | --- | --- | --- | --- |
| 205 | 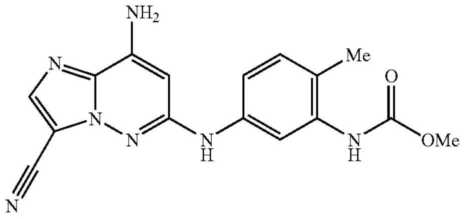 | Methyl (5-((8-amino-3-cyanoimidazo[1,2-b]pyridazin-6-yl)amino)-2-methylphenyl)carbamate | 338 | 2.377[b] |
| 206 | 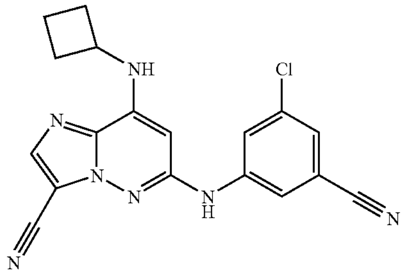 | 6-((3-Chloro-5-cyanophenyl)amino)-8-(cyclobutylamino)imidazo[1,2-b]pyridazine-3-carbonitrile | 364.30 | 1.030[e] |
| 207 | 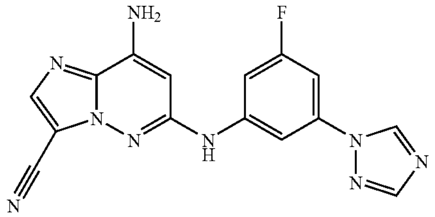 | 8-Amino-6-((3-fluoro-5-(1H-1,2,4-triazol-1-yl)phenyl) amino)imidazo[1,2-b]pyridazine-3-carbonitrile | 336.30 | 0.770[e] |
| 208 | 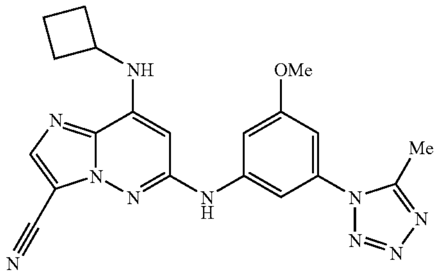 | 8-(Cyclobutylamino)-6-((3-methoxy-5-(5-methyl-1H-tetrazol-1-yl)phenyl)amino) imidazo[1,2-b]pyridazine-3-carbonitrile | 417.30 | 0.930[e] |
| 209 | 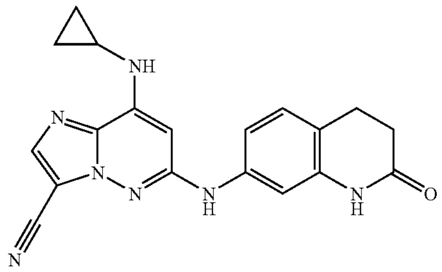 | 8-(Cyclopropylamino)-6-((2-oxo-1,2,3,4-tetrahydro-7-quinolinyl)amino)imidazo[1,2-b]pyridazine-3-carbonitrile | 360.14 | 1.69[c] |
| 210 | 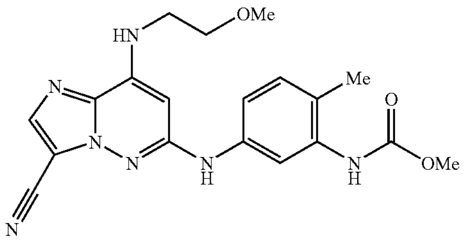 | Methyl (5-((3-cyano-8-((2-methoxyethyl)amino) imidazo[1,2-b]pyridazin-6-yl)amino)-2-methylphenyl) carbamate | 396 | 2.715[b] |

TABLE 9-continued

| Example No. | Structure | Name | [M + H]+ | HPLC Retention Time (min.)* |
|---|---|---|---|---|
| 211 | 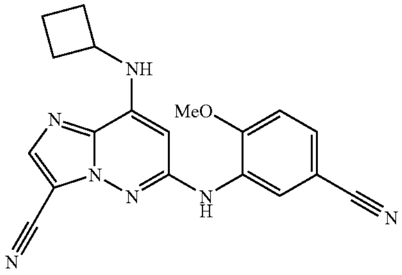 | 6-((5-Cyano-2-methoxyphenyl)amino)-8-(cyclobutylamino)imidazo[1,2-b]pyridazine-3-carbonitrile | 360.30 | 1.000[e] |
| 212 | 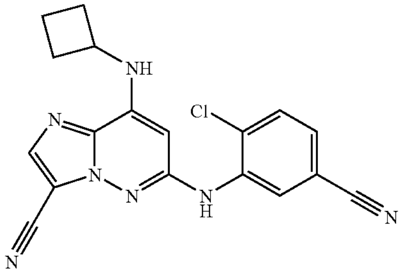 | 6-((2-Chloro-5-cyanophenyl) amino)-8-(cyclobutylamino) imidazo[1,2-b]pyridazine-3-carbonitrile | 364.30 | 1.030[e] |
| 213 | 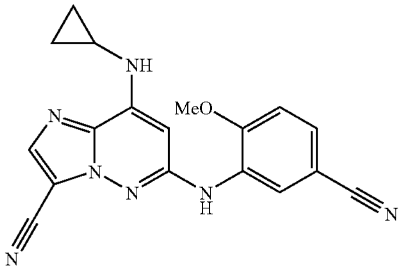 | 6-((5-Cyano-2-methoxyphenyl)amino)-8-(cyclopropylamino)imidazo [1,2-b]pyridazine-3-carbonitrile | 346.30 | 0.950[e] |
| 214 | 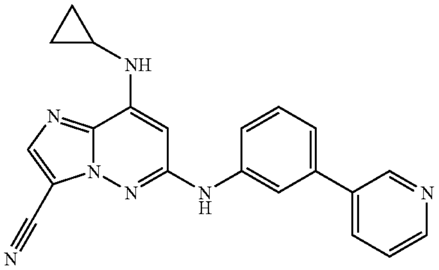 | 8-(Cyclopropylamino)-6-((3-(3-pyridinyl)phenyl)amino) imidazo[1,2-b]pyridazine-3-carbonitrile | 368.14 | 2.87[g] |
| 215 | 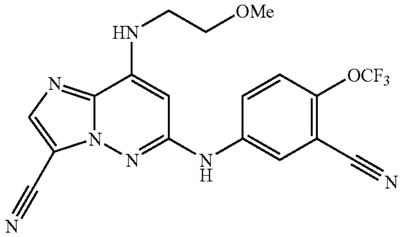 | 6-((3-Cyano-4-(trifluoromethoxy)phenyl) amino)-8-((2-methoxyethyl) amino)imidazo[1,2-b]pyridazine-3-carbonitrile | 418 | 3.321[b] |

TABLE 9-continued

| Example No. | Structure | Name | [M + H]+ | HPLC Retention Time (min.)* |
|---|---|---|---|---|
| 216 | 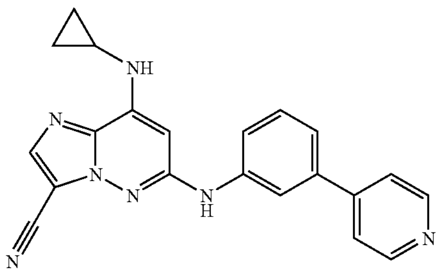 | 8-(Cyclopropylamino)-6-((3-(4-pyridinyl)phenyl)amino) imidazo[1,2-b]pyridazine-3-carbonitrile | 368.14 | 1.51[c] |
| 217 | 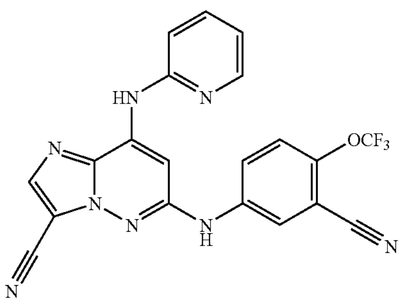 | 6-((3-Cyano-4-(trifluoromethoxy)phenyl) amino)-8-(2-pyridinylamino) imidazo[1,2-b]pyridazine-3-carbonitrile | 437 | 3.633[b] |
| 218 | 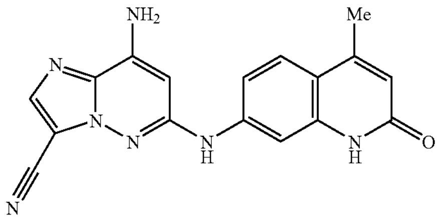 | 8-Amino-6-((4-methyl-2-oxo-1,2-dihydro-7-quinolinyl)amino)imidazo[1,2-b]pyridazine-3-carbonitrile | 332 | 2.681[b] |
| 219 | 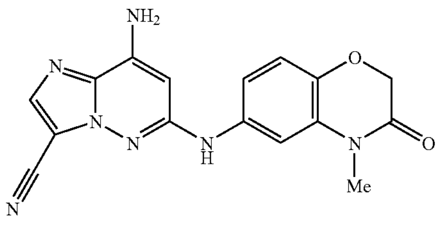 | 8-Amino-6-((4-methyl-3-oxo-3,4-dihydro-2H-1,4-benzoxazin-6-yl)amino) imidazo[1,2-b]pyridazine-3-carbonitrile | 336 | 2.725[b] |
| 220 | 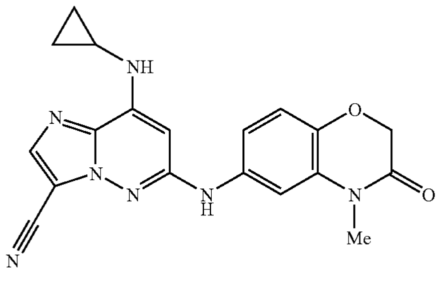 | 8-(Cyclopropylamino)-6-((4-methyl-3-oxo-3,4-dihydro-2H-1,4-benzoxazin-6-yl) amino)imidazo[1,2-b] pyridazine-3-carbonitrile | 376 | 3.17[b] |

TABLE 9-continued

| Example No. | Structure | Name | [M + H]$^+$ | HPLC Retention Time (min.)* |
|---|---|---|---|---|
| 221 | 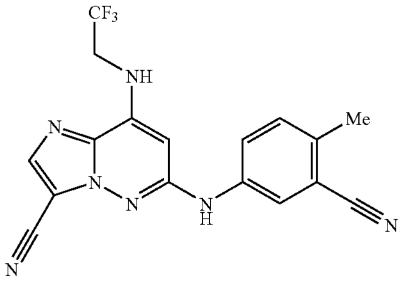 | 6-((3-Cyano-4-methylphenyl)amino)-8-((2,2,2-trifluoroethyl)amino) imidazo[1,2-b]pyridazine-3-carbonitrile | 372.10 | 1.070$^e$ |
| 222 | 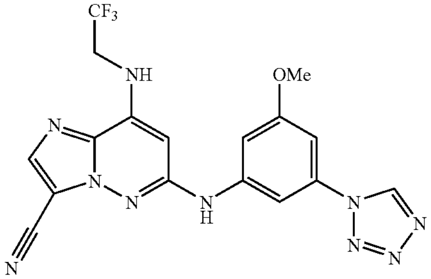 | 6-((3-Methoxy-5-(1H-tetrazol-1-yl)phenyl)amino)-8-((2,2,2-trifluoroethyl) amino)imidazo[1,2-b]pyridazine-3-carbonitrile | 431.10 | 1.010$^e$ |
| 223 | 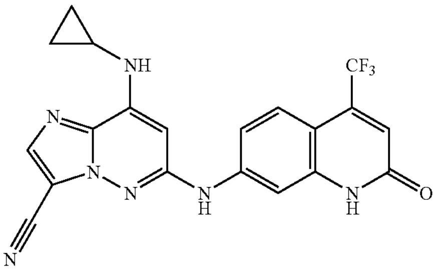 | 8-(Cyclopropylamino)-6-((2-oxo-4-(trifluoromethyl)-1,2-dihydro-7-quinolinyl)amino) imidazo[1,2-b]pyridazine-3-carbonitrile | 426.20 | 1.030$^e$ |
| 224 | 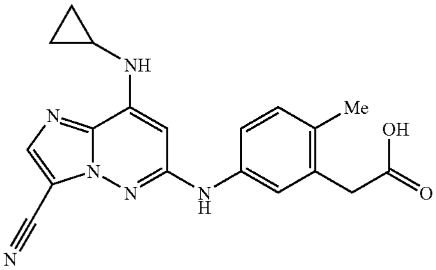 | (5-((3-Cyano-8-(cyclopropylamino)imidazo [1,2-b]pyridazin-6-yl) amino)-2-methylphenyl) acetic acid | 363 | 2.993$^e$ |
| 225 | 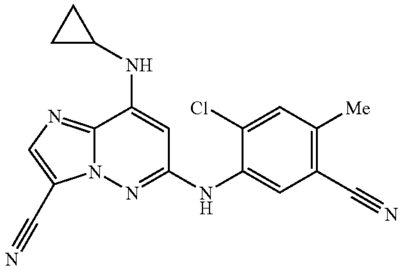 | 6-((2-Chloro-5-cyano-4-methylphenyl)amino)-8-(cyclopropylamino)imidazo [1,2-b]pyridazine-3-carbonitrile | 364 | 3.296$^e$ |

TABLE 9-continued

| Example No. | Structure | Name | [M + H]+ | HPLC Retention Time (min.)* |
|---|---|---|---|---|
| 226 | 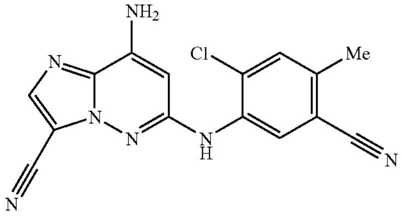 | 8-Amino-6-((2-chloro-5-cyano-4-methylphenyl) amino)imidazo[1,2-b]pyridazine-3-carbonitrile | 324 | 3.873[e] |
| 227 | 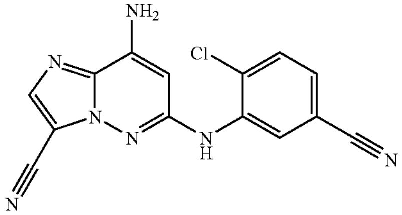 | 8-Amino-6-((2-chloro-5-cyanophenyl)amino)imidazo [1,2-b]pyridazine-3-carbonitrile | 310 | 2.678[e] |
| 228 | 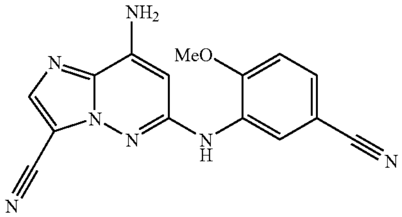 | 8-Amino-6-((5-cyano-2-methoxyphenyl)amino) imidazo[1,2-b]pyridazine-3-carbonitrile | 306 | 2.613[e] |
| 229 | 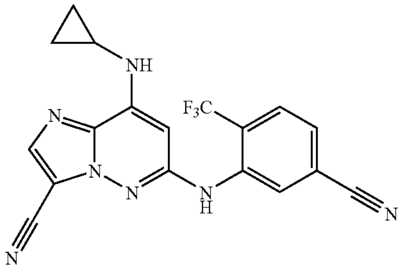 | 6-((5-Cyano-2-(trifluoromethyl)phenyl) amino)-8-(cyclopropylamino)imidazo [1,2-b]pyridazine-3-carbonitrile | 384.20 | 1.290[e] |
| 230 | 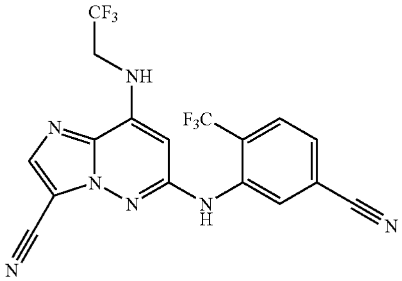 | 6-((5-Cyano-2-(trifluoromethyl)phenyl) amino)-8-((2,2,2-trifluoroethyl)amino) imidazo[1,2-b]pyridazine-3-carbonitrile | 426.10 | 1.280[e] |
| 231 | 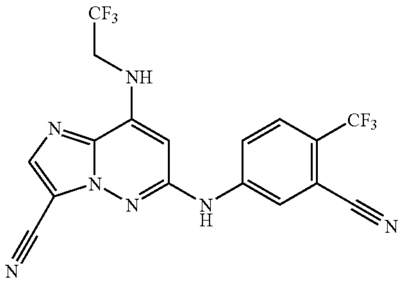 | 6-((3-Cyano-4-(trifluoromethyl)phenyl) amino)-8-((2,2,2-trifluoroethyl)amino)imidazo [1,2-b]pyridazine-3-carbonitrile | 426.10 | 1.090[e] |

TABLE 9-continued

| Example No. | Structure | Name | [M + H]+ | HPLC Retention Time (min.)* |
|---|---|---|---|---|
| 232 | 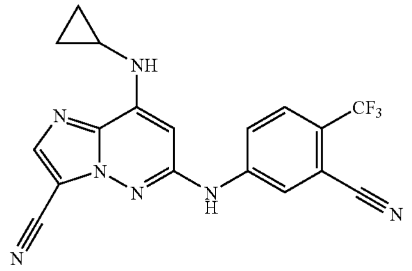 | 6-((3-Cyano-4-(trifluoromethyl)phenyl)amino)-8-(cyclopropylamino)imidazo[1,2-b]pyridazine-3-carbonitrile | 384.12 | 2.970[e] |
| 233 | 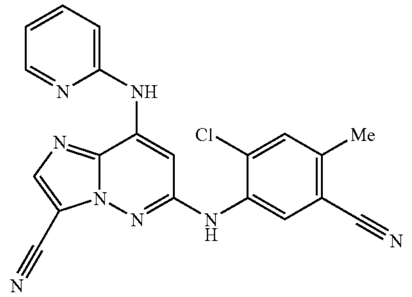 | 6-((2-Chloro-5-cyano-4-methylphenyl)amino)-8-(2-pyridinylamino)imidazo[1,2-b]pyridazine-3-carbonitrile | 401 | 3.228[b] |
| 234 | 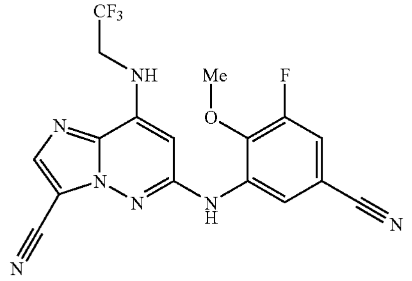 | 6-((5-Cyano-3-fluoro-2-methoxyphenyl)amino)-8-((2,2,2-trifluoroethyl)amino)imidazo[1,2-b]pyridazine-3-carbonitrile | 406.20 | 1.030[e] |
| 235 | 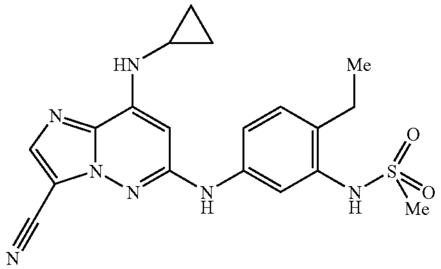 | N-(5-((3-Cyano-8-(cyclopropylamino)imidazo[1,2-b]pyridazin-6-yl)amino)-2-ethylphenyl)methanesulfonamide | 412 | 2.58[b] |
| 236 | 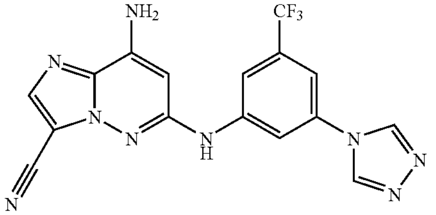 | 8-Amino-6-((3-(4H-1,2,4-triazol-4-yl)-5-(trifluoromethyl)phenyl)amino)imidazo[1,2-b]pyridazine-3-carbonitrile | 386 | 2.46[b] |

TABLE 9-continued

| Example No. | Structure | Name | [M + H]+ | HPLC Retention Time (min.)* |
|---|---|---|---|---|
| 237 | 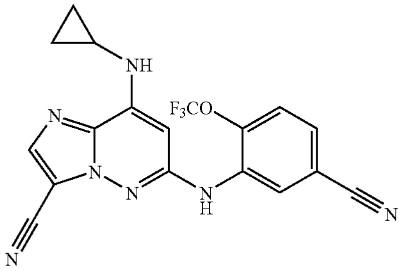 | 6-((5-Cyano-2-(trifluoromethoxy)phenyl) amino)-8-(cyclopropylamino)imidazo [1,2-b]pyridazine-3-carbonitrile | 400.20 | 1.150[e] |
| 238 | 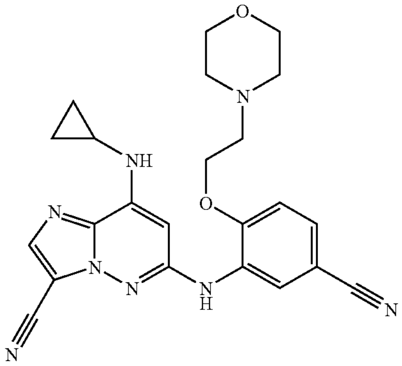 | 6-((5-Cyano-2-(2-(4-morpholinyl)ethoxy)phenyl) amino)-8-(cyclopropylamino) imidazo[1,2-b]pyridazine-3-carbonitrile | 445.30 | 0.870[e] |
| 239 | 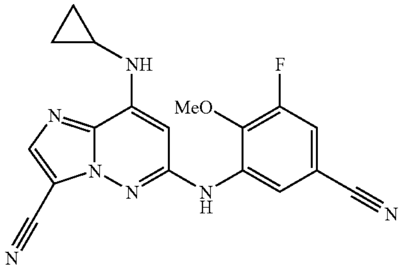 | 6-((5-Cyano-3-fluoro-2-methoxyphenyl)amino)-8-(cyclopropylamino)imidazo [1,2-b]pyridazine-3-carbonitrile | 364.20 | 0.970[e] |
| 240 | 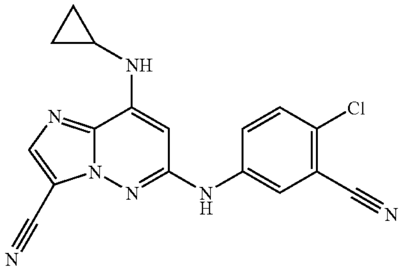 | 6-((4-Chloro-3-cyanophenyl)amino)-8-(cyclopropylamino)imidazo [1,2-b]pyridazine-3-carbonitrile | 350.90 | 1.91[c] |
| 241 | 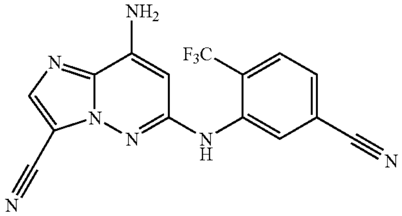 | 8-Amino-6-((5-cyano-2-(trifluoromethyl)phenyl) amino)imidazo[1,2-b]pyridazine-3-carbonitrile | 344.18 | 3.09[g] |

TABLE 9-continued

| Example No. | Structure | Name | [M + H]+ | HPLC Retention Time (min.)* |
|---|---|---|---|---|
| 242 | 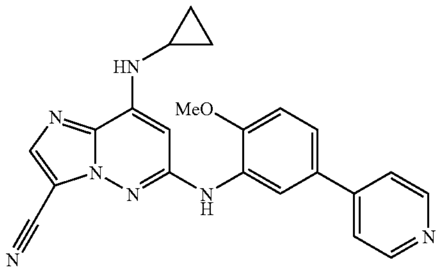 | 8-(Cyclopropylamino)-6-((2-methoxy-5-(4-pyridinyl) phenyl)amino)imidazo[1,2-b]pyridazine-3-carbonitrile | 398.22 | 1.59[c] |
| 243 | 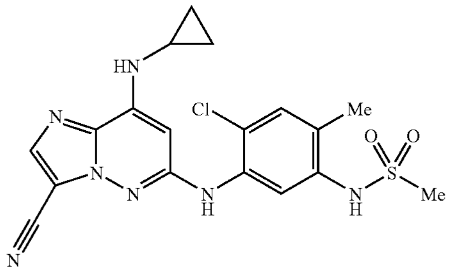 | N-(4-Chloro-5-((3-cyano-8-(cyclopropylamino)imidazo [1,2-b]pyridazin-6-yl) amino)-2-methylphenyl) methanesulfonamide | 432 | 2.67[b] |

*= HPLC conditions

[a]YMC S5 ODS 4.6 x 50 mm, 10-90% aqueous methanol containing 0.2% $H_3PO_4$, 4 min. gradient, monitored at 220 nm

[b]CHROMOLITH® column 4.6 x 50 mm eluting with 10-90% aqueous methanol over 4 min. containing 0.1% TFA, 4 mL/min, monitoring at 220 nm.

[c]PHENOMENEX® Luna 5 micron C18 4.6 x 30 mm, 0 to 100 B in 2 min. with 1 min. hold time, flow rate = 5 mL/min., detection at 254 nm, Solvent A: 10% methanol/90% water/0.1% TFA; Solvent B: 10% water/90% methanol/0.1% TFA

[d]YMC S5 ODS, 4.6 x 50 mm. 1 mL/min., 0-100% Water-Methanol 0.2% $H_3PO_4$, gradient over 15 min.

[e]BEH C18 2.1 x 50 mm, 1.7u, 0 to 100 B in 1 min. with 0.5 min. hold time, flow rate = 1 mL/min., detection at 254 nm, Solvent A: 100% water/0.1% TFA; Solvent B: 100% ACNl/0.1% TFA

[f]Column: PHENOMENEX® Luna C18 4.6 x 30 mm 3u, A10-90% aqueous methanol containing 0.1% TFA in 2 min; 4 mL/min flow

[g]Waters Sunfire C18 4.6 x 150 mm 5 micron. 1 mL/min., 0-100% Water-Methanol 0.2% $H_3PO_4$, gradient over 4 min.

[h]Sunfire-S5-C18 4.6 x 50 mm (4 min. grad) 10-90% aqueous methanol over 4 min. containing 0.1% TFA, 4 mL/min., monitoring at 220 nm.

[i]PHENOMENEX® Luna 4.6 x 50 mm S10 Solvent A = 5% ACN-95% H20-10 mM NH4Ac, Solvent B = 95% ACN-5% H20-10 mM NH4Ac, flow rate = 4 mL/min., detection at 220 nm, gradient over 4 min.

[j]PHENOMENEX® Luna 3.0 x 50 mm S10, 10-900% Water-Methanol 0.1% TFA, gradient over 2 min., monitoring at 254 nm.

Example 244

8-(Cyclopropylamino)-6-((4-(diethylamino)phenyl) amino)imidazo[1,2-b]pyridazine-3-carbonitrile

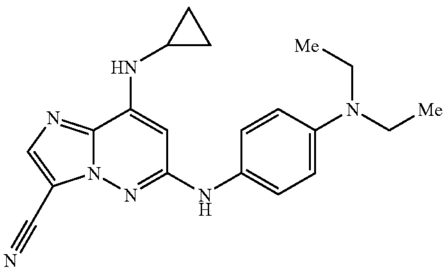

244A: 8-(Cyclopropyl(4-methoxybenzyl)amino)-6-(4-(diethylamino)phenylamino)imidazo[1,2-b]pyridazine-3-carbonitrile

244A

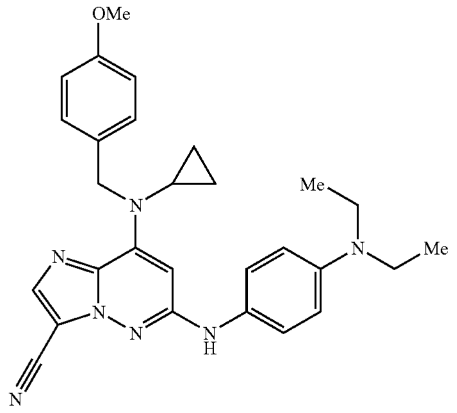

A microwave tube was charged with 1G (30 mg, 0.085 mmol), $N^1$,$N^1$-diethylbenzene-1,4-diamine (139 mg, 0.85 mmol), and NMP (1 mL). The mixture was irradiated in a microwave for three cycles of 15 min. (300W), 120° C. The crude reaction mixture was dissolved in a small amount of MeOH and purified by reversed phase HPLC (YMC ODS-A 5 um 30×250 mm, 10-90% aqueous methanol containing 0.1% TFA, 25 mL/min., 30 min. gradient, monitored at 220 nm) to afford 244A, (5 mg, 9.0% yield). HPLC: Rt=3.896 min. (YMC S5 ODS 4.6×50 mm, 10-90% aqueous methanol containing 0.2% $H_3PO_4$, 4 min. gradient, monitored at 220 nm). MS (ES): m/z=482.1 $[M+H]^+$.

Example 244

8-(Cyclopropylamino)-6-((4-(diethylamino)phenyl)amino)imidazo[1,2-b]pyridazine-3-carbonitrile

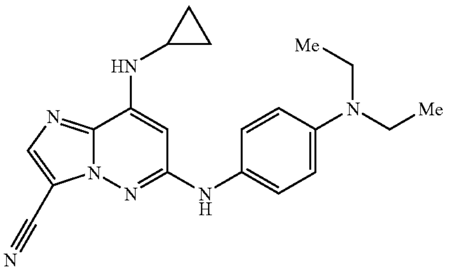

A solution of 244A (5 mg, 10.38 μmol) in DCM (1 mL) was treated with TFA (1 mL, 12.9 mmol) and stirred at room temperature for three hours. The reaction mixture was concentrated and dissolved in a small amount of MeOH and purified by reversed phase HPLC (YMC ODS-A 5 um 30×250 mm, 10-90% aqueous methanol containing 0.1% TFA, 25 mL/min., 20 min. gradient, monitored at 220 nm) to give Example 244, (1.2 mg, 22.12% yield). HPLC: Rt=3.178 min. (YMC S5 ODS 4.6×50 mm, 10-90% aqueous methanol containing 0.2% $H_3PO_4$, 4 min. gradient, monitored at 220 nm). MS (ES): m/z=362.1 $[M+H]^+$. $^1$H NMR (400 MHz, DMSO-$d_6$) δ ppm 11.09-11.33 (1H, m), 9.70 (1H, s), 8.15 (1H, s), 7.82-8.05 (2H, m), 7.51-7.67 (2H, m), 6.24 (1H, s), 1.01 (6H, t, J=6.80 Hz), 0.72-0.86 (2H, m, J=5.54 Hz), 0.53-0.72 (2H, m, J=2.77 Hz).

Example 245

8-(Cyclopropylamino)-6-((3-((2-(dimethylamino)ethyl)amino)-5-(4H-1,2,4-triazol-4-yl)phenyl)amino)imidazo[1,2-b]pyridazine-3-carbonitrile

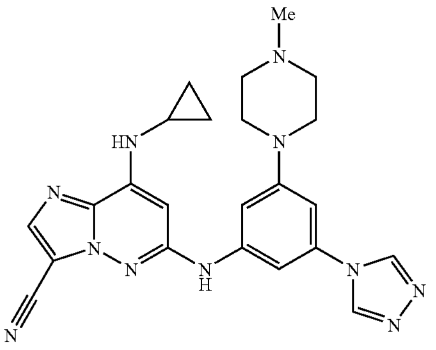

A mixture of Example 36 (30 mg, 0.090 mmol) and 1-methylpiperazine (100 μL) in NMP (1 mL) was heated in a microwave at 160° C. for 1 hour and 15 min. The reaction mixture was purified by prep HPLC. The fractions were concentrated, diluted with saturated aqueous $NaHCO_3$ and extracted with EtOAc. The organic phase was dried with $Na_2SO_4$, filtered, concentrated, and purified by flash chromatography, silica gel (4 g, stepwise gradient from 100% dichloromethane to 10% methanol/dichloromethane) to give Example 245 (8.0 mg, 21% yield) as a white solid. HPLC: Rt=2.608 min. (CHROMOLITH® column 4.6×50 mm eluting with 10-90% aqueous methanol over 4 min. containing 0.1% TFA, 4 mL/min., monitoring at 220 nm). MS (ES): m/z=414 $[M+H]^+$.

Example 246

6-((3-Cyano-5-(4-morpholinyl)phenyl)amino)-8-(cyclopropylamino)imidazo[1,2-b]pyridazine-3-carbonitrile

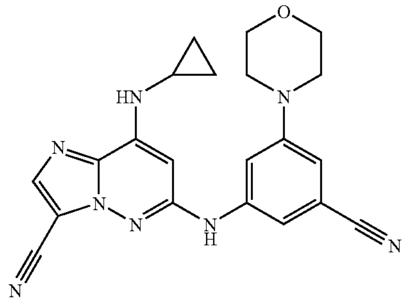

Example 246 was prepared from Example 36 and morpholine following the procedure employed for the preparation of Example 245. HPLC: Rt=3.466 min. (CHROMOLITH® column 4.6×50 mm eluting with 10-90% aqueous methanol over 4 min. containing 0.1% TFA, 4 mL/min., monitoring at 220 nm). MS (ES): m/z=401 $[M+H]^+$.

Example 247

6-((3-Cyano-4-(4-morpholinyl)phenyl)amino)-8-(cyclopropylamino)imidazo[1,2-b]pyridazine-3-carbonitrile

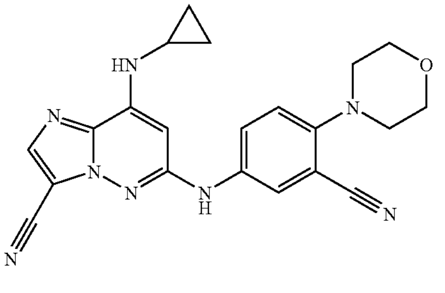

Example 247 was prepared from Example 25 and morpholine following the procedure employed for the preparation of Example 245. HPLC: Rt=3.188 min. (CHROMOLITH® column 4.6×50 mm eluting with 10-90% aqueous methanol over 4 min. containing 0.1% TFA, 4 mL/min., monitoring at 220 nm). MS (ES): m/z=401 $[M+H]^+$. $^1$H NMR (400 MHz, DMSO-$d_6$) δ ppm 9.52 (1H, s), 8.21 (1H, d, J=2.77 Hz), 8.14 (1H, s), 7.93 (1H, s), 7.77 (1H, dd, J=8.94, 2.64 Hz), 7.20 (1H, d, J=9.07 Hz), 6.18 (1H, s), 3.70-3.82 (4H, m), 3.03-3.11 (4H, m), 2.51-2.59 (1H, m), 0.76-0.86 (2H, m), 0.62-0.71 (2H, m).

Example 248

6-((3-Cyano-4-(4-methyl-1-piperazinyl)phenyl)amino)-8-(cyclopropylamino)imidazo[1,2-b]pyridazine-3-carbonitrile

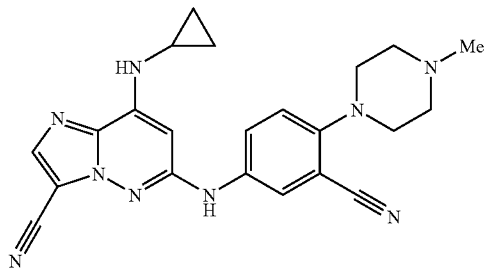

Example 248 was prepared from Example 25 and 1-methylpiperazine following the procedure employed for the preparation of Example 245. HPLC: Rt=3.188 min. (CHROMOLITH® column 4.6×50 mm eluting with 10-90% aqueous methanol over 4 min. containing 0.1% TFA, 4 mL/min., monitoring at 220 nm). MS (ES): m/z=401 $[M+H]^+$. $^1H$ NMR (400 MHz, DMSO-$d_6$) δ ppm 9.47 (1H, s), 8.19 (1H, d, J=2.77 Hz), 8.13 (1H, s), 7.92 (1H, s), 7.74 (1H, dd, J=9.06, 2.52 Hz), 7.18 (1H, d, J=9.06 Hz), 6.17 (1H, s), 3.01-3.13 (4H, m), 2.42-2.60 (5H, m), 2.25 (3H, s), 0.74-0.87 (2H, m), 0.61-0.71 (2H, m).

Example 249

N-(3-((3-Cyano-8-(cyclopropylamino)imidazo[1,2-b]pyridazin-6-yl)amino)phenyl)sulfamide

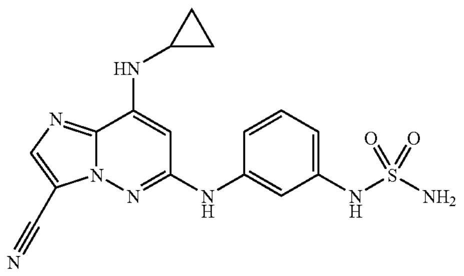

Sulfamoyl chloride (0.017 mL, 0.034 mmol; 2M solution in MeCN) was added to an ice-cold solution of 3A (0.0073 g, 0.017 mmol) and DIEA (6.59 μl, 0.038 mmol) in DCM (0.5 mL) under nitrogen. The resulting solution was stirred for 30 min. The reaction was quenched with water and partitioned between water and DCM, whereupon a precipitate formed. The reaction mixture was filtered, and the filtrate was concentrated. The residue was dissolved in DCM (0.2 mL) and treated with triethylsilane (10.9 μL, 0.069 mmol) and TFA (0.2 mL) and stirred at room temperature for 20 min. Volatiles were removed via a stream of nitrogen, and the solid was dissolved in DMF and purified via preparatory HPLC using an YMC ODS C-18 column (30×250 mm), 0%-100% B. Solvent B: (90% MeOH, 10% $H_2O$, 0.1% TFA). Solvent A: (10% MeOH, 90% $H_2O$, 0.1% TFA). Gradient, start % B=0, final % B=100, gradient time 180 min. (total run time 200 min.), flow rate 25 mL/min. (monitoring at 254 nm). The appropriate fractions were concentrated in vacuo, and the remaining residue was suspended in 2 mL 1:1 MeCN/1N HCl and lyophilized overnight, furnishing Example 249 (0.002 g, 28% yield) as a light yellow solid. HPLC: Rt=3.390 min. (YMC S5ODS-A column (4.6×50 mm). 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min., hold at 100% 1 min., flow rate 4 mL/min.). MS (ES): m/z=385.1 $[M+H]^+$. $^1H$ NMR (400 MHz, $CD_3OD$) δ ppm 7.99 (1H, s), 7.57 (1H, s), 7.44 (1H, d, J=1.76 Hz), 7.23 (1H, d, J=8.06 Hz), 6.84 (1H, d, J=1.51 Hz), 6.36 (1H, s), 3.68-3.74 (1H, m), 2.86 (1H, s), 2.62 (1H, s), 1.82-1.89 (1H, m), 1.39 (1H, s), 1.27-1.34 (1H, m), 0.85-0.94 (2H, m), 0.67 (2H, s).

Example 250

1-(3-((3-Cyano-8-(cyclopropylamino)imidazo[1,2-b]pyridazin-6-yl)amino)phenyl)-3-methylurea

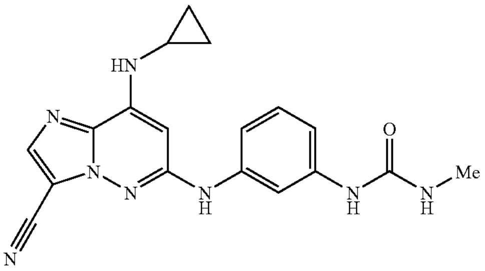

To a solution of 3A (0.065 g, 0.153 mmol) in DCM (1 mL) at 0° C. was added methylisocyanate (9.15 mg, 0.16 mmol). The reaction was slowly warmed to 22° C. and stirred overnight. The reaction mixture was filtered, and the solid was washed with cold DCM. The solid was then dissolved in THF and concentrated in vacuo, revealing a light tan solid, which was dissolved in a solution containing 1:1 TFA/DCM and 0.1 mL triethylsilane. The mixture was stirred at 22° C. for 30 min. The volatiles were removed via a stream of nitrogen, and the residue was taken up in EtOAc/DCM, whereupon a precipitate formed. The solid was filtered and washed with DCM and dried overnight. The resulting solid was taken up in 1N HCl (2 mL) and lyophilized overnight, furnishing Example 250 (0.041 g, 67% yield) as a white solid. HPLC: Rt=3.573 min. (YMC S5ODS-A column (4.6×50 mm). 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min., hold at 100% 1 min., flow rate 4 mL/min.). MS (ES): m/z=363.1 $[M+H]^+$. $^1H$ NMR (400 MHz, DMSO-$d_6$) δ ppm 9.24 (1H, s), 8.45 (1H, s), 8.11 (1H, s), 7.81 (1H, s), 7.62 (1H, dd, J=8.06, 1.26 Hz), 7.50 (1H, d, J=1.76 Hz), 7.12 (1H, t, J=8.18 Hz), 6.82-6.92 (1H, m), 6.29 (1H, s), 5.95-6.13 (1H, m), 2.60-2.67 (3H, m), 2.43-2.55 (1H, m), 0.73-0.83 (2H, m), 0.58-0.69 (2H, m).

Example 251

N-(5-((3-Cyano-8-((5-hydroxy-2-pyridinyl)amino) imidazo[1,2-b]pyridazin-6-yl)amino)-2-methylphenyl)acetamide

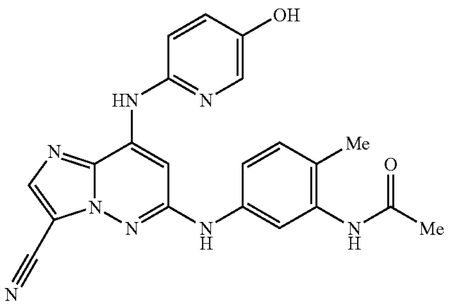

To a suspension of Example 5 (65 mg, 0.15 mmol) in DCM (4 mL) was added $BBr_3$ (1.0 M solution, 1.52 mL, 1.52 mmol) dropwise at room temperature under nitrogen, and the resulting suspension stirred at ambient temperature for 1 hour. An additional amount of $BBr_3$ (1.0 M solution, 0.5 mL, 0.5 mmol) was added and the mixture was stirred at ambient temperature for 18 hours. The reaction was quenched with water, and neutralized to pH 8 with 1 N NaOH. The resulting mixture was stirred at ambient temperature for 40 minutes, and the solid was collected by filtration, rinsed with water and air dried. The residue was purified by reverse phase HPLC, and lyophilized with 1.0 N HCl to give Example 251, (34.5 mg, 0.083 mmol, 54.8% yield). HPLC: Rt=3.428 min. (YMC S5 ODS (4.6×50 mm). 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min., hold at 100% 1 min., flow rate 4 mL/min.). MS (ES): m/z=415.0 $[M+H]^+$. $^1H$ NMR (400 MHz, DMSO-$d_6$) δ ppm 9.74 (1H, s), 9.37 (1H, s), 9.20 (1H, s), 8.16 (1H, s), 7.95 (1H, s), 7.91 (1H, d, J=2.76 Hz), 7.59-7.67 (2H, m), 7.32 (1H, d, J=9.04 Hz), 7.19 (1H, dd, J=8.78, 3.01 Hz), 7.07 (1H, d, J=8.28 Hz), 6.88-6.95 (1H, m).

Example 252

N-(5-((3-Cyano-8-((5-(2-hydroxyethoxy)-2-pyridinyl)amino)imidazo[1,2-b]pyridazin-6-yl)amino)-2-methylphenyl)acetamide

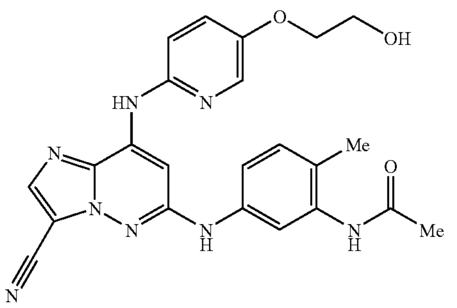

To a solution of Example 251 (15 mg, 0.036 mmol) in DMF (0.5 mL) was added 2-bromoethanol (0.013 mL, 0.18 mmol), followed by $K_2CO_3$ (20.01 mg, 0.145 mmol), and the resulting suspension was stirred at 100° C. overnight. The insoluble material was filtered off, and the mother liquor was purified by reverse phase HPLC. The appropriate fractions were concentrated. The residue was dissolved in a small amount of $CH_3CN$, diluted with 0.5 N HCl, and lyophilized to yield Example 252 (6.86 mg, 0.012 mmol, 33.2%). HPLC: Rt=3.481 min. (YMC S5 ODS column (4.6×50 mm). 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min., hold at 100% 1 min., flow rate 4 mL/min.). MS (ES): m/z=459.1 $[M+H]^+$. $^1H$ NMR (400 MHz, DMSO-$d_6$) δ ppm 9.94 (1H, s), 9.49 (1H, s), 9.29 (1H, s), 8.25 (1H, s), 8.05-8.12 (2H, m), 7.71 (2H, s), 7.50 (2H, d, J=1.76 Hz), 7.15 (1H, d, J=8.28 Hz), 4.06-4.10 (2H, m), 3.74 (2H, t, J=4.89 Hz), 3.51 (1H, s), 2.17 (3H, s), 2.07 (3H, s).

Example 253

3-(6-(3-Acetamido-4-methylphenylamino)-3-cyanoimidazo[1,2-b]pyridazin-8-ylamino)-N-(2-(dimethylamino)ethyl)benzamide

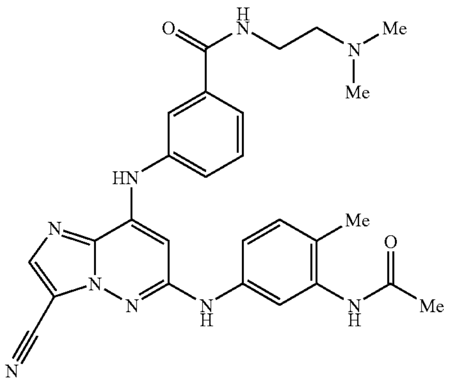

253A: tert-Butyl 3-(4-methoxybenzylamino)benzoate

253A

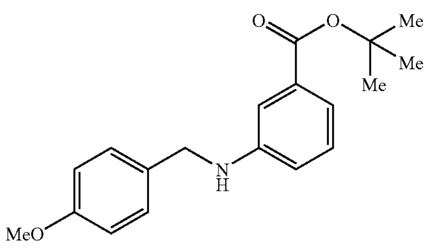

253A was prepared from 4-methoxybenzaldehyde and tert-butyl 3-aminobenzoate following the procedure as described in 4A. HPLC: Rt=3.82 min. (PHENOMENEX® Luna C18 4.6×30 mm 3 u, A10-90% aqueous methanol containing 0.1% TFA in 2 min; 4 mL/min flow). MS (ES): m/z=314.0 $[M+H]^+$.

253B: tert-Butyl 3-((6-chloro-3-cyanoimidazo[1,2-b]pyridazin-8-yl) (4-methoxybenzyl)amino)benzoate

253B

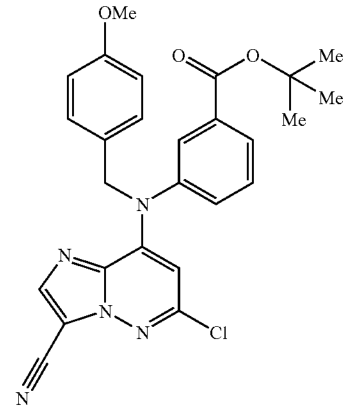

253B was prepared from 253A and a mixture of 1F following the procedure as described in 1G. HPLC: Rt=4.99 min. (PHENOMENEX® Luna C18 4.6×30 mm 3 u, A10-90% aqueous methanol containing 0.1% TFA in 2 min; 4 mL/min flow). MS (ES): m/z=490.1 [M+H]$^+$.

253C: 3-((6-Chloro-3-cyanoimidazo[1,2-b]pyridazin-8-yl)(4-methoxybenzyl)amino)benzoic acid

253C

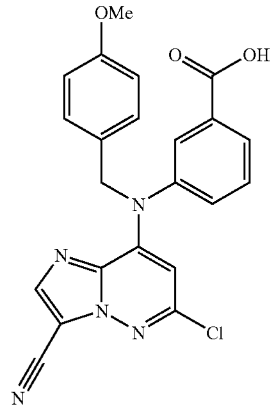

A solution of 253B (100 mg, 0.20 mmol) in acetonitrile (5 mL) was treated with iodine (15.54 mg, 0.061 mmol) and water (50 μL, 2.78 mmol). The reaction mixture was stirred at 80° C. for 8 hours. The reaction mixture was diluted with ethyl acetate, and washed with water. The aqueous layer was extracted with ethyl acetate (4×20 mL). The pooled organic phase was dried over $Na_2SO_4$ and concentrated. The residue was triturated with DCM and filtered. The filtrate was concentrated, dissolved in DCM, and purified by flash chromatography, silica column (12 g, gradient elution from hexanes-ethyl acetate in 15 min.). The appropriate fraction was concentrated under reduced pressure and dried in vacuo to yield 253C (57.5 mg, 64.9% yield) as a yellow solid. HPLC: Rt=4.23 min. (PHENOMENEX® Luna C18 4.6×30 mm 3 u, A10-90% aqueous methanol containing 0.1% TFA in 2 min; 4 mL/min flow). MS (ES): m/z=434.0 [M+H]$^+$.

253D: 3-((6-Chloro-3-cyanoimidazo[1,2-b]pyridazin-8-yl)(4-methoxybenzyl)amino)-N-(2-(dimethylamino)ethyl)benzamide

253D

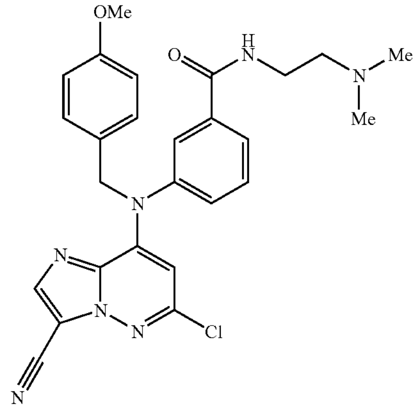

A stirred solution of 253C (55 mg, 0.127 mmol) in DMF (1.0 mL) was treated with $N^1$,$N^1$-dimethylethane-1,2-diamine (0.021 mL, 0.190 mmol), BOP (72.9 mg, 0.165 mmol) and TEA (0.035 mL, 0.254 mmol), and the reaction mixture was stirred at ambient temperature for 1 hour. The reaction mixture was concentrated, triturated with water, and the resulting white solid was collected by filtration to yield 253D (60.0 mg, 93.7% yield). HPLC: Rt=3.47 min. (PHENOMENEX® Luna C18 4.6×30 mm 3 u, A10-90% aqueous methanol containing 0.1% TFA in 2 min; 4 mL/min flow). MS (ES): m/z=504.1 [M+H]$^+$.

Example 253

3-(6-(3-Acetamido-4-methylphenylamino)-3-cyanoimidazo[1,2-b]pyridazin-8-ylamino)-N-(2-(dimethylamino)ethyl)benzamide

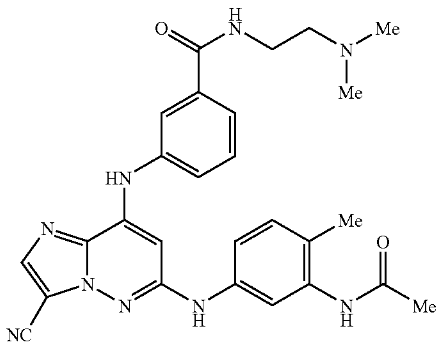

Example 253 was prepared from 253D and N-(5-amino-2-methylphenyl)acetamide following the procedure as described in Example 6. HPLC: Rt=3.110 min. (YMC S5 ODS (4.6×50 mm). 0%-100% B. Solvent B: (90% MeOH, 10% $H_2O$, 0.2% $H_3PO_4$). Solvent A: (10% MeOH, 90% $H_2O$, 0.2% $H_3PO_4$). Gradient, start % B=0, final % B=100, gradient time 4 min., hold at 100% 1 min., flow rate 4 mL/min.). MS (ES): m/z=512.2 [M+H]$^+$. $^1$H NMR (400 MHz, DMSO-$d_6$) δ ppm 10.04 (1H, br. s.), 9.52-9.58 (2H, m), 9.21 (1H, s), 8.94 (1H, t, J=5.52 Hz), 8.18 (1H, s), 7.87 (1H, s), 7.59-7.63 (2H, m), 7.44-7.54 (2H, m), 7.06 (1H, d, J=8.28 Hz), 6.81-6.85 (1H, m), 3.59 (3H, q, J=5.69 Hz), 3.24 (2H, q, J=5.86 Hz), 2.73-2.84 (6H, m), 2.08 (3H, s), 1.98 (3H, s).

Example 254

3-((3-Cyano-6-((3-methoxy-5-(5-methyl-1H-tetrazol-1-yl)phenyl)amino)imidazo[1,2-b]pyridazin-8-yl)amino)-N-methyl-N-(1-methyl-3-pyrrolidinyl) benzamide

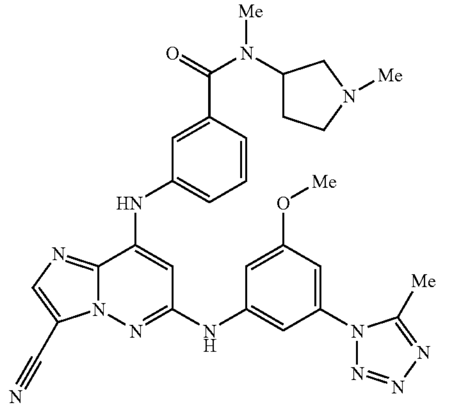

254A: 3-((6-Chloro-3-cyanoimidazo[1,2-b]pyridazin-8-yl)(4-methoxybenzyl)amino)-N-methyl-N-(1-methylpyrrolidin-3-yl)benzamide

254A

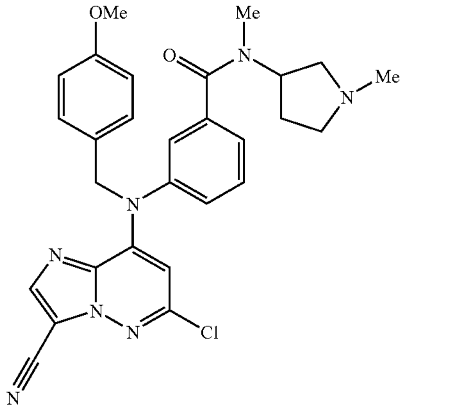

A stirred solution of 253C (500 mg, 1.152 mmol) in DMF (1 mL) was treated with N,1-dimethylpyrrolidin-3-amine (0.217 mL, 1.73 mmol), BOP (663 mg, 1.5 mmol) and TEA (0.32 mL, 2.30 mmol), and the reaction mixture was stirred at room temperature for 1 hour. The reaction mixture was triturated with water, and the solid was collected by filtration and dried in vacuo to obtain 254A (337 mg, 0.636 mmol, 55.2% yield) as a light grey solid. HPLC: Rt=1.56 min. (PHENOMENEX® Luna 5 micron C18 4.6×30 mm, 0 to 100 B in 2 min. with 1 min. hold time, flow rate=5 mL/min., detection at 254 nm, Solvent A: 10% methanol/90% water/0.1% TFA; solvent B: 10% water/90% methanol/0.1% TFA). MS (ES): m/z=531.97 [M+H]$^+$.

Example 254

3-((3-Cyano-6-((3-methoxy-5-(5-methyl-1H-tetrazol-1-yl)phenyl)amino)imidazo[1,2-b]pyridazin-8-yl)amino)-N-methyl-N-(1-methyl-3-pyrrolidinyl) benzamide

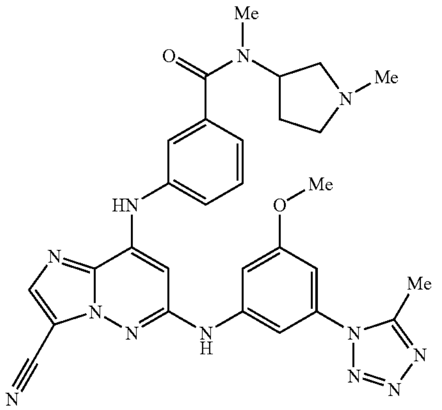

Example 254 was prepared from 254A and 3-methoxy-5-(5-methyl-1H-tetrazol-1-yl)aniline by utilizing the procedure as described in Example 6. HPLC: Rt=1.53 min. (PHENOMENEX® Luna 5 micron C18 4.6×30 mm, 0 to 100 B in 2 min. with 1 min. hold time, flow rate=5 mL/min., detection at 254 nm, Solvent A: 10% methanol/90% water/0.1% TFA; Solvent B: 10% water/90% methanol/0.1% TFA). MS (ES): m/z=579.13 [M+H]$^+$.

Example 255

3-((3-Cyano-6-((3-methoxy-5-(5-methyl-1H-tetrazol-1-yl)phenyl)amino)imidazo[1,2-b]pyridazin-8-yl)amino)-N-(2-(dimethylamino)ethyl)benzamide

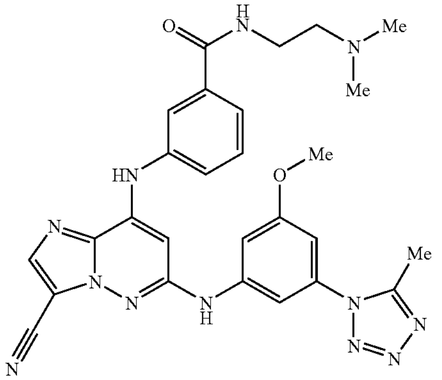

Example 255 was prepared from 253D and 3-methoxy-5-(5-methyl-1H-tetrazol-1-yl)aniline following the procedure as described in Example 6. HPLC: Rt=3.11 min. (YMC S5

ODS 4.6×50 mm, 10-90% aqueous methanol containing 0.2% $H_3PO_4$, 4 min. gradient, monitored at 220 nm). MS (ES): m/z=512.2 $[M+H]^+$.

Example 256

2-(5-((3-Cyano-8-(cyclopropylamino)imidazo[1,2-b]pyridazin-6-yl)amino)-2-methylphenyl)acetamide

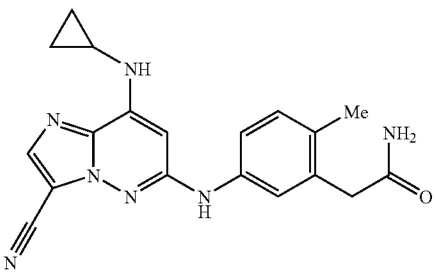

A mixture of 1G (50 mg, 0.14 mmol), 2-(5-amino-2-methylphenyl)acetic acid (46.7 mg, 0.17 mmol), $Pd_2(dba)_3$ (12.9 mg, 0.014 mmol), xantphos (16.4 mg, 0.028 mmol), copper (I) iodide (13.5 mg, 0.071 mmol) and $Cs_2CO_3$ (184 mg, 0.56 mmol) in DMA (1 mL) was purged with nitrogen and heated at 125° C. After 5 hours, the reaction mixture was diluted with 10% methanol/chloroform and filtered through a short silica gel column washing with 10% methanol/dichloromethane wash. The filtrate was concentrated and purified by reverse phase HPLC. The fractions were concentrated and dissolved in DCM (0.5 mL) and treated with (2,4-dimethoxyphenyl)methanamine (31.2 mg, 0.19 mmol), TEA (0.043 m, 0.31 mmol) and HATU (47.3 mg, 0.12 mmol). The reaction mixture was at room temperature for 30 minutes, concentrated, and then dissolved in DCM (0.5 mL), and treated with triethylsilane (0.2 mL) and TFA (1 mL) and heated at 60° C. for 40 min. The reaction mixture was concentrated and purified using reverse phase HPLC to isolate Example 256 (6.2 mg, 12% yield) as a white solid. HPLC: Rt=2.77 min. (BEH C18 2.1×50 mm, 1.7 u, 0 to 100 B in 1 min. with 0.5 min. hold time, flow rate=1 mL/min., detection at 254 nm, Solvent A:100% water/0.1% TFA; Solvent B: 100% ACN1/0.1% TFA). MS (ES): m/z=362 $[M+H]^+$.

What is claimed is:

1. A compound according to Formula (I):

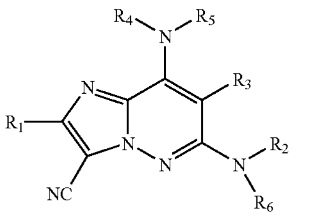

(I)

or a pharmaceutically acceptable salt thereof, wherein $R_1$ is selected from H, F, Cl, Br, CN, and $C_{1-6}$alkyl;

$R_2$ is selected from aryl substituted with 0-5 $R_{2a}$ and heteroaryl substituted with 0-5 $R_{2a}$;

$R_{2a}$, at each occurrence, is independently selected from H, F, Cl, Br, =O, CN, $NO_2$, —$OR_b$, —$S(O)_pR_c$, —C(=O)$R_d$, —$NR_aR_a$, —$(CR_{2b}R_{2c})_r$C(=O)$NR_aR_a$, —$NR_a$C(=O)$R_d$, —$NR_a$C(=O)$OR_b$, —OC(=O)$NR_aR_a$, —$NR_a$C(=O)$NR_aR_a$, —$(CR_{2b}R_{2c})_r$C(=O)$OR_b$, —$S(O)_2NR_aR_a$, —$NR_aS(O)_2NR_aR_a$, —$NR_aS(O)_2R_c$, $C_{1-6}$ alkyl substituted with 0-5 $R_e$, —$(CR_{2b}R_{2c})_r$—$C_{3-6}$ carbocyclyl substituted with 0-5 $R_e$, and —$(CR_{2b}R_{2c})_r$-heterocyclyl substituted with 0-5 $R_e$;

$R_{2b}$, at each occurrence, is independently selected from H and $C_{1-6}$alkyl substituted with 0-5 $R_e$;

$R_{2c}$, at each occurrence, is independently selected from H and $C_{1-6}$alkyl substituted with 0-5 $R_e$;

$R_3$ is selected from H, F, Cl, Br, CN, —$OR_b$, —$NR_aR_a$, —C(=O)$NR_aR_a$, —$NR_aS(O)_2R_c$, —$NR_a$C(=O)$R_d$, —$NR_a$C(=O)$OR_b$, and $C_{1-6}$alkyl substituted with 0-5 $R_e$;

$R_4$ is selected from H, $C_{1-6}$alkyl substituted with 0-5 $R_e$, —$(CR_{4b}R_{4c})_rOR_b$, —$(CR_{4b}R_{4c})_rS(O)_pR_c$, —$(CR_{4b}R_{4c})_r$C(=O)$R_d$, —$(CR_{4b}R_{4c})_rNR_aR_a$, —$(CR_{4b}R_{4c})_r$C(=O)$NR_aR_a$, —$(CR_{4b}R_{4c})_rNR_a$C(=O)$R_d$, —$(CR_{4b}R_{4c})_rNR_a$C(=O)$OR_b$, —$(CR_{4b}R_{4c})_r$OC(=O)$NR_aR_a$, —$(CR_{4b}R_{4c})_rNR_a$C(=O)$NR_aR_a$, —$(CR_{4b}R_{4c})_r$C(=O)$OR_b$, —$(CR_{4b}R_{4c})_rS(O)_2NR_aR_a$, —$(CR_{4b}R_{4c})_rNR_aS(O)_2NR_aR_a$, —$(CR_{4b}R_{4c})_rNR_aS(O)_2R_c$—$(CR_{4b}R_{4c})_r$—$C_{3-6}$carbocyclyl substituted with 0-5 $R_{4a}$, —$(CR_{4b}R_{4c})_r$-heterocyclyl substituted with 0-5 $R_{4a}$;

$R_{4a}$, at each occurrence, is independently selected from F, Cl, Br, $C_{1-6}$alkyl substituted with 0-5 $R_e$, $C_{2-6}$alkenyl, $C_{2-6}$alkynyl, $NO_2$, =O, CN, —$SO_3H$, —$S(O)_pR_c$, —$S(O)_2NR_aR_a$, —$NR_aS(O)_2R_c$, —$OR_b$, —$NR_aR_a$, —$NR_a$C(=O)$R_d$, —$NR_a$C(=O)$NR_aR_a$, —C(=O)$OR_b$, —C(=O)$R_d$, —OC(=O)$R_d$, —C(=O)$NR_aR_a$, $C_{3-6}$cycloalkyl, heterocyclyl, and aryl;

$R_{4b}$, at each occurrence, is independently selected from H and $C_{1-6}$alkyl substituted with 0-5 $R_e$;

$R_{4c}$, at each occurrence, is independently selected from H and $C_{1-6}$alkyl substituted with 0-5 $R_e$;

$R_5$ is selected from hydrogen and $C_{1-6}$alkyl substituted with 0-5 $R_e$;

$R_6$ is selected from hydrogen and $C_{1-6}$alkyl substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H, $C_{1-6}$ alkyl substituted with 0-5 $R_e$, $C_{2-6}$alkenyl substituted with 0-5 $R_e$, $C_{2-6}$alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOC_{1-5}$ alkyl, —$(CH_2)_r$OH, SH, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring;

p, at each occurrence, is independently selected from zero, 1, and 2; and r, at each occurrence, is independently selected from zero, 1, 2, 3, and 4;

wherein said heteroaryl or heterocyclyl is a 4-, 5-, 6-, or 7-membered monocyclic or bicyclic or 7-, 8-, 9-, 10-, 11-, 12-, 13-, or 14-membered bicyclic heterocyclic ring which is saturated, partially unsaturated or fully unsaturated or aromatic, and which consists of carbon atoms and 1, 2, 3 or 4 heteroatoms independently selected from N, O and S.

2. The compound according to claim 1 of the Formula (II) or salt thereof, (II)

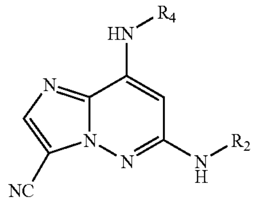

wherein $R_2$ is selected from aryl substituted with 0-4 $R_{2a}$ and heteroaryl substituted with 0-4 $R_{2a}$, wherein said heteroaryl comprises carbon atoms and 1-4 heteroatoms selected from N, O, and $S(O)_p$;

$R_{2a}$, at each occurrence, is independently selected from H, F, Cl, Br, =O, CN, $—OR_b$, $—S(O)_pR_c$, $—C(=O)R_d$, $—NR_aR_a$, $—(CR_{2b}R_{2c})_rC(=O)NR_aR_a$, $—NR_aC(=O)R_d$, $—NR_aC(=O)OR_b$, $—OC(=O)NR_aR_a$, $—NR_aC(=O)NR_aR_a$, $—(CR_{2b}R_{2c})_rC(=O)OR_b$, $—S(O)_2NR_aR_a$, $—NR_aS(O)_2NR_aR_a$, $—NR_2S(O)_2R_c$, $C_{1-4}$ alkyl substituted with 0-3 $R_e$, $—(CR_{2b}R_{2c})_r—C_{3-6}$carbocyclyl substituted with 0-3 $R_e$, and $—(CR_{2b}R_{2c})_r$-heterocyclyl substituted with 0-3 $R_e$;

$R_{2b}$, at each occurrence, is independently selected from H and $C_{1-4}$alkyl;

$R_{2c}$, at each occurrence, is independently selected from H and $C_{1-4}$alkyl;

$R_4$ is selected from H, $C_{1-4}$alkyl substituted with 0-5 $R_e$, $—(CR_{4b}R_{4c})_rOR_b$, $—(CR_{4b}R_{4c})_rS(O)_pR_c$, $—(CR_{4b}R_{4c})_rC(=O)R_d$, $—(CR_{4b}R_{4c})_rNR_aR_a$, $—(CR_{4b}R_{4c})_rC(=O)NR_aR_a$, $—(CR_{4b}R_{4c})_rNR_aC(=O)R_d$, $—(CR_{4b}R_{4c})_rNR_aC(=O)OR_b$, $—(CR_{4b}R_{4c})_rOC(=O)NR_aR_a$, $—(CR_{4b}R_{4c})_rNR_aC(=O)NR_aR_a$, $—(CR_{4b}R_{4c})_rC(=O)OR_b$, $—(CR_{4b}R_{4c})_rNR_aS(O)_2R_c$, $—(CR_{4b}R_{4c})_r—C_{3-6}$carbocyclyl substituted with 0-4 $R_{4a}$, $—(CR_{4b}R_{4c})_r$-heterocyclyl substituted with 0-4 $R_{4a}$;

$R_{4a}$, at each occurrence, is independently selected from F, Cl, Br, $C_{1-6}$-alkyl substituted with 0-3 $R_e$, $C_{2-6}$-alkynyl substituted with 0-3 $R_e$, $—SR_c$, $—S(O)_2R_c$, $—S(O)_2NR_aR_a$, $—NR_aS(O)_2R_c$, $—OR_b$, $—NR_aR_a$, $—NR_aC(=O)R_d$, $—NR_aC(=O)NR_aR_a$, $—C(=O)OR_b$, $—C(=O)R_d$, $—OC(=O)R_d$, $—C(=O)NR_aR_a$, $C_{3-6}$cycloalkyl, heterocyclyl, and aryl;

$R_{4b}$, at each occurrence, is independently selected from H and $C_{1-4}$alkyl;

$R_{4c}$, at each occurrence, is independently selected from H and $C_{1-4}$alkyl; and r, at each occurrence, is independently selected from zero, 1, 2, and 3.

3. The compound according to claim 2, wherein $R_2$ is selected from 4- to 7-membered monocyclic or 8- to 12-membered bicyclic aryl substituted with 1-4 $R_{2a}$ and 4- to 7-membered monocyclic or 7- to 12-membered bicyclic heteroaryl substituted with 0-4 $R_{2a}$;

$R_{2a}$, at each occurrence, is independently selected from H, F, Cl, Br, =O, CN, $—OR_b$, $—S(O)_pR_c$, $—C(=O)R_d$, $—NR_aR_a$, $—(CH_2)_rC(=O)NR_aR_a$, $—NHC(=O)R_d$, $—NHC(=O)OR_b$, $—OC(=O)NR_aR_a$, $—NHC(=O)NR_aR_a$, $—(CH_2)_rC(=O)OR_b$, $—S(O)_2NR_aR_a$, $—NHS(O)_2NR_aR_a$, $—NHS(O)_2R_c$, or $C_{1-6}$ alkyl substituted with 0-3 $R_e$, $—(CH_2)_r—C_{3-6}$ carbocyclyl substituted with 0-3 $R_e$, and $—(CH_2)_r$-heterocyclyl substituted with 0-3 $R_e$;

$R_4$ is selected from H, $C_{1-4}$alkyl substituted with 0-5 $R_e$, $—(CH_2)_rOR_b$, $—(CH_2)_rS(O)_pR_c$, $—(CH_2)_rC(=O)R_d$, $—(CH_2)_rNR_aR_a$, $—(CH_2)_rC(=O)NR_aR_a$, $—(CH_2)_rNR_aC(=O)R_d$, $—(CH_2)_rNR_aC(=O)OR_b$, $—(CH_{2c})_rOC(=O)NR_aR_a$, $—(CH_2)_rNR_aC(=O)NR_aR_a$, $—(CH_2)_rC(=O)OR_b$, $—(CH_2)_rNR_aS(O)_2R_c$, $—(CH_2)_r—C_{3-6}$ cycloalkyl substituted with 0-3 $R_{4a}$, $—(CH_2)_r$-aryl substituted with 0-3 $R_{4a}$, $—(CH_2)_r$-heterocyclyl substituted with 0-3 $R_e$;

$R_{4a}$, at each occurrence, is independently selected from $C_{1-6}$alkyl substituted with 0-3 $R_e$, $—SR_c$, $—S(O)_2R_c$, $—S(O)_2NR_aR_a$, $—NHS(O)_2R_c$, $—OR_b$, $—NR_aR_a$, $—NHC(=O)R_d$, $—NHC(=O)NR_aR_a$, $—C(=O)OR_b$, $—C(=O)R_d$, $—OC(=O)R_d$, $—C(=O)NR_aR_a$, $C_{3-6}$cycloalkyl, heterocyclyl, and aryl.

4. The compound according to claim 3 of the Formula (III) or salt thereof, (III)

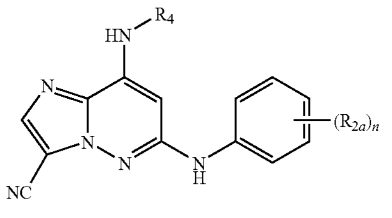

wherein $R_{2a}$, at each occurrence, is independently selected from H, F, Cl, Br, =O, CN, $—OR_b$, $—S(O)_pR_c$, $—C(=O)R_d$, $—NR_aR_a$, $—(CH_2)_rC(=O)NR_aR_a$, $—NHC(=O)R_d$, $—NHC(=O)OR_b$, $—OC(=O)NR_aR_a$, $—NHC(=O)NR_aR_a$, $—(CH_2)_rC(=O)OR_b$, $—S(O)_2NR_aR_a$, $—NHS(O)_2NR_aR_a$, $—NHS(O)_2R_c$, or $C_{1-4}$ alkyl substituted with 0-3 $R_e$, $—(CH_2)_r—C_{3-6}$ carbocyclyl substituted with 0-3 $R_e$, and $—(CH_2)_r$-heterocyclyl substituted with 0-3 $R_e$;

$R_4$ is selected from H, $C_{1-6}$alkyl substituted with 0-5 $R_e$, $—(CH_2)_rOR_b$, $—(CH_2)_rNR_aR_a$, $—(CH_2)_r—C_{3-6}$cycloalkyl substituted with 0-3 $R_{4a}$, $—(CH_2)_r$-aryl substituted with 0-3 $R_{4a}$, and $—(CH_2)_r$-heterocyclyl substituted with 0-3 $R_{4a}$;

$R_{4a}$, at each occurrence, is independently selected from $C_{1-6}$alkyl substituted with 0-3 $R_e$, $—SR_c$, $—S(O)_2NR_aR_a$, $—NHS(O)_2R_e$, $—OR_b$, $—NR_aR_a$, $—NHC(=O)R_d$, $—NHC(=O)NR_aR_a$, $—C(=O)OR_b$, —C(═O)$R_d$, —OC(═O)$R_d$, —C(═O)$NR_aR_a$, $C_{3-6}$cycloalkyl, heterocyclyl, and aryl $R_a$, at each occurrence, is independently selected from H, CN, $C_{1-6}$ alkyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$$C_{3-10}$-carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{3-6}$-carbocyclyl, and heterocyclyl;

$R_d$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, —$(CH_2)_r$—$C_{3-6}$ cycloalkyl, F, Cl, Br, CN, $NO_2$, ═O, $CO_2H$, —$(CH_2)_r$$OC_{1-5}$alkyl, —$(CH_2)_r$OH, SH, and —$(CH_2)_r$$NR_fR_f$;

$R_f$, at each occurrence, is independently selected from H, $C_{1-5}$ alkyl, and phenyl, or $R_f$ and $R_f$ together with the nitrogen atom to which they are both attached form a heterocyclic ring; and n, at each occurrence, is independently selected from zero, 1, 2, 3, and 4.

5. The compound according to claim 4, wherein $R_4$ is selected from H, $C_{1-6}$alkyl substituted with 0-3 $R_e$, —$(CH_2)_r$$OR_b$, —$(CH_2)_r$$NR_aR_a$, —$C_{3-6}$cycloalkyl substituted with 0-3 $R_{4a}$, aryl substituted with 0-3 $R_{4a}$, 4-, 5-, or 6-membered non-aromatic monocyclic heterocyclyl substituted with 0-3 $R_{4a}$, and 5- to 6-membered heteroaryl substituted with 0-3 $R_{4a}$;

$R_{4a}$, at each occurrence, is independently selected from $C_{1-6}$alkyl substituted with 0-3 $R_e$, —$S(O)_2NR_aR_a$, —$NHS(O)_2R_c$, —$OR_b$, —$NR_aR_a$, —NHC(═O)$R_d$, —NHC(═O)$NR_aR_a$, —C(═O)$OR_b$, —C(═O)$R_d$, —OC(═O)$R_d$, —C(═O)$NR_aR_a$, $C_{3-6}$cycloalkyl, heterocyclyl, and aryl;

$R_a$, at each occurrence, is independently selected from H, CN, $C_{1-4}$ alkyl substituted with 0-3 $R_e$, —$(CH_2)_r$-heterocyclyl substituted with 0-3 $R_e$; or $R_a$ and $R_a$ together with the nitrogen atom to which they are both attached form a monocyclic heterocyclic ring substituted with 0-3 $R_e$;

$R_b$, at each occurrence, is independently selected from H and $C_{1-4}$ alkyl substituted with 0-3 $R_e$, and heterocyclyl;

$R_c$, at each occurrence, is independently selected from $C_{1-4}$ alkyl substituted with 0-3 $R_e$ and heterocyclyl;

$R_d$, at each occurrence, is independently selected from H, $C_{1-4}$ alkyl substituted with 0-3 $R_e$, —$(CH_2)_r$—$C_{3-10}$carbocyclyl substituted with 0-3 $R_e$, and —$(CH_2)_r$-heterocyclyl substituted with 0-3 $R_e$;

$R_e$, at each occurrence, is independently selected from $C_{1-4}$ alkyl substituted with 0-4 $R_f$, F, Cl, Br, CN, $NO_2$, ═O, $CO_2H$, —$(CH_2)_r$$OC_{1-5}$ alkyl, —$(CH_2)_r$OH, SH, and —$(CH_2)_r$$NR_fR_f$;

$R_f$, at each occurrence, is independently selected from H and $C_{1-4}$-alkyl or $R_f$ and $R_f$ together with the nitrogen atom to which they are both attached form a heterocyclic ring.

6. The compound according to claim 4, wherein $R_{2a}$, at each occurrence, is independently selected from H, F, Cl, Br, CN, ═O, O—$C_{1-4}$-alkyl substituted with 0-3 $R_e$, —$O(CH_2)_r$$NR_aC_{1-4}$alkyl —O—$(CH_2)_r$$OC_{1-4}$alkyl, —$O(CH_2)_r$-heterocyclyl, —$S(O)_2C_{1-4}$alkyl, —C(═O)$C_{1-4}$alkyl, —$NH_2$, —$N(C_{1-4}alkyl)_2$, —NHCN, —$NR_a$$(CH_2)_r$$NR_aC_{1-4}$alkyl, —$NR_a(CH_2)_r$$OC_{1-4}$alkyl, —NH$(CH_2)_r$-heterocyclyl, —$(CH_2)_r$C(═O)$NH_2$, —C(═O)NH-heterocyclyl, —C(═O)NH$(CH_2)_r$$N(C_{1-4}alkyl)_2$, —C(═O)-heterocyclyl, —NHC(═O)$C_{1-4}$alkyl, —NHC(═O)$OC_{1-4}$alkyl, —NHC(═O)$NHC_{1-4}$alkyl, C(═O)$OC_{1-4}$alkyl, —$(CH_2)_r$C(═O)OH, —$S(O)_2NH_2$, —$S(O)_2$NH-heterocyclyl, —$S(O)_2NHC_{1-4}$alkyl, —$S(O)_2$-heterocyclyl substituted with 0-3 $R_e$, —$NH_2S(O)_2NH_2$, —$NHS(O)_2C_{1-4}$alkyl, $C_{1-4}$alkyl, $CF_3$, —$(CH_2)_r$OH, $C_{3-6}$carbocyclyl substituted with 0-3 $R_e$, non-aromatic heterocyclyl substituted with 0-3 $R_e$, and 5- or 6-membered heteroaryl substituted with 0-3 $R_e$.

7. The compound according to claim 3, wherein $R_2$ is selected from

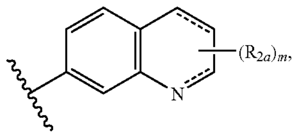

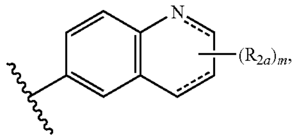

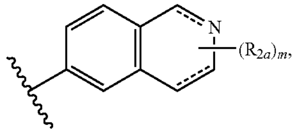

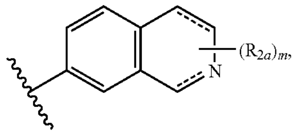

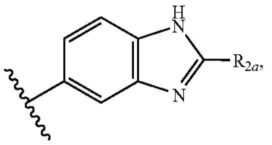

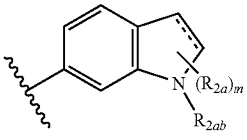

,

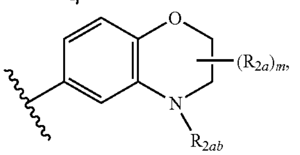

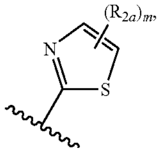

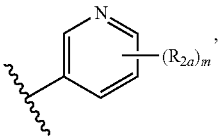

,

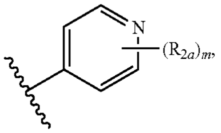

and

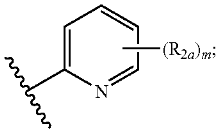

---- represents an optional bond;

$R_{2ab}$, at each occurrence, is independently selected from $C_{1-4}$ alkyl substituted with 0-3 $R_e$, —$S(O)_pR_c$, —C(═O)$R_d$, C(═O)$OR_b$; and m, at each occurrence, is independently selected from zero, 1, 2, and 3.

8. The compound according to claim 7, wherein $R_4$ is selected from H, $C_{1-4}$alkyl substituted with 0-5 $R_e$, —$(CH_2)_r$$OR_b$, —$(CH_2)_r$$NR_aR_a$, —$(CH_2)_r$—$C_{3-6}$cycloalkyl substituted with 0-3 $R_{4a}$, —$(CH_2)_r$-aryl substituted with 0-3 $R_{4a}$, and —$(CH_2)_r$-heterocyclyl substituted with 0-3 $R_{4a}$.

9. The compound according to claim 2, wherein $R_2$ is selected from phenyl substituted with 1-3 $R_{2a}$ and heteroaryl substituted with 0-3 $R_{2a}$;

$R_{2a}$, at each occurrence, is independently selected from H, F, Cl, Br, =O, CN, —$OR_b$, —$S(O)_2R_c$, —C(=O)$R_d$, —$NR_aR_a$, —$(CH_2)_r$C(=O)$NR_aR_a$, —NHC(=O)$R_d$, —NHC(=O)$OR_b$, —NHC(=O)$NR_aR_a$, —$(CH_2)_r$C(=O)$OR_b$, —$S(O)_2NR_aR_a$, —NHS$(O)_2NR_aR_a$, —NHS$(O)_2R_c$, $C_{1-4}$alkyl substituted with 0-3 $R_e$, non-aromatic heterocyclyl substituted with 0-3 $R_e$, and heteroaryl substituted with 0-3 $R_e$;

$R_4$ is selected from H, $C_{1-6}$alkyl substituted with 0-3 $R_e$, —$(CH_2)_rOR_b$, —$C_{3-6}$cycloalkyl substituted with 0-3 $R_{4a}$, aryl substituted with 0-3 $R_{4a}$, —$(CH_2)_r$-4, 5-, or 6-membered saturated monocyclic heterocyclyl substituted with 0-3 $R_{4a}$, and —$(CH_2)_r$-5- to 6-membered heteroaryl substituted with 0-3 $R_{4a}$;

$R_{4a}$, at each occurrence, is independently selected from $C_{1-4}$alkyl substituted with 0-3 $R_e$, —$OR_b$, and C(=O)$NR_aR_a$;

$R_a$, at each occurrence, is independently selected from H, CN, $C_{1-4}$ alkyl substituted with 0-5 $R_e$, —$(CH_2)_r$-heterocyclyl substituted with 0-3 $R_e$; or $R_a$ and $R_a$ together with the nitrogen atom to which they are both attached form a heterocyclic ring, having 1 to 3 heteroatoms selected from N, O, S, and substituted with 0-3 $R_e$;

$R_b$, at each occurrence, is independently selected from H, $C_{1-4}$ alkyl substituted with 0-3 $R_e$, and heterocyclyl;

$R_c$, at each occurrence, is independently $C_{1-4}$ alkyl substituted with 0-3 $R_e$;

$R_d$, at each occurrence, is independently selected from H and $C_{1-4}$ alkyl substituted with 0-3 $R_e$;

$R_e$, at each occurrence, is independently selected from $C_{1-4}$ alkyl substituted with 0-4 $R_f$, F, Cl, Br, =O, —$(CH_2)_r$-$OC_{1-5}$ alkyl, —$(CH_2)_r$OH, and —$(CH_2)_rNR_fR_f$; and $R_f$, at each occurrence, is independently selected from H and $C_{1-3}$alkyl or $R_f$ and $R_f$ together with the nitrogen atom to which they are both attached form a heterocyclic ring;

r, at each occurrence, is independently selected from zero, 1, 2, and 3; and m, at each occurrence, is independently selected from zero, 1, 2, and 3.

10. A compound selected from the group consisting of:

N-(5-((3-Cyano-8-(cyclopropylamino)imidazo[1,2-b]pyridazin-6-yl)amino)-2-methylphenyl)acetamide;

N-(6-(3-Cyano-8-(cyclopropylamino)imidazo[1,2-b]pyridazin-6-ylamino)pyridin-2-yl)acetamide;

N-(3-(3-Cyano-8-(cyclopropylamino)imidazo[1,2-b]pyridazin-6-ylamino)phenyl)methanesulfonamide;

8-(Cyclobutylamino)-6-((4-((2-(dimethylamino)ethyl)amino)-3-(4H-1,2,4-triazol-4-yl)phenyl)amino)imidazo[1,2-b]pyridazine-3-carbonitrile;

N-(5-(3-Cyano-8-(5-methoxypyridin-2-ylamino)imidazo[1,2-b]pyridazin-6-ylamino)-2-methylphenyl)acetamide;

N-(5-((8-(3-Azetidinylamino)-3-cyanoimidazo[1,2-b]pyridazin-6-yl)amino)-2-methylphenyl)acetamide;

N-(3-(3-Cyano-8-(phenylamino)imidazo[1,2-b]pyridazin-6-ylamino)phenyl)acetamide;

Methyl (5-((3-cyano-8-(2-pyridinylamino)imidazo[1,2-b]pyridazin-6-yl)amino)-2-fluorophenyl)carbamate;

6-((5-Cyano-2-methoxyphenyl)amino)-8-((2,2,2-trifluoroethyl)amino)imidazo[1,2-b]pyridazine-3-carbonitrile;

6-(3-Cyano-5-(trifluoromethyl)phenylamino)-8-(isopropylamino)imidazo[1,2-b]pyridazine-3-carbonitrile;

N-(5-(3-Cyano-8-(2-hydroxyethylamino)imidazo[1,2-b]pyridazin-6-ylamino)-2-methylphenyl)acetamide;

8-((1-(2-Hydroxyethyl)-1H-pyrazol-3-yl)amino)-6-((3-methoxy-5-(5-methyl-1H-tetrazol-1-yl)phenyl)amino)imidazo[1,2-b]pyridazine-3-carbonitrile;

8-(Ethylamino)-6-((3-(1H-1,2,4-triazol-1-yl)-5-(trifluoromethyl)phenyl)amino)imidazo[1,2-b]pyridazine-3-carbonitrile;

8-Amino-6-((3-chloro-5-cyanophenyl)amino)imidazo[1,2-b]pyridazine-3-carbonitrile;

6-((3-Cyano-5-(trifluoromethyl)phenyl)amino)-8-((2-methoxyethyl)amino)imidazo[1,2-b]pyridazine-3-carbonitrile;

6-((3-Cyano-5-(trifluoromethyl)phenyl)amino)-8-(methylamino)imidazo[1,2-b]pyridazine-3-carbonitrile;

8-((2-(4-Morpholinyl)ethyl)amino)-6-((3-(4H-1,2,4-triazol-4-yl)-4-(trifluoromethoxy)phenyl)amino)imidazo[1,2-b]pyridazine-3-carbonitrile;

6-((3-Amino-5-(trifluoromethyl)phenyl)amino)-8-(cyclopropylamino)imidazo[1,2-b]pyridazine-3-carbonitrile;

6-((3-Amino-5-cyanophenyl)amino)-8-(cyclopropylamino)imidazo[1,2-b]pyridazine-3-carbonitrile;

N-(3-Cyano-5-((3-cyano-8-(cyclopropylamino)imidazo[1,2-b]pyridazin-6-yl)amino)phenyl)acetamide;

N-(3-((3-Cyano-8-(cyclopropylamino)imidazo[1,2-b]pyridazin-6-yl)amino)-5-(trifluoromethyl)phenyl)acetamide;

N-(3-Chloro-5-((3-cyano-8-(cyclopropylamino)imidazo[1,2-b]pyridazin-6-yl)amino)phenyl)acetamide;

Methyl (3-chloro-5-((3-cyano-8-(cyclopropylamino)imidazo[1,2-b]pyridazin-6-yl)amino)phenyl)carbamate;

6-((3-Cyanophenyl)amino)-8-(cyclopropylamino)imidazo[1,2-b]pyridazine-3-carbonitrile;

6-((3-Cyano-4-fluorophenyl)amino)-8-(cyclopropylamino)imidazo[1,2-b]pyridazine-3-carbonitrile;

6-((3-Cyano-4-methylphenyl)amino)-8-(cyclopropylamino)imidazo[1,2-b]pyridazine-3-carbonitrile;

8-(Cyclopropylamino)-6-((3-(trifluoromethyl)phenyl)amino)imidazo[1,2-b]pyridazine-3-carbonitrile;

8-(Cyclopropylamino)-6-((3-(difluoromethoxy)phenyl)amino)imidazo[1,2-b]pyridazine-3-carbonitrile;

6-((5-Cyano-2-methylphenyl)amino)-8-(cyclopropylamino)imidazo[1,2-b]pyridazine-3-carbonitrile;

(3-((3-Cyano-8-(cyclopropylamino)imidazo[1,2-b]pyridazin-6-yl)amino)-5-methoxyphenyl)cyanamide;

6-((4-Cyano-3-(trifluoromethyl)phenyl)amino)-8-(cyclopropylamino)imidazo[1,2-b]pyridazine-3-carbonitrile;

6-((3-Cyano-2-fluorophenyl)amino)-8-(cyclopropylamino)imidazo[1,2-b]pyridazine-3-carbonitrile;

Methyl (3-((3-cyano-8-(cyclopropylamino)imidazo[1,2-b]pyridazin-6-yl)amino)-5-(trifluoromethyl)phenyl)carbamate;

6-((3-Cyano-4-(trifluoromethoxy)phenyl)amino)-8-(cyclopropylamino)imidazo[1,2-b]pyridazine-3-carbonitrile;

6-((3-Cyano-5-methoxyphenyl)amino)-8-(cyclopropylamino)imidazo[1,2-b]pyridazine-3-carbonitrile;

6-((3-Cyano-5-fluorophenyl)amino)-8-(cyclopropylamino)imidazo[1,2-b]pyridazine-3-carbonitrile;

8-(Cyclopropylamino)-6-((3-methoxy-5-(5-methyl-1H-tetrazol-1-yl)phenyl)amino)imidazo[1,2-b]pyridazine-3-carbonitrile;

N-(3-((3-Cyano-8-(cyclopropylamino)imidazo[1,2-b]pyridazin-6-yl)amino)phenyl)acetamide;

Methyl (5-((3-cyano-8-(cyclopropylamino)imidazo[1,2-b]pyridazin-6-yl)amino)-2-fluorophenyl)carbamate;

8-(Cyclopropylamino)-6-((3-(1H-imidazol-4-yl)phenyl)amino)imidazo[1,2-b]pyridazine-3-carbonitrile;

8-(Cyclopropylamino)-6-((3-(2-methyl-1H-imidazol-1-yl)phenyl)amino)imidazo[1,2-b]pyridazine-3-carbonitrile;

8-(Cyclopropylamino)-6-((3-(1H-imidazol-1-yl)phenyl)amino)imidazo[1,2-b]pyridazine-3-carbonitrile;

Methyl 6-((3-cyano-8-(cyclopropylamino)imidazo[1,2-b]pyridazin-6-yl)amino)-1-indolinecarboxylate;

3-((3-Cyano-8-(cyclopropylamino)imidazo[1,2-b]pyridazin-6-yl)amino)benzoic acid;

Methyl 6-((3-cyano-8-(cyclopropylamino)imidazo[1,2-b]pyridazin-6-yl)amino)-3,3-dimethyl-1-indolinecarboxylate;

8-(Cyclopropylamino)-6-((4-fluoro-3-(4H-1,2,4-triazol-4-yl)phenyl)amino)imidazo[1,2-b]pyridazine-3-carbonitrile;

6-((2-Chloro-5-cyanophenyl)amino)-8-(cyclopropylamino)imidazo[1,2-b]pyridazine-3-carbonitrile;

8-(Cyclopropylamino)-6-((3-(4-methyl-4H-1,2,4-triazol-3-yl)phenyl)amino)imidazo[1,2-b]pyridazine-3-carbonitrile;

8-(Cyclopropylamino)-6-((3-(1H-pyrazol-5-yl)phenyl)amino)imidazo[1,2-b]pyridazine-3-carbonitrile;

6-((3-Amino-4-(trifluoromethoxy)phenyl)amino)-8-(cyclopropylamino)imidazo[1,2-b]pyridazine-3-carbonitrile;

6-((3-Amino-4-methylphenyl)amino)-8-(cyclopropylamino)imidazo[1,2-b]pyridazine-3-carbonitrile;

8-(Cyclopropylamino)-6-((3-(4H-1,2,4-triazol-4-yl)-4-(trifluoromethoxy)phenyl)amino)imidazo[1,2-b]pyridazine-3-carbonitrile;

N-(5-((3-Cyano-8-((2-methoxyethyl)amino)imidazo[1,2-b]pyridazin-6-yl)amino)-2-methylphenyl)acetamide;

N-(5-((3-Cyano-8-((2-(4-morpholinyl)ethyl)amino)imidazo[1,2-b]pyridazin-6-yl)amino)-2-methylphenyl)acetamide;

N-(5-((3-Cyano-8-((2-hydroxy-2-methylpropyl)amino)imidazo[1,2-b]pyridazin-6-yl)amino)-2-methylphenyl)acetamide;

8-(Cyclopropylamino)-6-((3,4-dimethoxyphenyl)amino)imidazo[1,2-b]pyridazine-3-carbonitrile;

6-((5-Cyano-1,3-thiazol-2-yl)amino)-8-(cyclopropylamino)imidazo[1,2-b]pyridazine-3-carbonitrile;

8-(Cyclopropylamino)-6-((4-methyl-2-oxo-1,2-dihydro-7-quinolinyl)amino)imidazo[1,2-b]pyridazine-3-carbonitrile;

N-(5-((3-Cyano-8-(cyclopropylamino)imidazo[1,2-b]pyridazin-6-yl)amino)-2-fluorophenyl acetamide; 6-((3-Aminophenyl)amino)-8-(cyclopropylamino)imidazo[1,2-b]pyridazine-3-carbonitrile;

N-(3-((3-Cyano-8-(cyclopropylamino)imidazo[1,2-b]pyridazin-6-yl)amino)-4-fluorophenyl)acetamide;

8-(Cyclopropylamino)-6-((2-methyl-1H-benzimidazol-5-yl)amino)imidazo[1,2-b]pyridazine-3-carbonitrile;

Methyl (3-((3-cyano-8-(cyclopropylamino)imidazo[1,2-b]pyridazin-6-yl)amino)phenyl)carbamate;

6-((1-Acetyl-2,3-dihydro-1H-indol-6-yl)amino)-8-(cyclopropylamino)imidazo[1,2-b]pyridazine-3-carbonitrile;

N-(3-((3-Cyano-8-(2-pyridinylamino)imidazo[1,2-b]pyridazin-6-yl)amino)phenyl)acetamide;

N-(3-((3-Cyano-8-(cyclopropylamino)imidazo[1,2-b]pyridazin-6-yl)amino)phenyl)-2-methylpropanamide;

N-(3-((3-Cyano-8-(cyclopropylamino)imidazo[1,2-b]pyridazin-6-yl)amino)phenyl)propanamide;

Methyl (5-((3-cyano-8-(cyclopropylamino)imidazo[1,2-b]pyridazin-6-yl)amino)-2-fluorophenyl)carbamate;

N-(4-((3-Cyano-8-(cyclopropylamino)imidazo[1,2-b]pyridazin-6-yl)amino)-2-pyridinyl)acetamide;

N-(5-((3-Cyano-8-(cyclopropylamino)imidazo[1,2-b]pyridazin-6-yl)amino)-2-fluorophenyl)methanesulfonamide;

3-((3-Cyano-8-(cyclopropylamino)imidazo[1,2-b]pyridazin-6-yl)amino)benzamide;

8-(Cyclopropylamino)-6-((4-methyl-2-oxo-1,2-dihydro-6-quinolinyl)amino)imidazo[1,2-b]pyridazine-3-carbonitrile;

8-(Cyclopropylamino)-6-((3-(2-oxo-1-pyrrolidinyl)phenyl)amino)imidazo[1,2-b]pyridazine-3-carbonitrile;

N-(3-((3-Cyano-8-(cyclopropylamino)imidazo[1,2-b]pyridazin-6-yl)amino)phenyl)-N-methylacetamide;

8-(Cyclopropylamino)-6-((1-(methylsulfonyl)-1H-indol-6-yl)amino)imidazo[1,2-b]pyridazine-3-carbonitrile;

N-(5-((3-Cyano-8-(cyclopropylamino)imidazo[1,2-b]pyridazin-6-yl)amino)-2,4-difluorophenyl)acetamide;

Methyl (5-((3-cyano-8-(cyclopropylamino)imidazo[1,2-b]pyridazin-6-yl)amino)-2,4-difluorophenyl)carbamate;

Methyl (3-((3-cyano-8-(cyclopropylamino)imidazo[1,2-b]pyridazin-6-yl)amino)-4-fluorophenyl)carbamate;

6-((4-Chloro-3-(1,3-oxazol-5-yl)phenyl)amino)-8-(cyclopropylamino)imidazo[1,2-b]pyridazine-3-carbonitrile;

8-(Cyclopropylamino)-6-((3-(2-methyl-1,3-thiazol-4-yl)phenyl)amino)imidazo[1,2-b]pyridazine-3-carbonitrile;

6-((4-Chloro-3-(1,3-oxazol-2-yl)phenyl)amino)-8-(cyclopropylamino)imidazo[1,2-b]pyridazine-3-carbonitrile;

8-(Cyclopropylamino)-6-((3-(1,3,4-oxadiazol-2-yl)phenyl)amino)imidazo[1,2-b]pyridazine-3-carbonitrile;

8-(Cyclopropylamino)-6-((3-(1-methyl-1H-tetrazol-5-yl)phenyl)amino)imidazo[1,2-b]pyridazine-3-carbonitrile;

N-(5-((3-Cyano-8-(cyclopropylamino)imidazo[1,2-b]pyridazin-6-yl)amino)-2-methoxyphenyl)acetamide;

N-(2-Chloro-5-((3-cyano-8-(cyclopropylamino)imidazo[1,2-b]pyridazin-6-yl)amino)phenyl)acetamide;

8-(Cyclopropylamino)-6-((3-(methylsulfonyl)phenyl)amino)imidazo[1,2-b]pyridazine-3-carbonitrile;

3-((3-Cyano-8-(cyclopropylamino)imidazo[1,2-b]pyridazin-6-yl)amino)-N-methylbenzenesulfonamide;

N-(5-((3-Cyano-8-(cyclopropylamino)imidazo[1,2-b]pyridazin-6-yl)amino)-2-(trifluoromethoxy)phenyl)acetamide;

6-((3-Amino-4-((4-methyl-1-piperazinyl)carbonyl)phenyl)amino)-8-(cyclopropylamino)imidazo[1,2-b]pyridazine-3-carbonitrile;

Methyl (5-((3-cyano-8-(cyclopropylamino)imidazo[1,2-b]pyridazin-6-yl)amino)-2-(trifluoromethoxy)phenyl)carbamate;

Methyl (3-((3-cyano-8-(cyclopropylamino)imidazo[1,2-b]pyridazin-6-yl)amino)-4-(trifluoromethoxy)phenyl)carbamate;

Methyl (5-((3-cyano-8-(cyclopropylamino)imidazo[1,2-b]pyridazin-6-yl)amino)-2-(4-methyl-1-piperazinyl)phenyl)carbamate;

Methyl (5-((3-cyano-8-(cyclopropylamino)imidazo[1,2-b]pyridazin-6-yl)amino)-2-((4-methyl-1-piperazinyl)carbonyl)phenyl)carbamate;

Methyl (3-((3-cyano-8-(cyclopropylamino)imidazo[1,2-b]pyridazin-6-yl)amino)-4-(4-methyl-1-piperazinyl)phenyl)carbamate;

Methyl (5-((3-cyano-8-(cyclopropylamino)imidazo[1,2-b]pyridazin-6-yl)amino)-2-methylphenyl)carbamate;

Methyl (3-((3-cyano-8-(cyclopropylamino)imidazo[1,2-b]pyridazin-6-yl)amino)-4-methylphenyl)carbamate;

N-(5-((3-Cyano-8-(cyclopropylamino)imidazo[1,2-b]pyridazin-6-yl)amino)-2-methylphenyl)methanesulfonamide;

N-(3-((3-Cyano-8-(cyclopropylamino)imidazo[1,2-b]pyridazin-6-yl)amino)-4-methylphenyl)acetamide;

N-(5-((3-Cyano-8-(cyclopropylamino)imidazo[1,2-b]pyridazin-6-yl)amino)-2-(trifluoromethyl)phenyl)acetamide;

Methyl (5-((3-cyano-8-(cyclopropylamino)imidazo[1,2-b]pyridazin-6-yl)amino)-2-(trifluoromethyl)phenyl)carbamate;

N-(5-((3-Cyano-8-((2-methoxyethyl)amino)imidazo[1,2-b]pyridazin-6-yl)amino)-2-methylphenyl)acetamide;

8-(Cyclopropylamino)-6-((3-methoxy-5-(5-methyl-1H-tetrazol-1-yl)phenyl)amino)imidazo[1,2-b]pyridazine-3-carbonitrile;

8-(Cyclopropylamino)-6-((3-(1H-pyrazol-1-yl)-5-(trifluoromethyl)phenyl)amino)imidazo[1,2-b]pyridazine-3-carbonitrile;

8-(Cyclopropylamino)-6-((3-(1H-1,2,4-triazol-1-yl)-5-(trifluoromethyl)phenyl)amino)imidazo[1,2-b]pyridazine-3-carbonitrile;

8-(Cyclopropylamino)-6-((3-(3-ethyl-1H-1,2,4-triazol-5-yl)phenyl)amino)imidazo[1,2-b]pyridazine-3-carbonitrile;

8-(Cyclopropylamino)-6-((4-methyl-3-(4H-1,2,4-triazol-4-yl)phenyl)amino)imidazo[1,2-b]pyridazine-3-carbonitrile;

8-(Cyclopropylamino)-6-((3-(1,3-thiazol-2-yl)phenyl)amino)imidazo[1,2-b]pyridazine-3-carbonitrile;

8-(Cyclopropylamino)-6-((3-(1,3-oxazol-4-yl)phenyl)amino)imidazo[1,2-b]pyridazine-3-carbonitrile;

8-((2-Methoxyethyl)amino)-6-((3-methoxy-5-(5-methyl-1H-tetrazol-1-yl)phenyl)amino)imidazo[1,2-b]pyridazine-3-carbonitrile;

N-(5-((3-Cyano-8-(cyclopropylamino)imidazo[1,2-b]pyridazin-6-yl)amino)-2-methylphenyl)-2-methylpropanamide;

8-((5-Methoxy-2-pyridinyl)amino)-6-((3-(4H-1,2,4-triazol-4-yl)-4-(trifluoromethoxy)phenyl)amino)imidazo[1,2-b]pyridazine-3-carbonitrile;

6-((3-Methoxy-5-(5-methyl-1H-tetrazol-1-yl)phenyl)amino)-8-((5-methoxy-2-pyridinyl)amino)imidazo[1,2-b]pyridazine-3-carbonitrile;

N-(5-((3-Cyano-8-(isopropylamino)imidazo[1,2-b]pyridazin-6-yl)amino)-2-methylphenyl)acetamide;

6-((4-Fluoro-3-(4H-1,2,4-triazol-4-yl)phenyl)amino)-8-((5-methoxy-2-pyridinyl)amino)imidazo[1,2-b]pyridazine-3-carbonitrile;

8-(Cyclopropylamino)-6-((3-methoxy-5-(4H-1,2,4-triazol-4-yl)phenyl)amino)imidazo[1,2-b]pyridazine-3-carbonitrile;

8-(Cyclopropylamino)-6-((4-(4-morpholinyl)-3-(4H-1,2,4-triazol-4-yl)phenyl)amino)imidazo[1,2-b]pyridazine-3-carbonitrile;

8-((5-Methoxy-2-pyridinyl)amino)-6-((3-methoxy-5-(4H-1,2,4-triazol-4-yl)phenyl)amino)imidazo[1,2-b]pyridazine-3-carbonitrile;

8-((5-Methoxy-2-pyridinyl)amino)-6-((4-(4-morpholinyl)-3-(4H-1,2,4-triazol-4-yl)phenyl)amino)imidazo[1,2-b]pyridazine-3-carbonitrile;

8-((2-Methoxyethyl)amino)-6-((4-(4-morpholinyl)-3-(4H-1,2,4-triazol-4-yl)phenyl)amino)imidazo[1,2-b]pyridazine-3-carbonitrile;

8-((2-Methoxyethyl)amino)-6-((3-methoxy-5-(4H-1,2,4-triazol-4-yl)phenyl)amino)imidazo[1,2-b]pyridazine-3-carbonitrile;

8-(Cyclopropylamino)-6-((4-(4-methyl-1-piperazinyl)-3-(4H-1,2,4-triazol-4-yl)phenyl)amino)imidazo[1,2-b]pyridazine-3-carbonitrile;

8-(Cyclopropylamino)-6-((4-((2-(dimethylamino)ethyl)amino)-3-(4H-1,2,4-triazol-4-yl)phenyl)amino)imidazo[1,2-b]pyridazine-3-carbonitrile;

8-(Cyclopropylamino)-6-((4-((2-methoxyethyl)amino)-3-(4H-1,2,4-triazol-4-yl)phenyl)amino)imidazo[1,2-b]pyridazine-3-carbonitrile;

6-((3-Cyano-5-methoxyphenyl)amino)-8-((2-methoxyethyl)amino)imidazo[1,2-b]pyridazine-3-carbonitrile;

6-((3-Cyano-5-methoxyphenyl)amino)-8-((5-methoxy-2-pyridinyl)amino)imidazo[1,2-b]pyridazine-3-carbonitrile;

8-(Cyclopropylamino)-6-((4-(2-methoxyethoxy)-3-(4H-1,2,4-triazol-4-yl)phenyl)amino)imidazo[1,2-b]pyridazine-3-carbonitrile;

8-(Cyclopropylamino)-6-((4-(2-(dimethylamino)ethoxy)-3-(4H-1,2,4-triazol-4-yl)phenyl)amino)imidazo[1,2-b]pyridazine-3-carbonitrile;

8-(Cyclopropylamino)-6-((4-((1-methyl-4-piperidinyl)oxy)-3-(4H-1,2,4-triazol-4-yl)phenyl)amino)imidazo[1,2-b]pyridazine-3-carbonitrile;

8-(Cyclopropylamino)-6-((4-((3-(dimethylamino)propyl)amino)-3-(4H-1,2,4-triazol-4-yl)phenyl)amino)imidazo[1,2-b]pyridazine-3-carbonitrile;

8-(Cyclopropylamino)-6-((3-(4-methyl-1-piperazinyl)-5-(4H-1,2,4-triazol-4-yl)phenyl)amino)imidazo[1,2-b]pyridazine-3-carbonitrile;

8-(Cyclopropylamino)-6-((3-((2-(dimethylamino)ethyl)amino)-5-(4H-1,2,4-triazol-4-yl)phenyl)amino)imidazo[1,2-b]pyridazine-3-carbonitrile;

8-(Cyclopropylamino)-6-((4-((2-(dimethylamino)ethyl)(methyl)amino)-3-(4H-1,2,4-triazol-4-yl)phenyl)amino)imidazo[1,2-b]pyridazine-3-carbonitrile;

8-(Cyclopropylamino)-6-(3-(4-(2-hydroxyethyl)-1-piperazinyl)-5-(4H-1,2,4-triazol-4-yl)phenyl)amino)imidazo[1,2-b]pyridazine-3-carbonitrile;

8-(Cyclopropylamino)-6-((3-(2-(dimethylamino)ethoxy)-5-(4H-1,2,4-triazol-4-yl)phenyl)amino)imidazo[1,2-b]pyridazine-3-carbonitrile;

8-(Cyclopropylamino)-6-((4-((2-methoxyethyl)(methyl)amino)-3-(4H-1,2,4-triazol-4-yl)phenyl)amino)imidazo[1,2-b]pyridazine-3-carbonitrile;

8-(Cyclopropylamino)-6-((3-methoxy-5-(1H-1,2,4-triazol-1-yl)phenyl)amino)imidazo[1,2-b]pyridazine-3-carbonitrile;

8-(Cyclopropylamino)-6-((3-(1H-1,2,4-triazol-1-yl)-4-(trifluoromethoxy)phenyl)amino)imidazo[1,2-b]pyridazine-3-carbonitrile;

8-(Cyclobutylamino)-6-((3-methoxy-5-(4H-1,2,4-triazol-4-yl)phenyl)amino)imidazo[1,2-b]pyridazine-3-carbonitrile;

8-(Cyclopropylamino)-6-((4-((2-(1-pyrrolidinyl)ethyl)amino)-3-(4H-1,2,4-triazol-4-yl)phenyl)amino)imidazo[1,2-b]pyridazine-3-carbonitrile;

8-(Cyclopropylamino)-6-((4-(3-(dimethylamino)propoxy)-3-(4H-1,2,4-triazol-4-yl)phenyl)amino)imidazo[1,2-b]pyridazine-3-carbonitrile;

8-(Cyclopropylamino)-6-((3-(4-hydroxy-1-piperidinyl)-5-(4H-1,2,4-triazol-4-yl)phenyl)amino)imidazo[1,2-b]pyridazine-3-carbonitrile;

8-(Cyclopropylamino)-6-((3-((3aR,7aS)-2-oxohexahydro[1,3]oxazolo[5,4-c]pyridin-5-(2H)-yl)-5-(4H-1,2,4-triazol-4-yl)phenyl)amino)imidazo[1,2-b]pyridazine-3-carbonitrile;

8-(Cyclopropylamino)-6-((4-(2-(1-pyrrolidinyl)ethoxy)-3-(4H-1,2,4-triazol-4-yl)phenyl)amino)imidazo[1,2-b]pyridazine-3-carbonitrile;

6-((4-(4-Amino-1-piperidinyl)-3-(4H-1,2,4-triazol-4-yl)phenyl)amino)-8-(cyclopropylamino)imidazo[1,2-b]pyridazine-3-carbonitrile;

8-(Cyclopropylamino)-6-((5-(1H-1,2,4-triazol-1-yl)-3-pyridinyl)amino)imidazo[1,2-b]pyridazine-3-carbonitrile;

8-(Cyclopropylamino)-6-((3-(2-(dimethylamino)ethoxy)-5-(1H-1,2,4-triazol-1-yl)phenyl)amino)imidazo[1,2-b]pyridazine-3-carbonitrile;

8-Anilino-6-((3-(2-(dimethylamino)ethoxy)-5-(1H-1,2,4-triazol-1-yl)phenyl)amino)imidazo[1,2-b]pyridazine-3-carbonitrile;

8-(Cyclopropylamino)-6-((4-((2-(4-morpholinyl)ethyl)amino)-3-(1H-1,2,4-triazol-1-yl)phenyl)amino)imidazo[1,2-b]pyridazine-3-carbonitrile;

8-(Cyclopropylamino)-6-((4-(4-(2-hydroxyethyl)-1-piperazinyl)-3-(4H-1,2,4-triazol-4-yl)phenyl)amino)imidazo[1,2-b]pyridazine-3-carbonitrile;

8-(Cyclopropylamino)-6-((4-(2-(4-morpholinyl)ethoxy)-3-(4H-1,2,4-triazol-4-yl)phenyl)amino)imidazo[1,2-b]pyridazine-3-carbonitrile;

8-(Cyclopropylamino)-6-((4-((3-morpholinylmethyl)amino)-3-(4H-1,2,4-triazol-4-yl)phenyl)amino)imidazo[1,2-b]pyridazine-3-carbonitrile;

8-(Cyclobutylamino)-6-((3-(4-methyl-1-piperazinyl)-5-(4H-1,2,4-triazol-4-yl)phenyl)amino)imidazo[1,2-b]pyridazine-3-carbonitrile;

8-(Cyclopropylamino)-6-((4-(2-(methylamino)ethoxy)-3-(4H-1,2,4-triazol-4-yl)phenyl)amino)imidazo[1,2-b]pyridazine-3-carbonitrile;

8-(Cyclopropylamino)-6-((3-(4-hydroxy-1-piperidinyl)phenyl)amino)imidazo[1,2-b]pyridazine-3-carbonitrile;

8-(Cyclopropylamino)-6-((3-methyl-5-(1H-1,2,4-triazol-1-yl)phenyl)amino)imidazo[1,2-b]pyridazine-3-carbonitrile;

6-((3-Chloro-5-(1H-1,2,4-triazol-1-yl)phenyl)amino)-8-(cyclopropylamino)imidazo[1,2-b]pyridazine-3-carbonitrile;

8-(Cyclopropylamino)-6-((3-((1H-1,2,4-triazol-1-yl)-5-(2,2,2-trifluoroethoxy)phenyl)amino)imidazo[1,2-b]pyridazine-3-carbonitrile;

8-(Cyclopropylamino)-6-((4-(tetrahydro-2H-pyran-4-ylamino)-3-(1H-1,2,4-triazol-1-yl)phenyl)amino)imidazo[1,2-b]pyridazine-3-carbonitrile;

8-(Cyclopropylamino)-6-((3-(hydroxymethyl)-5-(1H-1,2,4-triazol-1-yl)phenyl)amino)imidazo[1,2-b]pyridazine-3-carbonitrile;

8-(Cyclopropylamino)-6-((2-methoxy-5-(1H-1,2,4-triazol-1-yl)phenyl)amino)imidazo[1,2-b]pyridazine-3-carbonitrile;

6-((3-Cyano-5-(trifluoromethyl)phenyl)amino)-8-(cyclopropylamino)imidazo[1,2-b]pyridazine-3-carbonitrile;

8-(Cyclopropylamino)-6-((2-methyl-5-(1H-1,2,4-triazol-1-yl)phenyl)amino)imidazo[1,2-b]pyridazine-3-carbonitrile;

8-(Cyclopropylamino)-6-((4-fluoro-3-(1H-1,2,4-triazol-1-yl)phenyl)amino)imidazo[1,2-b]pyridazine-3-carbonitrile;

8-(Cyclopropylamino)-6-((1,4-dimethyl-2-oxo-1,2-dihydro-7-quinolinyl)amino)imidazo[1,2-b]pyridazine-3-carbonitrile;

8-(Cyclobutylamino)-6-((3-(1H-1,2,4-triazol-1-yl)-5-(trifluoromethyl)phenyl)amino)imidazo[1,2-b]pyridazine-3-carbonitrile;

8-Anilino-6-((4-((2-(dimethylamino)ethyl)amino)-3-(4H-1,2,4-triazol-4-yl)phenyl)amino)imidazo[1,2-b]pyridazine-3-carbonitrile;

8-(Cyclopropylamino)-6-((5-(1H-1,2,4-triazol-1-yl)-2-(trifluoromethoxy)phenyl)amino)imidazo[1,2-b]pyridazine-3-carbonitrile;

6-((4-Cyano-2-pyridinyl)amino)-8-(cyclopropylamino)imidazo[1,2-b]pyridazine-3-carbonitrile;

8-(Cyclopropylamino)-6-((3-(4H-1,2,4-triazol-4-yl)-5-(trifluoromethyl)phenyl)amino)imidazo[1,2-b]pyridazine-3-carbonitrile;

8-(Cyclopropylamino)-6-((2-fluoro-5-(1H-1,2,4-triazol-1-yl)phenyl)amino)imidazo[1,2-b]pyridazine-3-carbonitrile;

3-((3-Cyano-8-(cyclopropylamino)imidazo[1,2-b]pyridazin-6-yl)amino)-N-(tetrahydro-2H-pyran-4-yl)-5-(1H-1,2,4-triazol-1-yl)benzamide;

8-(Cyclopropylamino)-6-((3-fluoro-5-(1H-1,2,4-triazol-1-yl)phenyl)amino)imidazo[1,2-b]pyridazine-3-carbonitrile;

8-(Cyclopropylamino)-6-((3,5-di-1H-1,2,4-triazol-1-ylphenyl)amino)imidazo[1,2-b]pyridazine-3-carbonitrile;

8-(Cyclopropylamino)-6-((3-(2-(methylamino)ethoxy)-5-(1H-1,2,4-triazol-1-yl)phenyl)amino)imidazo[1,2-b]pyridazine-3-carbonitrile;

8-Amino-6-((3-(1H-1,2,4-triazol-1-yl)-5-(trifluoromethyl)phenyl)amino)imidazo[1,2-b]pyridazine-3-carbonitrile;

N-(3-((3-Cyano-8-(cyclopropylamino)imidazo[1,2-b]pyridazin-6-yl)amino)-5-(trifluoromethyl)phenyl)methanesulfonamide;

Methyl (3-((3-cyano-8-(cyclopropylamino)imidazo[1,2-b]pyridazin-6-yl)amino)-5-(tetrahydro-2H-pyran-4-ylcarbamoyl)phenyl)carbamate;

3-Cyano-5-((3-cyano-8-(cyclopropylamino)imidazo[1,2-b]pyridazin-6-yl)amino)-N-methylbenzenesulfonamide;

N-(3-Cyano-5-((3-cyano-8-(cyclopropylamino)imidazo[1,2-b]pyridazin-6-yl)amino)phenyl)methanesulfonamide;

3-Cyano-5-((3-cyano-8-(cyclopropylamino)imidazo[1,2-b]pyridazin-6-yl)amino)-N-ethylbenzenesulfonamide;

6-((3-Amino-4-fluorophenyl)amino)-8-(cyclopropylamino)imidazo[1,2-b]pyridazine-3-carbonitrile;

Methyl (3-((3-cyano-8-(cyclopropylamino)imidazo[1,2-b]pyridazin-6-yl)amino)-5-(methylsulfonyl)phenyl)carbamate;

3-((3-Cyano-8-(cyclopropylamino)imidazo[1,2-b]pyridazin-6-yl)amino)-N-(2-(diethylamino)ethyl)-5-(1H-1,2,4-triazol-1-yl)benzamide;

6-((3-Chloro-5-cyanophenyl)amino)-8-(cyclopropylamino)imidazo[1,2-b]pyridazine-3-carbonitrile;

3-Cyano-5-((3-cyano-8-(cyclopropylamino)imidazo[1,2-b]pyridazin-6-yl)amino)-N-(tetrahydro-2H-pyran-4-yl)benzenesulfonamide;

6-((3-Cyano-5-((4-methyl-1-piperazinyl)sulfonyl)phenyl)amino)-8-(cyclopropylamino)imidazo[1,2-b]pyridazine-3-carbonitrile;

3-Cyano-5-((3-cyano-8-(cyclopropylamino)imidazo[1,2-b]pyridazin-6-yl)amino)benzenesulfonamide;

3-((3-Cyano-8-(cyclopropylamino)imidazo[1,2-b]pyridazin-6-yl)amino)-5-(methylsulfonyl)benzoic acid;

8-Anilino-6-((3-cyano-5-(trifluoromethyl)phenyl)amino)imidazo[1,2-b]pyridazine-3-carbonitrile;

6-((3-Cyano-5-(trifluoromethyl)phenyl)amino)-8-((2-hydroxyethyl)amino)imidazo[1,2-b]pyridazine-3-carbonitrile;

6-((3-Cyano-5-(trifluoromethyl)phenyl)amino)-8-((2-(4-morpholinyl)ethyl)amino)imidazo[1,2-b]pyridazine-3-carbonitrile;

3-((3-Cyano-8-(cyclopropylamino)imidazo[1,2-b]pyridazin-6-yl)amino)-5-(1H-1,2,4-triazol-1-yl)benzamide;

8-Amino-6-((3-cyano-5-(trifluoromethyl)phenyl)amino)imidazo[1,2-b]pyridazine-3-carbonitrile;

3-((3-Cyano-8-(cyclopropylamino)imidazo[1,2-b]pyridazin-6-yl)amino)-N-methyl-5-(1H-1,2,4-triazol-1-yl)benzamide;

6-((3-Cyano-5-fluorophenyl)amino)-8-(2-pyridinylamino)imidazo[1,2-b]pyridazine-3-carbonitrile;

6-((3-Cyano-4-methylphenyl)amino)-8-(2-pyridinylamino)imidazo[1,2-b]pyridazine-3-carbonitrile;

8-Amino-6-((3-cyano-5-fluorophenyl)amino)imidazo[1,2-b]pyridazine-3-carbonitrile;

8-Amino-6-((3-cyano-4-methylphenyl)amino)imidazo[1,2-b]pyridazine-3-carbonitrile;

6-((3-Cyano-5-fluorophenyl)amino)-8-((2-methoxyethyl)amino)imidazo[1,2-b]pyridazine-3-carbonitrile;

6-((3-Cyano-4-methylphenyl)amino)-8-((2-methoxyethyl)amino)imidazo[1,2-b]pyridazine-3-carbonitrile;

6-((3-Cyano-5-fluorophenyl)amino)-8-((2,2,2-trifluoroethyl)amino)imidazo[1,2-b]pyridazine-3-carbonitrile;

6-((3-Cyano-5-(trifluoromethyl)phenyl)amino)-8-((2,2,2-trifluoroethyl)amino)imidazo[1,2-b]pyridazine-3-carbonitrile;

6-((3-Cyano-5-(trifluoromethyl)phenyl)amino)-8-(cyclobutylamino)imidazo[1,2-b]pyridazine-3-carbonitrile;

8-Amino-6-((3-cyano-4-(trifluoromethoxy)phenyl)amino)imidazo[1,2-b]pyridazine-3-carbonitrile;

Methyl (5-((8-amino-3-cyanoimidazo[1,2-b]pyridazin-6-yl)amino)-2-methylphenyl)carbamate;

6-((3-Chloro-5-cyanophenyl)amino)-8-(cyclobutylamino)imidazo[1,2-b]pyridazine-3-carbonitrile;

8-Amino-6-((3-fluoro-5-(1H-1,2,4-triazol-1-yl)phenyl)amino)imidazo[1,2-b]pyridazine-3-carbonitrile;

8-(Cyclobutylamino)-6-((3-methoxy-5-(5-methyl-1H-tetrazol-1-yl)phenyl)amino)imidazo[1,2-b]pyridazine-3-carbonitrile;

8-(Cyclopropylamino)-6-((2-oxo-1,2,3,4-tetrahydro-7-quinolinyl)amino)imidazo[1,2-b]pyridazine-3-carbonitrile;

Methyl (5-((3-cyano-8-((2-methoxyethyl)amino)imidazo[1,2-b]pyridazin-6-yl)amino)-2-methylphenyl)carbamate;

6-((5-Cyano-2-methoxyphenyl)amino)-8-(cyclobutylamino)imidazo[1,2-b]pyridazine-3-carbonitrile;

6-((2-Chloro-5-cyanophenyl)amino)-8-(cyclobutylamino)imidazo[1,2-b]pyridazine-3-carbonitrile;

6-((5-Cyano-2-methoxyphenyl)amino)-8-(cyclopropylamino)imidazo[1,2-b]pyridazine-3-carbonitrile;

8-(Cyclopropylamino)-6-((3-(3-pyridinyl)phenyl)amino)imidazo[1,2-b]pyridazine-3-carbonitrile;

6-((3-Cyano-4-(trifluoromethoxy)phenyl)amino)-8-((2-methoxyethyl)amino)imidazo[1,2-b]pyridazine-3-carbonitrile;

8-(Cyclopropylamino)-6-((3-(4-pyridinyl)phenyl)amino)imidazo[1,2-b]pyridazine-3-carbonitrile;

6-((3-Cyano-4-(trifluoromethoxy)phenyl)amino)-8-(2-pyridinylamino)imidazo[1,2-b]pyridazine-3-carbonitrile;

8-Amino-6-((4-methyl-2-oxo-1,2-dihydro-7-quinolinyl)amino)imidazo[1,2-b]pyridazine-3-carbonitrile;

8-Amino-6-((4-methyl-3-oxo-3,4-dihydro-2H-1,4-benzoxazin-6-yl)amino)imidazo[1,2-b]pyridazine-3-carbonitrile;

8-(Cyclopropylamino)-6-((4-methyl-3-oxo-3,4-dihydro-2H-1,4-benzoxazin-6-yl)amino)imidazo[1,2-b]pyridazine-3-carbonitrile;

6-((3-Cyano-4-methylphenyl)amino)-8-((2,2,2-trifluoroethyl)amino)imidazo[1,2-b]pyridazine-3-carbonitrile;

6-((3-Methoxy-5-(1H-tetrazol-1-yl)phenyl)amino)-8-((2,2,2-trifluoroethyl)amino)imidazo[1,2-b]pyridazine-3-carbonitrile;

8-(Cyclopropylamino)-6-((2-oxo-4-(trifluoromethyl)-1,2-dihydro-7-quinolinyl)amino)imidazo[1,2-b]pyridazine-3-carbonitrile;

(5-((3-Cyano-8-(cyclopropylamino)imidazo[1,2-b]pyridazin-6-yl)amino)-2-methylphenyl)acetic acid;

6-((2-Chloro-5-cyano-4-methylphenyl)amino)-8-(cyclopropylamino)imidazo[1,2-b]pyridazine-3-carbonitrile;

8-Amino-6-((2-chloro-5-cyano-4-methylphenyl)amino)imidazo[1,2-b]pyridazine-3-carbonitrile;

8-Amino-6-((2-chloro-5-cyanophenyl)amino)imidazo[1,2-b]pyridazine-3-carbonitrile;

8-Amino-6-((5-cyano-2-methoxyphenyl)amino)imidazo[1,2-b]pyridazine-3-carbonitrile;

6-((5-Cyano-2-(trifluoromethyl)phenyl)amino)-8-(cyclopropylamino)imidazo[1,2-b]pyridazine-3-carbonitrile;

6-((5-Cyano-2-(trifluoromethyl)phenyl)amino)-8-((2,2,2-trifluoroethyl)amino)imidazo[1,2-b]pyridazine-3-carbonitrile;

6-((3-Cyano-4-(trifluoromethyl)phenyl)amino)-8-((2,2,2-trifluoroethyl)amino)imidazo[1,2-b]pyridazine-3-carbonitrile;

6-((3-Cyano-4-(trifluoromethyl)phenyl)amino)-8-(cyclopropylamino)imidazo[1,2-b]pyridazine-3-carbonitrile;

6-((2-Chloro-5-cyano-4-methylphenyl)amino)-8-(2-pyridinylamino)imidazo[1,2-b]pyridazine-3-carbonitrile;

6-((5-Cyano-3-fluoro-2-methoxyphenyl)amino)-8-((2,2,2-trifluoroethyl)amino)imidazo[1,2-b]pyridazine-3-carbonitrile;

N-(5-((3-Cyano-8-(cyclopropylamino)imidazo[1,2-b]pyridazin-6-yl)amino)-2-ethylphenyl)methanesulfonamide;

8-Amino-6-((3-(4H-1,2,4-triazol-4-yl)-5-(trifluoromethyl)phenyl)amino)imidazo[1,2-b]pyridazine-3-carbonitrile;

6-((5-Cyano-2-(trifluoromethoxy)phenyl)amino)-8-(cyclopropylamino)imidazo[1,2-b]pyridazine-3-carbonitrile;

6-((5-Cyano-2-(2-(4-morpholinyl)ethoxy)phenyl)amino)-8-(cyclopropylamino)imidazo[1,2-b]pyridazine-3-carbonitrile;

6-((5-Cyano-3-fluoro-2-methoxyphenyl)amino)-8-(cyclopropylamino)imidazo[1,2-b]pyridazine-3-carbonitrile;

6-((4-Chloro-3-cyanophenyl)amino)-8-(cyclopropylamino)imidazo[1,2-b]pyridazine-3-carbonitrile;

8-Amino-6-((5-cyano-2-(trifluoromethyl)phenyl)amino)imidazo[1,2-b]pyridazine-3-carbonitrile;

8-(Cyclopropylamino)-6-((2-methoxy-5-(4-pyridinyl)phenyl)amino)imidazo[1,2-b]pyridazine-3-carbonitrile;

N-(4-Chloro-5-((3-cyano-8-(cyclopropylamino)imidazo[1,2-b]pyridazin-6-yl)amino)-2-methylphenyl)methanesulfonamide;

8-(Cyclopropylamino)-6-((4-(diethylamino)phenyl)amino)imidazo[1,2-b]pyridazine-3-carbonitrile;

8-(Cyclopropylamino)-6-((3-((2-(dimethylamino)ethyl)amino)-5-(4H-1,2,4-triazol-4-yl)phenyl)amino)imidazo[1,2-b]pyridazine-3-carbonitrile;

6-((3-Cyano-5-(4-morpholinyl)phenyl)amino)-8-(cyclopropylamino)imidazo[1,2-b]pyridazine-3-carbonitrile;

6-((3-Cyano-4-(4-morpholinyl)phenyl)amino)-8-(cyclopropylamino)imidazo[1,2-b]pyridazine-3-carbonitrile;

6-((3-Cyano-4-(4-methyl-1-piperazinyl)phenyl)amino)-8-(cyclopropylamino)imidazo[1,2-b]pyridazine-3-carbonitrile;

N-(3-((3-Cyano-8-(cyclopropylamino)imidazo[1,2-b]pyridazin-6-yl)amino)phenyl)sulfamide;

1-(3-((3-Cyano-8-(cyclopropylamino)imidazo[1,2-b]pyridazin-6-yl)amino)phenyl)-3-methylurea;

N-(5-((3-Cyano-8-((5-hydroxy-2-pyridinyl)amino)imidazo[1,2-b]pyridazin-6-yl)amino)-2-methylphenyl)acetamide;

N-(5-((3-Cyano-8-((5-(2-hydroxyethoxy)-2-pyridinyl)amino)imidazo[1,2-b]pyridazin-6-yl)amino)-2-methylphenyl)acetamide;

3-(6-(3-Acetamido-4-methylphenylamino)-3-cyanoimidazo[1,2-b]pyridazin-8-ylamino)-N-(2-(dimethylamino)ethyl)benzamide;

3-((3-Cyano-6-((3-methoxy-5-(5-methyl-1H-tetrazol-1-yl)phenyl)amino)imidazo[1,2-b]pyridazin-8-yl)amino)-N-methyl-N-(1-methyl-3-pyrrolidinyl)benzamide;

3-((3-Cyano-6-((3-methoxy-5-(5-methyl-1H-tetrazol-1-yl)phenyl)amino)imidazo[1,2-b]pyridazin-8-yl)amino)-N-(2-(dimethylamino)ethyl)benzamide;

2-(5-((3-Cyano-8-(cyclopropylamino)imidazo[1,2-b]pyridazin-6-yl)amino)-2-methylphenyl)acetamide; or a pharmaceutically acceptable salt thereof.

11. A pharmaceutical composition comprising one or more compounds of claim 1 or 10 and a pharmaceutically acceptable carrier.

* * * * *

UNITED STATES PATENT AND TRADEMARK OFFICE

CERTIFICATE OF CORRECTION

PATENT NO. : 8,252,795 B2
APPLICATION NO. : 12/575589
DATED : August 28, 2012
INVENTOR(S) : Brian E. Fink et al.

It is certified that error appears in the above-identified patent and that said Letters Patent is hereby corrected as shown below:

In the Claims:

Claim 1:

Column 232, line 23, change "$(O)_2R_c$" to -- $(O)_2R_c$, --.

Claim 3:

Column 234, line 23, change "$-(CH_{2c})_rOC$" to -- "$-(CH_2)_rOC$ --.

Claim 4:

Column 234, line 66, change "$-NHS(O)_2R_e$," to -- $-NHS(O)_2R_c$, --.

Column 235, lines 10 and 11, change "$-(CH_2)_rC_{3-10}$-carbocyclyl" to -- $-(CH_2)_r-C_{3-10}$carbocyclyl --.

Column 235, line 14, change "$C_{3-6}$-carbocyclyl," to -- $C_{3-6}$carbocyclyl, --.

Claim 5:

Column 235, line 62, change "$C_{1-4}$-alkyl" to -- $C_{1-4}$alkyl --.

Claim 6:

Column 235, line 67, change "O—$C_{1-4}$-alkyl" to -- O—$C_{1-4}$alkyl --.

Column 236, line 1, after "—$O(CH_2)_rNR_aC_{1-4}$alkyl", insert -- , --.

Signed and Sealed this
Seventeenth Day of March, 2015

Michelle K. Lee
*Director of the United States Patent and Trademark Office*